(12) United States Patent
Arioli et al.

US009121074B2

(10) Patent No.: US 9,121,074 B2
(45) Date of Patent: Sep. 1, 2015

(54) *GOSSYPIUM HIRSUTUM* PLANTS WITH INCREASED FIBER STRENGTH COMPRISING A FIBER STRENGTH ALLELE SPANNING THE GLUC1.1A GENE FROM *GOSSYPIUM BARBADENSE*

(75) Inventors: Tony Arioli, Lubbock, TX (US); Steven Engelen, Lokeren (BE); John Jacobs, Merelbeke (BE); Michel Van Thournout, Sint-Michiels (BE); Stephane Bourot, Comines (FR)

(73) Assignee: Bayer CropScience N.V., Diegem (BE)

( * ) Notice: Subject to any disclaimer, the term of this patent is extended or adjusted under 35 U.S.C. 154(b) by 632 days.

(21) Appl. No.: 12/992,907

(22) PCT Filed: May 25, 2009

(86) PCT No.: PCT/EP2009/003674
§ 371 (c)(1),
(2), (4) Date: Nov. 16, 2010

(87) PCT Pub. No.: WO2009/143995
PCT Pub. Date: Dec. 3, 2009

(65) Prior Publication Data
US 2011/0093970 A1 Apr. 21, 2011

Related U.S. Application Data

(60) Provisional application No. 61/128,938, filed on May 27, 2008.

(30) Foreign Application Priority Data

May 26, 2008 (EP) .................................. 08075514

(51) Int. Cl.
*C12N 15/82* (2006.01)
*C12N 9/24* (2006.01)
*C12Q 1/68* (2006.01)

(52) U.S. Cl.
CPC ....... *C12Y 302/01039* (2013.01); *C12N 9/2402* (2013.01); *C12N 15/8246* (2013.01); *C12Q 1/6895* (2013.01)

(58) Field of Classification Search
USPC ........................................................ 800/281
See application file for complete search history.

(56) References Cited

U.S. PATENT DOCUMENTS

| | | | |
|---|---|---|---|
| 5,004,863 A | 4/1991 | Umbeck | |
| 5,792,933 A | 8/1998 | Ma | |
| 5,985,557 A | 11/1999 | Prudent et al. | |
| 6,001,567 A | 12/1999 | Brow et al. | |
| 6,166,294 A | 12/2000 | Kasukabe et al. | |
| 6,259,003 B1 | 7/2001 | Fujisawa et al. | |
| 6,483,013 B1 | 11/2002 | Reynaerts et al. | |
| 2003/0106097 A1 | 6/2003 | Haigler et al. | |
| 2005/0138683 A1 | 6/2005 | Mahill et al. | |

FOREIGN PATENT DOCUMENTS

| | | |
|---|---|---|
| EP | 0534858 | 3/1993 |
| EP | 1339859 | 9/2003 |
| WO | 9215675 | 9/1992 |
| WO | 9830698 | 7/1998 |
| WO | 9953050 | 10/1999 |
| WO | 0001133 | 1/2000 |
| WO | 0210377 | 2/2002 |
| WO | 0210413 | 2/2002 |
| WO | 02059294 | 8/2002 |
| WO | 03076619 | 9/2003 |
| WO | 2005017157 | 2/2005 |
| WO | WO 2005/017157 | * 2/2005 |
| WO | WO 2005/017157 A1 | * 2/2005 |
| WO | 2005047505 | 5/2005 |
| WO | 2006044322 | 4/2006 |
| WO | 2008083969 | 7/2008 |

OTHER PUBLICATIONS

Hsieh et al., Single Fiber Strength Variations of Developing Cotton Fibers—Strength and Structure of *G.hirsutum* and *G.barbedense*, 70 Textile Res. J., 682-690 (2000).*
Saha et al., Breeding and Genetics: Effect of Chromosome Substitutions from *Gossypium barbadense* L.3-79 into *G.hirsutum* L. TM-1 on Agronomic and Fiber Traits, 8 Journal of Cotton Science, 162-169 (2004).*
Park et al., Genetic mapping of new cotton fiber loci using EST-derived microsatellites in an interspecific recombinant inbred line cotton population, 274 Mol Gen Genomics, 428-441 (2005).*
Kohel et al., Molecular mapping and characterization of traits controlling fiber quality in cotton, 121 Euphytica, 163-172 (2001).*
Saha et al., Effect of Chromosome Substitutions from *Gossypium barbadense* L.3-79 into *G. hirsutum* L. TM-1 on Agronomic and Fiber Traits, 8 J of Cotton Science, 162-169 (2004).*
Van Ooijen, Johan W. et al., "MapQTL Version 3.0: Software for the Calculation of QTL Positions on Genetic Maps", Plant Genome IV Conference, Town & Country Conference Center, San Diego, CA, Jan. 1995.
Vos, Pieter et al., "AFLP: a new technique for DNA fingerprinting", Nucleic Acids Research, vol. 23, No. 21, p. 4407-4414, 1995.
Wang, Kai et al., "Complete assignment of the chromosomes of *Gossypium hirsutum* L. by translocation and fluorescence in situ hybridiation mapping", Theor Appl Genet, vol. 113, p. 73-80, 2006.
Wendel, Jonathan et al., "Allozyme Diversity and Introgression in the Galapagos Islands Endemic *Gossypium darwinii* and its Relationship to Continental *G. barbadense*", Biochemical Systematics and Ecology, vol. 18, No. 7/8, p. 517-528, 1990.

(Continued)

*Primary Examiner* — Cynthia Collins
*Assistant Examiner* — Rebecca Stephens

(57) ABSTRACT

This invention relates to the field of agriculture, more specifically to the use of molecular biology techniques to alter fiber-producing plants, particularly cotton plants, and/or accelerate breeding of such fiber-producing plants. Methods and means are provided to alter fiber qualities, such as increasing fiber strength. Methods are also provided to identify molecular markers associated with fiber strength in a population of cotton varieties and related progenitor plants.

13 Claims, 20 Drawing Sheets

(56) References Cited

OTHER PUBLICATIONS

Williams, John G. K. et al., "DNA polymorphisms amplified by arbitrary primers are useful as genetic markers", Nucleic Acids Research, vol. 18, No. 22, p. 6531-6535, 1990.

Xu, Mingliang et al., "Development of sequence-characterized amplified regions (SCARs) from amplified fragment length polymorphism (AFLP) markers tightly linked to the Vf gene in apple", Genome, vol. 44, p. 63-70, 2001.

Yanxin, Zhang et al., "Studies of new EST-SSRs derived from *Gossypium barbadense*", Chinese Science Bulletin, vol. 52, No. 18, p. 2522-2531, Sep. 2007.

Allard, R. W., "Reproductive Systems and Plant Breeding Methods", Principles of Plant Breeding, John Wiley & Sons, New York 1999.

Arioli, Tony et al., "Molecular Analysis of Cellulose Biosynthesis in *Arabidopsis*", Science, vol. 279, p. 717, 1998.

Barret, P. et al., "Development of a SCAR (sequence characterised amplified region) marker for molecular tagging of the dwarf BREIZH (BZH) gene in *Brassica napus* L.", Theor Appl Genet, vol. 97, p. 828-833. 1998.

Botstein, David et al., "Construction of a Genetic Linkage Map in Man Using Restriction Fragment Length Polymorphisms", Am J Hum Genet, vol. 32, p. 314-331, 1980.

Delanghe, Edmond A. L. et al., "Lint Development", The Cotton Foundation, Memphis, TN, p. 325-349, 1986.

Dussle, C. M. et al., "Conversion of AFLP fragments tightly linked to SCMV resistance genes Scmv1 and Scmv2 into Simple PCR-based markers", Theor Appl Genet, vol. 105, p. 1190-1195, 2002.

Fehr W. R., "Genetic Male Sterility for Population Improvement", Principles of Cultivar Development, vol. 1, Theory and Techniques, Collier Macmillan Publishers, London, ISBN 0-02-949920-8 1998.

Guo, P.-G. et al., "AFLP and STS tagging of a major QTL for *Fusarium* head blight resistance in wheat", Theor Appl Genet, vol. 106, p. 1011-1017, 2003.

Haigler, Candace H., "Substrate Supply for Cellulose Synthesis and Its Stress Sensitivity in the Cotton Fiber", Molecular and Structural Biology, p. 147-168, 2007.

Hayashi, Takahisa et al., "Xyloglucan in the cell walls of cotton fiber", Carbohydrate Research, vol. 181, p. 273-277, 1988.

Henikoff, Steven et al., "TILLING. Tradition Mutagenesis Meets Functional Genomics", Plant Physiology, vol. 135, p. 630-636, Jun. 2004.

Hsieh, You-Lo, "Structural Development of Cotton Fibers and Linkages to Fiber Quality", Developmental Biology, Quality Improvement, and Textile Processing, The Haworth PRess, New York, p. 137-165, 1999.

Huwyler, H. R., et al., "Changes in the Composition of Cotton Fibre Cell Walls during Development", Planta, vol. 146, p. 635-642, 1979.

Jansen, Ritsert C. et al., "High Resolution of Quantitative Traits Into Multiple Loci via Interval Mapping", Genetics, vol. 136, p. 1447-1455, Apr. 1994.

Jansen, Ritsert C., "Interval Mapping of Multiple Quantitative Trait Loci", Genetics, vol. 135, p. 205-211, Sep. 1993.

Jiang, Chun-Xiao et al., "Polyploid formation created unique avenues for response to selection in *Gossypium* (cotton)", Proc. Natl. Acad. Sci., vol. 95, p. 4419-4424, Apr. 1998.

Keller, Greg et al., "Transgenic cotton resistant to herbicide bialaphos", Transgenic Research, vol. 6, p. 385-392, 1997.

Kim, Hee Jin et al., "Cotton Fiber Growth in Planta and in Vitro. Models for Plant Cell Elongation and Cell Wall Biogenesis", Plant Physiology, vol. 127, p. 1361-1366, 2001.

Kosambi, D. D. "The Estimation of Map Distances From Recombination Values", Ann. Eugenet, vol. 12, p. 172-175, 1944.

Lacape, Jean-Marc et la., "QTL Analysis of Cotton Fiber Quality Using Multiple *Gossypium hirsutum* X *Gossypium barbadense* Backcross Generation", Crop. Sci., vol. 45, p. 123-140, 2005.

Li, Xin et al., "A fast neutron deletion mutagenesis-based reverse genetics system for plants", The Plant Journal, vol. 27, No. 3, p. 235-242, 2001.

Li, Xin et al., "Reverse genetics by fast neutron mutagenesis in higher plants", Funct Integr Genomics, vol. 2, p. 254-258, 2002.

Maltby, David et al., "B-1,3-Glucan in Developing Cotton Fibers", Plant Physiol. vol. 63, p. 1158-1164. 1979.

McCallum, Claire M. et al., "Targeted screening for induced mutations", Nature Biotechnology, vol. 18, p. 455-457, Apr. 2000.

McCallum, Claire M. et al., "Targeting Induced Local Lesions in Genomes (TILLING) for Plant Functional Genomics", Plant Physiology, vol. 123, p. 439-442, Jun. 2000.

Mei, M. et al., "Genetic mapping and QTL analysis of fiber-related traits in cotton (*Gossypium*)", Theor Appl Genet, vol. 108, pg. 280-291, 2004.

Meier, H. et al., "(1-3)-B-D-Glucan (callose) is a probable intermediate in biosynthesis of cellulose of cotton fibres", Nature, vol. 289, p. 821-822 1981.

Meinert, Maureen C. et al., "Changes in Biochemical Composition of the Cell Wall of the Cotton Fiber During Development", Plant Physiol. vol. 59, p. 1088-1097, 1977.

Meksem, K. et al., "Conversion of AFLP bands into high-throughput DNA markers", Mol Genet Genomics, vol. 265, p. 207-214, 2001.

Muller, Jurgen et al., "Crystal Structure of Barley 1,3-1, 4-B-Glucanase at 2.0-A Resolution and Comparison with *Bacillus* 1,3-1, 4-B-Glucanase", The Journal of Biological Chemistry, vol. 273, No. 6, p. 3438-3446, Feb. 1998.

Needleman, Saul B. et al., "A General Method Applicable to the Search for Similarities in the Amino Acid Sequence of Two Proteins", J. Mol. Biol., vol. 48, p. 443-453, 1970.

Negi, M. S. et al., "Identification of AFLP fragments linked to seed coat colur in *Brassica juncea* and conversion to a SCAR marker for rapid selection", Theor Appl Genet, vol. 101, p. 146-152, 2000.

Paran, I. et al., "Development of reliable PCR-based markers linked to downy mildew resistance genes in lettuce", Theor Appl Genet, vol. 85, p. 985-993, 1993.

Park, Young-Hoon et al., "Genetic mapping of new cotton fiber loci using EST-derived microsatellites in an interspecific recombinant inbred line cotton population", Mol Gen Genomics, vol. 274, p. 428-441, 2005.

Peng, Liangcai et al., "Sitosterol-B-glucoside as Primer for Cellulose Synthesis in Plants", Science, vol. 295, p. 147-150, 2002.

Pfluger, Jennifer et al., "Cell growth: The power of symplastic isolation", Current Biology, vol. 11, R436-R439, 2001.

Rice, Peter et al., "EMBOSS: The European Molecular Biology Open Software Suite", TIG, vol. 16, No. 6, p. 276-277, 2000.

Ruan, Yong-Ling et al., "A Fiberless Seed Mutation in Cotton is Associated with Lack of Fiber Cell Initiation in Ovule Epidermis and Alterations in Sucrose Synthase Expression and Carbon Partitioning in Developing Seeds", Plant Physiol., vol. 118, p. 399-406, 1998.

Ruan, Yong-Ling et al., "Pathway and control of sucrose import into initiating cotton fibre cells", Aust. J. Plant Physiol, vol. 27, p. 795-800, 2000.

Ruan, Yong-Ling et al., "The Control of Single-Celled Cotton Fiber Elongation by Developmentally Reversible Gating of Plasmodesmata and Coordinated Expression of Sucrose and K Transporters and Expansin", The Plant Cell, vol. 13, p. 47-60, Jan. 2001.

Ruan, Yong-Ling et al., "Genotypic and Developmental Evidence for the Role of Plasmodesmatal Regulation in Cotton Fiber Elongation Mediated by Callose Turnover", Plant Physiology, vol. 136, p. 4104-4113, Dec. 2004.

Schwab, Rebecca et al., "Highly Specific Gene Silencing by Artificial MicroRNAs in *Arabidopsis*", The Plant Cell, vol. 18, p. 1121-1133, May 2006.

Siebert, Paul D. et al., "An improved PCR method of walking in uncloned genomic DNA", Nucleic Acids Reserach, vol. 23, No. 6, p. 1087-1088, 1995.

Stam, Piet, "Construction of integrated genetic linkage maps by means of a new computer package: JoinMap", The Plant Journal, vol. 3, No. 5, p. 739-744, 1993.

Stelly D. M. et al., "Registration of 17 Upland (*Gossypium hirsutum*) Cotton Germplasm Lines Disomic for Different *G. Barbadense* Chromosome or Arm Substitutions", Crop Science, vol. 45, No. 6, p. 2663-2665, 2005.

Tanksley, S. D. et al., "RFLP Mapping in Plant Breeding: New Tools for an Old Science", Bio/Technology, vol. 7, p. 257-263, Mar. 1989.

(56) References Cited

OTHER PUBLICATIONS

Tautz, Diethard, "Hypervariablity of simple sequences as a general source for polymorphic DNA markers", Nucleic Acids Research, vol. 17, No. 16, p. 6463-6471, 1989.

Taylor, Neil G., "Cellulose biosynthesis and deposition in higher plants", New Phytologist, vol. 178, p. 239-252, 2008.

Triplett, B. A., "Using biotechnology to improve cotton fiber quality: progess and perspectives", Cellulosics, p. 135-140, 1993.

Van'T Hof, Jack, "Increased Nuclear DNA Content in Developing Cotton Fiber Cells", American Journal of Botany, vol. 86, No. 6, p. 776-779, 1999.

\* cited by examiner

```
                 putative signal peptide      ><: Putative post-translational splicing site
GhGLUC1.1A     1 -----------mlfltqilsltdgr><digvcygingnlpspgdvinlfktsginnirlyqpypevleaargsgislsms
GbGLUC1.1A     1 -----------mlfltqilsltdgr><digvcygingnlpspgdvinlfktsginnirlyqpypevleaargsgislsms
GhGLUC1.1D     1 mgptfsgflisamvfltqilsltdgr><digvcygingnlpspgdvinlrlyqpypevleaargsgislsmg
GbGLUC1.1D     1 mgptfsgflisamvfltqilsltdgr><digvcygingnlpspgdvinlyktsginnirlyqsypevleaargsgislsmg GhGLUC1.1A    69 ttnediqslatdq---saadawvntnivpykedvqfrfliigneaipgqsssyipgamnnimnslasfgigtttkvttvvp
GbGLUC1.1A    69 ttnediqslatdqthqsaadawvntnivpykedvqfrfliigneaipgqsssyipgamnnimnslasfgigtttkvttvvp
GhGLUC1.1D    81 prnediqslakdq---saadawvntnivpykddvqfkliitigneaisgqssyipdamnnimslalfgigtttkvttvvp
GbGLUC1.1D    81 prnediqslakdq---saadawvntnivpykddvqfkliitigneaisgqssyipdamnnimslalfgigtttkvttvvp GhGLUC1.1A   146 mnalstsyppsdgafgsditsimtsimaillvrqdspllinvypyfayasdpthislnyalftstapvvvdqgleynlfd
GbGLUC1.1A   149 mnalstsyppsdgafgsditsimtsimaillv-------------------------------------------------
GhGLUC1.1D   158 mnalstsyppsdgafgsditsimtsimaillavqdspllinvypyfayasdpthisldyalftstapvvvdqgleynlfd
GbGLUC1.1D   158 mnalstsyppsdgafgsditsimtsimaillavqdspllinvypyfayasdpthisldyalftstapvvvdqgleynlfd GH17 signature
GhGLUC1.1A   226 gmvdafnaaldkigfgqitlivaetgwptagnepytsvanaqtynknllnhvtqkgtpkrpeyimptfffemfnenlkqp
GbGLUC1.1A       -----------------------------------------------------------------------------
GhGLUC1.1D   238 gmvdafnaaldkigfgqitlivaetgwptagnepytsvanaqtynknllnhvtqkgtpkrpeyimptfffemfnedlkqp
GbGLUC1.1D   238 gmvdafnaaldkigfgqitlivaetgwptagnepytsvanaqtynknllnhvtqkgtpkrpeyimptfffemfnedlkqp GhGLUC1.1A   306 tveqnfgfffpnmnpvypfw
GbGLUC1.1A       --------------------
GhGLUC1.1D   318 tveqnfgfffpnmnpvypfw
GbGLUC1.1D   318 tveqnfgfffpnmnpvypfw
```

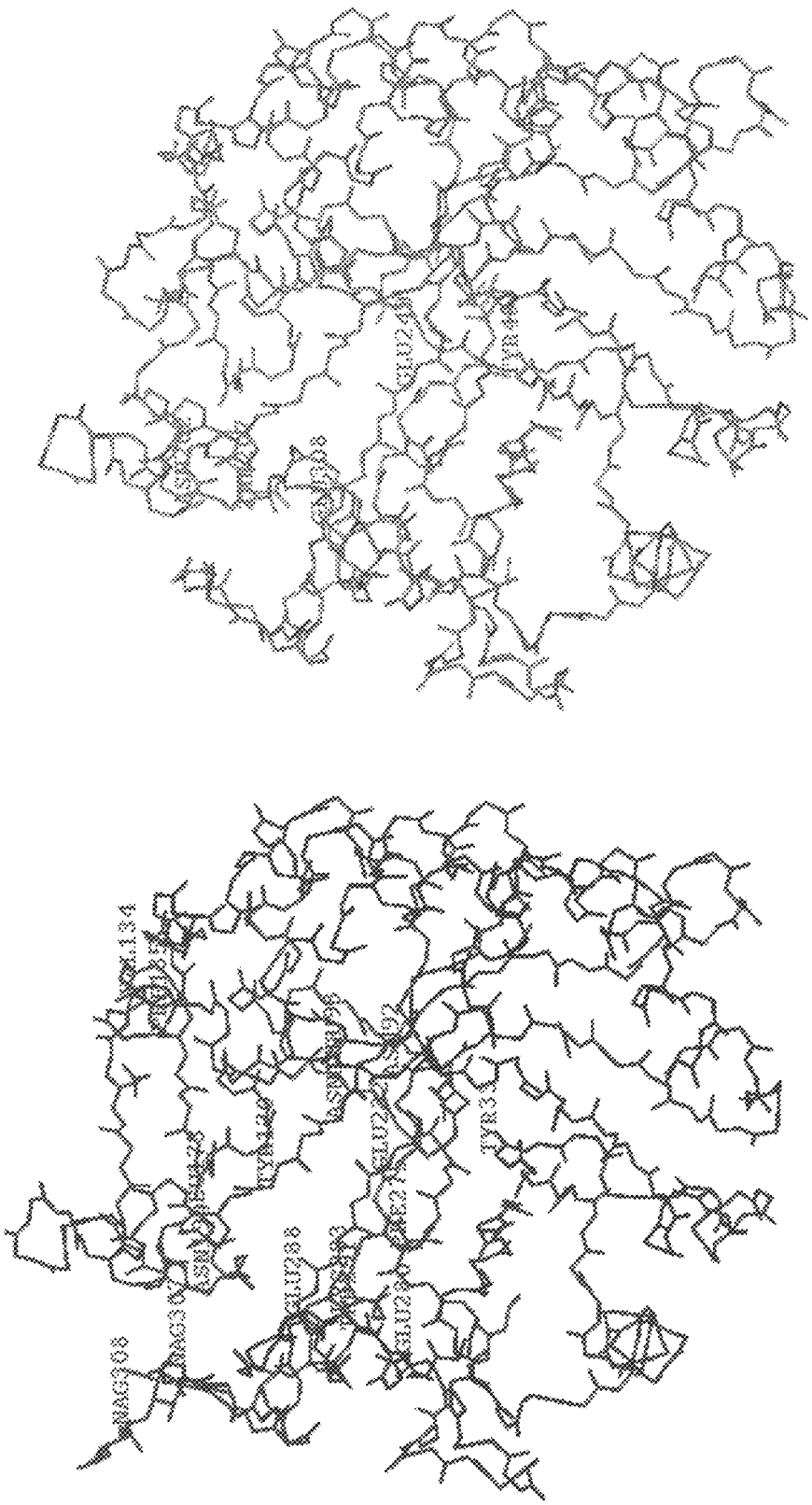

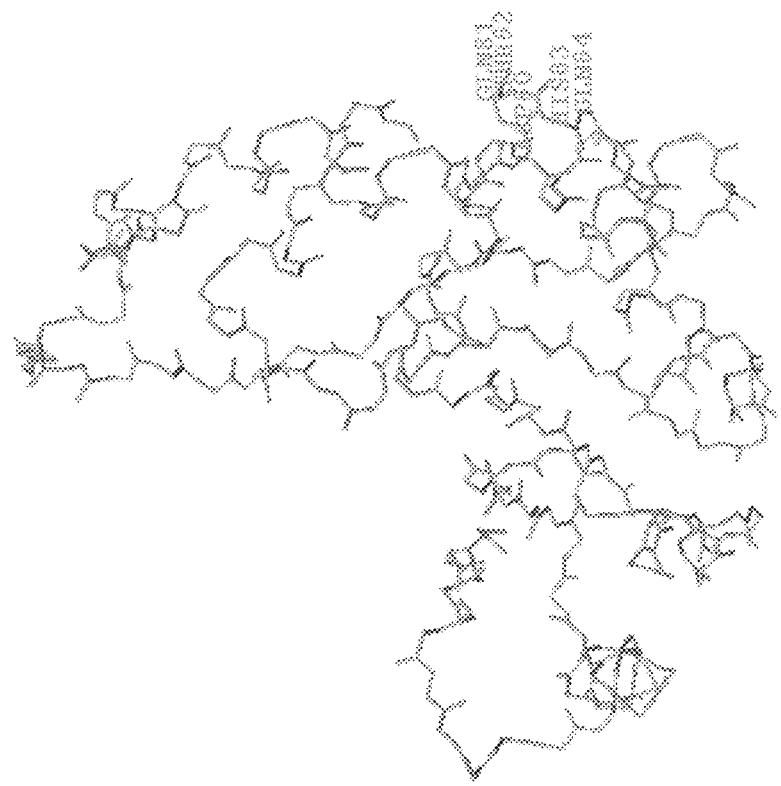
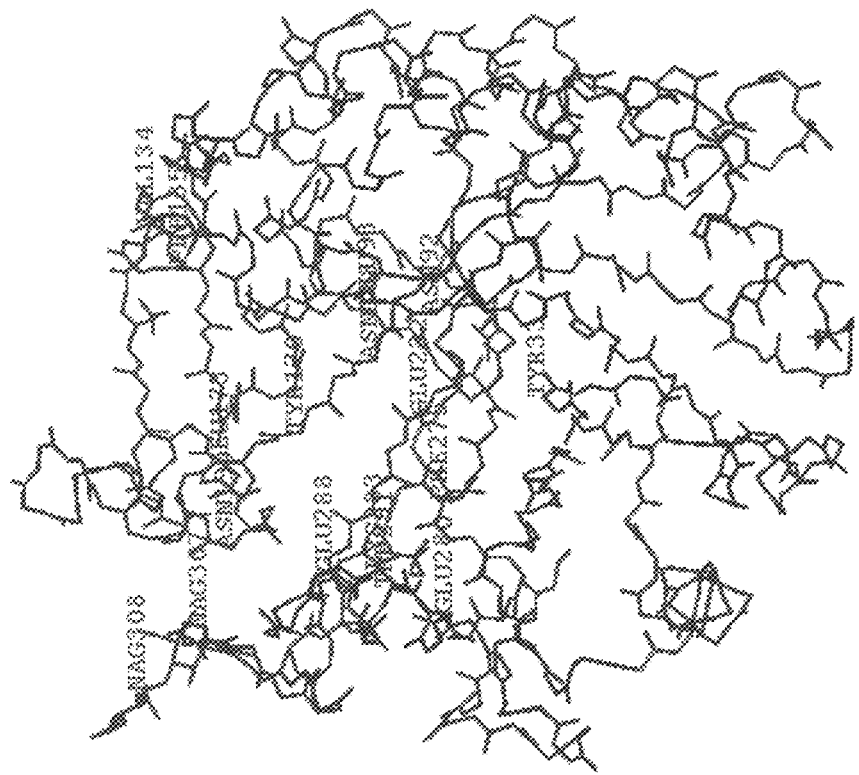
Figure 3b

```
GhGLUC1.1A_gDNA    712  tcgcccctcctgatcaatgtgtaccctatttgcctatgcctcagacccactcatatttccctcaactacgccttgtt
GtGLUC1.1A_gDNA    470  tcgcccctcctgatcaatgtgtaccctatttgcctatgcctcagacccactcatatttccctcaactacgccttgtt
GbGLUC1.1A_gDNA    721  tcgcccctcctgatcaatgtgtaccctatttgcctatgcctcagacccactcatatttccctcaactacgccttgtt
GdGLUC1.1A_gDNA    721  tcgcccctcctgatcaatgtgtaccctatttgcctatgcctcagacccactcatatttccctcaactacgccttgtt
GmGLUC1.1A-gDNA    470  tcgcccctcctgatcaatgtgtaccctatttgcctatgcctcagacccactcatatttccctcaactacgccttgtt
GaGLUC1.1A-gDNA    711  tcgcccctcctgatcaatgtgtaccctatttgcctatgcctcagacccactcatatttccctcaactacgccttgtt
GheGLUC1.1A-gDNA   712  tcgcccctcctgatcaatgtgtaccctatttgcctatgcctcagacccactcatatttccctcaactacgccttgtt
GhGLUC1.1D_gDNA    694  tcgcccctcctgatcaatgtgtaccctatttgcctatgcctcagacccactcatatttccctca a acgccttgtt
GtGLUC1.1D_gDNA    470  tcgcccctcctgatcaatgtgtaccctatttgcctatgcctcagacccactcatatttccctca a acgccttgtt
GbGLUC1.1D_gDNA    694  tcgcccctcctgatcaatgtgtaccctatttgcctatgcctcagacccactcatatttccctca a acgccttgtt
GdGLUC1.1D_gDNA    694  tcgcccctcctgatcaatgtgtaccctatttgcctatgcctcagacccactcatatttccctca a acgccttgtt
GmGLUC1.1D-gDNA    470  tcgcccctcctgatcaatgtgtaccctatttgcctatgcctcagacccactcatatttccctca a acgccttgtt
GrGLUC1.1D-gDNA    470  tcgcccctcctgatcaatgtgtaccctatttgcctatgcctcagacccactcatatttccctca a acgccttgtt
                                                                                       GLUC1.1A-SNP6 [g/a]
                                GLUC1.1A-SNP8 [c/g]                                        →
                                    →

GhGLUC1.1A_gDNA    792  cacctcgaccgcgcaccggtggtcgaccaaggcttggaatactacaacctctcttgacggcatgtcgatgctttcaatg
GtGLUC1.1A_gDNA    550  cacctcgaccgcgcaccggtggtcgaccaaggcttggaatactacaacctctcttgacggcatgtcgatgctttcaatg
GbGLUC1.1A_gDNA    801  cacctcgaccgcgcaccggtggtcgaccaa g gcttggaatactacaacctctcttgacggcat g tcgatgctttcaatg
GdGLUC1.1A_gDNA    801  cacctcgaccgcgcaccggtggtcgaccaaggcttggaatactacaacctctcttgacggcatgtcgatgctttcaatg
GmGLUC1.1A-gDNA    550  cacctcgaccgcgcaccggtggtcgaccaaggcttggaatactacaacctctcttgacggcatgtcgatgctttcaatg
GaGLUC1.1A-gDNA    791  cacctcgaccgcgcaccggtggtcgaccaaggcttggaatactacaacctctcttgacggcatgtcgatgctttcaatg
GheGLUC1.1A-gDNA   792  cacctcgaccgcgcaccggtggtcgaccaaggcttggaatactacaacctctcttgacggcatgtcgatgctttcaatg
GhGLUC1.1D_gDNA    774  cacctcgaccgcgcaccggtggtcgaccaaggcttggaatactacaacctctcttgacggcatgtcgatgctttcaatg
GtGLUC1.1D_gDNA    550  cacctcgaccgcgcaccggtggtcgaccaaggcttggaatactacaacctctcttgacggcatgtcgatgctttcaatg
GbGLUC1.1D_gDNA    774  cacctcgaccgcgcaccggtggtcgaccaaggcttggaatactacaacctctcttgacggcatgtcgatgctttcaatg
GdGLUC1.1D_gDNA    774  cacctcgaccgcgcaccggtggtcgaccaaggcttggaatactacaacctctcttgacggcatgtcgatgctttcaatg
GmGLUC1.1D-gDNA    550  cacctcgaccgcgcaccggtggtcgaccaaggcttggaatactacaacctctcttgacggcatgtcgatgctttcaatg
GrGLUC1.1D-gDNA    550  cacctcgaccgcgcaccggtggtcgaccaaggcttggaatactacaacctctcttgacggcatgtcgatgctttcaatg
                                                              ←------SE002-------

GhGLUC1.1A_gDNA    872  ccgcccctagataagatcggcttcggccttcggcc---------------------------------------------
GtGLUC1.1A_gDNA    630  ccgcccctagataagatcggcttcggccttcggcc---------------------------------------------
GbGLUC1.1A_gDNA    881  ccgcccctagataagatcggcttcggccttcggcc---------------------------------------------
GdGLUC1.1A_gDNA    881  ccgcccctagataagatcggcttcggccttcggcc---------------------------------------------
GmGLUC1.1A-gDNA    630  ccgcccctagataagatcggcttcggccttcggcc---------------------------------------------
GaGLUC1.1A-gDNA    871  ccgcccctagataagatcggcttcggccttcggcc---------------------------------------------
GheGLUC1.1A-gDNA   872  ccgcccctagataagatcggcttcggccttcggcc---------------------------------------------
GhGLUC1.1D_gDNA    854  ccgcccctagataagatcggcttcggccaattactctcattgtagccgaaactgatgccgaccgcggtaacgagcct
GtGLUC1.1D_gDNA    630  ccgcccctagataagatcggcttcggccaattactctcattgtagccgaaactgatgccgaccgcggtaacgagcct
GbGLUC1.1D_gDNA    854  ccgcccctagataagatcggcttcggccaattactctcattgtagccgaaactgatgccgaccgcggtaacgagcct
GdGLUC1.1D_gDNA    854  ccgcccctagataagatcggcttcggccaattactctcattgtagccgaaactgatgccgaccgcggtaacgagcct
GmGLUC1.1D-gDNA    630  ccgcccctagataagatcggcttcggccaattactctcattgtagccgaaactgatgccgaccgcggtaacgagcct
GrGLUC1.1D-gDNA    630  ccgcccctagataagatcggcttcggccaattactctcattgtagccgaaactgatgccgaccgcggtaacgagcct
```

| | | |
|---|---|---|
| GhGLUC1.1A_gDNA | 1192 | gagacgcttcatatag |
| GtGLUC1.1A-gDNA | | |
| GbGLUC1.1A-gDNA | 1175 | gagacgcttca |
| GdGLUC1.1A-gDNA | 1175 | gagacgcttca |
| GmGLUC1.1A-gDNA | | |
| GaGLUC1.1A-gDNA | 1191 | gagacgcttcatatag |
| GheGLUC1.1A-gDNA | 1192 | gagacgcttcatatag |
| GhGLUC1.1D_gDNA | 1171 | gagacgcttcatatag |
| GtGLUC1.1D_gDNA | | |
| GbGLUC1.1D_gDNA | 1171 | gagacgcttcatatag |
| GdGLUC1.1D_gDNA | 1171 | gagacgcttcatatag |
| GmGLUC1.1D-gDNA | | |
| GrGLUC1.1D-gDNA | | |

```
                    putative signal peptide      ><: Putative post-translational splicing site
GhGLUC1.1A-prot   1 ------------mlfitqlsltdgr><digvcyglngnnipspdvinlfktsginnirlyqpypevleaargsgisisms
GtGLUC1.1A-prot   1 -------------------------><digvcyglngnnipspdvinlfktsginnirlyqpypevleaargsgisisms
GbGLUC1.1A-prot   1 -------------mifliqlsltdgr><digvcyglngnnipspdvinlfktsginnirlyqpypevleaargsgisisms
GdGLUC1.1A-prot   1 -------------mifliqlsltdgr><digvcyglngnnipspdvinlfktsginnirlyqpypevleaargsgisisms
GmGLUC1.1A-prot   1 -------------------------><-gnnipspgdvinlfktsginnirlyqpypevleaargsgisisms
GaGLUC1.1A-prot   1 -------------------------><-gnnipspgdvinlfktsginnirlyqpypevleaargsgisisms
GheGLUC1.1A-prot  1 mgprfsgflisamlfitqlsltdgr><digvcyglngnnipspqdvinlfktsginnirlyqpypevleaargsgisisms
GhGLUC1.1D-prot   1 mgprfsgflisamifitqlsltdgr><digvcyglngnnipspqdvinlfktsginnirlyqpypevleaargsgisisms
GtGLUC1.1D-prot   1 mgprfsgflisamfitqlsltdgr><digvcyglngnnipspqdvinlfktsginnirlyqpypevleaargsgisisms
GbGLUC1.1D-prot   1 mgprfsgflisamflicqlsltdgr><digvcyglngnnipspqdvinlfktsginnirlyqpypevleaargsgisisms
GdGLUC1.1D-prot   1 mgprfsgflisamflicqlsltdgr><digvcyglngnnipspqdvinlfktsginnirlyqpypevleaargsgisisms
GmGLUC1.1D-prot   1 -------------------------><-gnnipspgdvinlfktsginnirlyqpypevleaargsgisisms
GrGLUC1.1D-prot   1 -------------------------><-gnnipspgdvinlfktsginnirlyqpypevleaargsgisisms GhGLUC1.1A-prot   69 ttnediqslatd---qsaadawvntnivpykedvqfrfliigneaipgqsssyipgamnimnslasfgigttkvttvvp
GtGLUC1.1A-prot   46 ttnediqslatd---qsaadawvntnivpykedvqfrfliigneaipgqsssyipgamnimnslasfgigttkvttvvp
GbGLUC1.1A-prot   69 ttnediqslatd---qsaadawvntnivpykedvqfrfliigneaipgqsssyipgamnimnslasfgigttkvttvvp
GdGLUC1.1A-prot   69 ttnediqslatd---qsaadawvntnivpykedvqfrfliigneaipgqsssyipgamnimnslasfgigttkvttvvp
GmGLUC1.1A-prot   46 ttnediqslatd---qsaadawvntnivpykedvqfrfliigneaipgqsssyipgamnimnslasfgigttkvttvvp
GaGLUC1.1A-prot   46 -----------------------------------------------------------------------------
GheGLUC1.1A-prot  81 ttnediqslatd---qsaadawvntnivpykdvqfrfliigneaipgqsssyipgamnimnslasfgigttkvttvvp
GhGLUC1.1D-prot   81 ttnediqsland---qsaadawvntnivpykdvqfkitigneaigqsssyipamnimnslafgigttkvttvvp
GtGLUC1.1D-prot   46 ttnediqsland---qsaadawvntnivpykdvqfkitigneaigqsssyipamnimnslafgigttkvttvvp
GbGLUC1.1D-prot   69 ttnediqsland---qsaadawvntnivpykdvqfkitigneaigqsssyipamnimnslafgigttkvttvvp
GdGLUC1.1D-prot   81 ttnediqsland---qsaadawvntnivpykdvqfkitigneaigqsssyipamnimnslafgigttkvttvvp
GmGLUC1.1D-prot   46 ttnediqsland---qsaadawvntnivpykdvqfkitigneaigqsssyipamnimnslafgigttkvttvvp
GrGLUC1.1D-prot   46 ttnediqsland---qsaadawvntnivpykdvqfkitigneaigqsssyipamnimnslafgigttkvttvvp GhGLUC1.1A-prot  146 mnaistsyppsdgafgsditsimtsimailvrqdspllinvypyfayasdpthislnyalftstapvvvdqgieyynlfd
GtGLUC1.1A-prot  123 mnaistsyppsdgafgsditsimtsimailvrqdspllinvypyfayasdpthislnyalftstapvvvdqgieyynlfd
GbGLUC1.1A-prot  149 mnaistsyppsdgafgsditsimtsimailv-----------------------------------------------
GdGLUC1.1A-prot  149 mnaistsyppsdgafgsditsimtsimailv-----------------------------------------------
GmGLUC1.1A-prot  123 mnaistsyppsdgafgsditsimtsimailv-----------------------------------------------
GaGLUC1.1A-prot   69 -----------------------------------------------------------------------------
GheGLUC1.1A-prot 158 mnaistsyppsdgafgsditsimtsimailqdspllinvypyfayasdpthislyalftstapvvvdqgieyynlfd
GhGLUC1.1D-prot  158 mnaistsyppsdgafgsditsimtsimailqdspllinvypyfayasdpthislyalftstapvvvdqgieyynlfd
GtGLUC1.1D-prot  123 mnaistsyppsdgafgsditsimtsimailqdspllinvypyfayasdpthislyalftstapvvvdqgieyynlfd
GbGLUC1.1D-prot  158 mnaistsyppsdgafgsditsimtsimailqdspllinvypyfayasdpthislyalftstapvvvdqgieyynlfd
GdGLUC1.1D-prot  158 mnaistsyppsdgafgsditsimtsimailqdspllinvypyfayasdpthislyalftstapvvvdqgieyynlfd
GmGLUC1.1D-prot  123 mnaistsyppsdgafgsditsimtsimailqdspllinvypyfayasdpthislyalftstapvvvdqgieyynlfd
GrGLUC1.1D-prot  123 mnaistsyppsdgafgsditsimtsimailqdspllinvypyfayasdpthislyalftstapvvvdqgieyynlfd
```

Figure 7b

```
                    GH17 signature
GhGLUC1.1A-prot 226 gmvdafnaaldkigfgqitlivaetgwptagnepytsvanaqtynknilnhvtqkgtpkrpeyimptfffemfnenlkqp
GtGLUC1.1A-prot 203 gmvdaaldkigfg-----------------------------------------------------------------
GbGLUC1.1A-prot     ------------------------------------------------------------------------------
GdGLUC1.1A-prot     ------------------------------------------------------------------------------
GmGLUC1.1A-prot 203 gmvdafnaaldkigfg--------------------------------------------------------------
GaGLUC1.1A-prot  76 ------------------------------------------------------------------------------
GheGLUC1.1A-prot 238 gmvdafnaaldkigfgqitlivaetgwptagnepytsvanaqtynknilnhvtqkgtpkrpeyimptfffemfnenlkqp
GhGLUC1.1D-prot 238 gmvdafnaaldkigfgqitlivaetgwptagnepytsvanaqtynknilnhvtqkgtpkrpeyimptfffemfnelkqp
GtGLUC1.1D-prot 203 gmvdafnaaldkigfg--------------------------------------------------------------
GbGLUC1.1D-prot 238 gmvdafnaaldkigfgqitlivaetgwptagnepytsvanaqtynknilnhvtqkgtpkrpeyimptfffemfnelkqp
GdGLUC1.1D-prot 238 gmvdafnaaldkigfgqitlivaetgwptagnepytsvanaqtynknilnhvtqkgtpkrpeyimptfffemfnelkqp
GmGLUC1.1D-prot 203 gmvdafnaaldkigfg--------------------------------------------------------------
GrGLUC1.1D-prot 203 gmvdafnaaldkigfg--------------------------------------------------------------

GhGLUC1.1A-prot 306 tveqnfgfffpnmnpvypfw
GtGLUC1.1A-prot     --------------------
GbGLUC1.1A-prot     --------------------
GdGLUC1.1A-prot     --------------------
GmGLUC1.1A-prot     --------------------
GaGLUC1.1A-prot     --------------------
GheGLUC1.1A-prot 318 tveqnfgfffpnmnpvypfw
GhGLUC1.1D-prot 318 tveqnfgfffpnmnpvypfw
GtGLUC1.1D-prot     --------------------
GbGLUC1.1D-prot 318 tveqnfgfffpnmnpvypfw
GdGLUC1.1D-prot 318 tveqnfgfffpnmnpvypfw
GmGLUC1.1D-prot     --------------------
GrGLUC1.1D-prot     --------------------
```

GOSSYPIUM HIRSUTUM PLANTS WITH INCREASED FIBER STRENGTH COMPRISING A FIBER STRENGTH ALLELE SPANNING THE GLUC1.1A GENE FROM GOSSYPIUM BARBADENSE

CROSS REFERENCE TO RELATED APPLICATION

This application is a §371 U.S. National Stage of International Application No. PCT/EP09/003674, which claims the benefit of U.S. Provisional Application Ser. No. 61/128,938, filed May 27, 2008, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "CS9046PCTUSSequenceListingST25.txt", created on Nov. 11, 2010, and having a size of 358 kilobytes and is filed concurrently with the specification. The sequence listing contained in this ASCII formatted document is part of the specification and is herein incorporated by reference in its entirety.

FIELD OF THE INVENTION

This invention relates to the field of agriculture, more specifically to the use of molecular biology techniques to alter fiber-producing plants, particularly cotton plants, and/or accelerate breeding of such fiber-producing plants. Methods and means are provided to alter fiber qualities, such as increasing fiber strength. Methods are also provided to identify molecular markers associated with fiber strength in a population of cotton varieties and related progenitor plants.

BACKGROUND OF THE INVENTION

Cotton provides much of the high quality fiber for the textile industry. The modification of cotton fiber characteristics to better suit the requirements of the industry is a major effort in breeding by either classical methods or by genetically altering the genome of cotton plants.

About 90% of cotton grown worldwide is *Gossypium hirsutum* L., whereas *Gossypium barbadense* accounts for about 8%. As in most flowering plants, cotton genomes are thought to have incurred one or more polyploidization events and to have evolved by the joining of divergent genomes in a common nucleus. The cotton commerce is dominated by improved forms of two "AD" allotetraploid species, *Gossypium hirsutum* L. and *Gossypium barbadense* L (both 2n=4x=52). Allotetraploid cottons are thought to have formed about 1-2 million years ago, in the New World, by hybridization between a maternal Old World "A" genome taxon resembling *Gossypium herbaceum* (2n=2x=26) and paternal New World "D" genome taxon resembling *Gossypium raimondii* or *Gossypium gossypioides* (both 2n=2x=26). Wild A genome diploid and AD allotetraploid *Gossypium* taxa produce spinnable fibers. One A genome diploid species, *Gossypium arboreum* (2n=2x=26), remains intensively bred and cultivated in Asia. Its close relative and possible *Gossypium* progenitor, the A genome diploid species *G. herbaceum*, also produces spinnable fiber. Although the seeds of D genome diploids are pubescent, none produce spinnable fibers. No taxa from the other recognized diploid *Gossypium* genomes (B, C, E, F, G and K) have been domesticated. Intense directional selection by humans has consistently produced AD allotetraploid cottons that have superior yield and/or quality characteristics compared to the A genome diploid cultivars. Selective breeding of *G. hirsutum* (AADD; "Upland" cotton) has emphasized maximum yield, whereas *G. barbadense* (AADD; "Sea Island", "Pima", or "Egyptian" cotton) is prized for its fibers of superior length, strength, and fineness (Jiang et al., 1998, Proc Natl Acad Sci USA. 95(8): 4419-4424).

A cotton fiber is a single cell that initiates from the epidermis of the outer integument of the ovules, at or just prior to anthesis. Thereafter, the fibers elongate rapidly for about 3 weeks before they switch to intensive secondary cell wall cellulose synthesis. Fiber cells interconnect only to the underlying seed coat at their basal ends and influx of solute, water and other molecules occurs through either plasmodesmata or plasma membrane. Ruan et al. 2001 (Plant Cell 13: 47-63) demonstrated a transient closure of plasmodesmata during fiber elongation. Ruan et al. 2004 (Plant Physiology 136: 4104-4113) compared the duration of plasmodesmata closure among different cotton genotypes differing in fiber length and found a positive correlation between the duration of the plasmodesmata closure and fiber length. Furthermore, microscopic evidence was presented showing callose deposition and degradation at the fiber base, correlating with the timing of plasmodesmata closure and reopening. Expression of a endo-1,3-beta-glucanase gene in the fibers, allowing to degrade callose, correlated with the reopening of the plasmodesmata at the fiber base.

WO2005/017157 describes methods and means for modulating fiber length in fiber producing plants such as cotton by altering the fiber elongation phase. The fiber elongation phase may be increased or decreased by interfering with callose deposition in plasmodesmata at the base of the fiber cells.

WO2008/083969 (claiming priority of European patent application EP 07000550) discloses isolated DNA molecules comprising a nucleotide sequence encoding cotton endo-1,3-beta-glucanases and fiber cell preferential promoter or promoter regions, as well as methods for modifying the length of a fiber of a cotton plant using these sequences or promoters. WO2008/083969 also describes that the timing of expression of the A and D subgenome specific alleles of the fiber specific endo-1,3-beta-glucanase gene in *Gossypium hirsutum* is different. Whereas the onset of the expression of the D subgenome specific allele correlates with the end of the rapid elongation phase (about 14 to 17 days post-anthesis, hereinafter abbreviated "DPA"), onset of the expression of the A subgenome specific allele is delayed until the beginning of the late fiber maturation phase (about 35-40 DPA) depending on growth conditions.

One fiber characteristic that is of special interest for the cotton industry is fiber strength. There is not only a high correlation between fiber strength and yarn strength, but also cotton with high fiber strength is more likely to withstand breakage during the manufacturing process.

Fiber strength is, among many other textile properties of cotton fibers (e.g., fiber wall thickness or maturity, dyeability, extensibility . . . ), described to be directly dependent on the amount and properties (e.g., degree of polymerization, crystallite size, and microfibril orientation) of cellulose (Ramey, 1986, In: Mauney J. R. and Stewart J. McD. (eds.) *Cotton Physiology. The Cotton Foundation*, Memphis, Tenn., pp. 351-360; Triplett, 1993, In: *Cellulosics: Pulp, Fibre, and Environmental Aspects*. Ellis Horwood, Chichester, UK, pp. 135-140; Hsieh, 1999, In: Basra A. S. (ed.) *Cotton Fibers: Developmental Biology, Quality Improvement, and Textile*

*Processing.* The Haworth Press, New York, pp. 137-166). Advances in the past decade, particularly using the model plant *Arabidopsis* (Arioli et al., 1998, Science 279(5351): 717-720), have led to a great increase in the knowledge of the proteins involved in cellulose synthesis. Despite this, there is still much to learn about cellulose synthesis, especially about how it is regulated at both transcriptional and post-transcriptional levels (Taylor, 2008, New Phytologist 178 (2), 239-252).

Typical primary fiber cell walls in *G. hirsutum*, which are about 0.5 μM thick and contain 20-25% cellulose along with pectin, xyloglucan, and protein (Meinert and Delmer 1977, Plant Physiol 59:1088-1097), are synthesized during fiber elongation (Haigler, 2007, In: R. M. Brown, Jr. and I. M. Saxena (eds.), *Cellulose: Molecular and Structural Biology*, 147-168, Springer). Primary wall deposition proceeds alone until 14-17 DPA, then a transition phase with concurrent primary and secondary wall deposition occurs between 15-24 DPA (representing deposition of the "winding layer"), followed by predominantly secondary wall synthesis until at least 40 DPA. The first period of wall thickening (12-16 DPA) is accomplished by continued synthesis in the same proportions of primary wall components (Meinert and Delmer, 1977, supra), an observation that is consistent with increasing wall birefringence while the cellulose microfibrils remain transversely oriented (Seagull, 1986, Can J Bot 64:1373-1381). The secondary wall finally attains a thickness of 3-6 μM around the whole circumference of the fiber, becoming thinner only at the fiber tip. In *G. barbadense*, there is an overlap between primary and secondary wall deposition within each fiber rather than in the fiber population because the overlapping period is greatly prolonged, and 90% of secondary wall deposition is complete before elongation ceases (DeLanghe, 1986, In: Mauney J. R. and Stewart J. McD. (eds.) cotton Physiology. The Cotton Foundation, Memphis, Tenn., pp. 325-350). It is thought that elongation continues exclusively at the fiber tip as secondary wall is deposited over most of the cell surface.

Maltby et al. (1979, Plant Physiol. 63, 1158-1164) describe that developing fibers of *Gossypium hirsutum* transiently synthesize 1,3-beta-D-glucan (callose) at the onset of secondary wall deposition followed by massive synthesis of cellulose. Meier et al. (1981, Nature 289: 821-822) describe that callose may be a probable intermediate in biosynthesis of cellulose of cotton fibers. DeLanghe (1986, supra) describes that callose may be required in cotton fiber secondary walls to provide a space for the crystallization and final orientation of cellulose microfibrils in the exoplasmic zone in the absence of typical matrix molecules.

The inventions described hereinafter in the different embodiments, examples, figures and claims provide improved methods and means for modulating fiber strength. More specifically, the present invention describes how to increase fiber strength and at the same time maintain a high fiber yield in plants. In particular, the invention describes how to increase fiber strength in cotton species selected for high yield, such as *Gossypium hirsutum*, by introgression of fiber strength determining genes from other cotton species selected for high fiber strength, such as *Gossypium barbadense*. Methods are also provided to identify molecular markers associated with fiber strength in a population of cotton varieties and related progenitor plants. The inventions described hereinafter also provide novel nucleic acid molecules encoding fiber-specific *Gossypium* glucanase proteins (GLUC1.1) and the proteins as such.

SUMMARY OF THE INVENTION

The inventors identified a quantitative trait locus for fiber strength on chromosome A05 of *Gossypium* and found that *Gossypium barbadense* comprises an allele of this fiber strength locus that is superior to the allele of this QTL from *Gossypium hirsutum*, i.e. the presence of the *Gossypium barbadense* fiber strength allele in a *Gossypium* plant results in a higher fiber strength as compared to the fiber strength of a *Gossypium* plant comprising the *Gossypium hirsutum* fiber strength allele.

Thus, in a first aspect, the present invention provides a non-naturally occurring *Gossypium* plant, and parts and progeny thereof, comprising at least one superior allele of a fiber strength locus on chromosome A05.

In one embodiment, the plant is a plant from an A genome diploid *Gossypium* species, such as *Gossypium herbaceum* or *Gossypium arboreum*, or an AD genome allotetraploid *Gossypium* species, such as *Gossypium hirsutum* and *Gossypium barbadense*, and the superior fiber strength allele is derived from a different A or AD genome *Gossypium* species.

In another embodiment, the plant is a *Gossypium hirsutum*, a *Gossypium herbaceum* or a *Gossypium arboreum* plant, preferably a *Gossypium hirsutum* plant, and the superior fiber strength allele is derived from *Gossypium barbadense*.

In one aspect, the *Gossypium barbadense* fiber strength allele is located on chromosome A05 of *Gossypium barbadense* between AFLP marker P5M50-M126.7 and SSR marker CIR280. In another aspect, between AFLP marker P5M50-M126.7 and SSR marker BNL3992. In still another aspect, between AFLP marker P5M50-M126.7 and SSR marker CIR401c. In yet another aspect, is the LOD peak of the *Gossypium barbadense* fiber strength allele located between SSR marker NAU861 or the GLUC1.1 gene and SSR marker CIR401c. In a further aspect, is the LOD peak of the *Gossypium barbadense* fiber strength allele located at about 0 to 5 cM, more specifically at about 4.008 cM, from SSR marker NAU861 or the GLUC1.1 gene. In still a further aspect, is the LOD peak of the *Gossypium barbadense* fiber strength allele is located at about 0 to 12 cM, more specifically at about 10 cM, especially at about 10.52 cM, from SSR marker CIR401c.

In another aspect, the *Gossypium barbadense* fiber strength allele comprises at least one *Gossypium barbadense* ortholog of a nucleotide sequence comprised in the genomic DNA sequence spanning the *Gossypium hirsutum* GLUC1.1A gene represented in SEQ ID NO: 53.

In still another aspect, the *Gossypium barbadense* fiber strength allele comprises a GLUC1.1 gene encoding a non-functional GLUC1.1 protein. In one aspect, the *Gossypium barbadense* GLUC1.1 gene is characterised by the presence of a T nucleotide at a nucleotide position corresponding to nucleotide position 712 of SEQ ID NO: 5. In a further aspect, the *Gossypium barbadense* GLUC1.1 gene is located at about 0 to 5 cM, more specifically at about 4 cM, from the LOD peak of the *Gossypium barbadense* fiber strength allele. In yet a further aspect, the *Gossypium barbadense* GLUC1.1 gene is located at about 0 to 2 cM, at about 0 to 1 cM, more specifically at about 0.008 cM of the NAU861 marker.

In yet another embodiment, the plant is a *Gossypium hirsutum*, *Gossypium barbadense*, a *Gossypium herbaceum* or a *Gossypium arboreum* plant, preferably a *Gossypium hirsutum* plant, and the superior fiber strength allele is derived from *Gossypium darwinii*. In one aspect, the *Gossypium darwinii* fiber strength allele comprises a GLUC1.1 gene encoding a non-functional GLUC1.1 protein. In another aspect, the *Gossypium darwinii* GLUC1.1 gene is characterised by the presence of a T nucleotide at a nucleotide position corresponding to nucleotide position 761 of SEQ ID NO: 56.

In still another embodiment, the plant is a *Gossypium hirsutum*, *Gossypium barbadense* or a *Gossypium herbaceum* plant, preferably a *Gossypium hirsutum* plant, and the superior fiber strength allele is derived from *Gossypium arboreum*. In one aspect, the *Gossypium arboreum* fiber strength allele comprises a GLUC1.1 gene encoding a nonfunctional GLUC1.1 protein. In another aspect, the *Gossypium arboreum* GLUC1.1 gene is characterised by the absence of a C nucleotide at a nucleotide position corresponding to the nucleotide position between position 327 and 328 of SEQ ID NO: 21.

In a further embodiment, the callose content of the fibers is increased in the plant compared to the callose content of the fibers of an equivalent *Gossypium* plant that does not comprise the at least one superior allele of the fiber strength locus.

In yet a further embodiment, the strength of the fibers is increased in the plant compared to the strength of the fibers of an equivalent *Gossypium* plant that does not comprise the at least one superior allele of the fiber strength locus. In one aspect, the strength of the fibers is on average between about 5% and about 10%, preferably about 7.5%, higher. In another aspect, the strength of the fibers is on average between about 1.6 g/tex and about 3.3 g/tex, preferably about 2.5 g/tex, higher. In still another aspect, the strength of the fibers is on average between about 34.6 g/tex and about 36.3 g/tex, preferably about 35.5 g/tex.

In another embodiment, the plant is a *Gossypium hirsutum* plant homozygous for the *Gossypium barbadense* fiber strength allele.

In still another embodiment, the invention provides a fiber obtainable from the plant of any one of paragraphs 13 to 23.

In a further embodiment, the invention provides a method of identifying a *Gossypium barbadense* allele of a fiber strength locus on chromosome A05 in a plant, preferably a *Gossypium* plant, such as a *Gossypium hirsutum* plant, comprising the step of determining the presence of a *Gossypium barbadense* allele of a marker linked to the fiber strength locus in the genomic DNA of the plant selected from the group consisting of: AFLP marker P5M50-M126.7, SSR marker CIR280, SSR marker BNL3992, SSR marker CIR401c, SSR marker NAU861, a polymorphic site in an ortholog of a nucleotide sequence comprised in the genomic DNA sequence spanning a *Gossypium hirsutum* GLUC1.1A gene represented in SEQ ID NO: 53 of the plant; and a polymorphic site in a nucleotide sequence of a GLUC1.1A gene of the plant, such as SNP marker GLUC1.1A-SNP2 located at a nucleotide position corresponding to nucleotide position 418 to 428 in SEQ ID NO: 5, SNP marker GLUC1.1A-SNP3 located at a nucleotide position corresponding to nucleotide position 573 in SEQ ID NO: 5, SNP marker GLUC1.1A-SNP5 located at a nucleotide position corresponding to nucleotide position 712 in SEQ ID NO: 5, SNP marker GLUC1.1A-SNP6 located at a nucleotide position corresponding to nucleotide position 864 in SEQ ID NO: 5 or SNP marker GLUC1.1A-SNP8 located at a nucleotide position corresponding to nucleotide position 832 in SEQ ID NO: 5.

In a particular aspect, the *Gossypium barbadense* allele of AFLP marker P5M50-M126.7 is detected by amplification of a DNA fragment of about 126.7 bp with at least two primers comprising at their extreme 3' end SEQ ID NO: 43 and 44, respectively; the *Gossypium barbadense* allele of SSR marker CIR280 is detected by amplification of a DNA fragment of about 205 bp with at least two primers comprising at their extreme 3' end SEQ ID NO: 51 and 52, respectively; the *Gossypium barbadense* allele of SSR marker BNL3992 is detected by amplification of a DNA fragment of about 140 bp to about 145 bp with at least two primers comprising at their extreme 3' end SEQ ID NO: 49 and 50, respectively; the *Gossypium barbadense* allele of SSR marker CIR401c is detected by amplification of a DNA fragment of about 245 to about 250 bp with at least two primers comprising at their extreme 3' end SEQ ID NO: 47 and 48, respectively; the *Gossypium barbadense* allele of SSR marker NAU861 is detected by amplification of a DNA fragment of about 215 bp to about 220 bp with at least two primers comprising at their extreme 3' end SEQ ID NO: 45 and 46, respectively; the *Gossypium barbadense* allele of SNP marker GLUC1.1A-SNP2 is detected by detecting a CTCATCAAA nucleotide sequence at a position corresponding to the position of SNP marker GLUC1.1A-SNP2 or by amplification of a DNA fragment of about 143 bp with at least two primers comprising at their extreme 3' end SEQ ID NO: 37 and 38, respectively; the *Gossypium barbadense* allele of SNP marker GLUC1.1A-SNP3 is detected by detecting a C nucleotide at a position corresponding to the position of SNP marker GLUC1.1A-SNP3; the *Gossypium barbadense* allele of SNP marker GLUC1.1A-SNP5 is detected by detecting a T nucleotide at a position corresponding to the position of SNP marker GLUC1.1A-SNP5; the *Gossypium barbadense* allele of SNP marker GLUC1.1A-SNP6 is detected by detecting an A nucleotide at a position corresponding to the position of SNP marker GLUC1.1A-SNP6; the *Gossypium barbadense* allele of SNP marker GLUC1.1A-SNP8 is detected by detecting a C nucleotide at a position corresponding to the position of SNP marker GLUC1.1A-SNP8.

In a further embodiment, the invention provides a method of identifying a *Gossypium darwinii* allele of a fiber strength locus on chromosome A05 in a plant, preferably a *Gossypium* plant, such as a *Gossypium hirsutum* plant, comprising the step of determining the presence of a *Gossypium darwinii* specific polymorphic site in a nucleotide sequence of a GLUC1.1A gene in the genomic DNA of the plant corresponding to the nucleotide sequence of a GLUC1.1A gene of SEQ ID NO: 56, such as SNP marker GLUC1.1A-SNP2 located at a nucleotide position corresponding to nucleotide position 476 to 477 in SEQ ID NO: 56, SNP marker GLUC1.1A-SNP3 located at a nucleotide position corresponding to nucleotide position 622 in SEQ ID NO: 56, SNP marker GLUC1.1A-SNP5 located at a nucleotide position corresponding to nucleotide position 761 in SEQ ID NO: 56, SNP marker GLUC1.1A-SNP6 located at a nucleotide position corresponding to nucleotide position 913 in SEQ ID NO: 56 or SNP marker GLUC1.1A-SNP8 located at a nucleotide position corresponding to nucleotide position 881 in SEQ ID NO: 56.

In a particular aspect, the *Gossypium darwinii* allele of SNP marker GLUC1.1A-SNP2 is detected by detecting a CTCATCAAA nucleotide sequence at a position corresponding to the position of SNP marker GLUC1.1A-SNP2 or by amplification of a DNA fragment of about 143 bp with at least two primers comprising at their extreme 3' end SEQ ID NO: 37 and 38, respectively; the *Gossypium darwinii* allele of SNP marker GLUC1.1A-SNP3 is detected by detecting a C nucleotide at a position corresponding to the position of SNP marker GLUC1.1A-SNP3; the *Gossypium darwinii* allele of SNP marker GLUC1.1A-SNP5 is detected by detecting a T nucleotide at a position corresponding to the position of SNP marker GLUC1.1A-SNP5; the *Gossypium darwinii* allele of SNP marker GLUC1.1A-SNP6 is detected by detecting an A nucleotide at a position corresponding to the position of SNP marker GLUC1.1A-SNP6, and the *Gossypium darwinii* allele of SNP marker GLUC1.1A-SNP8 is detected by detecting a G nucleotide at a position corresponding to the position of SNP marker GLUC1.1A-SNP8.

In a further embodiment, the invention provides a method of identifying a *Gossypium arboreum* allele of a fiber strength locus on chromosome A05 in a plant, preferably a *Gossypium* plant, such as a *Gossypium hirsitum* plant, comprising the step of determining the presence of a *Gossypium arboreum* specific polymorphic site in a nucleotide sequence of a GLUC1.1A gene in the genomic DNA of the plant corresponding to the nucleotide sequence of a GLUC1.1A gene of SEQ ID NO: 21, such as SNP marker GLUC1.1A-SNP7 located at a nucleotide position corresponding to a nucleotide position between nucleotide position 327 and 328 in SEQ ID NO: 21. In a particular aspect, the *Gossypium arboreum* allele of SNP marker GLUC1.1A-SNP7 is detected by detecting the absence of a C nucleotide at a position corresponding to the position of SNP marker GLUC1.1A-SNP7.

In a further embodiment, the invention provides a method of distinguishing a *Gossypium barbadense* allele of a fiber strength locus on chromosome A05 from a *Gossypium hirsutum* allele of the fiber strength locus in a plant, preferably a *Gossypium* plant, such as a *Gossypium hirsitum* plant, comprising the step of determining the presence of *Gossypium barbadense* alleles and/or *Gossypium hirsutum* alleles of markers linked to the fiber strength locus in the genomic DNA of the plant selected from the group consisting of: AFLP marker P5M50-M126.7, SSR marker CIR280, SSR marker BNL3992, SSR marker CIR401, SSR marker NAU861; a polymorphic site in an ortholog of a nucleotide sequence comprised in the genomic DNA sequence spanning the *Gossypium hirsutum* GLUC1.1A gene represented in SEQ ID NO: 53 of the plant; and a polymorphic site in a nucleotide sequence of a GLUC1.1A gene in the genomic DNA of the plant, such as SNP marker GLUC1.1A-SNP2 located at a nucleotide position corresponding to nucleotide position 418 to 428 in SEQ ID NO: 5, SNP marker GLUC1.1A-SNP3 located at a nucleotide position corresponding to nucleotide position 573 in SEQ ID NO: 5, SNP marker GLUC1.1A-SNP5 located at a nucleotide position corresponding to nucleotide position 712 in SEQ ID NO: 5, SNP marker GLUC1.1A-SNP6 located at a nucleotide position corresponding to nucleotide position 864 in SEQ ID NO: 5 or SNP marker GLUC1.1A-SNP8 located at a nucleotide position corresponding to nucleotide position 832 in SEQ ID NO: 5.

In a particular aspect, the *Gossypium hirsutum* allele is distinguished from the *Gossypium barbadense* allele of AFLP marker P5M50-M126.7 bp amplification of, respectively, no DNA fragment and a DNA fragment of about 126.7 bp with at least two primers comprising at their extreme 3' end SEQ ID NO: 43 and 44, respectively; the *Gossypium hirsutum* allele is distinguished from the *Gossypium barbadense* allele of SSR marker CIR280 by amplification of, respectively, no DNA fragment and a DNA fragment of about 205 bp with at least two primers comprising at their extreme 3' end SEQ ID NO: 51 and 52, respectively; the *Gossypium hirsutum* allele is distinguished from the *Gossypium barbadense* allele of SSR marker BNL3992 by amplification of, respectively, two DNA fragments, one of about 160 bp to about 165 bp and one of about 85 bp to about 90 bp, and a DNA fragment of about 140 bp to about 145 bp with at least two primers comprising at their extreme 3' end SEQ ID NO: 49 and 50, respectively; the *Gossypium hirsutum* allele is distinguished from the *Gossypium barbadense* allele of SSR marker CIR401 bp amplification of, respectively, a DNA fragment of about 255 bp (CIR401b) and a DNA fragment of about 245 bp to about 250 bp (CIR401c) with at least two primers comprising at their extreme 3' end SEQ ID NO: 47 and 48, respectively; the *Gossypium hirsutum* allele is distinguished from the *Gossypium barbadense* allele of SSR marker NAU861 by amplification of, respectively, a DNA fragment of about 205 bp to about 210 bp and a DNA fragment of about 215 bp to about 220 bp with at least two primers comprising at their extreme 3' end SEQ ID NO: 45 and 46, respectively; the *Gossypium hirsutum* allele is distinguished from the *Gossypium barbadense* allele of SNP marker GLUC1.1A-SNP2 by detecting, respectively, no nucleotide or a CTCATCAAA nucleotide sequence at a position corresponding to the position of SNP marker GLUC1.1A-SNP2, or by amplification of, respectively, a DNA fragment of about 134 bp and a DNA fragment of about 143 bp with at least two primers comprising at their extreme 3' end SEQ ID NO: 37 and 38, respectively; the *Gossypium hirsutum* allele is distinguished from the *Gossypium barbadense* allele of SNP marker GLUC1.1A-SNP3 by detecting, respectively, a G or a C nucleotide at a position corresponding to the position of SNP marker GLUC1.1A-SNP3; the *Gossypium hirsutum* allele is distinguished from the *Gossypium barbadense* allele of SNP marker GLUC1.1A-SNP5 by detecting, respectively, a C or a T nucleotide at a position corresponding to the position of SNP marker GLUC1.1A-SNP5; the *Gossypium hirsutum* allele is distinguished from the *Gossypium barbadense* allele of SNP marker GLUC1.1A-SNP6 by detecting, respectively, a G or an A nucleotide at a position corresponding to the position of SNP marker GLUC1.1A-SNP6; and the *Gossypium hirsutum* allele is distinguished from the *Gossypium barbadense* allele of SNP marker GLUC1.1A-SNP8 by detecting, respectively, a G or a C nucleotide at a position corresponding to the position of SNP marker GLUC1.1A-SNP8.

In another embodiment, the invention provides a method for generating and/or selecting a non-naturally occurring *Gossypium* plant, and parts and progeny thereof, comprising at least one superior allele of a fiber strength locus on chromosome A05, wherein the superior fiber strength allele is derived from *Gossypium barbadense*, comprising the steps of crossing a plant from an A genome diploid *Gossypium* species, such as *Gossypium herbaceum* or *Gossypium arboreum*, or an AD genome allotetraploid *Gossypium* species, such as *Gossypium hirsutum*, with a *Gossypium barbadense* plant, and identifying the *Gossypium barbadense* fiber strength allele according to paragraph 25 or 26.

In another embodiment, the invention provides a method for generating and/or selecting a non-naturally occurring *Gossypium* plant, and parts and progeny thereof, comprising at least one superior allele of a fiber strength locus on chromosome A05, wherein the superior fiber strength allele is derived from *Gossypium darwinii*, comprising the steps of crossing a plant from an A genome diploid *Gossypium* species, such as *Gossypium herbaceum* or *Gossypium arboreum*, or an AD genome allotetraploid *Gossypium* species, such as *Gossypium hirsutum* or *Gossypium barbadense*, with a *Gossypium darwinii* plant, and identifying the *Gossypium darwinii* fiber strength allele according to paragraph 27 or 28.

In another embodiment, the invention provides a method for generating and/or selecting a non-naturally occurring *Gossypium* plant, and parts and progeny thereof, comprising at least one superior allele of a fiber strength locus on chromosome A05, wherein the superior fiber strength allele is derived from *Gossypium arboreum*, comprising the steps of crossing a plant from an A genome diploid *Gossypium* species, such as *Gossypium herbaceum*, or an AD genome allotetraploid *Gossypium* species, such as *Gossypium hirsutum* or *Gossypium barbadense*, with a *Gossypium arboreum* plant, and identifying the *Gossypium arboreum* fiber strength allele according to paragraph 29.

In still another embodiment, the invention provides a method for altering the callose content of a fiber in a *Gossypium* plant, particularly increasing the callose content of a fiber, comprising the steps of: introgressing a superior allele of the fiber strength locus on chromosome A05 in the *Gossypium* plant according to any one of paragraph 32 to 34, and selecting a plant with an altered callose content in its fibers, in particular an increased callose content.

In yet another embodiment, the invention provides a method for altering the properties of a fiber in a *Gossypium* plant, particularly increasing the strength of a fiber, comprising the steps of: introgressing a superior allele of the fiber strength locus on chromosome A05 in the *Gossypium* plant according to any one of paragraph 32 to 34, selecting a plant with an altered fiber strength, in particular an increased fiber strength.

In a further embodiment, the invention provides a kit for of identifying a *Gossypium barbadense* allele of a fiber strength locus on chromosome A05 or for distinguishing a *Gossypium barbadense* allele of a fiber strength locus on chromosome A05 from a *Gossypium hirsutum* allele of the fiber strength locus in a plant, preferably a *Gossypium* plant, such as a *Gossypium hirsutum* plant, comprising primers and/or probes for determining the presence of *Gossypium barbadense* alleles and/or *Gossypium hirsutum* alleles of markers linked to the fiber strength locus in the genomic DNA of the plant selected from the group consisting of: AFLP marker P5M50-M126.7, SSR marker CIR280, SSR marker BNL3992, SSR marker CIR401, SSR marker NAU861, a polymorphic site in an ortholog of a nucleotide sequence comprised in the genomic DNA sequence spanning the *Gossypium hirsutum* GLUC1.1A gene represented in SEQ ID NO: 53, and a polymorphic site in a nucleotide sequence of the GLUC1.1A gene in the genomic DNA of the plant, such as SNP marker GLUC1.1A-SNP2 located at a nucleotide position corresponding to nucleotide position 418 to 428 in SEQ ID NO: 5, SNP marker GLUC1.1A-SNP3 located at a nucleotide position corresponding to nucleotide position 573 in SEQ ID NO: 5, SNP marker GLUC1.1A-SNP5 located at a nucleotide position corresponding to nucleotide position 712 in SEQ ID NO: 5, SNP marker GLUC1.1A-SNP6 located at a nucleotide position corresponding to nucleotide position 864 in SEQ ID NO: 5 or SNP marker GLUC1.1A-SNP8 located at a nucleotide position corresponding to nucleotide position 832 in SEQ ID NO: 5.

In one aspect, the kit comprises at least two primers and/or probes selected from the group consisting of: primers comprising at their extreme 3' end SEQ ID NO: 43 and 44, respectively; primers comprising at their extreme 3' end SEQ ID NO: 51 and 52, respectively; primers comprising at their extreme 3' end SEQ ID NO: 49 and 50, respectively; primers comprising at their extreme 3' end SEQ ID NO: 47 and 48, respectively; primers comprising at their extreme 3' end SEQ ID NO: 45 and 46, respectively; primers comprising at their extreme 3' end SEQ ID NO: 37 and 38, respectively.

The inventors have further found that the properties of fibers in cotton plants can be controlled by controlling the number of endo-1,3-beta-glucanase genes/alleles that are "functionally expressed", i.e. that result in functional (biologically active) endo-1,3-beta-glucanase protein (GLUC), in fibers during the secondary cell wall synthesis phase and the maturation phase, herein commonly referred to as fiber strength building phase, of fiber development. By abolishing the functional expression of a number of endo-1,3-beta-glucanase genes/alleles that are functionally expressed in fibers during the fiber strength building phase, in particular during the maturation phase, of fiber development, such as the A-subgenome specific endo-1,3-beta-glucanase gene in *G. hirsutum*, while maintaining the functional expression of a number of such endo-1,3-beta-glucanase genes/alleles, such as the D-subgenome specific endo-1,3-beta-glucanase gene in *G. hirsutum*, it is believed that the degradation of callose can be decreased to a level allowing a higher fiber strength, while maintaining a level of callose degradation sufficient to obtain an industrially relevant fiber length.

Thus, in another aspect, the present invention provides a non-naturally occurring fiber-producing plant, and parts and progeny thereof, characterized in that the functional expression of at least one allele of at least one fiber-specific GLUC gene that is functionally expressed during the fiber strength building phase, in particular the fiber maturation phase, of fiber development is abolished. Such plants, and parts and progeny thereof, can be used for obtaining plants with modified callose content and/or modified fiber properties, in particular for obtaining fiber-producing plants with increased callose content in the fibers and/or increased fiber strength that preferably maintain an industrially relevant fiber length. As used herein, "plant part" includes anything derived from a plant of the invention, including plant parts such as cells, tissues, organs, seeds, fibers, seed fats or oils.

In one embodiment, the GLUC gene is a GLUC1.1 gene encoding a GLUC protein that has at least 90% sequence identity to SEQ ID NO: 4.

In another embodiment, the plant is a *Gossypium* plant, wherein the GLUC gene is a GLUC1.1A gene encoding a GLUC protein that has at least 97% sequence identity to SEQ ID NO: 4 or a GLUC1.1D gene encoding a GLUC protein that has at least 97% sequence identity to SEQ ID NO: 10, preferably the GLUC1.1A gene.

In still another embodiment, the plant is a *Gossypium hirsutum* plant.

In a further embodiment, the amount of functional GLUC protein is significantly reduced in fibers during the fiber strength building phase, in particular the fiber maturation phase, of fiber development in the plant compared to the amount of functional GLUC protein produced in fibers during the fiber strength building phase, in particular the fiber maturation phase, of fiber development in a plant in which the functional expression of the at least one GLUC allele is not abolished.

In still a further embodiment, the callose content is significantly increased in fibers of the plant compared to the callose content in fibers in a plant in which the functional expression of the at least one GLUC allele is not abolished.

In yet a further embodiment, the strength of the fibers is significantly increased compared to the strength of the fibers in a plant in which the functional expression of the at least one GLUC allele is not abolished. In one aspect, the strength of the fibers is on average between about 5% and about 10%, preferably about 7.5%, higher. In another aspect, the strength of the fibers is on average between about 1.6 g/tex and about 3.3 g/tex, preferably about 2.5 g/tex, higher. In still another aspect, the strength of the fibers is on average between about 34.6 g/tex and about 36.3 g/tex.

In still a further embodiment, the plant is a *Gossypium hirsutum* plant characterized in that the functional expression of at least two alleles of at least one fiber-specific GLUC gene is abolished.

In another embodiment, the present invention provides a fiber obtainable from the fiber-producing plant of any one of paragraphs 40 to 47.

In a further embodiment, the present invention provides a nucleic acid molecule encoding a non-functional GLUC1.1 protein having an amino acid sequence wherein at least one amino acid residue similar to the active site residues or to the glycosylation site residues of the GLUC1.1 protein of SEQ ID NO: 4 is lacking or is substituted for a non-similar amino acid residue. In one aspect, the active site residues of the GLUC1.1 protein of SEQ ID NO: 4 are selected from the group consisting of Tyr48, Glu249, Trp252, and Glu308, and wherein the glycosylation site residue of the GLUC1.1 protein of SEQ ID NO: 4 is Asn202. In another aspect, the non-functional GLUC1.1 protein comprises an amino acid sequence at least 90% identical to the amino acid sequence of SEQ ID NO: 6, SEQ ID NO: 18, SEQ ID NO: 57 or SEQ ID NO: 22. In another aspect, the nucleic acid molecule comprises a nucleic acid sequence having at least 92% sequence identity to SEQ ID NO: 3 from nucleotide 101 to 1078, wherein at least one nucleic acid residue is deleted, inserted or substituted. In yet another aspect, the nucleic acid molecule comprises a nucleotide sequence at least 92% identical to the nucleic acid sequence of SEQ ID NO: 54 from nucleotide 50 to 589. In still a further aspect, the nucleic acid molecule comprises the nucleic acid sequence of SEQ ID NO: 54 from nucleotide 50 to 589. In still another aspect, the nucleic acid molecule comprises a nucleic acid sequence having at least 92% sequence identity to SEQ ID NO: 1 from nucleotide 2410 to 3499, wherein at least one nucleic acid residue is deleted, inserted or substituted. In yet another aspect, the nucleic acid molecule comprises a nucleotide sequence at least 92% identical to the nucleic acid sequence of SEQ ID NO: 5 from nucleotide 63 to 711, SEQ ID NO: 17 from nucleotide 2 to 472, SEQ ID NO: 56 from nucleotide 112 to 760 or SEQ ID NO: 21 from nucleotide 27 to 372. In still a further aspect, the nucleic acid molecule comprises the nucleic acid sequence of SEQ ID NO: 5 from nucleotide 63 to 711, SEQ ID NO: 17 from nucleotide 2 to 472, SEQ ID NO: 56 from nucleotide 112 to 760, or SEQ ID NO: 21 from nucleotide 27 to 372.

In another embodiment, the present invention provides a non-functional GLUC1.1 protein encoded by the nucleic acid molecule of paragraph 49.

In still another embodiment, the present invention provides a method for identifying a GLUC1.1 gene encoding a non-functional GLUC1.1 protein in a plant, preferably a *Gossypium* plant, such as a *Gossypium hirsutum* plant, said GLUC1.1 gene comprising a nucleic acid sequence having at least 92% sequence identity to SEQ ID NO: 1 from nucleotide 2410 to 3499, comprising the step of identifying a polymorphic site in the nucleotide sequence of the GLUC1.1 gene in the genomic DNA of the plant that results in the production of a non-functional GLUC1.1 protein. In one aspect, the present invention provides a method for identifying a GLUC1.1 gene from *Gossypium barbadense* or from *Gossypium darwinii* comprising the step of identifying a T nucleotide at a nucleotide position corresponding to nucleotide position 3050 in SEQ ID NO: 1. In another aspect, the present invention provides a method for identifying a GLUC1.1 gene from *Gossypium arboreum* comprising the step of identifying a deletion of a C nucleotide at a nucleotide position corresponding to nucleotide position 2674, 2675 or 2676 in SEQ ID NO: 1.

In a further embodiment, the present invention provides a method of distinguishing a GLUC1.1 gene encoding a non-functional GLUC1.1 protein from a GLUC1.1 gene encoding a functional GLUC1.1 protein, said GLUC1.1 genes both comprising a nucleic acid sequence having at least 92% sequence identity to SEQ ID NO: 1 from nucleotide 2410 to 3499, comprising the step of identifying a polymorphic site in the nucleotide sequences of the GLUC1.1 genes. In one aspect, the present invention provides a method of distinguishing a GLUC1.1 from *Gossypium barbadense*, from *Gossypium darwinii* or from *Gossypium arboreum* from a GLUC1.1 gene from *Gossypium hirsutum*, respectively, comprising the step of identifying a polymorphic site selected from the group consisting of: polymorphic sequence marker GLUC1.1A-SNP2 located between the nucleotide at position 2765 and 2766 in SEQ ID NO: 1, SNP marker GLUC1.1A-SNP3 located at nucleotide position 2911 in SEQ ID NO: 1, SNP marker GLUC1.1A-SNP5 located at nucleotide position 3050 in SEQ ID NO: 1, SNP marker GLUC1.1A-SNP6 located at nucleotide position 3202 in SEQ ID NO: 1, SNP marker GLUC1.1A-SNP7 located at nucleotide position 2674, 2675 or 2676 in SEQ ID NO: 1 and SNP marker GLUC1.1A-SNP8 located at nucleotide position 3170 in SEQ ID NO: 1. In another aspect, polymorphic sequence marker GLUC1.1A-SNP2 from *Gossypium barbadense* or *Gossypium darwinii* and from *Gossypium hirsutum*, respectively, is detected by amplification of a DNA fragment of about 143 bp and about 134 bp, respectively, with primers comprising at their extreme 3' end SEQ ID NO: 37 and 38, respectively. In still another aspect, SNP marker GLUC1.1A-SNP3 from *Gossypium barbadense* or *Gossypium darwinii* and from *Gossypium hirsutum*, respectively, is detected by amplification of a DNA fragment of about 57 bp with primers comprising SEQ ID NO: 41 and 42 and detection of the DNA fragment with fluorescently labeled probes comprising SEQ ID NO: 39 and 40, respectively.

In a further embodiment, the present invention provides a method for generating and/or selecting a non-naturally occurring fiber-producing plant, and parts and progeny thereof, wherein the functional expression of at least one allele of at least one fiber-specific GLUC gene that is functionally expressed during the fiber strength building phase, in particular the fiber maturation phase, of fiber development is abolished, comprising the step of: mutagenizing at least one allele of the GLUC gene, or introgressing at least one allele of a non-functionally expressed ortholog of the GLUC gene or at least one allele of a mutagenized GLUC gene, or introducing a chimeric gene comprises the following operably linked DNA elements: (a) a plant expressible promoter, (b) a transcribed DNA region, which when transcribed yields an inhibitory RNA molecule capable of reducing the expression of the GLUC allele, and (c) a 3' end region comprising transcription termination and polyadenylation signals functioning in cells of the plant. In one aspect, the GLUC gene is a GLUC1.1 gene encoding a GLUC protein that has at least 90% sequence identity to SEQ ID NO: 4. In another aspect, the fiber-producing plant is a *Gossypium* plant, and the GLUC gene is a GLUC1.1A gene encoding a GLUC protein that has at least 97% sequence identity to SEQ ID NO: 4 or a GLUC1.1D gene encoding a GLUC protein that has at least 97% sequence identity to SEQ ID NO: 9, preferably a GLUC1.1A gene. In still another aspect, the fiber-producing plant is a *Gossypium* plant, and the non-functionally expressed ortholog of the GLUC gene is a GLUC1.1A gene which is derived from a *Gossypium barbadense*, from a *Gossypium darwinii* or a *Gossypium arboreum* plant, preferably from a *Gossypium barbadense*. In a further aspect, the method further comprises the step of identifying the non-functionally expressed ortholog of the GLUC gene or the mutagenized GLUC gene according to the method of paragraph 51.

In a further embodiment, the present invention provides a method for altering the callose content of a fiber in a fiber-producing plant, particularly increasing the callose content of a fiber, comprising the steps of: generating and/or selecting a non-naturally occurring fiber-producing plant, and parts and progeny thereof, wherein the functional expression of at least one allele of at least one fiber-specific GLUC gene that is functionally expressed during the fiber strength building phase, in particular the fiber maturation phase, of fiber development is abolished, according to the method of paragraph 53, and selecting a plant with an altered callose content in its fibers, in particular an increased callose content.

In a further embodiment, the present invention provides a method for altering the properties of a fiber in a fiber-producing plant, particularly increasing the strength of a fiber, comprising the steps of: generating and/or selecting a non-naturally occurring fiber-producing plant, and parts and progeny thereof, wherein the functional expression of at least one allele of at least one fiber-specific GLUC gene that is functionally expressed during the fiber strength building phase, in particular the fiber maturation phase, of fiber development is abolished, according to the method of paragraph 53, and selecting a plant with an altered fiber strength, in particular an increased fiber strength.

In another embodiment, the present invention provides a kit for identifying a GLUC1.1 gene encoding a non-functional GLUC1.1 protein in a plant, said GLUC1.1 gene comprising a nucleic acid sequence having at least 92% sequence identity to SEQ ID NO: 1 from nucleotide 2410 to 3499, comprising primers and/or probes for determining the presence of a polymorphic site in the nucleotide sequence of the GLUC1.1 gene in the genomic DNA of the plant that results in the production of a non-functional GLUC1.1 protein. In one aspect, the kit comprises primers and/or probes for determining the presence of a T nucleotide at a nucleotide position corresponding to nucleotide position 3050 in SEQ ID NO: 1 or for determining a deletion of a C nucleotide at a nucleotide position corresponding to nucleotide position 2674, 2675 or 2676 in SEQ ID NO: 1.

In still another embodiment, the present invention provides a kit for distinguishing a GLUC1.1 gene encoding a non-functional GLUC1.1 protein from a GLUC1.1 gene encoding a functional GLUC1.1 protein, said GLUC1.1 genes both comprising a nucleic acid sequence having at least 92% sequence identity to SEQ ID NO: 1 from nucleotide 2410 to 3499, comprising primers and/or probes for determining the presence of a polymorphic site in the nucleotide sequences of the GLUC1.1 genes. In one aspect, the present invention provides a kit comprising primers and/or probes for distinguishing *Gossypium barbadense*, *Gossypium darwinii* or *Gossypium arboreum* specific alleles from *Gossypium hirsutum* specific alleles of a polymorphic site selected from the group consisting of: polymorphic sequence marker GLUC1.1A-SNP2 located between the nucleotide at position 2765 and 2766 in SEQ ID NO: 1, SNP marker GLUC1.1A-SNP3 located at nucleotide position 2911 in SEQ ID NO: 1, SNP marker GLUC1.1A-SNP5 located at nucleotide position 3050 in SEQ ID NO: 1, SNP marker GLUC1.1A-SNP6 located at nucleotide position 3202 in SEQ ID NO: 1, SNP marker GLUC1.1A-SNP7 located at nucleotide position 2674, 2675 or 2676 in SEQ ID NO: 1 and SNP marker GLUC1.1A-SNP8 located at nucleotide position 3170 in SEQ ID NO: 1. In another aspect, the kit comprises at least two primers and/or probes selected from the group consisting of: primers comprising at their extreme 3' end SEQ ID NO: 37 and 38, respectively, to identify polymorphic sequence marker GLUC1.1A-SNP2, primers comprising SEQ ID NO: 41 and 42, respectively, to identify SNP marker GLUC1.1A-SNP3, probes comprising SEQ ID NO: 39 and 40, respectively, to identify SNP marker GLUC1.1A-SNP3, primers comprising SEQ ID NO: 62 and 63, respectively, to identify SNP marker GLUC1.1A-SNP5, and probes comprising SEQ ID NO: 60 and 61, respectively, to identify SNP marker GLUC1.1A-SNP5.

BRIEF DESCRIPTION OF THE FIGURES

Figure 1A:
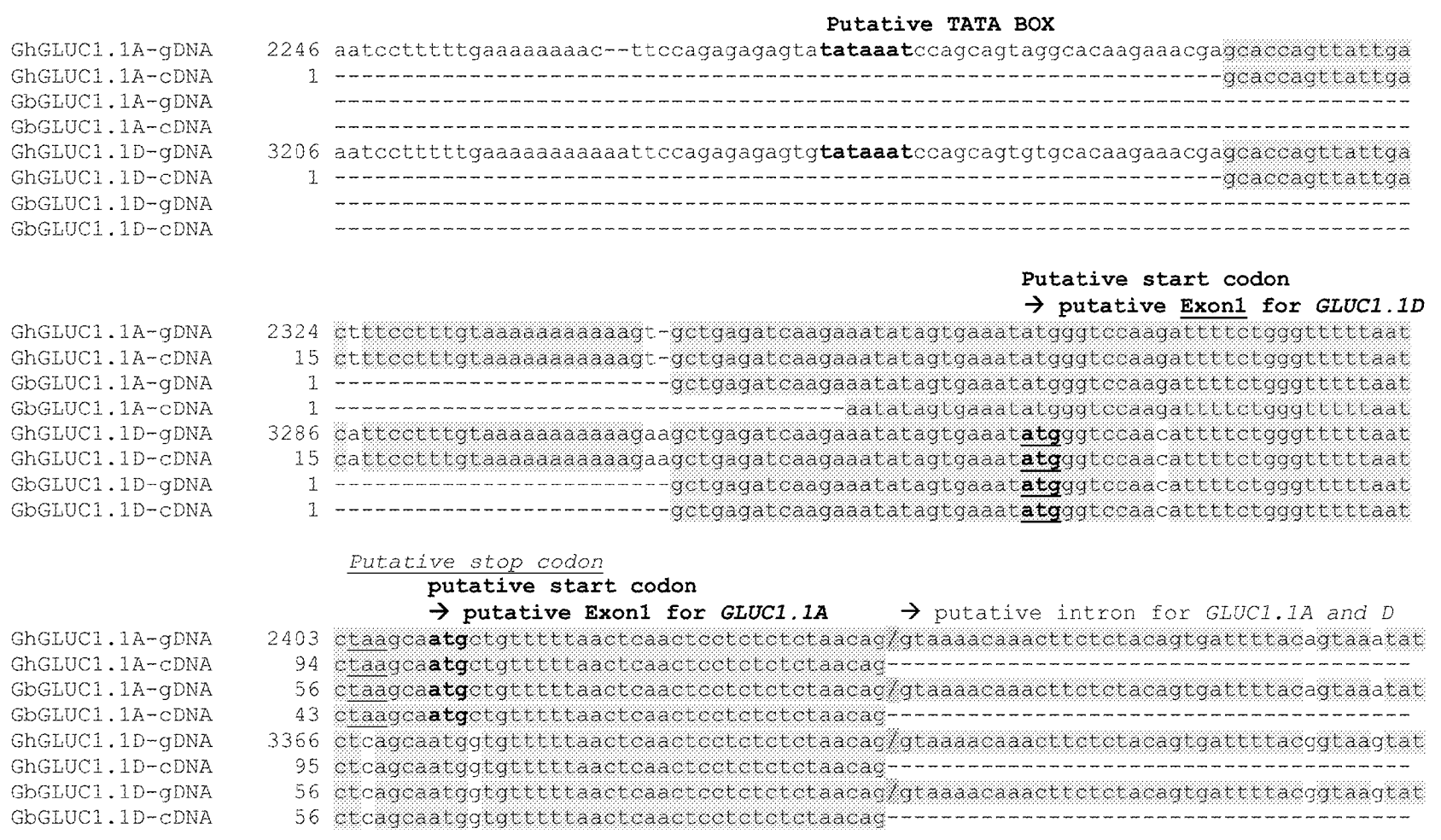
Figure 1C:
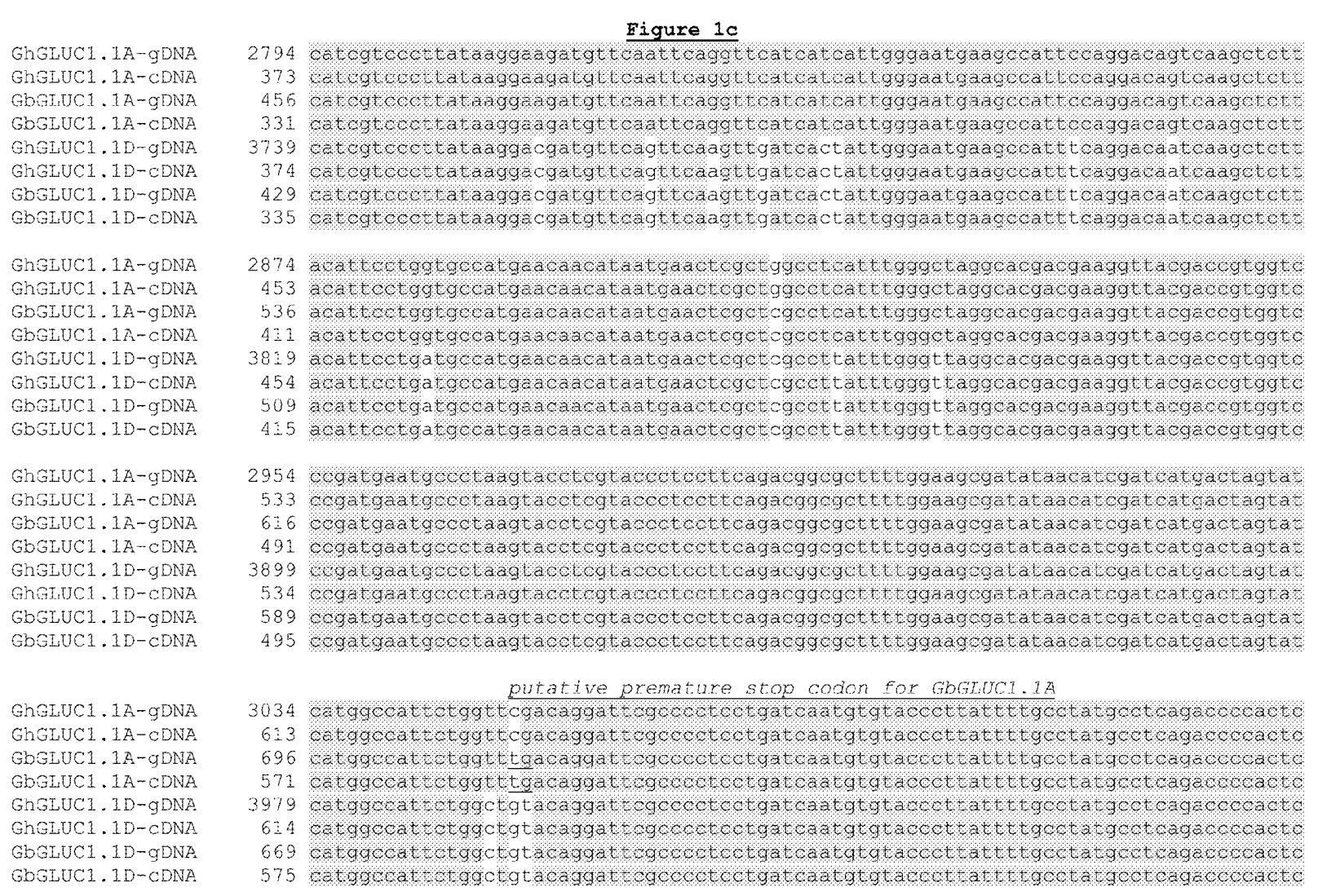
Figure 1D:
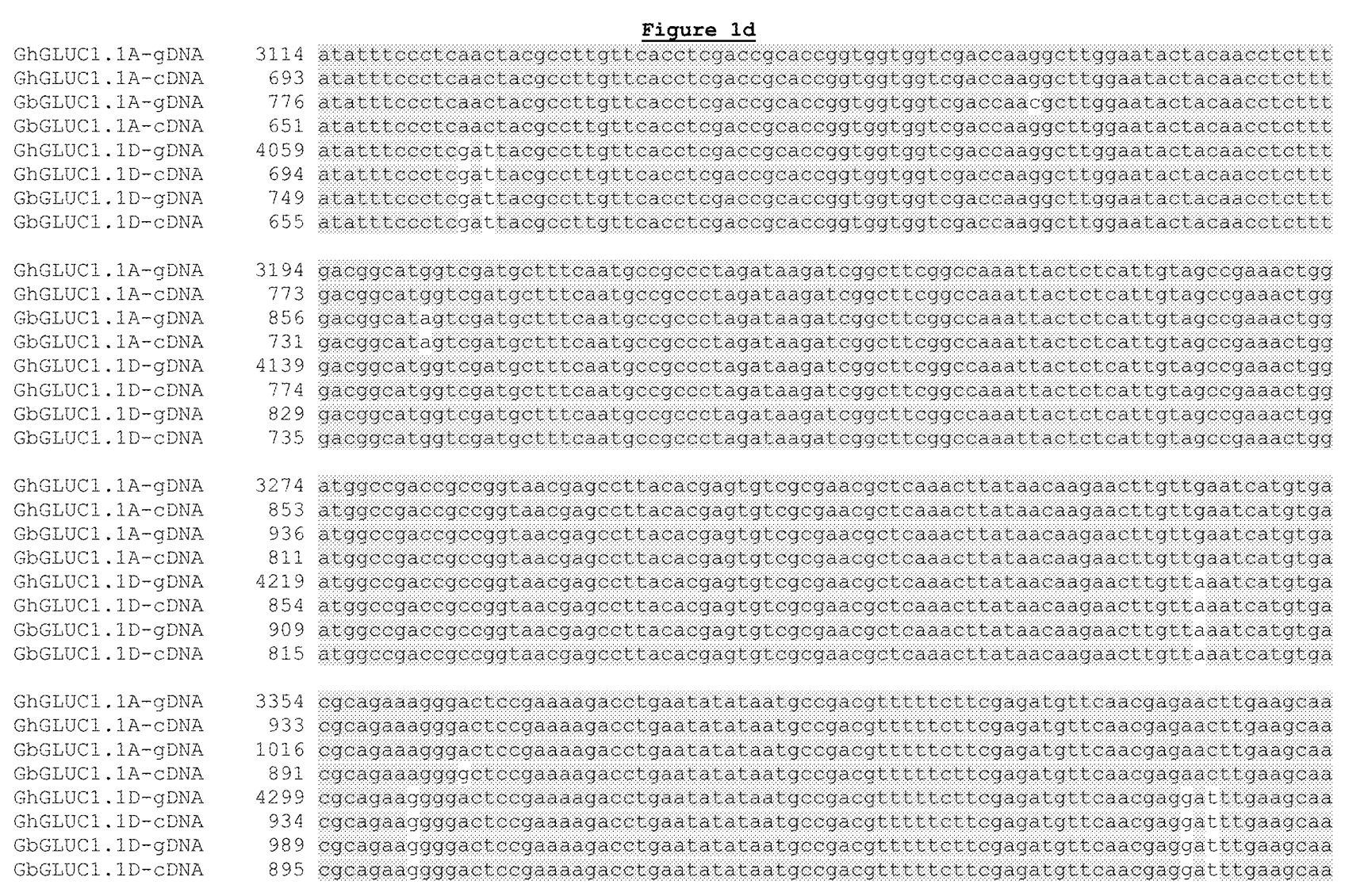
Figure 1E:
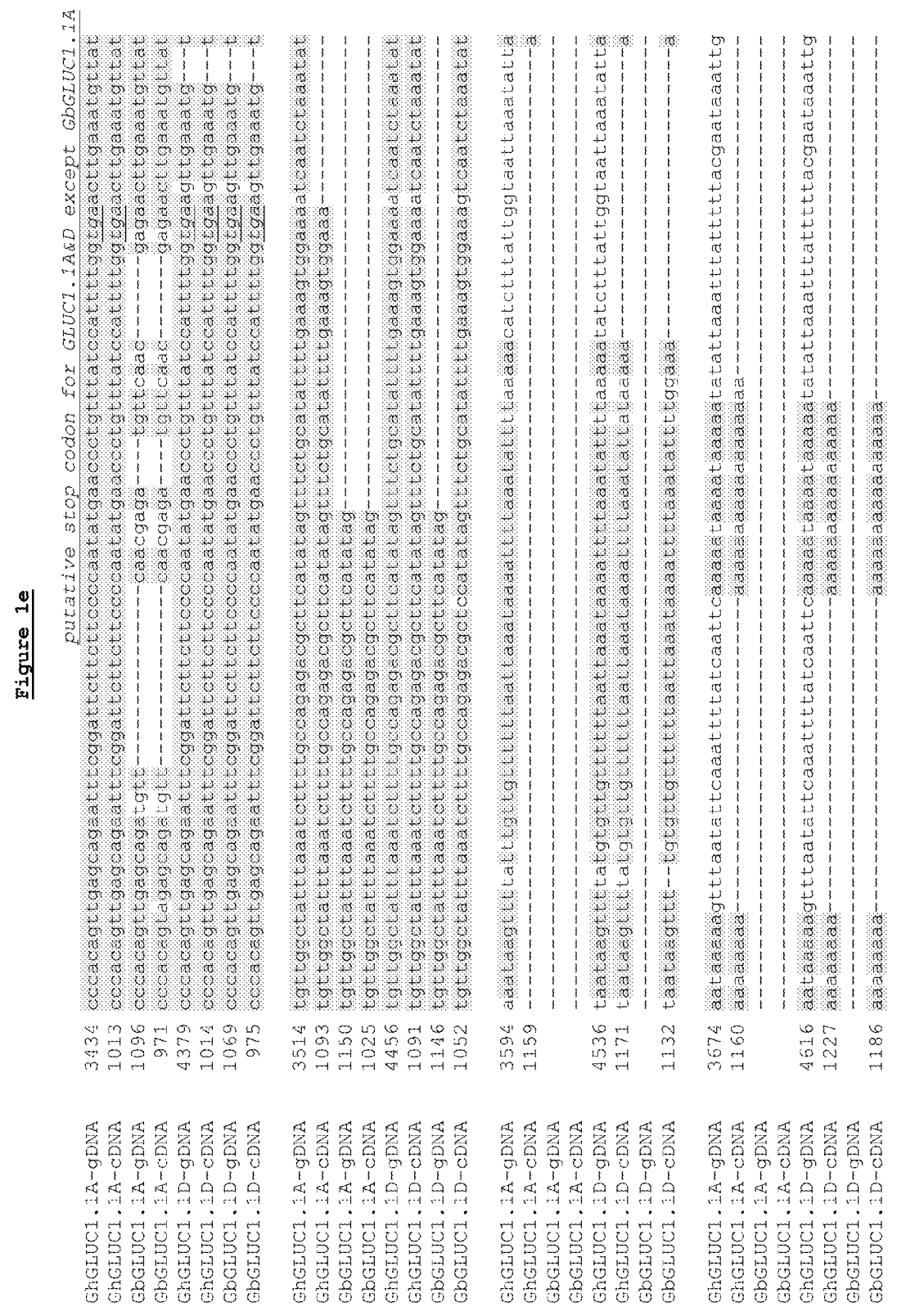

FIG. 1: Alignment of genomic and cDNA sequences of A and D subgenome-specific GLUC1.1 genes from *Gossypium hirsutum* ('GhGLUC1.1A-gDNA' corresponds to SEQ ID NO: 1 from nucleotide 2246 to 3753, 'GhGLUC1.1A-cDNA' corresponds to SEQ ID NO: 3, 'GhGLUC1.1D-gDNA' corresponds to SEQ ID NO: 7 from nucleotide 3206 to 4694, and 'GhGLUC1.1D-cDNA' corresponds to SEQ ID NO: 9) and *Gossypium barbadense* ('GbGLUC1.1A-gDNA' corresponds to SEQ ID NO: 5, 'GbGLUC1.1A-cDNA' corresponds to SEQ ID NO: 54, 'GbGLUC1.1D-gDNA' corresponds to SEQ ID NO: 11, and 'GbGLUC1.1D-cDNA' corresponds to SEQ ID NO: 13). The putative TATA box is indicated in bold, the putative start codons and the putative first exons are indicated in bold and in bold with an arrow, respectively, the putative intron and second exon sequences are indicated in regular with an arrow, the putative intron sequences are further indicated between '/', the putative (premature) STOP codons are indicated in italic and underlined.

FIG. 2: Alignment of amino acid sequences of A and D subgenome-specific GLUC1.1 proteins from *Gossypium hirsutum* ('GhGLUC1.1A' corresponds to SEQ ID NO: 2 and 4 and 'GhGLUC1.1D' corresponds to SEQ ID NO: 8 and 10) and *Gossypium barbadense* ('GbGLUC1.1A' corresponds to SEQ ID NO: 6 and 55 and 'GbGLUC1.1D' corresponds to SEQ ID NO: 12 and 14). The putative signal peptide is indicated in italic, the putative post-translational splicing site is indicated as '><', the GH17 signature is indicated in bold. Amino acids that are identical between at least three of the four sequences are highlighted. The dashed line indicates the protein segment that is missing in GbGLUC1.1A.

FIG. 3: Protein model of GLUC1.1A protein of *G. hirsutum* (FIG. 3a; right) and *G. barbadense* (FIG. 3b; right) based on an X-ray structure of a barley 1,3-1,4-beta-glucanase (1aq0; FIG. 3a &b; left). The active site of 1aq0 is located in an open cleft at the bottom of the barrel defined by the C-terminal ends of the parallel intra-barrel beta-strands (Müller et al., 1998, J. Biol. Chem. 273 (6): 3438-3446) and is indicated by the amino acids and their position numbers displayed in the upper left part of the protein model of 1aq0 in FIG. 3a and b at the left. Active site residues Glu288, Glu232 and Tyr33 in 1aq0 (FIG. 3a, left) correspond to Glu308, Glu249 and Tyr48 in GhGLUC1.1A (FIG. 3a, right) and are absent in GbGLUC1.1A (FIG. 3b, right). The glycosylation site Asn190 in 1aq0 (FIG. 3A, left) corresponds to Asn 202 in GhGLUC1.1A (FIG. 3a, right) and is also absent in GbGLUC1.1A (FIG. 3b, right). FIG. 3b further shows that the threonine, histidine and glutamine amino acids at position 82, 83 and 84 of GbGLUC1.1A (FIG. 3b; right) that are not present in GhGLUC1.1A (see for example FIG. 7) are located in a distant loop which is not part of the active site and not involved in glycosylation.

Figure 6A:
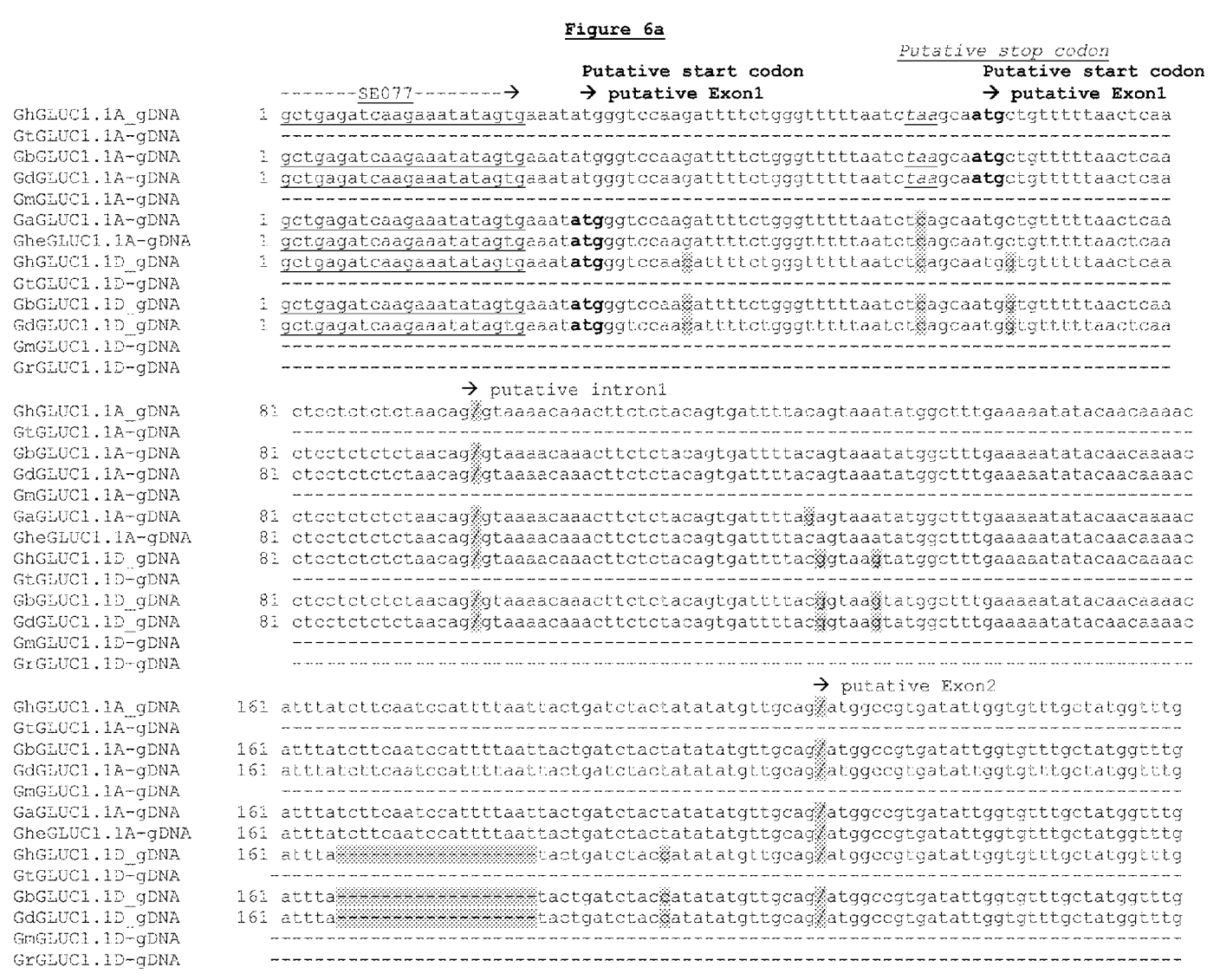
Figure 6B:
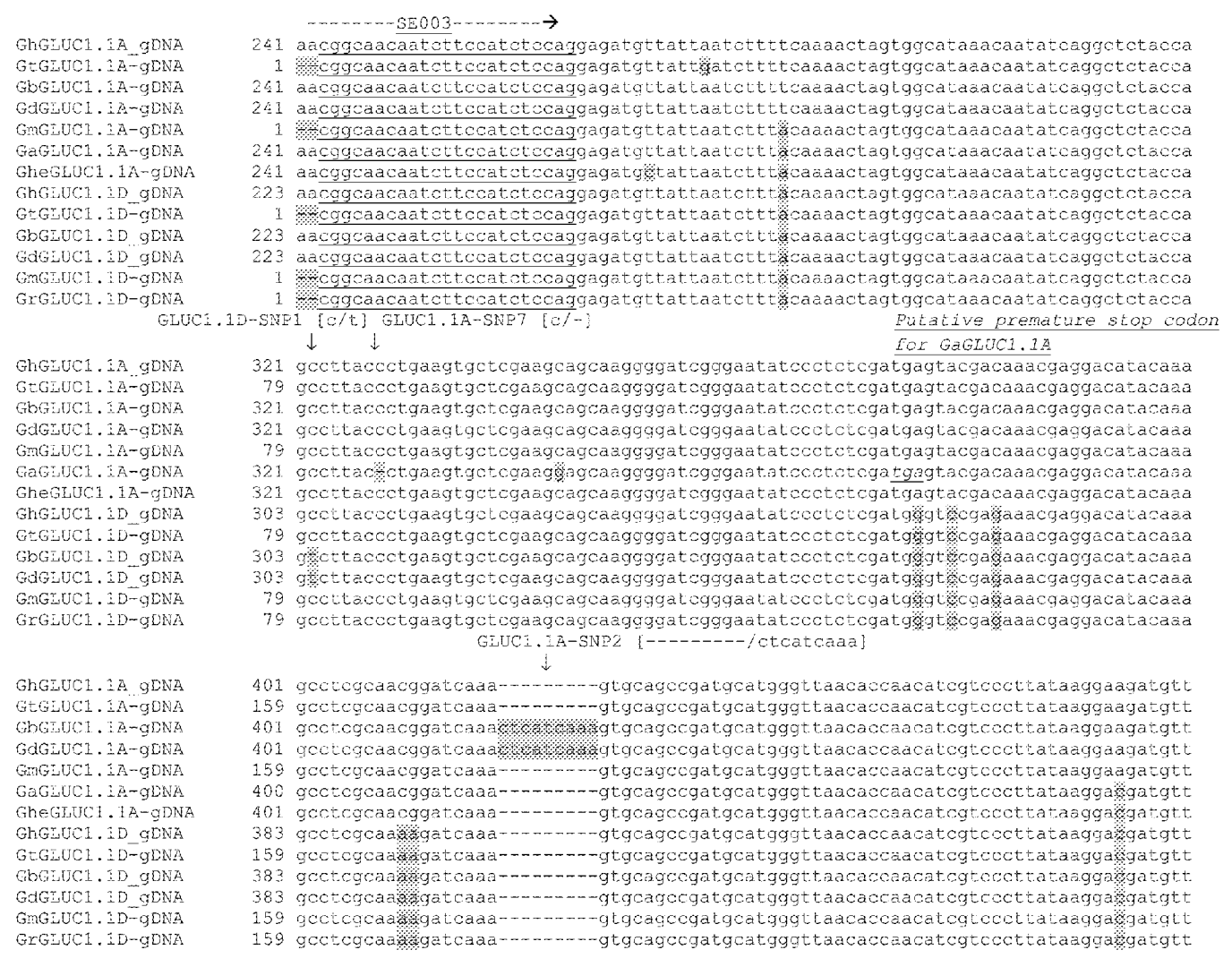
Figure 6E:
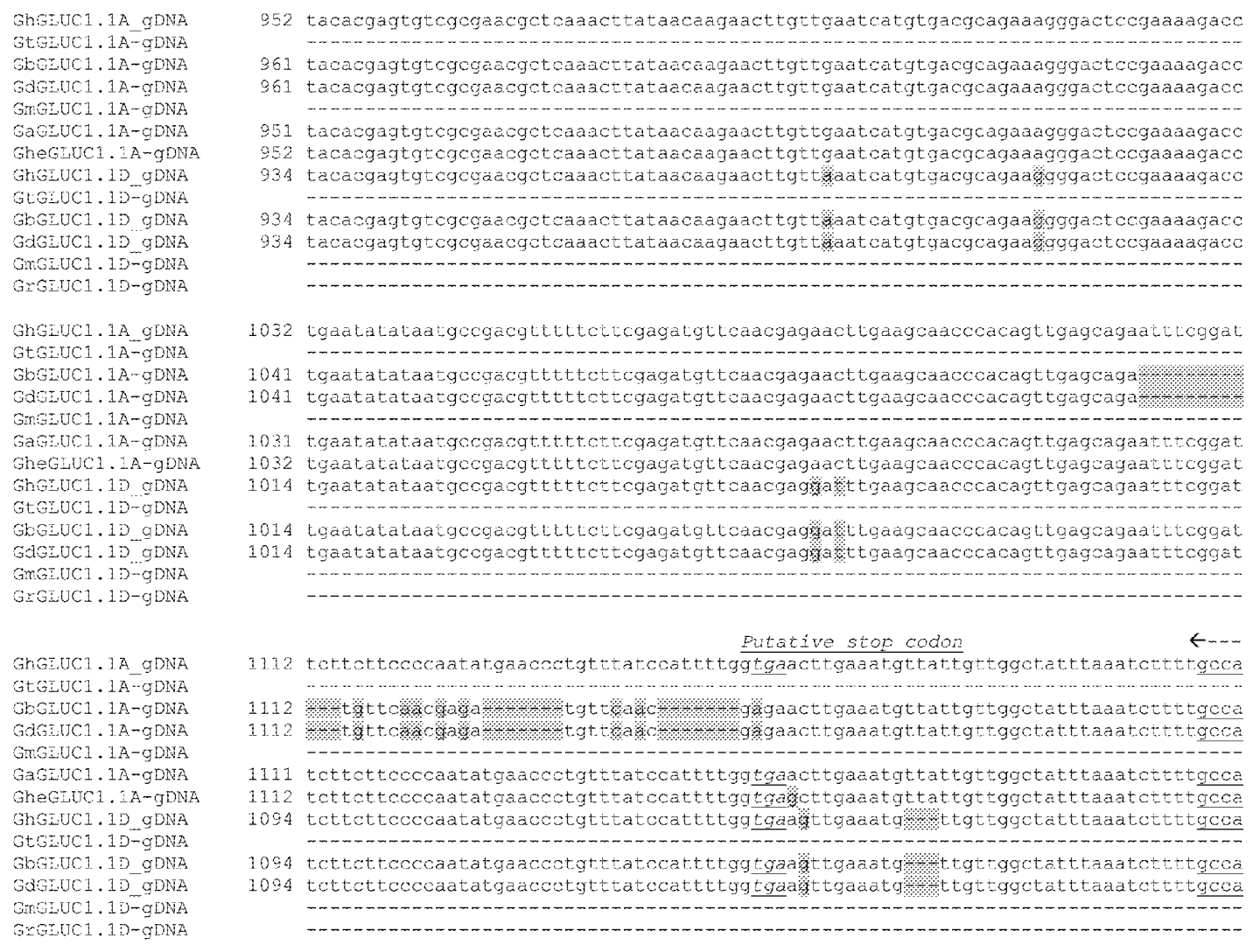

FIG. 6: Alignment of genomic DNA sequences of A and D subgenome-specific GLUC1.1 genes from *Gossypium hirsutum* ('GhGLUC1.1A_gDNA' corresponds to SEQ ID NO: 1 from nucleotide 2348 to 3554 and 'GhGLUC1.1D_gDNA' corresponds to SEQ ID NO: 7 from nucleotide 3311 to 4496), *Gossypium tomentosum* ('GtGLUC1.1A_gDNA' corresponds to SEQ ID NO: 15 and 'GtGLUC1.1D_gDNA' corresponds to SEQ ID NO: 25), *Gossypium barbadense* ('GbGLUC1.1A_gDNA' corresponds to SEQ ID NO: 5 and 'GbGLUC1.1D_gDNA' corresponds to SEQ ID NO: 11), *Gossypium darwinii* ('GdGLUC1.1A_gDNA' corresponds to SEQ ID NO: 17 and 'GdGLUC1.1D_gDNA' corresponds to SEQ ID NO: 27), *Gossypium mustelinum*, ('GmGLUC1.1A_gDNA' corresponds to SEQ ID NO: 19 and 'GmGLUC1.1D_gDNA' corresponds to SEQ ID NO: 29), *Gossypium arboreum* ('GaGLUC1.1A_gDNA' corresponds to SEQ ID NO: 21), *Gossypium herbaceum* ('GheGLUC1.1A_gDNA' corresponds to SEQ ID NO: 23), and *Gossypium raimondii* ('GrGLUC1.1D_gDNA' corresponds to SEQ ID NO: 31). The positions of primers SE077 and SE078, used to generate the complete coding sequence from start to stop codon, and the positions of primers SE003 and SE002, used to generate partial coding sequences, are underlined. The putative start codons and the putative first exons are indicated in bold and in bold with an arrow, respectively, the putative intron and second exon sequences are indicated in regular with an arrow, the putative intron sequences are further indicated between '/', the putative (premature) STOP codons are indicated in italic and underlined. Five polymorphic sites (4 single nucleotide polymorphisms (SNPs) and one extended indel) that exist between the GLUC1.1A or GLUC1.1D sequences of, e.g., *G. hirsutum* FM966 and *G. barbadense* Pima S7 or *G. darwinii*, are indicated with arrows and named 'GLUC1.1D-SNP1' and 'GLUC1.1A-SNP2, 3, 5 and 6'. Allelic variants are indicated as follows: [*G. hirsutum* allele/*G. barbadense* or *G. darwinii* allele]. One polymorphic site (1 SNP) that exist between the GLUC1.1A sequences of, e.g., *G. hirsutum* FM966 and *G. arboreum* is indicated with an arrow and named 'GLUC1.1A-SNP7'. Allelic variants are indicated as follows: [*G. hirsutum* allele/*G. arboreum* allele]. One polymorphic site (1 SNP) that exist between the GLUC1.1A sequences of, e.g., *G. barbadense* Pima S7 or *G. darwinii* is indicated with an arrow and named 'GLUC1.1A-SNP8'. Allelic variants are indicated as follows: [*G. barbadense* allele/*G. darwinii* allele].

FIG. 7: Alignment of amino acid sequences of A and D subgenome-specific GLUC1.1 proteins from *Gossypium hirsutum* (GhGLUC1.1A_prot' corresponds to SEQ ID NO: 2 and 4 and GhGLUC1.1D_ prot' corresponds to SEQ ID NO: 8 and 10; full-length sequences), *Gossypium tomentosum* (GtGLUC1.1A_prot' corresponds to SEQ ID NO: 16 and GtGLUC1.1D_prot' corresponds to SEQ ID NO: 26; partial sequences), *Gossypium barbadense* (GbGLUC1.1A_prot' corresponds to SEQ ID NO: 6 and 55 and GbGLUC1.1D_prot' corresponds to SEQ ID NO: 12 and 14; full-length sequences), *Gossypium darwinii* (GdGLUC1.1A_prot' corresponds to SEQ ID NO: 57 and GdGLUC1.1D_prot' corresponds to SEQ ID NO: 59; full-length sequences), *Gossypium mustelinum*, (GmGLUC1.1A_prot' corresponds to SEQ ID NO: 20 and GmGLUC1.1D_prot' corresponds to SEQ ID NO: 30; partial sequences), *Gossypium arboreum* (GaGLUC1.1A_prot' corresponds to SEQ ID NO: 22; full-length sequence), *Gossypium herbaceum* (GheGLUC1.1A_proe corresponds to SEQ ID NO: 24; full-length sequence), and *Gossypium raimondii* (GrGLUC1.1D_prot' corresponds to SEQ ID NO: 32; partial sequences). The putative signal peptide is indicated in italic, the putative post-translational splicing site is indicated as '><', the GH17 signature is indicated in bold. Amino acids that differ from the amino acids in the upper sequence, i.e. GhGLUC1.1A_prot, are highlighted.

FIG. 8: Expression of GLUC1.1A and GLUC1.1D in *G. barbadense*. DNA from a cDNA library from (developing) fibers in *Gossypium barbadense* was extracted and equalized. PCR fragments were amplified using oligonucleotide primers SE002 and SE003 (SEQ ID NO: 35 and 36) and digested with restriction enzyme AlwI. A PCR amplified product for GLUC1.1A yields 3 fragments (479 bp118 bp+59 bp) while for GLUC1.1D it only yields 2 fragments (538 bp+118 bp). The 59 bp fragment is not visible. Lane 1 and 12: 1 kb size markers; lanes 2 to 9: GbGLUC1.1A and D expression at 0, 5, 10, 15, 20, 25, 30 and 40 DPA; lane 10: negative (no template; NTC); lane 11: positive control (genomic DNA from Pima S7).

DETAILED EMBODIMENTS

Figure 4:
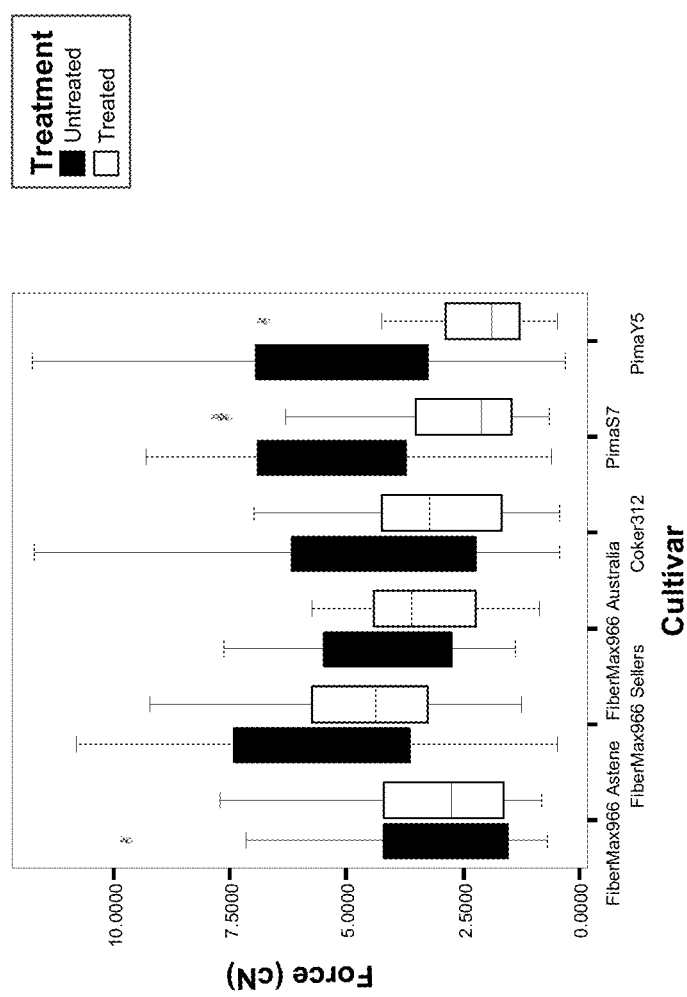
FIG. 4: Box plot indicating the difference in fiber strength (as determined by measuring the breaking force of single fibers; indicated in cN on the Y-axis) between untreated fibers ('untreated') and fibers treated with exogenous glucanase ('treated') derived from *Gossypium hirsutum* cultivar FM966 grown in a greenhouse in Europe ('FM966 Astene'), in the field in the US ('FM966 Sellers') and in the field in Australia ('FM966 Australia'), from *Gossypium hirsutum* cultivar Coker 312 grown in a greenhouse in Europe ('Coker 312'), from *Gossypium barbadense* cultivar PimaS7 grown in a greenhouse in Europe ('PimaS7'), and from *Gossypium barbadense* cultivar PimaY5 grown in the field in Australia ('PimaY5').

The current invention is based on the unexpected finding that the presence of the *Gossypium barbadense* ortholog of a fiber strength locus on chromosome A05, hereinafter called *Gossypium barbadense* fiber strength allele, in *Gossypium hirsutum* plants results in an increased strength of the fibers of the *Gossypium hirsutum* plants compared to the strength of the fibers of *Gossypium hirsutum* plants comprising the *Gossypium hirsutum* ortholog of the fiber strength locus.

Thus, in a first aspect, the present invention provides a non-naturally occurring *Gossypium* plant, and parts and progeny thereof, comprising at least one superior allele of a quantitative trait locus (QTL) for fiber strength located on chromosome A05.

As used herein, the term "non-naturally occurring" or "cultivated" when used in reference to a plant, means a plant with a genome that has been modified by man. A transgenic fiber-producing plant, for example, is a non-naturally occurring fiber-producing plant that contains an exogenous nucleic acid molecule, e.g., a chimeric gene comprising a transcribed region which when transcribed yields a biologically active RNA molecule capable of reducing the expression of a GLUC gene according to the invention and, therefore, has been genetically modified by man. In addition, a fiber-producing plant that contains, for example, a mutation in an endogenous GLUC gene (e.g. in a regulatory element or in the coding sequence) as a result of an exposure to a mutagenic agent is also considered a non-naturally occurring fiber-producing plant, since it has been genetically modified by man. Furthermore, a fiber-producing plant of a particular species, such as *Gossypium hirsutum*, that contains, for example, a mutation in an endogenous GLUC gene that in nature does not occur in that particular plant species, as a result of, for example, directed breeding processes, such as marker-assisted breeding and selection or introgression, with another species of that fiber-producing plant, such as *Gossypium barbadense*, is also considered a non-naturally occurring fiber-producing plant. In contrast, a fiber-producing plant containing only spontaneous or naturally occurring mutations, i.e. a plant that has not been genetically modified by man, is not a "non-naturally occurring plant" as defined herein and, therefore, is not encompassed within the invention. One skilled in the art understands that, while a non-naturally occurring fiber-producing plant typically has a nucleotide sequence that is altered as compared to a naturally occurring fiber-producing plant, a non-naturally occurring fiber-producing plant also can be genetically modified by man without altering its nucleotide sequence, for example, by modifying its methylation pattern.

The term "quantitative trait" refers herein to a trait, such as fiber strength, whose phenotypic characteristics vary in degree and can be attributed to the interactions between two or more genes and their environment.

As used herein, the term "locus" (loci plural) or "site" means a specific place or places on a chromosome where, for example, a gene, a genetic marker or a QTL is found.

A "quantitative trait locus (QTL)" is a stretch of DNA (such as a chromosome arm, a chromosome region, a nucleotide sequence, a gene, and the like) that is closely linked to a gene that underlies the trait in question. "QTL mapping" involves the creation of a map of the genome using genetic or molecular markers, like AFLP, RAPD, RFLP, SNP, SSR, and the like, visible polymorphisms and allozymes, and determining the degree of association of a specific region on the genome to the inheritance of the trait of interest. As the markers do not necessarily involve genes, QTL mapping results involve the degree of association of a stretch of DNA with a trait rather than pointing directly at the gene responsible for that trait. Different statistical methods are used to ascertain whether the degree of association is significant or not. A molecular marker is said to be "linked" to a gene or locus, if the marker and the gene or locus have a greater association in inheritance than would be expected from independent assortment, i.e. the marker and the locus co-segregate in a segregating population and are located on the same chromosome. "Linkage" refers to the genetic distance of the marker to the locus or gene (or two loci or two markers to each other). The closer the linkage, the smaller the likelihood of a recombination event taking place, which separates the marker from the gene or locus. Genetic distance (map distance) is calculated from recombination frequencies and is expressed in centiMorgans (cM) [Kosambi (1944), *Ann. Eugenet.* 12:172-175].

"Fiber strength locus" or "strength locus", as used herein, refers to a stretch of DNA on chromosome A05 of *Gossypium* species that is closely linked to (a) gene(s) that is(are) involved in the regulation of fiber strength. The "fiber strength locus" is a QTL said to be linked to the "(fiber strength) causal gene(s)".

A "fiber", such as a "cotton fiber", as used herein, refers to a seed trichome, more specifically a single cell of a fiber-producing plant, such as cotton, that initiates from the epidermis of the outer integument of the ovules, at or just prior to anthesis. The morphological development of cotton fibers has been well documented (Basra and Malik, 1984, Int Rev of Cytology 89: 65-113; Graves and Stewart, 1988, supra; Ramsey and Berlin, 1976, American Journal of Botany 63 (6): 868-876; Ruan and Chourey, 1998, Plant Physiology 118: 399-406; Ruan et al. 2000, Aust. J. Plant Physiol. 27:795-800; Stewart, 1975, Am. J. Bot. 62, 723-730). Cotton fibers, in particular from *Gossypium hirsutum*, undergo four overlapping developmental stages: fiber cell initiation, elongation, secondary cell wall biosynthesis, and maturation. Fiber cell initiation is a rapid process. White fuzzy fibers begin to develop immediately after anthesis and continue up to about 3 days post-anthesis (DPA), which is followed by fiber cell elongation (until about 10 to about 17 DPA). Depending upon growth conditions, secondary cell wall biosynthesis initiates and continues to about 25 to about 40 DPA, followed by a maturation process until about 45 to about 60 DPA. The secondary cell wall synthesis and maturation phase are herein commonly referred to as "fiber strength building phase". Only about 25 to 30% of the epidermal cells differentiate into the commercially important lint fibers (Kim and Triplett, 2001). The majority of cells does not differentiate into fibers or develop into short fibers or fuzz. During fiber elongation and secondary wall metabolism, the fiber cells elongate rapidly, synthesize secondary wall components, and show dramatic cellular, molecular and physiological changes. Fiber elongation is coupled with rapid cell growth and expansion (Seagull, 1991. In *Biosynthesis and biodegradation of cellulose* (Haigler, C. H. & Weimer, P. J., eds) pp. 1432163, MarcelDekker, New York) and constant synthesis of a large amount of cell metabolites and cell wall components such as cellulose. About 95% of the dry-weight in mature cotton fibers is cellulose (Pfluger and Zambryski, 2001, Curr Biol 11: R436-R439; Ruan et al., 2001, Plant Cell 13: 47-63). Non-celluloid components are also important to fiber cell development (Hayashi and Delmer, 1988, Carbohydr. Res. 181: 273-277; Huwyler et al., 1979, Planta 146: 635-642; Meinert and Delmer, 1977, Plant Physiol 59: 1088-1097; Peng et al., 2002, Science 295: 147-150). Compared to other plant cells, cotton fibers do not contain lignin in secondary walls but have large vacuoles that are presumably related to rapid cell growth and expansion (Basra and Malik, 1984, supra; Kim and Triplett, 2001, Plant Physiology 127: 1361-1366; Mauney, 1984, supra; Ruan and Chourey, 1998, supra; Ruan et al., 2000, supra; Van't H of, 1999, American Journal of Botany 86: 776-779).

"Fiber strength", as used herein, can be determined by determining the strength of a bundle of fibers, i.e. "fiber bundle strength", or by determining the strength of single fibers. The higher the single fiber strength and the lower the variations of single fiber breaking elongation, the closer the bundle and yarn tensile strength would be to the sum of single fiber strength; ideally, fiber bundle tenacity would equal the total single fiber breaking tenacity had all fibers within the bundle equal breaking elongation and no slack (Liu et al., February 2005, Textile Res. J.).

"Fiber bundle strength", as used herein, refers to a measure that is usually expressed in terms of grams per tex. This commercial High Volume Instruments (HVI) measure of fiber bundle strength ("HVI strength") is also called "tenacity". A tex unit is equal to the weight in grams of 1,000 meters of fiber. Therefore, the strength reported is the force in grams required to break a bundle of fibers one tex unit in size. Measurements of cotton fiber bundle strength can, for example, be made according to USDA standards. A beard of cotton is clamped in two sets of jaws, one eighth inch apart, and the force required to break the fibers is determined. Table 1 can be used as a guide in interpreting fiber strength measurements.

TABLE 1

Interpretation of HVI fiber strength measurements

| Degree of Strength | HVI* Strength (grams per tex) |
| --- | --- |
| Very Strong | 31 or more |
| Strong | 29-30 |
| Average | 26-28 |
| Intermediate | 24-25 |
| Weak | 23 or less |

*High Volume Precision Instruments

Alternatively, the strength of fibers can be compared by determining the "single fiber strength" by performing single fiber tensile tests, for example, on a FAVIMAT Robot (Textechno) as described on the World Wide Web at textechno.com in the Examples. Briefly, a single fiber is clamped between two fiber clamps with a continuously adjustable gauge length between 5 and 100 mm (set e.g. on 8 mm) and a draw-off clamp speed between 0.1 and 100 mm/min (set e.g. on 4 mm/min), and the force (cN) required to break the fibers ("breaking force") is determined. Average breaking forces of specific cotton varieties can be found in the Examples.

"Chromosome A05", as used herein, refers to chromosome A05 (numbering according to Wang et al., 2006, Theor Appl Genet. 113(1):73-80) in an A genome diploid *Gossypium* plant, such as *Gossypium herbaceum* or *Gossypium arboreum*, or in an AD allotetraploid *Gossypium* plant, such as *Gossypium hirsutum, Gossypium barbadense* and *Gossypium darwinii*. In one embodiment, the *Gossypium* plant is an A genome diploid *Gossypium* plant comprising 13 A genome chromosome pairs, numbered A01 to A13 according to Wang et al. (2006, Theor Appl Genet. 113(1):73-80), such as *Gossypium herbaceum* or *Gossypium arboreum*. In another embodiment, the *Gossypium* plant is an AD genome allotetraploid *Gossypium* plant comprising 13 A genome and 13 D genome chromosome pairs, numbered A01 to A13 and D01 to D13, respectively, according to Wang et al. (supra), such as *Gossypium hirsutum, Gossypium barbadense* and *Gossypium darwinii*.

In one embodiment, the non-naturally occurring *Gossypium* plant is a *Gossypium hirsutum*, a *Gossypium herbaceum* or a *Gossypium arboreum* plant, preferably a *Gossypium hirsutum* plant, and the superior allele of the fiber strength locus is derived from *Gossypium barbadense*.

*Gossypium barbadense*, in particular *Gossypium barbadense* cv. Pima S7, seeds are publicly available and can be obtained for example from the Cotton Collection (USDA, ARS, Crop Germplasm Research, 2765 F&B Road, College Station, Tex. 77845 on the World Wide Web at ars.grin.gov).

The term "superior allele" of the fiber strength locus refers herein to an allele of the fiber strength locus the presence of which in the genome of a fiber-producing plant results in a higher fiber strength compared to the fiber strength in such fiber-producing plant not comprising the superior allele (i.e., comprising a non-superior allele).

As used herein, the term "allele(s)" means any of one or more alternative forms of a gene or a marker at a particular locus or of a quantitative trait locus (QTL). In a diploid or allotetraploid (amphidiploid) cell of an organism, alleles of a given gene, marker or QTL are located at a specific location or locus (loci plural) on a chromosome. One allele is present on each chromosome of the pair of homologous chromosomes. As used herein, the term "homologous chromosomes" means chromosomes that contain information for the same biological features and contain the same genes or markers at the same loci and the same quantitative trait loci but possibly different alleles of those genes, markers or quantitative trait loci. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In allotetraploid (amphidiploid) species, like cotton, essentially two sets of diploid genomes exist, whereby the chromosomes of the two genomes are referred to as "homeologous chromosomes" (and similarly, the genes, markers and loci of the two genomes are referred to as homeologous genes, markers or loci). A diploid, or allotetraploid (amphidiploid), plant species may comprise a large number of different alleles at a particular locus.

The term "ortholog" of a gene or protein or QTL refers herein to the homologous gene or protein or QTL found in another species, which has the same function as the gene or protein or QTL, but is (usually) diverged in sequence from the time point on when the species harboring the genes or quantitative trait loci diverged (i.e. the genes or quantitative trait loci evolved from a common ancestor by speciation). Orthologs of, e.g., the *Gossypium barbadense* GLUC genes or fiber strength locus may thus be identified in other plant species (e.g. *Gossypium arboreum, Gossypium darwinii*, etc.) based on both sequence comparisons (e.g. based on percentages sequence identity over the entire sequence or over specific domains) and/or functional analysis.

In one embodiment, the superior allele of the fiber strength locus is obtainable from *Gossypium barbadense*, in particular *Gossypium barbadense* cv. PimaS7, i.e. the presence of the *Gossypium barbadense* fiber strength allele in a *Gossypium* plant, such as a *Gossypium hirsutum* plant, results in an increased fiber strength compared to the fiber strength in the *Gossypium* plant, such as the *Gossypium hirsutum* plant, not comprising the *Gossypium barbadense* allele, but, for example, the *Gossypium hirsutum* allele.

In still another embodiment, the *Gossypium barbadense* fiber strength allele is located on chromosome A05 of *Gossypium barbadense* between AFLP marker P5M50-M126.7 and SSR marker CIR280. In another embodiment, the *Gossypium barbadense* fiber strength allele is located on chromosome A05 of *Gossypium barbadense* between AFLP marker P5M50-M126.7 and SSR marker BNL3992. In yet another embodiment, the *Gossypium barbadense* allele is located on chromosome A05 of *Gossypium barbadense* between AFLP marker P5M50-M126.7 and SSR marker CIR401c. In a further embodiment, the LOD peak of the fiber strength QTL allele of *Gossypium barbadense* is located between SSR marker NAU861 or the GLUC1.1 marker and SSR marker CIR401c, in particular at about 0 to 5 cM, more specifically at about 4 cM, especially at about 4.008 cM, from SSR marker NAU861 or the GLUC1.1 marker and at about 0 to 12 cM, more specifically at about 10 cM, especially at about 10.52 cM, from SSR marker CIR401c.

A "(genetic or molecular) marker", as used herein, refers to a polymorphic locus, i.e. a polymorphic nucleotide (a so-called single nucleotide polymorphism or SNP) or a polymorphic DNA sequence at a specific locus. A marker refers to a measurable, genetic characteristic with a fixed position in the genome, which is normally inherited in a Mendelian fashion, and which can be used for mapping of a trait of interest. For example, the fiber strength trait was mapped on chromosome A05 of *Gossypium barbadense* between, amongst others, markers P5M50-M126.7 and CIR280, P5M50-M126.7 and BNL3992, P5M50-M126.7 and CIR401, and linked to markers NAU861, GLUC1.1, and others, as indicated, e.g., in Table 6 in the Examples. Thus, a genetic marker may be a short DNA sequence, such as a sequence surrounding a single base-pair change, i.e. a single nucleotide polymorphism or SNP, or a long DNA sequence, such as microsatellites or Simple Sequence Repeats (SSRs). The nature of the marker is dependent on the molecular analysis used and can be detected at the DNA, RNA or protein level. Genetic mapping can be performed using molecular markers such as, but not limited to, RFLP (restriction fragment length polymorphisms; Botstein et al. (1980), Am J Hum Genet. 32:314-331; Tanksley et al. (1989), Bio/Technology 7:257-263), RAPD [random amplified polymorphic DNA; Williams et al. (1990), NAR 18:6531-6535], AFLP [Amplified Fragment Length Polymorphism; Vos et al. (1995) *NAR* 23:4407-4414], SSRs or microsatellites [Tautz et al. (1989), *NAR* 17:6463-6471]. Appropriate primers or probes are dictated by the mapping method used.

The term "AFLP®" (AFLP® is a registered trademark of KeyGene N.V., Wageningen, The Netherlands), "AFLP analysis" and "AFLP marker" is used according to standard terminology [Vos et al. (1995), *NAR* 23:4407-4414; EP0534858; on the World Wide Web at keygene.com/keygene/techs-apps]. Briefly, AFLP analysis is a DNA fingerprinting technique which detects multiple DNA restriction fragments by means of PCR amplification. The AFLP technology usually comprises the following steps: (i) the restriction of the DNA with two restriction enzymes, preferably a hexa-cutter and a tetra-cutter, such as EcoRI, PstI and MseI; (ii) the ligation of double-stranded adapters to the ends of the restriction fragments, such as EcoRI, PstI and MseI adaptors; (iii) the amplification of a subset of the restriction fragments using two primers complementary to the adapter and restriction site sequences, and extended at their 3' ends by one to three "selective" nucleotides, i.e., the selective amplification is achieved by the use of primers that extend into the restriction fragments, amplifying only those fragments in which the primer extensions match the nucleotides flanking the restriction sites. AFLP primers thus have a specific sequence and each AFLP primer has a specific code (the primer codes and their sequences can be found at the Keygene website keygene.com/keygene/pdf/PRIMERCO.pdf; (iv) gel electrophoresis of the amplified restriction fragments on denaturing slab gels or capillaries; (v) the visualization of the DNA fingerprints by means of autoradiography, phospho-imaging, or other methods. Using this method, sets of restriction fragments may be visualized by PCR without knowledge of nucleotide sequence. An AFLP marker, as used herein, is a DNA fragment of a specific size, which is generated and visualized as a band on a gel by carrying out an AFLP analysis. Each AFLP marker is designated by the primer combination used to amplify it, followed by the approximate size (in base pairs) of the amplified DNA fragment, e.g. P5M50-M126.7 refers to AFLP primer combination P05 (or Keygene code P11, which is a PstI primer with additional nucleotides AA; see Table 2) and M50 (which is a MseI primer with additional nucleotides CAT; see Table 2), the use of which in *Gossypium barbadense* results in an amplified DNA fragment of 126.7 bp (see Table 2). It is understood that the size of these fragments may vary slightly depending on laboratory conditions and equipment used. Every time reference is made herein to an AFLP marker by referring to a primer combination and the specific size of a fragment, it is to be understood that such size is approximate, and comprises or is intended to include the slight variations observed in different labs. Each AFLP marker represents a certain locus in the genome.

The term "SSR" refers to Simple Sequence Repeats or microsatellite [Tautz et al. (1989), *NAR* 17:6463-6471]. Short Simple Sequence stretches occur as highly repetitive elements in all eukaryotic genomes. Simple sequence loci usually show extensive length polymorphisms. These simple sequence length polymorphisms (SSLP) can be detected by polymerase chain reaction (PCR) analysis and be used for identity testing, population studies, linkage analysis and genome mapping. "SSR marker", as used herein, refers to markers indicated as CIRx, NAUx and BNLx (wherein x is a number) that are publicly available markers which are used to create genetic maps of different *Gossypium* species (see Cotton Microsatellite Database on the World Wide Web at cottonmarket.org).

A "(genetic or molecular) marker", such as an AFLP or SSR marker, can be dominant (homozygous and heterozygous individuals are not distinguishable) or co-dominant (distinguishing homozygous and heterozygous individuals, e.g., by band intensity), as exemplified in Table 2 below. A "(genetic or molecular) marker", such as an AFLP or SSR marker, can be linked to a gene or locus in "coupling phase" or in "repulsion phase'. For example, a dominant marker linked in coupling to a gene or locus is present in individuals with the gene or locus and absent in individuals without the gene or locus, while a dominant marker linked in repulsion phase to a gene or locus is absent in individuals with the gene or locus and present in individuals without the gene or locus.

Different alleles of markers can exist in different plant species. "*Gossypium barbadense* or *Gossypium hirsutum* alleles of markers linked to the fiber strength locus", as used herein, refers to a form of a marker that is derived from and specific for *Gossypium barbadense* or *Gossypium hirsutum*, respectively. Table 2 examplifies how different alleles of different markers can be identified or distinguished: column 1 indicates different marker loci on chromosome A05 of *Gossypium barbadense* and/or *Gossypium hirsutum*, column 2 indicates for each marker locus a specific primer pair that can be used to identify the presence or absence of the specific marker locus, column 3 indicates whether a specific marker allele of *Gossypium barbadense* (in particular cv. Pima S7; indicated as 'Pima') and *Gossypium hirsutum* (in particular cv. FM966; indicated as 'FM') generates an amplified DNA fragment and, if so, the size of the amplified DNA fragment, column 4 indicates whether the marker indicated in column 1 is a dominant or a codominant marker as defined above.

TABLE 2

Detection of specific *Gossypium barbadense* or *Gossypium hirsutum* alleles of markers on chromosome A05

| Marker locus on chromosome A05 | Primer pair: | | Amplified fragment (in bp) from FM | Amplified fragment (in bp) From Pima | Codominant/ dominant marker |
|---|---|---|---|---|---|
| P5M50-M126.7 | P5 | 5' GACTGCGTACATGCAGAA 3' (SEQ ID NO: 43) | — | 126.7 | dominant |
|  | M50 | 5' GATGAGTCCTGAGTAACAT 3' (SEQ ID NO: 44) |  |  |  |
| GLUC1.1A-SNP2 | forward | 5' TAT CCC TCT CGA TGA GTA CGA C 3' (SEQ ID NO: 37) | 134 | 143 | codominant |
|  | reverse | 5'CCC AAT GAT GAT GAA CCT GAA TTG3' (SEQ ID NO: 38) |  |  |  |
| NAU861 | forward | 5' CCAAAACTTGTCCCATTAGC 3' (SEQ ID NO: 45) | 205-210 | 215-220 | codominant |
|  | reverse | 5' TTCATCTGTTGCCAGATCC 3' (SEQ ID NO: 46) |  |  |  |
| CIR401c | forward | 5' TGGCGACTCCCTTTT 3' (SEQ ID NO: 47) | — | 245-250 | dominant |
|  | reverse | 5' AAAAGATGTTACACACACAC 3' (SEQ ID NO: 48) |  |  |  |
| CIR401b | forward | 5' TGGCGACTCCCTTTT 3' (SEQ ID NO: 47) | 255 | — | dominant |
|  | reverse | 5' AAAAGATGTTACACACACAC 3' (SEQ ID NO: 48) |  |  |  |
| BNL3992 | forward | 5' CAGAAGAGGAGGAGGTGGAG 3' (SEQ ID NO: 49) | 160-165/ 85-90 | 140-145 | codominant |
|  | reverse | 5' TGCCAATGATGGAAAACTCA 3' (SEQ ID NO: 50) |  |  |  |
| CIR280 | forward | 5' ACTGCGTTCATTACACC 3' (SEQ ID NO: 51) | — | 205 | dominant |
|  | reverse | 5' GCTTCACCCATTCATC 3' (SEQ ID NO: 52) |  |  |  |

As indicated above, the location of the *Gossypium barbadense* fiber strength allele on chromosome A05 can be determined by linked AFLP and/or SSR markers, such as AFLP marker P5M50-M126.7, and SSR markers BNL3992, CIR401b and NAU861. However, it is understood that these AFLP and SSR markers can be converted into other types of molecular markers. When referring to a specific (molecular or genetic) marker in the present invention, it is understood that the definition encompasses other types of molecular markers used to detect the genetic variation originally identified by the AFLP and SSR markers. For example, if an AFLP marker is converted into another molecular marker using known methods, this other marker is included in the definition. For example, AFLP markers can be converted into sequence-specific markers such as, but not limited to STS (sequenced-tagged-site) or SCAR (sequence-characterized-amplified-region) markers using standard technology as described in Meksem et al. [(2001), *Mol Gen Genomics* 265(2):207-214], Negi et al. [(2000), *TAG* 101:146-152], Barret et al. (1989), *TAG* 97:828-833], Xu et al. [(2001), *Genome* 44(1):63-70], Dussel et al. [(2002), *TAG* 105:1190-1195] or Guo et al. [(2003), *TAG* 103:1011-1017]. For example, Dussel et al. [(2002), *TAG* 105:1190-1195] converted AFLP markers linked to resistance into PCR-based sequence tagged site markers such as indel (insertion/deletion) markers and CAPS (cleaved amplified polymorphic sequence) markers.

The conversion of an AFLP marker into an STS marker, for example, generally involves the purification of the DNA fragment from the AFLP gel and the cloning and sequencing of the DNA fragment. Cloning and sequencing of AFLP fragments (bands) can be carried out using known methods [Guo et al. *TAG* 103:1011-1017]. Based on the marker sequence (internal) locus specific PCR primers can be developed [Paran and Michelmore (1993), *TAG* 85:985-993], which amplify fragments of different sizes or wherein the PCR product is cleaved with a restriction enzyme after amplification to reveal a polymorphism. As internal PCR primers often do not reveal polymorphisms related to the EcoRI, MseI or PstI (or other enzymes) restriction site differences, inverse PCR [Hartl and Ochmann (1996), In: Harwood A, editor, *Methods in molecular biology vol 58: basic DNA and RNA protocols*, Humana Press, Totowa N.J. pp 293-301] or PCR-walking [Negi et al. (2000), *TAG* 101:146-152; Siebert et al, (1995), *NAR* 23:1087-1088] may be used to identify flanking sequences, which can then be used to generate simple, locus specific, PCR based markers. Primers can easily be designed using computer software programs such as provided by Sci-Ed (Scientific & Educational Software PO Box 72045, Durham, N.C. 27722-2045 USA). The polymorphism of the STS marker can be detected by gel electrophoresis, or can be detected using fluorometric assays, such as TaqMan® technology (Roche Diagnostics).

Figure 9:
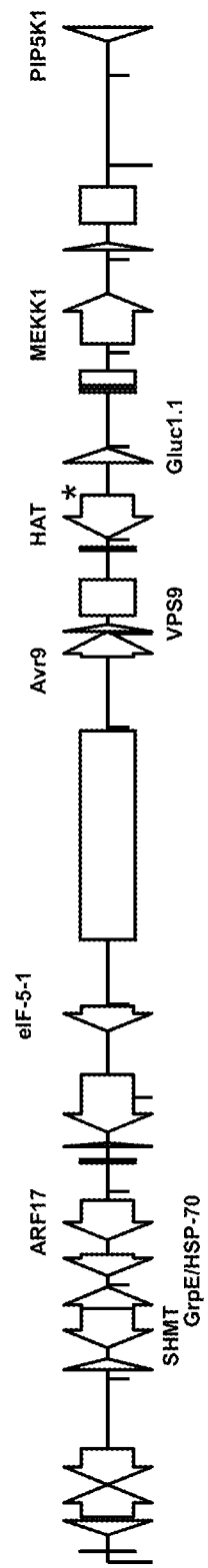
FIG. 9: Schematic representation of 165250 bps DNA fragment spanning the GLUC1.1A gene of *Gossypium hirsutum* (SEQ ID NO: 53). Box: retrotransposon region; *: position of CIR280 homology region; arrow: DNA fragment encoding protein indicated with following abbreviations: SHMT (Serine HydroxyMethylTransferase); GrpE/HSP-70 (GrpE protein/HSP-70 cofactor); ARF17: putative Auxin Response Factor similar to At-ARF17; eIF-5-1: probable eukaryotic translation Initiation Ffactor 5-1; Avr9: putative Avr9 elicitor response protein; VPS9: similar to Vacuolar Protein Sorting-associated protein VPS9; HAT: putative Histon Acetyl Transferase gene; Gluc1.1: GLUC1.1A encoding region; MEKK1: putative Mitogen-activated protein kinase kinase kinase 1; PIP5K1: Phosphatidylinositol-4-Phosphate 5-Kinase 1.

In another embodiment, the fiber strength QTL allele of *Gossypium barbadense* comprises at least one *Gossypium barbadense* ortholog of a nucleotide sequence comprised in the genomic DNA sequence spanning the *Gossypium hirsutum* GLUC1.1A gene represented in SEQ ID NO: 53 (see FIG. 9 and the sequence listing).

In another embodiment, the fiber strength QTL allele of *Gossypium barbadense* comprises at least a GLUC1.1 gene encoding a non-functional GLUC1.1 protein as further described below. In one aspect the *Gossypium barbadense* GLUC1.1 gene is located at about 0 to 5 cM, more specifically at about 4 cM, from the LOD peak of the fiber strength QTL allele of *Gossypium barbadense*. In another aspect the *Gossypium barbadense* GLUC1.1 gene is located at about 0 to 2 cM, at about 0 to 1 cM, more specifically at about 0.008 cM of the NAU861 marker located in the fiber strength QTL allele of *Gossypium barbadense*.

In another embodiment, the non-naturally occurring *Gossypium* plant is a *Gossypium hirsutum*, *Gossypium barbadense*, a *Gossypium herbaceum* or a *Gossypium arboreum* plant, preferably a *Gossypium hirsutum* plant, and wherein the superior fiber strength allele is derived from *Gossypium darwinii*. In one aspect, the fiber strength QTL allele of *Gossypium darwinii* comprises at least a GLUC1.1 gene as further described below.

In still another embodiment, the non-naturally occurring *Gossypium* plant is a *Gossypium hirsutum*, *Gossypium barbadense* or a *Gossypium herbaceum* plant, preferably a *Gossypium hirsutum* plant, and wherein the superior fiber strength allele is derived from *Gossypium arboreum*. In one aspect, the fiber strength QTL allele of *Gossypium arboreum* comprises at least a GLUC1.1 gene as further described below.

In a particular embodiment, the callose content of the fibers of the non-naturally occurring *Gossypium* plant is increased compared to the callose content of the fibers of an equivalent *Gossypium* plant that does not comprise the at least one superior allele of the fiber strength locus.

"Callose" refers to a plant polysaccharide that comprises glucose residues linked together through beta-1,3-linkages, and is termed a beta-glucan. It is thought to be manufactured at the cell wall by callose synthases and is degraded by beta-1,3-glucanases. The callose content of fibers can be measured by staining the fibers with aniline blue, a dye specific for 1,3-beta-glucans. Under UV, callose deposits present an intense yellow-green fluorescence. Images are analyzed and the ratio Green/Blue is used as a measure for callose. "Cellulose" is the major structural polysaccharide of higher plant cell walls. Chains of beta-1,4-linked glucosyl residues assemble soon after synthesis to form rigid, chemically resistant microfibrils. Their mechanical properties together with their orientation in the wall influence the relative expansion of cells in different directions and determine many of the final mechanical properties of mature cells and organs.

In a particular embodiment, the strength of the fibers of the non-naturally occurring *Gossypium* plant is increased compared to the strength of the fibers of an equivalent *Gossypium* plant that does not comprise the at least one superior allele of the fiber strength locus.

"Increase in fiber strength", as used herein, refers to an average strength of fibers of a specific fiber-producing plant species, such as cotton, which is significantly higher than the average strength of fibers of that specific plant species normally observed. Fiber strength is largely determined by variety. However, it may be affected by plant nutrient deficiencies and weather.

In one aspect of this embodiment, the non-naturally occurring *Gossypium* plant is a *Gossypium hirsutum* plant which is homozygous for the *Gossypium barbadense* fiber strength allele. In a further aspect of this embodiment, the strength of the fibers of the *Gossypium* plant is on average between about 5% and about 10%, more specifically about 7.5%, higher than the fiber strength of a *Gossypium hirsutum* plant which is homozygous for the *Gossypium hirsutum* fiber strength allele. In still a further aspect of this embodiment, the strength of the fibers of the *Gossypium* plant is on average between about 1.6 g/tex and about 3.3 g/tex, more specifically about 2.5 g/tex higher than the fiber strength of a *Gossypium hirsutum* plant which is homozygous for the *Gossypium hirsutum* fiber strength allele. In yet a further aspect of this embodiment, the strength of the fibers of the *Gossypium* plant is on average between about 34.6 g/tex and about 36.3 g/tex, more specifically about 35.5 g/tex, as compared to a fiber strength of on average between about 32.2 g/tex and about 33.8 g/tex, more specifically about 33.0 g/tex of a *Gossypium hirsutum* plant which is homozygous for the *Gossypium hirsutum* fiber strength allele.

A "variety" (abbreviated as var.) or "cultivar" (abbreviated as cv.) is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

A "fiber-producing plant" refers to a plant species that produces fibers as defined above, such as a cotton plant. Of the *Gossypium* species, the A genome diploid *Gossypium* species and AD genome allotetraploid *Gossypium* species are known to produce spinnable fiber. Botanically, there are three principal groups of cotton that are of commercial importance. The first, *Gossypium hirsutum* (AADD), is native to Mexico and Central America and has been developed for extensive use in the United States, accounting for more than 95% of U.S. production. This group is known in the United States as American Upland cotton, and their fibers vary in length from about ⅞ to about 1 5⁄16 inches (about 22-about 33 mm). Worldwide it accounts for about 90% of the cotton production. A second botanical group, *G. barbadense* (AADD), which accounts for about 5% of U.S. production and about 8% of the worldwide production, is of early South American origin. With fibers varying in length from about 1 ¼ to about 1 9⁄16 inches (about 32-about 40 mm), it is known in the United States as American Pima, but is also commonly referred to as Extra Long Staple (ELS) cotton. A third group, *G. herbaceum* (AA) and *G. arboreum* (AA), embraces cotton plants with fibers of shorter length, about ½ to about 1 inch (about 13-about 25 mm), that are native to India and Eastern Asia. None from this group is cultivated in the United States.

"Fiber length", as used herein, refers to the average length of the longer one-half of the fibers (upper half mean length). In the US, it is usually reported in 100 ths or 32 nds of an inch (see Table 3; 1 inch is 25.4 mm). It is measured, for example, according to United States Department of Agriculture (USDA) standards by passing a "beard" of parallel fibers through a sensing point. The beard is formed when fibers from a sample of cotton are grasped by a clamp, then combed and brushed to straighten and parallel the fibers. Fiber length is largely determined by variety, but the cotton plant's exposure to extreme temperatures, water stress, or nutrient deficiencies may shorten the length. Excessive cleaning and/or drying at the gin may also result in shorter fiber length. Fiber length affects yarn strength, yarn evenness, and the efficiency of the spinning process. The fineness of the yarn which can be successfully produced from given fibers is also influenced by the length of the fiber.

TABLE 3

Cotton fiber length conversion chart for American Upland and Pima cotton

| American Upland cotton | | | | American Pima cotton | |
|---|---|---|---|---|---|
| inches | 32nds | inches | 32nds | inches | 32nds |
| At least 0.79 | 24 | 1.11-1.13 | 36 | At least 1.20 | 40 |
| 0.80-0.85 | 26 | 1.14-1.17 | 37 | 1.21-1.25 | 42 |
| 0.86-0.89 | 28 | 1.18-1.20 | 38 | 1.26-1.31 | 44 |
| 0.90-0.92 | 29 | 1.21-1.23 | 39 | 1.32-1.36 | 46 |
| 0.93-0.95 | 30 | 1.24-1.26 | 40 | 1.37-1.42 | 48 |
| 0.96-0.98 | 31 | 1.27-1.29 | 41 | 1.43-1.47 | 50 |
| 0.99-1.01 | 32 | 1.30-1.32 | 42 | At least 1.48 | 52 |
| 1.02-1.04 | 33 | 1.33-1.35 | 43 | | |
| 1.05-1.07 | 34 | At least 1.36 | At least 44 | | |
| 1.08-1.10 | 35 | | | | |

Source: on the World Wide Web at cottoninc.com 1 inch = 2.54 cm

An "industrially relevant fiber length", as used herein, refers to a length of fibers of a specific cotton species which is on average at least equal to or not significantly smaller than the length of fibers of that specific cotton variety normally observed. For *G. hirsutum*, an industrially relevant fiber length is reported to vary from about ⅞ to 1 5/16 inches (about 22-about 33 mm). For *G. barbadense*, an industrially relevant fiber length is reported to vary from 1¼ to 1 9/16 inches (about 32-about 40 mm). For *G. herbaceum* (AA) and *G. arboreum* (AA), an industrially relevant fiber length is reported to vary from ½ to 1 inch (about 13-about 25 mm).

Whenever reference to a "plant" or "plants" according to the invention is made, it is understood that also plant parts (cells, tissues or organs, seeds, fibers, severed parts such as roots, leaves, flowers, pollen, etc.), progeny of the plants which retain the distinguishing characteristics of the parents (especially the fiber properties), such as seed obtained by selfing or crossing, e.g. hybrid seed (obtained by crossing two inbred parental lines), hybrid plants and plant parts derived there from are encompassed herein, unless otherwise indicated.

The term "fiber strength allele detection assay" refers herein to an assay that indicates (directly or indirectly) the presence or absence of specific alleles of the fiber strength locus of the present invention. In one embodiment it allows one to determine whether a particular fiber strength allele is homozygous or heterozygous at the locus in any individual plant.

In another aspect of the invention, methods are provided for generating and/or selecting *Gossypium* plants, and parts and progeny thereof, comprising at least one superior allele of the fiber strength locus.

In one embodiment, the superior allele of the fiber strength locus is the *Gossypium barbadense* allele and the method comprises the step of identifying a *Gossypium* plant that comprises the *Gossypium barbadense* fiber strength allele based on the presence of *Gossypium barbadense* alleles of markers linked to the fiber strength locus, such as the markers linked to the *Gossypium barbadense* fiber strength allele indicated above and in Table 6 and 13.

In a particular aspect, the method comprises the step of determining the presence of *Gossypium barbadense* alleles of markers linked to the fiber strength locus in the genomic DNA of a plant selected from the group consisting of: AFLP marker P5M50-M126.7, SSR marker CIR280, SSR marker BNL3992, SSR marker CIR401c, SSR marker NAU861, a polymorphic site in a genomic DNA sequence of the plant corresponding to a genomic DNA sequence comprised in SEQ ID NO: 53, and a polymorphic site in a nucleotide sequence of a GLUC1.1A gene in the genomic DNA of the plant corresponding to the nucleotide sequence of a GLUC1.1A gene of SEQ ID NO: 5, such as the SNP markers indicated as GLUC1.1A-SNP2, 3, 5, 6 and 8 below and in Table 13.

In a further embodiment, the superior allele of the fiber strength locus is the *Gossypium darwinii* allele and the method comprises the step of identifying a *Gossypium* plant that comprises the *Gossypium darwinii* fiber strength allele based on the presence of *Gossypium darwinii* alleles of markers linked to the fiber strength locus, such as the markers linked to the *Gossypium darwinii* fiber strength allele indicated above and in Table 13.

In a particular aspect, the method comprises the step of determining the presence of a *Gossypium darwinii* allele of a polymorphic site in a nucleotide sequence of a GLUC1.1A gene in the genomic DNA of the plant corresponding to the nucleotide sequence of a GLUC1.1A gene of SEQ ID NO: 56, such as the SNP markers indicated as GLUC1.1A-SNP2, 3, 5, 6 and 8 below and in Table 13.

In a further embodiment, the superior allele of the fiber strength locus is the *Gossypium arboreum* allele and the method comprises the step of identifying a *Gossypium* plant that comprises the *Gossypium arboreum* fiber strength allele based on the presence of *Gossypium arboreum* alleles of markers linked to the fiber strength locus, such as the markers linked to the *Gossypium arboreum* fiber strength allele indicated above and in Table 13.

In a particular aspect, the method comprises the step of determining the presence of a *Gossypium arboreum* allele of a polymorphic site in a nucleotide sequence of a GLUC1.1A gene in the genomic DNA of the plant corresponding to the nucleotide sequence of a GLUC1.1A gene of SEQ ID NO: 21, such as the SNP marker indicated as GLUC1.1A-SNP7 below and in Table 13.

Markers linked to the fiber strength locus can be used for marker assisted selection (MAS) or map based cloning of the fiber strength locus. MAS involves screening plants for the presence or absence of linked markers. In particular plants are screened for the presence of markers flanking the locus or gene or linked to the locus or gene. Based on the presence/absence of the marker(s) plants are selected or discarded during the breeding program. MAS can significantly speed up breeding programs and introgression of a particular locus or gene into another genetic background, and can also reduce problems with genotype x environment interactions. MAS is also useful in combining different fiber strength loci in one plant. The presence or absence of a specific fiber strength allele, such as the *Gossypium barbadense* fiber strength allele, can be inferred from the presence or absence of molecular markers, such as the AFLP and SSR markers indicated above (see for example Table 2) or markers derived from them, linked to the specific allele. For example, *Gossypium barbadense* plants, in particular *Gossypium barbadense* cv. Pima S7 plants, may be crossed to *Gossypium hirsutum* plants and progeny plants from this cross are then screened for the presence of one or more AFLP and/or SSR markers linked to the *Gossypium barbadense* fiber strength allele, for example, by using the *barbadense* allele identification protocol.

Breeding procedures such as crossing, selfing, and backcrossing are well known in the art [see Allard R W (1960) *Principles of Plant Breeding*. John Wiley & Sons, New York, and Fehr W R (1987) *Principles of Cultivar Development*, Volume 1, Theory and Techniques, Collier Macmillan Publishers, London. ISBN 0-02-949920-8]. Superior alleles of the fiber strength locus, such as the *Gossypium barbadense* fiber strength allele, can be transferred into other breeding lines or varieties either by using traditional breeding methods alone or by using additionally MAS. In traditional breeding methods the increased callose content and/or increased fiber strength phenotype is assessed in the field or in controlled environment tests in order to select or discard plants comprising or lacking the superior fiber strength allele. Different crosses can be made to transfer the superior fiber strength allele, such as the *Gossypium barbadense* fiber strength allele, into lines of other *Gossypium* species or varieties, such as A genome diploid *Gossypium* plant lines, such as *Gossypium herbaceum* or *Gossypium arboreum* plant lines, or in AD allotetraploid *Gossypium* plant lines, such as *Gossypium hirsutum* and *Gossypium barbadense* plant lines, in particularly in *Gossypium barbadense* plant lines different from the Pima S7 variety. The breeding program may involve crossing to generate an F1 (first filial generation), followed by several generations of selfing (generating F2, F3, etc.). The breeding program may also involve backcrossing (BC) steps, whereby the offspring are backcrossed to one of the parental lines (termed the recurrent parent). Breeders select for agronomically important traits, such as high yield, high fiber quality, disease resistance, etc., and develop thereby elite breeding lines (lines with good agronomic characteristics). In addition, plants are bred to comply with fiber quality standards, such as American Pima or American Upland fiber quality.

The "*barbadense* or *hirsutum* allele identification protocol", as used herein, refers to the identification of the *Gossypium barbadense* and/or *Gossypium hirsutum* allele of the fiber strength locus comprising the steps of: extracting DNA from plant tissue such as leaf tissue or seeds and carrying out an analysis of linked markers, such as an AFLP and/or SSR analysis for one or more of the linked AFLP and/or SSR markers, using, for example, specific primer pairs to identify the *barbadense* or *hirsutum* allele, such as those indicated in Table 2. The *barbadense* or *hirsutum* allele identification protocol may be carried out on DNA obtained from individual plants or on DNA obtained from bulks (or pools). In one embodiment kits for detecting the presence of the *Gossypium barbadense* and/or *Gossypium hirsutum* fiber strength allele in *Gossypium* DNA are provided. Such a kit comprises, for example, primers or probes able to detect a DNA marker, such as an AFLP and/or an SSR marker, linked to the *Gossypium barbadense* and/or *Gossypium hirsutum* fiber strength allele. The kit may further comprise samples, which can be used as positive or negative controls and additional reagents for AFLP and/or SSR analysis. The samples may be tissue samples or DNA samples. As positive control may, for example, *Gossypium barbadense* seeds, in particular from cv. Pima S7, be included. As negative controls may, for example, *Gossypium hirsutum* seeds, in particular from cv. FM966, be included.

In a further aspect, methods are provided to distinguish between the presence of superior and non-superior alleles of the fiber strength locus. In one embodiment, methods are provided to distinguish between the presence of the *Gossypium barbadense* allele and the *Gossypium hirsutum* allele comprising the step of determining the presence of *Gossypium barbadense* and/or *Gossypium hirsutum* alleles of markers linked to the fiber strength locus, such as the markers linked to the fiber strength locus indicated above, for example, those indicated in Table 2 and Table 13.

Thus, in one embodiment, a method is provided for distinguishing between the presence of the *Gossypium barbadense* and *Gossypium hirsutum* fiber strength alleles by determining the presence of *Gossypium barbadense* and *Gossypium hirsutum* alleles of markers linked to the fiber strength locus in the genomic DNA of a plant selected from the group consisting of: AFLP marker P5M50-M126.7, SSR marker CIR280, SSR marker BNL3992, SSR marker CIR401, SSR marker NAU861, a polymorphic site in a genomic DNA sequence of the plant corresponding to a genomic DNA sequence comprised in SEQ ID NO: 53, and a polymorphic site in a nucleotide sequence of a GLUC1.1A gene in the genomic DNA of the plant corresponding to the nucleotide sequence of a GLUC1.1A gene of SEQ ID NO: 5, such as the SNP markers indicated as GLUC1.1A-SNP2, 3, 5, 6 and 8 below and in Table 13.

According to another aspect of the invention, methods are provided for altering the callose content of a fiber in a *Gossypium* plant, particularly increasing the callose content of a fiber, comprising the step of introgressing a superior allele of the cotton fiber strength locus on chromosome A05, such as the *Gossypium barbadense* allele, in the *Gossypium* plant.

According to yet another aspect of the invention, methods are provided for altering the properties of a fiber in a *Gossypium* plant, particularly increasing the strength of a fiber, comprising the step of introgressing a superior allele of the cotton fiber strength locus on chromosome A05, such as the *Gossypium barbadense* allele, in the *Gossypium* plant.

The current invention is further based on the unexpected finding that the functionality and the timing of expression of the GLUC1.1A gene, which was located in the support interval of the strength locus, differ between *G. hirsutum* and *G. barbadense*. It was found that, while *G. hirsutum* plants comprise a GLUC1.1A gene which is functionally expressed during the fiber strength building stage of fiber development, more particularly during the fiber maturation phase, *G. barbadense* plants comprise a GLUC1.1A gene which is non-functionally expressed during the fiber strength building phase. The GLUC1.1D gene on the other hand is functionally expressed during the entire fiber strength building stage in both *Gossypium* species. It was further found that addition of exogenous endo-1,3-beta-glucanase to fibers of *Gossypium barbadense* reduces the callose content and the strength of the fibers. Based on these findings, it is believed that the renown strength of the fibers of *G. barbadense* might be, at least in part, caused by a higher callose content in the fibers and that this higher callose content might be caused by the absence of a functionally expressed A subgenome-specific fiber-specific endo-1,3-beta-glucanase gene. It is further believed that by abolishing the functional expression of specific alleles of GLUC genes during the fiber strength building stage in fiber-producing plants while maintaining the functional expression of specific other GLUC genes during the fiiber strength building stage, it is possible to fine tune the amount and/or type of functional GLUC proteins produced during the fiber strength building stage, thus influencing the degradation of callose in the fiber which in turn influences the strength and length of the fiber produced. It is believed that the absolute and relative amount of different GLUC proteins in fibers can thus be tuned in such a way so as to attain a proper balance between fiber length and strength.

Thus, in a further aspect, the present invention provides a non-naturally occurring fiber-producing plant, and parts and progeny thereof, characterized in that the functional expression of at least one allele of at least one fiber-specific GLUC gene that is functionally expressed during the fiber strength building phase, in particular during the maturation phase of fiber development, is abolished.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operable linked to regulatory regions (e.g. a promoter). A gene (genomic DNA) may thus comprise several operably linked sequences, such as a promoter, a 5' leader sequence comprising e.g. sequences involved in translation initiation, a (protein) coding region (with introns) and a 3' non-translated sequence comprising e.g. transcription termination sites. "cDNA sequence" refers to a nucleic acid sequence comprising the 5' untranslated region, the coding region without introns and the 3' untranslated region and a polyA tail. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection, introgressed from another plant species by, e.g., marker-assisted selection, or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional, i.e. biologically active, protein is produced; the term "not functionally expressed" to indicate that a protein with significantly reduced or no functionality (biological activity) is produced or that no or a significantly reduced amount of protein is produced.

The term "fiber specific" or "fiber cell specific", with respect to the expression of a gene, refers to, for practical purposes, the highly specific, expression of a gene in fiber cells of plants, such as cotton plants. In other words, transcript levels of a DNA in tissues different of fiber cells is either below the detection limit or very low (less than about 0.2 picogram per microgram total RNA).

The term "fiber strength building phase" commonly refers herein to the secondary cell wall synthesis and maturation phase of fiber development as defined above.

The term "GLUC gene" refers herein to a nucleic acid sequence encoding an endo-1,3-beta-glucanase (GLUC) protein.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous (allele of a) GLUC gene present within the nuclear genome of a plant cell. An "isolated nucleic acid sequence" is used to refer to a nucleic acid sequence that is no longer in its natural environment, for example in vitro or in a recombinant bacterial or plant host cell.

The terms "protein" and "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein that is no longer in its natural environment, for example in vitro or in a recombinant bacterial or plant host cell. "Amino acids" are the principal building blocks of proteins and enzymes. They are incorporated into proteins by transfer RNA according to the genetic code while messenger RNA is being decoded by ribosomes. During and after the final assembly of a protein, the amino acid content dictates the spatial and biochemical properties of the protein or enzyme. The amino acid backbone determines the primary sequence of a protein, but the nature of the side chains determines the protein's properties. "Similar amino acids", as used herein, refers to amino acids that have similar amino acid side chains, i.e. amino acids that have polar, non-polar or practically neutral side chains. "Non-similar amino acids", as used herein, refers to amino acids that have different amino acid side chains, for example an amino acid with a polar side chain is non-similar to an amino acid with a non-polar side chain. Polar side chains usually tend to be present on the surface of a protein where they can interact with the aqueous environment found in cells ("hydrophilic" amino acids). On the other hand, "non-polar" amino acids tend to reside within the center of the protein where they can interact with similar non-polar neighbors ("hydrophobic" amino acids"). Examples of amino acids that have polar side chains are arginine, asparagine, aspartate, cysteine, glutamine, glutamate, histidine, lysine, serine, and threonine (all hydrophilic, except for cysteine which is hydrophobic). Examples of amino acids that have non-polar side chains are alanine, glycine, isoleucine, leucine, methionine, phenylalanine, proline, and tryptophan (all hydrophobic, except for glycine which is neutral).

An "enzyme" is a protein comprising enzymatic activity, such as functional, i.e. biologically active, endo-1,3-beta-glucanase or glucan endo-1,3-beta-D-glucosidase (GLUC) proteins (EC 3.2.1.39). GLUC proteins belong to the glycosyl hydrolase family 17 (GH17) enzyme grouping and are capable of hydrolyzing 1,3-beta-D-glucosidic linkages in 1,3-beta-D-glucans, including long chain 1,3-beta-D-glucans called callose (see also on the World Wide Web at cazy.org/fam/GH17. The GH17 group is identified by the following amino acid recognition signature: [LIVMKS]-X-[LIVM-FYWA](3)-[STAG]-E-[STACVI]-G-[WY]*-P-[STN]-X-[SAGQ], where E, such as Glu249 in GhGLUC1.1A (SEQ ID NO: 2 and 4) and similar or identical amino acids in other GLUC1.1 proteins (for example as indicated in FIG. 7), is an active site residue. The GH17 recognition signal of GLUC1.1 enzymes, as described herein, further contains a conserved tryptophan (W) residue at the position indicated with *, such as Trp252 in GhGLUC1.1A (SEQ ID NO: 2 and 4) and similar or identical amino acids in other GLUC1.1 proteins (for example as indicated in FIG. 7), which is predicted to be involved in the interaction with the glucan substrate.

In one embodiment, the fiber-specific GLUC gene that is functionally expressed during the fiber strength building phase, is a GLUC1.1 gene.

The term "GLUC1.1 gene" refers herein to a nucleic acid sequence encoding a GLUC1.1 protein. In particular, a "GLUC1.1 gene", as used herein, refers to a GLUC gene encoding a cDNA sequence with at least 90%, at least 91%, at least 92%, at least 93%, at least 94%, at least 95%, at least 96%, at least 97%, at least 98%, at least 99%, 100% sequence identity to SEQ ID NO: 3 or comprises a coding sequence with at least 92%, at least 93%, at least 94%, at least 95%, at least 96%, at least 97%, at least 98%, at least 99%, 100% sequence identity to the nucleotide at position 2410 to the nucleotide at position 3499 of SEQ ID NO: 1.

A "GLUC1.1 protein", as used herein, refers to a GLUC protein that has at least 90%, at least 91%, at least 92%, at least 93%, at least 94%, at least 95%, at least 96%, at least 97%, at least 98%, at least 99%, 1000% sequence identity to SEQ ID NO: 4.

A functional "GLUC1.1 protein", as used herein, refers to a GLUC1.1 protein that is capable of hydrolyzing 1,3-beta-D-glucosidic linkages in 1,3-beta-D-glucans, that has at least 90%, at least 95%, at least 96%, at least 97%, at least 98%, at least 99% sequence identity to SEQ ID NO: 4 and that comprises amino acid residues similar to the active site residues of the GLUC1.1 protein of SEQ ID NO:4. A non-functional "GLUC1.1 protein", as used herein, refers to a GLUC1.1 protein that is not capable of hydrolyzing 1,3-beta-D-glucosidic linkages in 1,3-beta-D-glucans. In particular, a non-functional GLUC1.1 protein lacks one or more amino acid residues similar to the active site residues of the GLUC1.1 protein of SEQ ID NO:4.

An "active site" or "catalytic site", as used herein, refers to a position on the three-dimensional structure of an enzyme which is involved in substrate binding, such as binding of 1,3-beta-D-glucans to GLUC enzymes, and in the biological activity of the enzyme, such as the hydrolyzation of 1,3-beta-D-glucosidic linkages in 1,3-beta-D-glucans of GLUC enzymes. "Active site (amino acid) residues", as used herein, refer to amino acid residues that are located within the active site of an enzyme and play a crucial role in substrate binding or in enzyme activity. A "glycosylation site", as used herein, refers to a position on the three-dimensional structure of an enzyme which is glycosylated, i.e. a site to which (branched) oligosaccharides bind which may function in increasing stability, such as thermostability, of the protein. "Glycosylation site (amino acid) residues", as used herein, refer to amino acid residues within the glycosylation site of an enzyme to which (branched) oligosaccharides bind. Predictions of the three-dimensional structure of the endo-1,3-beta-glucanase enzymes as described herein indicate that the active site and the glycosylation site of the barley 1,3-1,4-beta-glucanase (as described by Müller et al., 1998, J of Biol Chem 273 (6): 3438-3446; called "1aq0" in the Protein Data Bank, which is freely available on the World Wide Web at rcsb.org/pdb) are conserved, for example, in the *Gossypium hirsutum* GLUC1.1A and D, the *Gossypium barbadense* GLUC1.1D and the *Gossypium herbaceum* GLUC1.1A proteins as described herein, while the *Gossypium barbadense* GLUC1.1A protein, the *Gossypium darwinii* GLUC1.1A protein, and the *Gossypium arboreum* GLUC1.1A protein as described herein lack most conserved amino acids located within these sites these sites (see, e.g., Table 4, FIG. 3 and Examples). Active site and glycosylation residues in other GLUC1.1 proteins can be determined by aligning the amino acid sequences of the different GLUC1.1 proteins with the GLUC1.1 proteins of the present invention, such as the amino acid sequence of GhGLUC1.1A in SEQ ID NO:4, and identifying identical or similar residues in the other GLUC1.1 proteins.

TABLE 4

Amino acid regions and positions of active site residues and glycosylation site residues in GLUC1.1A and D proteins of the three principal groups of cotton of commercial interest

| GLUC protein: barley 1,3-1,4-beta-glucanase | GhGLUC1.1 A | GhGLUC1.1 D | GbGLUC1.1 A | GbGLUC1.1 D | GheGLUC1.1 A | GaGLUC1.1 A |
|---|---|---|---|---|---|---|
| SEQ ID NO: | 2/4 | 8/10 | 6/55 | 12/14 | 24 | 22 |
| Protein size (aa) | 325 | 337 | 179 | 337 | 337 | 78 |
| Mature protein | 311 | 311 | 165 | 311 | 311 | 52 |
| aa encoded by exon 1 | 11 | 23 | 11 | 23 | 23 | 23 |
| aa encoded by exon 2 | 314 | 314 | 168 | 314 | 314 | 55 |
| Active site residue | | | | | | |
| Tyr33 | Tyr48 | Tyr60 | Tyr48 | Tyr60 | Tyr60 | Tyr60 |
| Glu232 | Glu249 | Glu261 | — | Glu261 | Glu261 | — |
|  | Trp252 | Trp264 | — | Trp264 | Trp264 | — |
| Glu288 | Glu308 | Glu320 | — | Glu320 | Glu320 | — |
| Glycosylation site residue: | | | | | | |
| Asn190 | Asn202 | ND | — | ND | Asn214 | — |

—: not present; ND: not determined

The terms "target peptide", "transit peptide" or "signal peptide" refer to amino acid sequences which target a protein to intracellular organelles. The GLUC1.1 proteins as described herein comprise a signal peptide at their N-terminal end, such as the amino acid sequence indicated before the putative post-translational splicing site in FIGS. 2 and 7. "Mature protein" refers to a protein without the signal peptide, such as the GLUC1.1 proteins as described herein without the amino acid sequence indicated before the putative post-translational splicing site in FIGS. 2 and 7. "Precursor protein" or "preproenzyme" refers to the mature protein with its signal peptide.

In another embodiment, the fiber-producing plant is a *Gossypium* plant. In a particular aspect, the *Gossypium* GLUC1.1 allele is a GLUC1.1A or D allele.

A "GLUC1.1A gene", as used herein, refers to a GLUC1.1 gene located on the A subgenome of a *Gossypium* diploid or allotetraploid species ("GLUC1.1A locus") and encoding a GLUC1.1A protein. In particular, a GLUC1.1A gene encodes a cDNA sequence with at least 97%, at least 98%, at least 99% sequence identity to SEQ ID NO: 3 or comprises a coding sequence with at least 95%, at least 96%, at least 97%, at least 98%, at least 99% sequence identity to the nucleotide at position 2410 to the nucleotide at position 3499 of SEQ ID NO: 1. Similarly, a "GLUC1.1D gene", as used herein, refers to a GLUC1.1 gene located on the D subgenome of a *Gossypium* diploid or allotetraploid species ("GLUCHD locus") and encoding a GLUC1.1D protein. In particular, a GLUC1.1D gene encodes a cDNA sequence with at least 97%, at least 98%, at least 99% sequence identity to SEQ ID NO: 9 or comprises a coding sequence with at least 95%, at least 96%, at least 97%, at least 98%, at least 99% sequence identity to the nucleotide at position 3337 to the nucleotide at position 4444 of SEQ ID NO: 7.

A "GLUC1.1A protein", as used herein, refers to a GLUC1.1 protein encoded by a GLUC1.1 gene located on the A subgenome of a *Gossypium* diploid or allotetraploid species and having at least 95%, at least 96%, at least 97%, at least 98%, at least 99% sequence identity to SEQ ID NO: 4. Similarly, a "GLUC1.1D protein", as used herein, refers to a GLUC protein encoded by a GLUC1.1 gene located on the D subgenome of a *Gossypium* diploid or allotetraploid species and having at least 95%, at least 96%, at least 97%, at least 98%, at least 99% sequence identity to SEQ ID NO: 10.

In another embodiment the fiber-producing plant is a *Gossypium hirsutum* plant. In a particular aspect, the *Gossypium hirsutum* GLUC1.1 allele is a GhGLUC1.1A or a GhGLUC1.1D allele, preferably a GhGLUC1.1A allele.

As described in WO2008/083969, the GLUC1.1A and GLUC1.1D genes of *Gossypium hirsutum* can be distinguished by the presence of a cleaved amplified polymorphic sequence (CAPS) marker using an AlwI restriction enzyme recognition site present in the nucleotide sequence of GhGLUC1.1A that is absent in the nucleotide sequence of GhGLUC1.1D and by their timing of expression: whereas the GhGLUC1.1D is expressed during the entire fiber strength building phase (from about 14 to 17 DPA on depending on growth conditions), onset of GhGLUC1.1A is delayed until the beginning of the late fiber maturation phase (about 30-40 DPA depending on growth conditions). The GLUC1.1A and GLUC1.1D genes of *Gossypium barbadense* can also be distinguished by the presence of the CAPS marker using the AlwI restriction enzyme recognition site present in the nucleotide sequence of GbGLUC1.1A that is absent in the nucleotide sequence of GbGLUC1.1D. Both genes are however expressed during the entire fiber strength building phase (from about 14 to 17 DPA on depending on growth conditions). The level of expression of GbGLUC1.1A is however much lower than the level of expression of GbGLUC1.1D.

In one embodiment, the functional expression of the at least one GLUC allele is abolished by mutagenesis.

"Mutagenesis", as used herein, refers to the process in which plant cells (e.g., *Gossypium* seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more GLUC alleles may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, *Gossypium* plants are regenerated from the treated cells using known techniques. For instance, the resulting *Gossypium* seeds may be planted in accordance with conventional growing procedures and following self-pollination seed is formed on the plants. Additional seed that is formed as a result of such self-pollination in the present or a subsequent generation may be harvested and screened for the presence of mutant GLUC alleles. Several techniques are known to screen for specific mutant alleles, e.g., Deleteagene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant GLUC alleles are described in the Examples below.

"Wild type" (also written "wildtype" or "wild-type"), as used herein, refers to a typical form of a plant or a gene as it most commonly occurs in nature. A "wild type plant" refers to a plant with the most common phenotype of such plant in the natural population. A "wild type allele" refers to an allele of a gene required to produce the wild-type phenotype. By contrast, a "mutant plant" refers to a plant with a different rare phenotype of such plant in the natural population or produced by human intervention, e.g. by mutagenesis, and a "mutant allele" refers to an allele of a gene required to produce the mutant phenotype.

As used herein, the term "wild type GLUC" (e.g. wild type GLUC1.1A or GLUC1.1D), means a naturally occurring GLUC allele found within plants, in particular *Gossypium* plants, which encodes a functional GLUC protein (e.g. a functional GLUC1.1A or GLUC1.1D, respectively). In contrast, the term "mutant GLUC" (e.g. mutant GLUC1.1A or GLUC1.1D), as used herein, refers to a GLUC allele, which does not encode a functional GLUC protein, i.e. a GLUC allele encoding a non-functional GLUC protein (e.g. a non-functional GLUC1.1A or GLUC1.1D, respectively), which, as used herein, refers to a GLUC protein having no biological activity or a significantly reduced biological activity as compared to the corresponding wild-type functional GLUC protein, or encoding no GLUC protein or a significantly reduced amount of GLUC protein. Such a "mutant GLUC allele" is a GLUC allele, which comprises one or more mutations in its nucleic acid sequence, whereby the mutation(s) preferably result in a significantly reduced (absolute or relative) amount of functional GLUC protein in the cell in vivo. As used herein, a "full knock-out GLUC1.1A allele" is a mutant GLUC1.1A allele the presence of which in homozygous state in the plant (e.g. a *Gossypium hirsutum* plant with two full knock-out GLUC1.1A alleles and two wild-type GLUC1.1D alleles) results in an increase of fiber strength in that plant. Mutant alleles of the GLUC protein-encoding nucleic acid sequences are designated as "gluc" (e.g. gluc1.1a or gluc1.1d, respectively) herein. Mutant alleles can be either "natural mutant" alleles, which are mutant alleles found in nature (e.g. produced spontaneously without human application of mutagens), such as the *Gossypium barbadense* GLUC1.1A allele, the *Gossypium darwinii* GLUC1.1A allele, and the *Gossypium arboreum* GLUC1.1A allele, or "induced mutant" alleles, which are induced by human intervention, e.g. by mutagenesis.

Thus in one aspect of the embodiment, GLUC mutant plants are provided herein, whereby the mutant alleles are selected from the GLUC1.1A and/or GLUC1.1D genes. Thus in a particular aspect, the genotype of these GLUC mutant plants can be described as: GLUC1.1A/gluc1.1a; GLUC1.1D/gluc1.1d; GLUC1.1A/gluc1.a, GLUC1.1D/GLUC1.1D; or GLUC1.1A/GLUC1.1A, GLUC1.1D/gluc1.1d.

In a further aspect of the embodiment, homozygous GLUC mutant plants or plant parts are provided, whereby the mutant alleles are selected from the GLUC1.1A and GLUC1.1D genes. Thus in a particular aspect, homozygous GLUC mutant plants are provided herein, wherein the genotype of the plant can be described as: gluc1.1a/gluc1.1a; gluc1.1d/gluc1.1d; gluc1.1a/gluc1.1a, GLUC1.1D/GLUC1.1D or GLUC1.1A/GLUC1.1A, gluc1.1d/gluc1.1d.

In a further aspect of the invention the homozygous GLUC mutant plants or plant parts comprise a further mutant allele, wherein the mutant plants or plant parts are heterozygous for the additional mutant GLUC allele. Thus in a further particular aspect, homozygous GLUC mutant plants comprising one further mutant GLUC allele are provided herein, wherein the genotype of the plant can be described as: GLUC1.1-A/gluc1.1-a, gluc1.1-d/gluc1.1-d or gluc1.1a/gluc1.1a, GLUC1.1D/gluc1.1d.

In another embodiment, the functional expression of the at least one GLUC allele is abolished by introgression of a non-functionally expressed orthologous GLUC allele or of a mutagenized allele of the GLUC gene.

In one aspect of this embodiment, the non-functionally expressed orthologous GLUC allele can be isolated from specific cotton species, for example from *Gossypium barbadense, darwinii* or *arboreum*.

In yet another embodiment, the functional expression of the at least one allele of the GLUC gene is abolished by introduction of a chimeric gene comprises the following operably linked DNA elements:
(a) a plant expressible promoter,
(b) a transcribed DNA region, which when transcribed yields an inhibitory RNA molecule capable of reducing the expression of the GLUC allele, and
(c) a 3' end region comprising transcription termination and polyadenylation signals functioning in cells of the plant.

Several methods are available in the art to produce an inhibitory or a silencing RNA molecule, i.e. an RNA molecule which when expressed reduces the expression of a particular gene or group of genes, including the so-called "sense" or "antisense" RNA technologies.

Thus in one embodiment, the inhibitory RNA molecule encoding chimeric gene is based on the so-called antisense technology. In other words, the coding region of the chimeric gene comprises a nucleotide sequence of at least 19 or 20 consecutive nucleotides of the complement of the nucleotide sequence of the GLUC allele. Such a chimeric gene may be constructed by operably linking a DNA fragment comprising at least 19 or 20 nucleotides from the GLUC allele, isolated or identified as described elsewhere in this application, in inverse orientation to a plant expressible promoter and 3' end formation region involved in transcription termination and polyadenylation.

In another embodiment, the inhibitory RNA molecule encoding chimeric gene is based on the so-called co-suppression technology. In other words, the coding region of the chimeric gene comprises a nucleotide sequence of at least 19 or 20 consecutive nucleotides of the nucleotide sequence of the GLUC allele. Such a chimeric gene may be constructed by operably linking a DNA fragment comprising at least 19 or 20 nucleotides from the GLUC allele, in direct orientation to a plant expressible promoter and 3' end formation region involved in transcription termination and polyadenylation.

The efficiency of the above mentioned chimeric genes in reducing the expression of the GLUC allele may be further enhanced by the inclusion of a DNA element which results in the expression of aberrant, unpolyadenylated inhibitory RNA molecules or results in the retention of the inhibitory RNA molecules in the nucleus of the cells. One such DNA element suitable for that purpose is a DNA region encoding a self-splicing ribozyme, as described in WO 00/01133 (incorporated by reference). Another such DNA element suitable for that purpose is a DNA region encoding an RNA nuclear localization or retention signal, as described in WO03/076619 (incorporated by reference).

A convenient and very efficient way of downregulating the expression of a gene of interest uses so-called double-stranded RNA (dsRNA) or interfering RNA (RNAi), as described e.g. in WO99/53050 (incorporated by reference). In this technology, an RNA molecule is introduced into a plant cell, whereby the RNA molecule is capable of forming a double stranded RNA region over at least about 19 to about 21 nucleotides, and whereby one of the strands of this double stranded RNA region is about identical in nucleotide sequence to the target gene ("sense region"), whereas the other strand is about identical in nucleotide sequence to the complement of the target gene or of the sense region ("antisense region"). It is expected that for silencing of the target gene expression, the nucleotide sequence of the 19 consecutive nucleotide sequences may have one mismatch, or the sense and antisense region may differ in one nucleotide. To achieve the construction of such RNA molecules or the encoding chimeric genes, use can be made of the vector as described in WO 02/059294.

Thus, in one aspect of the embodiment, the chimeric gene comprises the following operably linked DNA elements:
(a) a plant expressible promoter, preferably a plant expressible promoter which controls transcription preferentially in the fiber cells;
(b) a transcribed DNA region, which when transcribed yields a double-stranded RNA molecule capable of reducing the expression of the GLUC allele and the RNA molecule comprising a first and second RNA region wherein
  i) the first RNA region comprises a nucleotide sequence of at least 19 consecutive nucleotides having at least about 94% sequence identity to the nucleotide sequence of the GLUC allele;
  ii) the second RNA region comprises a nucleotide sequence complementary to the at least 19 consecutive nucleotides of the first RNA region;
  iii) the first and second RNA region are capable of basepairing to form a double stranded RNA molecule between at least the 19 consecutive nucleotides of the first and second region; and
(c) a 3' end region comprising transcription termination and polyadenylation signals functioning in cells of the plant.

The length of the first or second RNA region (sense or antisense region) may vary from about 19 nucleotides (nt) up to a length equaling the length (in nucleotides) of the GLUC allele. The total length of the sense or antisense nucleotide sequence may thus be at least about 25 nt, or at least about 50 nt, or at least about 100 nt, or at least about 150 nt, or at least about 200 nt, or at least about 500 nt. It is expected that there is no upper limit to the total length of the sense or the antisense nucleotide sequence. However for practical reasons (such as e.g. stability of the chimeric genes) it is expected that the length of the sense or antisense nucleotide sequence should not exceed 5000 nt, particularly should not exceed 2500 nt and could be limited to about 1000 nt.

It will be appreciated that the longer the total length of the sense or antisense region, the less stringent the requirements for sequence identity between these regions and the corresponding sequence in the GLUC allele or its complement. Preferably, the nucleic acid of interest should have a sequence identity of at least about 75% with the corresponding target sequence, particularly at least about 80%, more particularly at least about 85%, quite particularly about 90%, especially about 95%, more especially about 100%, quite especially be identical to the corresponding part of the target sequence or its complement. However, it is preferred that the nucleic acid of interest always includes a sequence of about 19 consecutive nucleotides, particularly about 25 nt, more particularly about 50 nt, especially about 100 nt, quite especially about 150 nt with 100% sequence identity to the corresponding part of the target nucleic acid. Preferably, for calculating the sequence identity and designing the corresponding sense or antisense sequence, the number of gaps should be minimized, particularly for the shorter sense sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. on the World Wide Web at ebi.ac.uk/emboss/align/index) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical", "essentially similar", or "corresponding to", as used herein, refers to sequences, which, when optimally aligned as defined above, share at least a certain minimal percentage of sequence identity (as defined further below). "(A nucleotide or a nucleotide sequence) at a position corresponding to a position of (a nucleotide or a nucleotide sequence in a specific nucleotide sequence)", as used herein, refers to (nucleotides or nucleotide sequences) of two essentially similar sequences, which are aligned with each other in an optimal alignment of the two essentially similar sequences.

dsRNA encoding chimeric genes according to the invention may comprise an intron, such as a heterologous intron, located e.g. in the spacer sequence between the sense and antisense RNA regions in accordance with the disclosure of WO 99/53050 (incorporated herein by reference).

It is preferred for the current invention that the target specific gene sequence included in the antisense, sense or double stranded RNA molecule comprises at least one nucleotide, and preferably more which are specific for the specific GLUC allele whose expression is to be downregulated. Such specific nucleotides are indicated at least in FIG. 6 by the gray boxes.

In a preferred embodiment, the inhibitory RNA molecule is specifically adapted to downregulate the A-subgenomic allele of the GLUC1.1 gene. In another preferred embodiment, the biologically active RNA is specifically adapted to downregulate the D subgenome-specific allele of the GLUC1.1 gene.

The use of synthetic micro-RNA's to downregulate expression of a particular gene in a plant cell, provides for very high sequence specificity of the target gene, and thus allows conveniently to discriminate between closely related alleles as target genes the expression of which is to be downregulated.

Thus, in another embodiment of the invention, the inhibitory RNA or silencing RNA or biologically active RNA molecule may be a microRNA molecule, designed, synthesized and/or modulated to target and cause the cleavage of specific subgenomic alleles, preferably the A subgenomic allele of the GLUC1.1 gene in a fiber producing plant, such as a cotton plant. Various methods have been described to generate and use miRNAs for a specific target gene (including but not limited to Schwab et al. (2006, Plant Cell, 18(5):1121-1133), WO2006/044322, WO2005/047505, EP 06009836, incorporated by reference). Usually, an existing miRNA scaffold is modified in the target gene recognizing portion so that the generated miRNA now guides the RISC complex to cleave the RNA molecules transcribed from the target nucleic acid. miRNA scaffolds could be modified or synthesized such that the miRNA now comprises 21 consecutive nucleotides of one of the subgenomic alleles of the fiber selective β-1,3 endoglucanase encoding nucleotide sequence, such as the sequences represented in the Sequence listing of WO2008/083969, and allowing mismatches according to the herein below described rules.

Thus, in one embodiment, the invention provides a chimeric gene comprising the following operably linked DNA regions:

(a) a plant expressible promoter;
(b) a DNA region which upon introduction and transcription in a plant cell is processed into a miRNA, whereby the miRNA is capable of recognizing and guiding the cleavage of the mRNA of a GLUC allele of the plant but not another GLUC allele, such as the mRNA of the A subgenome specific GLUC allele but not the D subgenome specific GLUC allele; and optionally,
(c) a 3' DNA region involved in transcription termination and polyadenylation.

The mentioned DNA region processed into a miRNA may comprise a nucleotide sequence which is essentially complementary to a nucleotide sequence of at least 21 consecutive nucleotides of a GLUC allele, provided that one or more of following mismatches are allowed: a mismatch between the nucleotide at the 5' end of the miRNA and the corresponding nucleotide sequence in the RNA molecule; a mismatch between any one of the nucleotides in position 1 to position 9 of the miRNA and the corresponding nucleotide sequence in the RNA molecule; three mismatches between any one of the nucleotides in position 12 to position 21 of the miRNA and the corresponding nucleotide sequence in the RNA molecule provided that there are no more than two consecutive mismatches.

As used herein, a "miRNA" is an RNA molecule of about 20 to 22 nucleotides in length which can be loaded into a RISC complex and direct the cleavage of another RNA molecule, wherein the other RNA molecule comprises a nucleotide sequence essentially complementary to the nucleotide sequence of the miRNA molecule whereby one or more of the following mismatches may occur: a mismatch between the nucleotide at the 5' end of said miRNA and the corresponding nucleotide sequence in the target RNA molecule; a mismatch between any one of the nucleotides in position 1 to position 9 of said miRNA and the corresponding nucleotide sequence in the target RNA molecule; three mismatches between any one of the nucleotides in position 12 to position 21 of said miRNA and the corresponding nucleotide sequence in the target RNA molecule provided that there are no more than two consecutive mismatches. no mismatch is allowed at positions 10 and 11 of the miRNA (all miRNA positions are indicated starting from the 5' end of the miRNA molecule).

A miRNA is processed from a "pre-miRNA" molecule by proteins, such as DCL proteins, present in any plant cell and loaded onto a RISC complex where it can guide the cleavage of the target RNA molecules.

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop and further comprising the nucleotide sequence of the miRNA (and its complement sequence) in the double stranded RNA stem. Preferably, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

The pre-miRNA molecules (and consequently also the miRNA molecules) can be conveniently introduced into a plant cell by providing the plant cells with a gene comprising a plant-expressible promoter operably linked to a DNA region, which when transcribed yields the pre-miRNA molecule. The plant expressible promoter may be the promoter naturally associated with the pre-miRNA molecule or it may be a heterologous promoter.

Suitable miRNA and pre microRNA molecules for the specific downregulation of the expression of the GhGLUC1.1A gene are set forth in the sequence listing entries SEQ ID NO: 13, 14, 17, 18 and 19 of WO2008/083969.

Suitable miRNA and pre microRNA molecules for the specific downregulation of the expression of the GhGLUC1.1D gene are set forth in the sequence listing entries SEQ ID NO: 15, 16, 20 and 21 of WO2008/083969.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No. 4 or No. 7, or T-DNA gene promoters and the like.

A plant-expressible promoter that controls initiation and maintenance of transcription preferentially in fiber cells is a promoter that drives transcription of the operably linked DNA region to a higher level in fiber cells and the underlying epidermis cells than in other cells or tissues of the plant. Such promoters include the promoter from cotton from a fiber-specific (3-tubulin gene (as described in WO0210377), the promoter from cotton from a fiber-specific actin gene (as described in WO0210413), the promoter from a fiber specific lipid transfer protein gene from cotton (as described in U.S. Pat. No. 5,792,933), a promoter from an expansin gene from cotton (WO9830698) or a promoter from a chitinase gene in cotton (US2003106097) or the promoters of the fiber specific genes described in U.S. Pat. No. 6,259,003 or U.S. Pat. No. 6,166,294. Fiber selective promoters as described herein may also be used.

The invention also encompasses the chimeric genes herein described, as well as plants, seeds, tissues comprising these chimeric genes, and fibers produced from such plants.

Methods to transform plants are well known in the art and are of minor relevance for the current invention. Methods to transform cotton plants are also well known in the art. *Agrobacterium*-mediated transformation of cotton has been described e.g. in U.S. Pat. No. 5,004,863 or in U.S. Pat. No. 6,483,013 and cotton transformation by particle bombardment is reported e.g. in WO 92/15675.

The chimeric genes according to the invention may be introduced into plants in a stable manner or in a transient manner using methods well known in the art. The chimeric genes may be introduced into plants, or may be generated inside the plant cell as described e.g. in EP 1339859.

The chimeric genes may be introduced by transformation in cotton plants from which embryogenic callus can be derived, such as Coker 312, Coker310, Coker 5Acala SJ-5, GSC25110, FIBERMAX 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 ORO BLANCO PIMA, FIBERMAX FM5013, FIBERMAX FM5015, FIBERMAX FM5017, FIBERMAX FM989, FIBERMAX FM832, FIBERMAX FM966, FIBERMAX FM958, FIBERMAX FM989, FIBERMAX FM958, FIBERMAX FM832, FIBERMAX FM991, FIBERMAX FM819, FIBERMAX FM800, FIBERMAX FM960, FIBERMAX FM966, FIBERMAX FM981, FIBERMAX FM5035, FIBERMAX FM5044, FIBERMAX FM5045, FIBERMAX FM5013, FIBERMAX FM5015, FIBERMAX FM5017 or FIBERMAX FM5024 and plants with genotypes derived thereof.

"Cotton" as used herein includes *Gossypium hirsutum*, *Gossypium barbadense*, *Gossypium arboreum* and *Gossypium herbaceum*. "Cotton progenitor plants" include *Gossypium arboreum*, *Gossypium herbaceum*, *Gossypium raimondii*, *Gossypium longicalyx* and *Gossypium kirkii*.

The methods and means of the current invention may also be employed for other plant species such as hemp, jute, flax and woody plants, including but not limited to *Pinus* spp., *Populus* spp., *Picea* spp., *Eucalyptus* spp. etc.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

In one embodiment, the amount of functional GLUC protein is significantly reduced in fibers of the fiber-producing plant during the fiber strength building phase of fiber development compared to the amount of functional GLUC protein produced during the fiber strength building phase in a plant in which the functional expression of the at least one GLUC allele is not abolished.

A "significantly reduced amount of functional GLUC protein" (e.g. functional GLUC1.1A or GLUC1.1D protein) refers to a reduction in the amount of a functional GLUC protein produced by the cell comprising a mutant GLUC allele by at least 30%, 40%, 50%, 60%, 70%, 80%, 90%, 95% or 100% (i.e. no functional GLUC protein is produced by the cell) as compared to the amount of the functional GLUC protein produced by the cell not comprising the mutant GLUC allele. This definition encompasses the production of a "non-functional" GLUC protein (e.g. truncated GLUC protein) having no biological activity in vivo, the reduction in the absolute amount of the functional GLUC protein (e.g. no functional GLUC protein being made due to the mutation in the GLUC gene), and/or the production of a GLUC protein with significantly reduced biological activity compared to the activity of a functional wild type GLUC protein (such as a GLUC protein in which one or more amino acid residues that are crucial for the biological activity of the encoded GLUC protein, as exemplified above and below, are substituted for another amino acid residue). The term "mutant GLUC protein", as used herein, refers to a GLUC protein encoded by a mutant GLUC nucleic acid sequence ("gluc allele") whereby the mutation results in a significantly reduced and/or no GLUC activity in vivo, compared to the activity of the GLUC protein encoded by a non-mutant, wild type GLUC sequence ("GLUC allele").

In yet a further embodiment, the fibers of the non-naturally occurring fiber-producing plant have a higher callose content compared to the callose content of the fibers of an equivalent fiber-producing plant wherein the expression of the at least one GLUC allele is not abolished.

In a particular aspect of this embodiment, the strength of the fibers of the non-naturally occurring fiber-producing plant is increased compared to the strength of the fibers of an equivalent fiber-producing plant wherein the expression of the at least one GLUC allele is not abolished.

In one aspect of this embodiment, the non-naturally occurring *Gossypium* plant is a *Gossypium hirsutum* plant which is homozygous for the *Gossypium barbadense* GLUC1.1A allele. In a further aspect of this embodiment, the strength of the fibers of the *Gossypium* plant is on average between about 5% and about 10%, more specifically about 7.5%, higher than the fiber strength of a *Gossypium hirsutum* plant which is homozygous for the *Gossypium hirsutum* GLUC1.1A allele. In still a further aspect of this embodiment, the strength of the fibers of the *Gossypium* plant is on average between about 1.6 g/tex and about 3.3 g/tex, more specifically about 2.5 g/tex higher than the fiber strength of a *Gossypium hirsutum* plant which is homozygous for the *Gossypium hirsutum* GLUC1.1A allele. In yet a further aspect of this embodiment, the strength of the fibers of the *Gossypium* plant is on average between about 34.6 g/tex and about 36.3 g/tex, more specifically about 35.5 g/tex, as compared to a fiber strength of on average between about 32.2 g/tex and about 33.8 g/tex, more specifically about 33.0 g/tex of a *Gossypium hirsutum* plant which is homozygous for the *Gossypium hirsutum* GLUC1.1A allele.

Further provided herein are nucleic acid sequences of wild type and mutant GLUC1.1 genes/alleles from *Gossypium* species, as well as the wild type and mutant GLUC1.1 proteins. Also provided are methods of generating and combining mutant and wild type GLUC1.1 alleles in *Gossypium* plants, as well as *Gossypium* plants and plant parts comprising specific combinations of wild type and mutant GLUC1.1 alleles in their genome, whereby these plants produce fibers with altered fiber strength and whereby the plants preferably grow normally and have a normal phenotype. The use of these plants for transferring mutant GLUC1.1 alleles to other plants is also an embodiment of the invention, as are the plant products of any of the plants described. In addition kits and methods for marker assisted selection (MAS) for combining or detecting GLUC genes and/or alleles are provided. Each of the embodiments of the invention is described in detail herein below.

Provided are both wild type (GLUC1.1) nucleic acid sequences, encoding functional GLUC1.1 proteins, and mutant (gluc1.1) nucleic acid sequences (comprising one or more mutations, preferably mutations which result in a significantly reduced biological activity of the encoded GLUC1.1 protein or in no GLUC1.1 protein being produced) of GLUC1.1 genes from *Gossypium* species, especially from *Gossypium hirsutum* and *Gossypium barbadense*, but also from other *Gossypium* species. For example, *Gossypium* species comprising an A and/or a D genome may comprise different alleles of GLUC1.1A or GLUC1.1D genes which can be identified and combined in a single plant according to the invention. In addition, mutagenesis methods can be used to generate mutations in wild type GLUC1.1A or GLUC1.1D alleles, thereby generating mutant alleles for use according to the invention. Because specific GLUC1.1 alleles are preferably combined in a *Gossypium* plant by crossing and selection, in one embodiment the GLUC1.1 and/or gluc1.1 nucleic acid sequences are provided within a *Gossypium* plant (i.e. endogenously).

However, isolated GLUC1.1 and gluc1.1 nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional protein or a protein with significantly reduced or no functionality (e.g. by expression in a recombinant host cell and enzyme assays) and for selection and transfer of specific alleles from one *Gossypium* plant into another, in order to generate a plant having the desired combination of functional and mutant alleles.

Nucleic acid sequences of GLUC1.1A and/or GLUC1.1D have been isolated from *Gossypium hirsutum*, from *Gossypium barbadense*, from *Gossypium tomentosum*, from *Gossypium darwinii*, from *Gossypium mustelinum*, from *Gossypium arboreum*, from *Gossypium herbaceum*, and from *Gossypium raimondii* as depicted in the sequence listing. The wild type GLUC1.1A sequences of *Gossypium hirsutum, tomentosum, mustelinum* and *herbaceum* and wild type GLUC1.1D sequences of *Gossypium hirsutum, tomentosum, barbadense, darwinii, mustelinum* and *raimondii* are depicted, while the mutant gluc1.1a and/or gluc1.1d sequences of these sequences, and of sequences essentially similar to these, are described herein below and in the Examples, with reference to the wild type GLUC1.1A and GLUC1.1D sequences. Further, the mutant GLUC1.1A sequences of *Gossypium barbadense, darwinii* and *arboreum* are depicted, while the alternative mutant gluc1.1a sequences of these sequences, and of sequences essentially similar to these, are described herein below and in the Examples. The genomic GLUC1.1A and D protein-encoding DNA, and corresponding pre-mRNA, comprises 2 exons (numbered exons 1 and 2 starting from the 5' end) interrupted by 1 intron. In the cDNA and corresponding processed mRNA (i.e. the spliced RNA), introns are removed and exons are joined, as depicted in the sequence listing and FIGS. 1 and 6. Exon sequences are more conserved evolutionarily and are therefore less variable than intron sequences.

"GLUC1.1A nucleic acid sequences" or "GLUC1.1A variant nucleic acid sequences" according to the invention are nucleic acid sequences encoding an amino acid sequence having at least 95%, at least 96%, at least 97%, at least 98%, at least 99% or 100% sequence identity to SEQ ID NO: 4 or nucleic acid sequences encoding a cDNA sequence with at least 97%, at least 98%, at least 99% sequence identity to SEQ ID NO: 3 or comprises a coding sequence with at least 95%, at least 96%, at least 97%, at least 98%, at least 99% sequence identity to the nucleotide at position 2410 to the nucleotide at position 3499 of SEQ ID NO: 1. These nucleic acid sequences may also be referred to as being "essentially similar" or "essentially identical" or "corresponding to" the GLUC1.1A sequences provided in the sequence listing.

"GLUC1.1D nucleic acid sequences" or "GLUC1.1D variant nucleic acid sequences" according to the invention are nucleic acid sequences encoding an amino acid sequence having at least 95%, at least 96%, at least 97%, at least 98%, at least 99% or 100% sequence identity to SEQ ID NO: 10 or nucleic acid sequences encoding a cDNA sequence with at least 97%, at least 98%, at least 99% sequence identity to SEQ ID NO: 3 or comprises a coding sequence with at least 95%, at least 96%, at least 97%, at least 98%, at least 99% sequence identity to the nucleotide at position 3337 to the nucleotide at position 4444 of SEQ ID NO: 7. These nucleic acid sequences may also be referred to as being "essentially similar" or "essentially identical" or "corresponding to" the GLUC1.1A sequences provided in the sequence listing.

Thus, the invention provides both nucleic acid sequences encoding wild type, functional GLUC1.1A and GLUC1.1D proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type protein. Preferably the mutation(s) in the nucleic acid sequence result in one or more amino acid changes (i.e. in relation to the wild type amino acid sequence one or more amino acids are inserted, deleted and/or substituted) whereby the biological activity of the GLUC1.1 protein is significantly reduced. A significant reduction in biological activity of the mutant GLUC1.1 protein, refers to a reduction in enzymatic activity by at least 30%, at least 40%, 50% or more, at least 90% or 100% (no biological activity) compared to the activity of the wild type protein.

Both endogenous and isolated nucleic acid sequences are provided herein. Also provided are fragments of the GLUC1.1 sequences and GLUC1.1 variant nucleic acid sequences defined above, for use as primers or probes and as components of kits according to another aspect of the invention (see further below). A "fragment" of a GLUC1.1 or gluc1.1 nucleic acid sequence or variant thereof (as defined) may be of various lengths, such as at least 10, 12, 15, 18, 20, 50, 100, 200, 500, 1000 contiguous nucleotides of the GLUC1.1 or gluc1.1 sequence (or of the variant sequence).

Nucleic acid sequences of GLUC1.1A and/or GLUC1.1D have been isolated from *Gossypium hirsutum*, from *Gossypium barbadense*, from *Gossypium tomentosum*, from *Gossypium darwinii*, from *Gossypium mustelinum*, from *Gossypium arboreum*, from *Gossypium herbaceum*, and from *Gossypium raimondii* as depicted in the sequence listing. The wild type GLUC1.1A sequences of *Gossypium hirsutum, tomentosum, mustelinum* and *herbaceum* and wild type GLUC1.1D sequences of *Gossypium hirsutum, tomentosum, barbadense, darwinii, mustelinum* and *raimondii* are depicted, while the mutant gluc1.1a and/or gluc1.1d sequences of these sequences, and of sequences essentially similar to these, are described herein below and in the Examples, with reference to the wild type GLUC1.1A and GLUC1.1D sequences. Further, the mutant GLUC1.1A sequences of *Gossypium barbadense, darwinii* and *arboreum* are depicted, while the alternative mutant gluc1.1a sequences of these sequences, and of sequences essentially similar to these, are described herein below and in the Examples. The genomic GLUC1.1A and D protein-encoding DNA, and corresponding pre-mRNA, comprises 2 exons (numbered exons 1 and 2 starting from the 5' end) interrupted by 1 intron. In the cDNA and corresponding processed mRNA (i.e. the spliced RNA), introns are removed and exons are joined, as depicted in the sequence listing and FIGS. 1 and 6. Exon sequences are more conserved evolutionarily and are therefore less variable than intron sequences.

The nucleic acid sequences of GLUC1.1A and/or GLUC1.1D from *Gossypium hirsutum*, from *Gossypium barbadense*, from *Gossypium tomentosum*, from *Gossypium darwinii*, from *Gossypium mustelinum*, from *Gossypium arboreum*, from *Gossypium herbaceum*, and from *Gossypium raimondii* depicted in the sequence listing encode wild type, functional GLUC1.1 proteins from these *Gossypium* species. Further, the mutant GLUC1.1A sequences of *Gossypium barbadense, darwinii* and *arboreum* depicted in the sequence listing encode wild type, non-functional GLUC1.1 proteins from these *Gossypium* species. Thus, these sequences are endogenous to the *Gossypium* species from which they were isolated. Other *Gossypium* species, varieties, breeding lines or wild accessions may be screened for other GLUC1.1A and GLUC1.1D alleles, encoding the same GLUC1.1A and GLUC1.1D proteins or variants thereof. For example, nucleic acid hybridization techniques (e.g. Southern blot, using for example stringent hybridization conditions) or PCR-based techniques may be used to identify GLUC1.1 alleles endogenous to other *Gossypium* plants. To screen such plants or plant tissues for the presence of GLUC1.1 alleles, the GLUC1.1 nucleic acid sequences provided in the sequence listing, or variants or fragments of any of these, may be used. For example whole sequences or fragments may be used as probes or primers. For example specific or degenerate primers may be used to amplify nucleic acid sequences encoding GLUC1.1 proteins from the genomic DNA of the plant or plant tissue. These GLUC1.1 nucleic acid sequences may be isolated and sequenced using standard molecular biology techniques. Bioinformatics analysis may then be used to characterize the allele(s), for example in order to determine which GLUC1.1 allele the sequence corresponds to and which GLUC1.1 protein or protein variant is encoded by the sequence.

Whether a nucleic acid sequence encodes a functional GLUC1.1 protein can be analyzed by recombinant DNA techniques as known in the art, e.g. expressing the nucleic acid molecule in a host cell (e.g. a bacterium, such as *E. coli*) and analyzing the endo-1,3-beta-glucanase activity of the resulting protein or cells.

In addition, it is understood that GLUC1.1 nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below. Fragments include nucleic acid sequences encoding only the mature protein, or smaller fragments comprising all or part of the exon and/or intron sequences, etc.

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as gluc1.1 sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded GLUC1.1 protein (i.e. it is not a "silent mutation"). In another embodiment, the mutation(s) in the nucleic acid sequence result in a significantly reduced or completely abolished biological activity of the encoded GLUC1.1 protein relative to the wild type protein.

The nucleic acid molecules may, thus, comprise one or more mutations, such as:

(a) a "missense mutation", which is a change in the nucleic acid sequence that results in the substitution of an amino acid for another amino acid;
(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
(c) an "insertion mutation" of one or more amino acids, due to one or more codons having been added in the coding sequence of the nucleic acid;
(d) a "deletion mutation" of one or more amino acids, due to one or more codons having been deleted in the coding sequence of the nucleic acid;
(e) a "frameshift mutation", resulting in the nucleic acid sequence being translated in a different frame downstream of the mutation. A frameshift mutation can have various causes, such as the insertion, deletion or duplication of one or more nucleotides, but also mutations which affect pre-mRNA splicing (splice site mutations) can result in frameshifts;
(f) a "splice site mutation", which alters or abolishes the correct splicing of the pre-mRNA sequence, resulting in a protein of different amino acid sequence than the wild type. For example, one or more exons may be skipped during RNA splicing, resulting in a protein lacking the amino acids encoded by the skipped exons. Alternatively, the reading frame may be altered through incorrect splicing, or one or more introns may be retained, or alternate splice donors or acceptors may be generated, or splicing may be initiated at an alternate position (e.g. within an intron), or alternate polyadenylation signals may be generated. Correct pre-mRNA splicing is a complex process, which can be affected by various mutations in the nucleotide sequence of the GLUC1.1-encoding gene. In higher eukaryotes, such as plants, the major spliceosome splices introns containing GU at the 5' splice site (donor site) and AG at the 3' splice site (acceptor site). This GU-AG rule (or GT-AG rule; see Lewin, Genes VI, Oxford University Press 1998, pp 885-920, ISBN 0198577788) is followed in about 99% of splice sites of nuclear eukaryotic genes, while introns containing other dinucleotides at the 5' and 3' splice site, such as GC-AG and AU-AC account for only about 1% and 0.1% respectively.

As already mentioned, it is desired that the mutation(s) in the nucleic acid sequence preferably result in a mutant protein comprising significantly reduced or no enzymatic activity in vivo. Basically, any mutation which results in a protein comprising at least one amino acid insertion, deletion and/or substitution relative to the wild type protein can lead to significantly reduced or no enzymatic activity. It is, however, understood that mutations in certain parts of the protein are more likely to result in a reduced function of the mutant GLUC1.1 protein, such as mutations leading to truncated proteins, whereby significant portions of the functional domains, such as the catalytic domain, are lacking.

The functional GLUC1.1 proteins of *Gossypium* described herein are about 325-337 amino acids in length and comprise a number of structural and functional domains. These include the following: An N-terminal plastid target peptide of about 14-26 amino acids followed by what constitutes the mature GLUC1.1 protein. The mature GLUC1.1 protein comprises active site and glycosylation amino acid residues as indicated in Table 4 above.

Thus in one embodiment, nucleic acid sequences comprising one or more of any of the types of mutations described above are provided. In another embodiment, gluc1.1 sequences comprising one or more deletion mutations, one or more stop codon (nonsense) mutations and/or one or more splice site mutations are provided. Any of the above mutant nucleic acid sequences are provided per se (in isolated form), as are plants and plant parts comprising such sequences endogenously.

A deletion mutation in a GLUC1.1 allele, as used herein, is a mutation in a GLUC1.1 allele whereby at least 1, at least 2, 3, 4, 5, 10, 20, 30, 50, 100, 200, 500, 1000 or more bases are deleted from the corresponding wild type GLUC1.1 allele, and whereby the deletion results in the mutant GLUC1.1 allele being transcribed and translated into a mutant protein which has significantly reduced or no activity in vivo. A deletion may lead to a frame-shift and/or it may introduce a premature stop codon, or may lead to one amino acid or more amino acids (e.g. large parts) of coding sequence being removed, etc. The exact underlying molecular basis by which the deletion results in a mutant protein having significantly reduced biological activity is not important. Also provided herein are plants and plant parts in which specific GLUC1.1 alleles are completely deleted, i.e. plants and plant parts lacking one or more GLUC1.1 alleles.

A nonsense mutation in a GLUC1.1 allele, as used herein, is a mutation in a GLUC1.1 allele whereby one or more translation stop codons are introduced into the coding DNA and the corresponding mRNA sequence of the corresponding wild type GLUC1.1 allele. Translation stop codons are TGA (UGA in the mRNA), TAA (UAA) and TAG (UAG). Thus, any mutation (deletion, insertion or substitution) which leads to the generation of an in-frame stop codon in the coding sequence (exon sequence) will result in termination of translation and truncation of the amino acid chain. In one embodiment, a mutant GLUC1.1 allele comprising a nonsense mutation is a GLUC1.1 allele wherein an in-frame stop codon is introduced in the GLUC1.1 codon sequence by a single nucleotide substitution, such as the mutation of CAG to TAG, TGG to TAG, TGG to TGA, or CGA to TGA. In another embodiment, a mutant GLUC1.1 allele comprising a nonsense mutation is a GLUC1.1 allele wherein an in-frame stop codon is introduced in the GLUC1.1 codon sequence by double nucleotide substitutions, such as the mutation of CAG to TAA, TGG to TAA, CGG to TAG or TGA, CGA to TAA. In yet another embodiment, a mutant GLUC1.1 allele comprising a nonsense mutation is a GLUC1.1 allele wherein an in-frame stop codon is introduced in the GLUC1.1 codon sequence by triple nucleotide substitutions, such as the mutation of CGG to TAA. The truncated protein lacks the amino acids encoded by the coding DNA downstream of the mutation (i.e. the C-terminal part of the GLUC1.1 protein) and maintains the amino acids encoded by the coding DNA upstream of the mutation (i.e. the N-terminal part of the GLUC1.1 protein). In one embodiment, the nonsense mutation is present anywhere in front of the second conserved Glu residue, the Trp residue, the first Glu residue, and/or the Tyr residue of the active site, so that at least the conserved Glu residue, the Trp residue, the first Glu residue, and/or the Tyr residue is lacking, resulting in significantly reduced activity of the truncated protein. The more truncated the mutant protein is in comparison to the wild type protein, the more likely it is that it will lack any enzymatic activity. Thus in another embodiment, a mutant GLUC1.1 allele comprising a nonsense mutation which result in a truncated protein lacking the second conserved Glu, a truncated protein lacking the second conserved Glu residue and the Trp residue, a truncated protein lacking the second conserved Glu residue, the Trp residue and the first Glu residue, a truncated protein lacking the second conserved Glu residue, the Trp residue, the first Glu residue and the Tyr residue, or a truncated protein with even less amino acids in length are provided. In yet another embodiment, the nonsense mutation results in one or more exons not being translated into protein, such as exon 1, exon 2 or exons 1 and 2.

A splice site mutation in a GLUC1.1 allele, as used herein, is a mutation in a GLUC1.1 allele whereby a mutation in the corresponding wild type functional GLUC1.1 allele results in aberrant splicing of the pre-mRNA thereby resulting in a mutant protein having significantly reduced or no activity. The mutation may be in the consensus splice site sequence. For example, Table 5 describes consensus sequences, which—if mutated—are likely to affect correct splicing. The GT-AG splice sites commonly have other conserved nucleotides, such as 2 highly conserved nucleotides on the 5' end of the intron (in the exon), often being 5'-AG-3'. On the 3'-side of the GT dinucleotide (thus in the intron) high conservation can be found for a tetranucleotide 5'-AAGT-3'. This means that 8 nucleotides can be identified as highly conserved at the donor site.

TABLE 5

Consensus splice site sequences

| Intron type | 5' splice junction (exon^intron) | Near 3'splice site | 3'splice junction (intron^exon) | Found in |
|---|---|---|---|---|
| GU-AG (Canonical introns; about 99%) | CRN^GU(A/G)AGU | A | YnAG^N | nuclear pre-mRNA |
| (about 1%) | ^GC | | AG^ | nuclear pre-mRNA |
| Non-canonical introns (< about 0.1%) | ^AU | | AC^ | nuclear pre-mRNA |
| Canonical branch sites | | CUPuAPy | | 20-50 nucleotides 5' to splice-site acceptor of nuclear pre mRNA |

^depicts the splice site; R = A or G; Y = C or T; N = A, C, G or T (but often G); n = multiple nucleotides; in bold = consensus dinucleotides in the intron sequence.
Pu = purine base; Py = pyrimidine base.

Splice site structure and consensus sequences are described in the art and computer programs for identifying exons and splice site sequences, such as NetPLAntgene, BDGP or Genio, est2genome, FgeneSH, and the like, are available. Comparison of the genomic sequence or premRNA sequence with the translated protein can be used to determine or verify splice sites and aberrant splicing.

Any mutation (insertion, deletion and/or substitution of one or more nucleotides) which alters pre-mRNA splicing and thereby leads to a protein with significantly reduced biological activity is encompassed herein. In one embodiment, a mutant GLUC1.1 allele comprising a splice site mutation is a GLUC1.1 allele wherein altered splicing is caused by the introduction in the GLUC1.1 transcribed DNA region of one or more nucleotide substitution(s) of the consensus dinucleotides depicted in bold above. For example, ˆGU may for example be mutated to ˆAU in the donor splice site and/or AGˆ may be mutated to AAˆ in the acceptor splice site sequence. In another embodiment, a mutant GLUC1.1 allele comprising a splice site mutation is a GLUC1.1 allele wherein altered splicing is caused by the introduction in the GLUC1.1 transcribed DNA region of one or more nucleotide substitution(s) in the conserved nucleotides in the exon sequences.

Further provided are both functional GLUC1.1 amino acid sequences and non-functional GLUC1.1 amino acid sequences (comprising one or more mutations, preferably mutations which result in a significantly reduced or no biological activity of the GLUC1.1 protein) from *Gossypium* species, especially from *Gossypium hirsutum* and *Gossypium barbadense*, but also from other *Gossypium* species, such as those indicated below. In addition, mutagenesis methods can be used to generate mutations in wild type functional GLUC1.1 alleles, thereby generating mutant non-functional GLUC1.1 alleles which can encode further non-functional GLUC1.1 proteins. In one embodiment the functional and/or non-functional GLUC1.1 amino acid sequences are provided within a *Gossypium* plant (i.e. endogenously). However, isolated GLUC1.1 amino acid sequences (e.g. isolated from the plant or made synthetically), as well as variants thereof and fragments of any of these are also provided herein.

Amino acid sequences of GLUC1.1A and GLUC1.1D proteins have been determined from *Gossypium hirsutum*, from *Gossypium barbadense*, from *Gossypium* tomentosum, from *Gossypium darwinii*, from *Gossypium mustilinum*, from *Gossypium arboreum*, from *Gossypium herbaceum*, and from *Gossypium raimondii* as depicted in the sequence listing and FIGS. 2 and 7. The wild type functional GLUC1.1A sequences of *Gossypium hirsutum, tomentosum, mustilinum* and *herbaceum* and wild type functional GLUC1.1D sequences of *Gossypium hirsutum, tomentosum, barbadense, darwinii, mustilinum* and *raimondii* are depicted, while mutant non-functional GLUC1.1A sequences of these, and of sequences essentially similar to these, are described herein below, with reference to the wild type functional GLUC1.1A and GLUC1.1D sequences. Further, the wild type non-functional GLUC1.1A sequences of *Gossypium barbadense, darwinii* and *arboreum* are depicted, while alternative (mutant) non-functional GLUC1.1A sequences of these sequences, and of sequences essentially similar to these, are described herein below and in the Examples.

As described above, the functional GLUC1.1 proteins of *Gossypium* described herein are about 325-337 amino acids in length and comprise a number of structural and functional domains. The sequences of the N-terminal part of the GLUC1.1 proteins are less conserved evolutionarily than the sequences of the mature GLUC1.1 proteins. The sequences of the mature GLUC1.1 proteins are therefore less variable than the sequences of the precursor proteins.

"GLUC1.1A amino acid sequences" or "GLUC1.1A variant amino acid sequences" according to the invention are amino acid sequences having at least 95%, at least 96%, at least 97%, at least 98%, at least 99% or at least 100% sequence identity to SEQ ID NO: 4. These amino acid sequences may also be referred to as being "essentially similar" or "essentially identical" or "corresponding to" the GLUC1.1A sequences provided in the sequence listing.

"GLUC1.1D amino acid sequences" or "GLUC1.1D variant amino acid sequences" according to the invention are amino acid sequences having at least 95%, at least 96%, at least 97%, at least 98%, at least 99% or at least 100% sequence identity to SEQ ID NO: 10. These amino acid sequences may also be referred to as being "essentially similar" or "essentially identical" or "corresponding to" the GLUC1.1D sequences provided in the sequence listing.

Thus, the invention provides both amino acid sequences of wild type functional and non-functional GLUC1.1A and GLUC1.1D proteins, including variants and fragments thereof (as defined further below), as well as mutant non-functional amino acid sequences of any of these, whereby the mutation in the amino acid sequence preferably results in a significant reduction in the biological activity of the GLUC1.1 protein. A significant reduction in biological activity of the (wild type or mutant) non-functional GLUC1.1 protein, refers to a reduction in enzymatic activity (i.e. in endo-1,3-beta-glucanase activity) by at least 30%, at least 40%, 50% or more, at least 90% or 100% (no biological activity) compared to the activity of the functional protein.

Both endogenous and isolated amino acid sequences are provided herein. A "fragment" of a GLUC1.1 amino acid sequence or variant thereof (as defined) may be of various lengths, such as at least 10, 12, 15, 18, 20, 50, 100, 200, 400 contiguous amino acids of the GLUC1.1 sequence (or of the variant sequence).

The amino acid sequences depicted in the sequence listing are wild type GLUC1.1 proteins from *Gossypium* species. Thus, these sequences are endogenous to the *Gossypium* plants from which they were isolated. Other *Gossypium* species, varieties, breeding lines or wild accessions may be screened for other (functional or non-functional) GLUC1.1 proteins with the same amino acid sequences or variants thereof, as described above.

In addition, it is understood that GLUC1.1 amino acid sequences and variants thereof (or fragments of any of these) may be identified in silico, by screening amino acid databases for essentially similar sequences. Fragments of amino acid molecules according to the invention are also provided. Fragments include amino acid sequences of the mature protein, or smaller fragments comprising all or part of the amino acid sequences, etc.

Amino acid sequences comprising one or more amino acid deletions, insertions or substitutions relative to the wild type (functional or non-functional) amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the GLUC1.1 protein relative to the wild type protein. As described above, basically, any mutation which results in a protein comprising at least one amino acid insertion, deletion and/or substitution relative to the wild type protein can lead to significantly reduced (or no) enzymatic activity. It is, however, understood that mutations in certain parts of the protein are more likely to result in a reduced function of the mutant GLUC1.1 protein, such as mutations leading to truncated proteins, whereby significant portions of the functional domains, such as the active site or glycosylation site (see above), are lacking or mutations whereby conserved amino acid residues which have a catalytic function or which are involved in substrate specificity are substituted.

Thus in one embodiment, mutant GLUC1.1 proteins are provided comprising one or more deletion or insertion mutations, whereby the deletion(s) or insertion(s) result(s) in a mutant protein which has significantly reduced or no activity in vivo. Such mutant GLUC1.1 proteins are GLUC1.1 proteins wherein at least 1, at least 2, 3, 4, 5, 10, 20, 30, 50, 100, 200, 300, 400 or more amino acids are deleted or inserted as compared to the wild type GLUC1.1 protein, whereby the deletion(s) or insertion(s) result(s) in a mutant protein which has significantly reduced or no activity in vivo.

In another embodiment, mutant GLUC1.1 proteins are provided which are truncated whereby the truncation results in a mutant protein which has significantly reduced or no activity in vivo. Such truncated GLUC1.1 proteins are GLUC1.1 proteins which lack functional domains, such as active site residues and/or glycosylation site residues, in the C-terminal part of the corresponding wild type (mature) GLUC1.1 protein and which maintain the N-terminal part of the corresponding wild type (mature) GLUC1.1 protein. Thus in one embodiment, a truncated GLUC1.1 protein comprising the N-terminal part of the corresponding wild type (mature) GLUC1.1 protein up to but not including the conserved second Glu residue (as described above) is provided. The more truncated the mutant protein is in comparison to the wild type protein, the more likely it is that it will lack any enzymatic activity. Thus in another embodiment, a truncated GLUC1.1 protein comprising the N-terminal part of the corresponding wild type (mature) GLUC1.1 protein up to but not including the conserved Trp and/or the first Glu residue (as described above) is provided. In yet another embodiment, a truncated GLUC1.1 protein comprising the N-terminal part of the corresponding wild type (mature) GLUC1.1 protein up to but not including the conserved Tyr residue (as described above), or lacking even more amino acids, is provided.

In yet another embodiment, mutant GLUC1.1 proteins are provided comprising one or more substitution mutations, whereby the substitution(s) result(s) in a mutant protein which has significantly reduced or no activity in vivo. Such mutant GLUC1.1 proteins are GLUC1.1 proteins whereby conserved amino acid residues which have a catalytic function or which are involved in substrate binding or specificity (for example, those described above) are substituted. Thus in one embodiment, a mutant GLUC1.1 protein comprising a substitution of a conserved amino acid residue which has a catalytic function, such as the conserved first or second Glu, Trp, and/or Tyr residues, is provided. In another embodiment, a mutant GLUC1.1 protein comprising a substitution of a conserved amino acid residue involved in glycosylation, such as the conserved Asn residue, is provided.

In another aspect of the invention, methods are provided for generating mutant gluc1.1 alleles (for example induced by mutagenesis) and/or identifying mutant gluc1.1 alleles using a range of methods, which are conventional in the art, for example using PCR based methods to amplify part or all of the gluc1.1 genomic or cDNA.

The term "mutagenesis", as used herein, refers to the process in which plant cells (e.g., a plurality of *Gossypium* seeds or other parts, such as pollen) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more GLUC1.1 alleles may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source.

Following mutagenesis, *Gossypium* plants are grown from the treated seeds, or regenerated from the treated cells using known techniques. For instance, the resulting *Gossypium* seeds may be planted in accordance with conventional growing procedures and following self-pollination seed is formed on the plants. Additional seed which is formed as a result of such self-pollination in the present or a subsequent generation may be harvested and screened for the presence of mutant GLUC1.1 alleles, using techniques which are conventional in the art, for example polymerase chain reaction (PCR) based techniques (amplification of the gluc1.1 alleles) or hybridization based techniques, e.g. Southern blot analysis, and/or direct sequencing of gluc1.1 alleles. To screen for the presence of point mutations (so called Single Nucleotide Polymorphisms or SNPs) in mutant GLUC1.1 alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type (functional or non-functional) GLUC1.1 allele results in the presence of one or more deleted, inserted, or substituted nucleotides (hereinafter called "mutation region") in the resulting mutant GLUC1.1 allele. The mutant GLUC1.1 allele can thus be characterized by the location and the configuration of the one or more deleted, inserted, or substituted nucleotides in the wild type GLUC1.1 allele. The site in the wild type GLUC1.1 allele where the one or more nucleotides have been inserted, deleted, or substituted, respectively, is also referred to as the "mutation region". A "5' or 3' flanking region or sequence" as used herein refers to a DNA region or sequence in the mutant (or the corresponding wild type) GLUC1.1 allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) GLUC1.1 allele which is located either immediately upstream of and contiguous with (5' flanking region or sequence") or immediately downstream of and contiguous with (3' flanking region or sequence") the mutation region in the mutant GLUC1.1 allele (or in the corresponding wild type GLUC1.1 allele).

The tools developed to identify a specific mutant GLUC1.1 allele or the plant or plant material comprising a specific mutant GLUC1.1 allele, or products which comprise plant material comprising a specific mutant GLUC1.1 allele are based on the specific genomic characteristics of the specific mutant GLUC1.1 allele as compared to the genomic characteristics of the corresponding wild type GLUC1.1 allele, such as, a specific restriction map of the genomic region comprising the mutation region, molecular markers or the sequence of the flanking and/or mutation regions.

Once a specific mutant GLUC1.1 allele has been sequenced, primers and probes can be developed which specifically recognize a sequence within the 5' flanking, 3' flanking and/or mutation regions of the mutant GLUC1.1 allele in the nucleic acid (DNA or RNA) of a sample by way of a molecular biological technique. For instance a PCR method can be developed to identify the mutant GLUC1.1 allele in biological samples (such as samples of plants, plant material or products comprising plant material). Such a PCR is based on at least two specific "primers": one recognizing a sequence within the 5' or 3' flanking region of the mutant GLUC1.1 allele and the other recognizing a sequence within the 3' or 5' flanking region of the mutant GLUC1.1 allele, respectively; or one recognizing a sequence within the 5' or 3' flanking region of the mutant GLUC1.1 allele and the other recognizing a sequence within the mutation region of the mutant GLUC1.1 allele; or one recognizing a sequence within the 5' or 3' flanking region of the mutant GLUC1.1 allele and the other recognizing a sequence spanning the joining region between the 3' or 5' flanking region and the mutation region of the specific mutant GLUC1.1 allele (as described further below), respectively.

The primers preferably have a sequence of between 15 and 35 nucleotides which under optimized PCR conditions "specifically recognize" a sequence within the 5' or 3' flanking region, a sequence within the mutation region, or a sequence spanning the joining region between the 3' or 5' flanking and mutation regions of the specific mutant GLUC1.1 allele, so that a specific fragment ("mutant GLUC1.1 specific fragment" or discriminating amplicon) is amplified from a nucleic acid sample comprising the specific mutant GLUC1.1 allele. This means that only the targeted mutant GLUC1.1 allele, and no other sequence in the plant genome, is amplified under optimized PCR conditions.

PCR primers suitable for the invention may be the following:

oligonucleotides ranging in length from 17 nt to about 200 nt, comprising a nucleotide sequence of at least 17 consecutive nucleotides, preferably 20 consecutive nucleotides selected from the 5' flanking sequence of a specific mutant GLUC1.1 allele (i.e., for example, the sequence 5' flanking the one or more nucleotides deleted, inserted or substituted in the mutant GLUC1.1 alleles of the invention, such as the sequence 5' flanking the deletion, non-sense or splice site mutations described above or the sequence 5' flanking the potential STOP codon or splice site mutations indicated above) at their 3' end (primers recognizing 5' flanking sequences); or oligonucleotides ranging in length from 17 nt to about 200 nt, comprising a nucleotide sequence of at least 17 consecutive nucleotides, preferably 20 consecutive nucleotides, selected from the 3' flanking sequence of a specific mutant GLUC1.1 allele (i.e., for example, the complement of the sequence 3' flanking the one or more nucleotides deleted, inserted or substituted in the mutant GLUC1.1 alleles of the invention, such as the complement of the sequence 3' flanking the deletion, non-sense or splice site mutations described above or the complement of the sequence 3' flanking the potential STOP codon or splice site mutations indicated above) at their 3' end (primers recognizing 3' flanking sequences); or oligonucleotides ranging in length from 17 nt to about 200 nt, comprising a nucleotide sequence of at least 17 consecutive nucleotides, preferably 20 nucleotides selected from the sequence of the mutation region of a specific mutant GLUC1.1 allele (i.e., for example, the sequence of nucleotides inserted or substituted in the GLUC1.1 genes of the invention, or the complement thereof) at their 3' end (primers recognizing mutation sequences).

The primers may of course be longer than the mentioned 17 consecutive nucleotides, and may e.g. be 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence at their 3' end spanning the joining region between flanking and mutation sequences (i.e., for example, the joining region between a sequence 5' flanking one or more nucleotides deleted, inserted or substituted in the mutant GLUC1.1 alleles of the invention and the sequence of the one or more nucleotides inserted or substituted or the sequence 3' flanking the one or more nucleotides deleted, such as the joining region between a sequence 5' flanking deletion, non-sense or splice site mutations in the GLUC1.1 genes of the invention described above and the sequence of the non-sense or splice site mutations or the sequence 3' flanking the deletion mutation, or the joining region between a sequence 5' flanking a potential STOP codon or splice site mutation as indicated above and the sequence of the potential STOP codon or splice site mutation), provided the mentioned 3'-located nucleotides are not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID NO: X" is the nucleotide sequence which can be derived from the represented nucleotide sequence by replacing the nucleotides through their complementary nucleotide according to Chargaff's rules (A⇔T; G⇔C) and reading the sequence in the 5' to 3' direction, i.e. in opposite direction of the represented nucleotide sequence.

Examples of primers suitable to identify specific mutant GLUC1.1 alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, a sequence within the mutation region, or a sequence spanning the joining region between the 3' or 5' flanking and mutation regions of the specific mutant GLUC1.1 allele, provided the mismatches still allow specific identification of the specific mutant GLUC1.1 allele with these primers under optimized PCR conditions. The range of allowable mismatches however, can easily be determined experimentally and are known to a person skilled in the art.

Detection and/or identification of a "mutant GLUC1.1 specific fragment" can occur in various ways, e.g., via size estimation after gel or capillary electrophoresis or via fluorescence-based detection methods. The mutant GLUC1.1 specific fragments may also be directly sequenced. Other sequence specific methods for detection of amplified DNA fragments are also known in the art.

Standard PCR protocols are described in the art, such as in 'PCR Applications Manual" (Roche Molecular Biochemicals, 2nd Edition, 1999) and other references. The optimal conditions for the PCR, including the sequence of the specific primers, is specified in a "PCR identification protocol" for each specific mutant GLUC1.1 allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of PCR identification protocols to identify specific mutant GLUC1.1 alleles are described in the Examples.

Alternatively, specific primers can be used to amplify a mutant GLUC1.1 specific fragment that can be used as a "specific probe" for identifying a specific mutant GLUC1.1 allele in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant GLUC1.1 allele. Such identification methods based on hybridization with a specific probe (either on a solid phase carrier or in solution) have been described in the art. The specific probe is preferably a sequence which, under optimized conditions, hybridizes specifically to a region within the 5' or 3' flanking region and/or within the mutation region of the specific mutant GLUC1.1 allele (hereinafter referred to as "GLUC1.1 mutation specific region"). Preferably, the specific probe comprises a sequence of between 20 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the specific mutant GLUC1.1 allele.

Specific probes suitable for the invention may be the following:
  oligonucleotides ranging in length from 20 nt to about 1000 nt, comprising a nucleotide sequence of at least 20 consecutive nucleotides selected from the 5' flanking sequence of a specific mutant GLUC1.1 allele (i.e., for example, the sequence 5' flanking the one or more nucleotides deleted, inserted or substituted in the mutant GLUC1.1 alleles of the invention, such as the sequence 5' flanking the deletion, non-sense or splice site mutations described above or the sequence 5' flanking the potential STOP codon or splice site mutations indicated above), or a sequence having at least 80% sequence identity therewith (probes recognizing 5' flanking sequences); or oligonucleotides ranging in length from 20 nt to about 1000 nt, comprising a nucleotide sequence of at least 20 consecutive nucleotides selected from the 3' flanking sequence of a specific mutant GLUC1.1 allele (i.e., for example, the sequence 3' flanking the one or more nucleotides deleted, inserted or substituted in the mutant GLUC1.1 alleles of the invention, such as the sequence 3' flanking the deletion, non-sense or splice site mutations described above or the sequence 3' flanking the potential STOP codon or splice site mutations indicated above), or a sequence having at least 80% sequence identity therewith (probes recognizing 3' flanking sequences); or oligonucleotides ranging in length from 20 nt to about 1000 nt, comprising a nucleotide sequence of at least 20 consecutive nucleotides selected from the mutation sequence of a specific mutant GLUC1.1 allele (i.e., for example, the sequence of nucleotides inserted or substituted in the GLUC1.1 genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be not longer than 50, more preferably not longer than 25 or even not longer than 20 or 15 nucleotides.

Moreover, suitable probes may comprise or consist of a nucleotide sequence spanning the joining region between flanking and mutation sequences (i.e., for example, the joining region between a sequence 5' flanking one or more nucleotides deleted, inserted or substituted in the mutant GLUC1.1 alleles of the invention and the sequence of the one or more nucleotides inserted or substituted or the sequence 3' flanking the one or more nucleotides deleted, such as the joining region between a sequence 5' flanking deletion, non-sense or splice site mutations in the GLUC1.1 genes of the invention described above and the sequence of the non-sense or splice site mutations or the sequence 3' flanking the deletion mutation, or the joining region between a sequence 5' flanking a potential STOP codon or splice site mutation indicated above and the sequence of the potential STOP codon or splice site mutation), provided the mentioned nucleotide sequence is not derived exclusively from either the mutation region or flanking regions.

Examples of specific probes suitable to identify specific mutant GLUC1.1 alleles are described in the Examples.

Detection and/or identification of a "mutant GLUC1.1 specific region" hybridizing to a specific probe can occur in various ways, e.g., via size estimation after gel electrophoresis or via fluorescence-based detection methods. Other sequence specific methods for detection of a "mutant GLUC1.1 specific region" hybridizing to a specific probe are also known in the art.

Alternatively, plants or plant parts comprising one or more mutant gluc1.1 alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants, seeds and tissues comprising one or more mutant gluc1.1 alleles in one or more tissues and methods for generating and identifying such plants is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in GLUC1.1 alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant gluc1.1 alleles. As for the mutagenesis techniques above, preferably *Gossypium* species are screened which comprise an A and/or a D genome, so that the identified gluc1.1 allele can subsequently be introduced into other *Gossypium* species, such as *Gossypium hirsutum*, by crossing (inter- or intraspecific crosses) and selection. In ECOTILLING natural polymorphisms in breeding lines or related species are screened for by the TILLING methodology described above, in which individual or pools of plants are used for PCR amplification of the gluc1.1 target, heteroduplex formation and high-throughput analysis. This can be followed up by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested by expression in a homologous or heterologous host and testing the mutant GLUC1.1 protein for functionality in an enzyme assay. Using this approach a plurality of mutant gluc1.1 alleles (and *Gossypium* plants comprising one or more of these) can be identified. The desired mutant alleles can then be combined with the desired wild type alleles by crossing and selection methods as described further below. Finally a single plant comprising the desired number of mutant gluc1.1 and the desired number of wild type GLUC1.1 alleles is generated.

Oligonucleotides suitable as PCR primers or specific probes for detection of a specific mutant GLUC1.1 allele can also be used to develop methods to determine the zygosity status of the specific mutant GLUC1.1 allele.

To determine the zygosity status of a specific mutant GLUC1.1 allele, a PCR-based assay can be developed to determine the presence of a mutant and/or corresponding wild type GLUC1.1 specific allele:

To determine the zygosity status of a specific mutant GLUC1.1 allele, two primers specifically recognizing the wild-type GLUC1.1 allele can be designed in such a way that they are directed towards each other and have the mutation region located in between the primers. These primers may be primers specifically recognizing the 5' and 3' flanking sequences, respectively. This set of primers allows simultaneous diagnostic PCR amplification of the mutant, as well as of the corresponding wild type GLUC1.1 allele.

Alternatively, to determine the zygosity status of a specific mutant GLUC1.1 allele, two primers specifically recognizing the wild-type GLUC1.1 allele can be designed in such a way that they are directed towards each other and that one of them specifically recognizes the mutation region. These primers may be primers specifically recognizing the sequence of the 5' or 3' flanking region and the mutation region of the wild type GLUC1.1 allele, respectively. This set of primers, together with a third primer which specifically recognizes the sequence of the mutation region in the mutant GLUC1.1 allele, allow simultaneous diagnostic PCR amplification of the mutant GLUC1.1 gene, as well as of the wild type GLUC1.1 gene.

Alternatively, to determine the zygosity status of a specific mutant GLUC1.1 allele, two primers specifically recognizing the wild-type GLUC1.1 allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type GLUC1.1 allele, respectively. This set of primers, together with a third primer which specifically recognizes the joining region between the mutation region and the 3' or 5' flanking region of the mutant GLUC1.1 allele, respectively, allow simultaneous diagnostic PCR amplification of the mutant GLUC1.1 gene, as well as of the wild type GLUC1.1 gene.

Alternatively, the zygosity status of a specific mutant GLUC1.1 allele can be determined by using alternative primer sets which specifically recognize mutant and wild type GLUC1.1 alleles.

If the plant is homozygous for the mutant GLUC1.1 gene or the corresponding wild type GLUC1.1 gene, the diagnostic PCR assays described above will give rise to a single PCR product typical, preferably typical in length, for either the mutant or wild type GLUC1.1 allele. If the plant is hemizygous for the mutant GLUC1.1 allele, two specific PCR products will appear, reflecting both the amplification of the mutant and the wild type GLUC1.1 allele.

Identification of the wild type and mutant GLUC1.1 specific PCR products can occur e.g. by size estimation after gel or capillary electrophoresis (e.g. for mutant GLUC1.1 alleles comprising a number of inserted or deleted nucleotides which results in a size difference between the fragments amplified from the wild type and the mutant GLUC1.1 allele, such that said fragments can be visibly separated on a gel); by evaluating the presence or absence of the two different fragments after gel or capillary electrophoresis, whereby the diagnostic PCR amplification of the mutant GLUC1.1 allele can, optionally, be performed separately from the diagnostic PCR amplification of the wild type GLUC1.1 allele; by direct sequencing of the amplified fragments; or by fluorescence-based detection methods.

Examples of primers suitable to determine the zygosity of specific mutant GLUC1.1 alleles are described in the Examples.

Alternatively, to determine the zygosity status of a specific mutant GLUC1.1 allele, a hybridization-based assay can be developed to determine the presence of a mutant and/or corresponding wild type GLUC1.1 specific allele:

To determine the zygosity status of a specific mutant GLUC1.1 allele, two specific probes recognizing the wild-type GLUC1.1 allele can be designed in such a way that each probe specifically recognizes a sequence within the GLUC1.1 wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type GLUC1.1 allele.

Alternatively, to determine the zygosity status of a specific mutant GLUC1.1 allele, two specific probes recognizing the wild-type GLUC1.1 allele can be designed in such a way that one of them specifically recognizes a sequence within the GLUC1.1 wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type GLUC1.1 allele, respectively. The use of one or, preferably, both of these probes, optionally, together with a third probe which specifically recognizes the sequence of the mutation region in the mutant GLUC1.1 allele, allow diagnostic hybridization of the mutant and of the wild type GLUC1.1 gene.

Alternatively, to determine the zygosity status of a specific mutant GLUC1.1 allele, a specific probe recognizing the wild-type GLUC1.1 allele can be designed in such a way that the probe specifically recognizes the joining region between the 5' or 3' flanking region, preferably the 5' flanking region, and the mutation region of the wild type GLUC1.1 allele. This probe, optionally, together with a second probe which specifically recognizes the joining region between the 5' or 3' flanking region, preferably the 5' flanking region, and the mutation region of the mutant GLUC1.1 allele, allows diagnostic hybridization of the mutant and of the wild type GLUC1.1 gene.

Alternatively, the zygosity status of a specific mutant GLUC1.1 allele can be determined by using alternative sets of probes which specifically recognize mutant and wild type GLUC1.1 alleles.

If the plant is homozygous for the mutant GLUC1.1 gene or the corresponding wild type GLUC1.1 gene, the diagnostic hybridization assays described above will give rise to a single specific hybridization product, such as one or more hybridizing DNA (restriction) fragments, typical, preferably typical in length, for either the mutant or wild type GLUC1.1 allele. If the plant is hemizygous for the mutant GLUC1.1 allele, two specific hybridization products will appear, reflecting both the hybridization of the mutant and the wild type GLUC1.1 allele.

Identification of the wild type and mutant GLUC1.1 specific hybridization products can occur e.g. by size estimation after gel or capillary electrophoresis (e.g. for mutant GLUC1.1 alleles comprising a number of inserted or deleted nucleotides which results in a size difference between the hybridizing DNA (restriction) fragments from the wild type and the mutant GLUC1.1 allele, such that said fragments can be visibly separated on a gel); by evaluating the presence or absence of the two different specific hybridization products after gel or capillary electrophoresis, whereby the diagnostic hybridization of the mutant GLUC1.1 allele can, optionally, be performed separately from the diagnostic hybridization of the wild type GLUC1.1 allele; by direct sequencing of the hybridizing DNA (restriction) fragments; or by fluorescence-based detection methods.

Examples of probes suitable to determine the zygosity of specific mutant GLUC1.1 alleles are described in the Examples.

Furthermore, detection methods specific for a specific mutant GLUC1.1 allele which differ from PCR- or hybridization-based amplification methods can also be developed using the specific mutant GLUC1.1 allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex.

In another aspect of the invention, kits are provided. A "kit" as used herein refers to a set of reagents for the purpose of performing the methods of the invention, more particularly, the identification of a specific mutant GLUC1.1 allele in biological samples or the determination of the zygosity status of plant material comprising a specific mutant GLUC1.1 allele. More particularly, a preferred embodiment of the kit of the invention comprises at least two specific primers, as described above, for identification of a specific mutant GLUC1.1 allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant GLUC1.1 allele therein, as described above, for identification of a specific mutant GLUC1.1 allele, or at least two or three specific probes for the determination of the zygosity status. Optionally, the kit can further comprise any other reagent (such as but not limited to hybridizing buffer, label) for identification of a specific mutant GLUC1.1 allele in biological samples, using the specific probe.

The kit of the invention can be used, and its components can be specifically adjusted, for purposes of quality control (e.g., purity of seed lots), detection of the presence or absence of a specific mutant GLUC1.1 allele in plant material or material comprising or derived from plant material, such as but not limited to cotton seeds, raw cotton, cotton bales, yarn, fabric, apparel, etc.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant GLUC1.1 allele under the conditions set forth in the method (such as the conditions of the PCR identification protocol), whereby the specificity is determined by the presence of positive and negative controls.

The term "hybridizing" as used herein when referring to specific probes, refers to the fact that the probe binds to a specific region in the nucleic acid sequence of a specific mutant GLUC1.1 allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass *Gossypium* plant tissues, at any stage of maturity, as well as any cells, tissues, or organs taken from or derived from any such plant, including without limitation, any fibers, seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products, such as raw cotton, cotton bales, yarn, fabric, apparel, etc., which are produced using plant material or can be contaminated by plant material. It is understood that, in the context of the present invention, such biological samples are tested for the presence of nucleic acids specific for a specific mutant GLUC1.1 allele, implying the presence of nucleic acids in the samples. Thus the methods referred to herein for identifying a specific mutant GLUC1.1 allele in biological samples, relate to the identification in biological samples of nucleic acids which comprise the specific mutant GLUC1.1 allele.

The present invention also relates to the transfer of one or more specific mutant GLUC1.1 allele(s) in one *Gossypium* plant to another *Gossypium* plant, to the combination of specific GLUC1.1 alleles in one plant, to the plants comprising one or more specific mutant GLUC1.1 allele(s), the progeny obtained from these plants and to the plant cells, or plant material derived from these plants.

Thus, in one embodiment of the invention a method for transferring a non-functionally expressed GLUC1.1 allele from one *Gossypium* plant to another *Gossypium* plant is provided comprising the steps of:
(a) crossing a *Gossypium* plant comprising a non-functionally expressed GLUC1.1 allele, as described above, with a second *Gossypium* plant,
(b) collecting F1 hybrid seeds from the cross,
(c) optionally, backcrossing the F1 plants, derived from the F1 seeds, for one or more generations (x), collecting BCx seeds from the crosses, and identifying in every generation BCx plants, derived from the BCx seeds, comprising the non-functionally expressed GLUC1.1 allele as described above,
(d) selfing the F1 or BCx plants, derived from the F1 or BCx seeds,
(e) collecting F1 S1 or BCx S1 seeds from the selfing,
(f) identifying F1 S1 or BCx S1 plants, derived from the F1 S1 or BCx S1 seeds, comprising the non-functionally expressed GLUC1.1 allele as described above.

In another embodiment of the invention a method for combining at least two non-functionally expressed GLUC1.1 alleles in one *Gossypium* plant is provided comprising the steps of:
(a) transferring a non-functionally expressed GLUC1.1 allele(s) from one *Gossypium* plant to another *Gossypium* plant as described above,
(b) repeating step (a) until the desired number and/or types of non-functionally expressed GLUC1.1 alleles are combined in the second plant.

In yet another embodiment of the invention, a method is provided for altering the callose content of a fiber in a fiber producing plant, such as *Gossypium* plants, comprising the steps of:
(a) abolishing the functional expression of at least one allele of at least one fiber specific GLUC gene that is functionally expressed during the fiber strength building phase of fiber development,
(b) identifying a plant, which produces fibers, the callose content of which is increased as compared to the callose content of the fibers of a corresponding plant in which the functional expression of the GLUC gene is not abolished.

In still another embodiment of the invention, a method is provided for altering the properties of a fiber, particularly increasing the strength of a fiber, in a fiber producing plant, such as a *Gossypium* plant, comprising the steps of:
(c) abolishing the functional expression of at least one allele of at least one fiber specific GLUC gene that is functionally expressed during the fiber strength building phase of fiber development,
(d) identifying a plant, which produces fibers, the strength of which is increased as compared to the strength of fibers of a corresponding plant in which the functional expression of the GLUC gene is not abolished.

In another aspect of the invention, plant fibers with increased fiber strength are are provided derived from fiber-producing plants according to the invention, especially of *Gossypium hirsutum* plants as provided herein, but also from other *Gossypium* species. For example, *Gossypium* species wherein the expression of at least one fiber specific GLUC gene that is functionally expressed during the fiber strength building phase of fiber development, such as a GLUC1.1A and/or GLUC1.1D gene, can be abolished, for example *Gossypium tomentosum*, *Gossypium mustilinum*, *Gossypium herbaceum*, or *Gossypium raimondii*.

Also included in the invention is the use of the fibers of this invention, for example, in the production of raw cotton, cotton bales, yarn, fabric, apparel, etc.

Other applications, such as mixing fibers with a specific callose content and/or a specific modified strength according to the invention with other fibers with a lower callose content and/or a lower fiber to increase the average callose content and/or fiber strength in, for example, cotton bales, yarn, fabric, apparel, etc; thus making it more suitable for certain applications, such as but not limited to, the production of biodiesel, stronger textile, etc., are also included in the invention.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc. A plant comprising a certain trait may thus comprise additional traits etc.

The following non-limiting Examples describe the identification of a fiber strength locus on chromosome A05 in cotton and the characterization of a GLUC1.1 gene located in the 1-LOD support interval of the Strength QTL. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:

SEQ ID NO: 1: amplified genomic DNA fragment of endo-1,3-beta-glucanase gene from *Gossypium hirsutum* cv. Fiber Max966, A-subgenome specific
SEQ ID NO: 2: endo-1,3-beta-glucanase protein encoded by SEQ ID NO: 1
SEQ ID NO: 3: amplified cDNA fragment of endo-1,3-beta-glucanase gene from *Gossypium hirsutum* cv. Fiber Max966, A-subgenome specific
SEQ ID NO: 4: endo-1,3-beta-glucanase protein encoded by SEQ ID NO: 3
SEQ ID NO: 5: amplified genomic DNA fragment of endo-1,3-beta-glucanase gene from *Gossypium barbadense* cv. PimaS7, A-subgenome specific
SEQ ID NO: 6: endo-1,3-beta-glucanase protein encoded by SEQ ID NO: 5
SEQ ID NO: 7: amplified genomic DNA fragment of endo-1,3-beta-glucanase gene from *Gossypium hirsutum* cv. Fiber Max966, D-subgenome specific
SEQ ID NO: 8: endo-1,3-beta-glucanase protein encoded by SEQ ID NO: 7
SEQ ID NO: 9: amplified cDNA fragment of endo-1,3-beta-glucanase gene from *Gossypium hirsutum* cv. Fiber Max966, D-subgenome specific
SEQ ID NO: 10: endo-1,3-beta-glucanase protein encoded by SEQ ID NO: 9
SEQ ID NO: 11: amplified genomic DNA fragment of endo-1,3-beta-glucanase gene from *Gossypium barbadense* cv. PimaS7, D-subgenome specific
SEQ ID NO: 12: endo-1,3-beta-glucanase protein encoded by SEQ ID NO: 11
SEQ ID NO: 13: amplified cDNA fragment of endo-1,3-beta-glucanase gene from *Gossypium barbadense* cv. PimaS7, D-subgenome specific
SEQ ID NO: 14: endo-1,3-beta-glucanase protein encoded by SEQ ID NO: 13
SEQ ID NO: 15: amplified genomic DNA fragment of endo-1,3-beta-glucanase gene from *Gossypium tomentosum*, A-subgenome specific
SEQ ID NO: 16: endo-1,3-beta-glucanase protein encoded by SEQ ID NO: 15
SEQ ID NO: 17: amplified genomic DNA fragment of endo-1,3-beta-glucanase gene from *Gossypium darwinii*, A-subgenome specific
SEQ ID NO: 18: endo-1,3-beta-glucanase protein encoded by SEQ ID NO: 17
SEQ ID NO: 19: amplified genomic DNA fragment of endo-1,3-beta-glucanase gene from *Gossypium mustelinum*, A-subgenome specific
SEQ ID NO: 20: endo-1,3-beta-glucanase protein encoded by SEQ ID NO: 19
SEQ ID NO: 21: amplified genomic DNA fragment of endo-1,3-beta-glucanase gene from *Gossypium arboreum*, A-subgenome specific
SEQ ID NO: 22: endo-1,3-beta-glucanase protein encoded by SEQ ID NO: 21
SEQ ID NO: 23: amplified genomic DNA fragment of endo-1,3-beta-glucanase gene from *Gossypium herbaceum*, A-subgenome specific
SEQ ID NO: 24: endo-1,3-beta-glucanase protein encoded by SEQ ID NO: 23
SEQ ID NO: 25: amplified genomic DNA fragment of endo-1,3-beta-glucanase gene from *Gossypium tomentosum*, D-subgenome specific
SEQ ID NO: 26: endo-1,3-beta-glucanase protein encoded by SEQ ID NO: 25
SEQ ID NO: 27: amplified genomic DNA fragment of endo-1,3-beta-glucanase gene from *Gossypium darwinii*, D-subgenome specific
SEQ ID NO: 28: endo-1,3-beta-glucanase protein encoded by SEQ ID NO: 27
SEQ ID NO: 29: amplified genomic DNA fragment of endo-1,3-beta-glucanase gene from *Gossypium mustelinum*, D-subgenome specific
SEQ ID NO: 30: endo-1,3-beta-glucanase protein encoded by SEQ ID NO: 29
SEQ ID NO: 31: amplified genomic DNA fragment of endo-1,3-beta-glucanase gene from *Gossypium raimondii*, D-subgenome specific
SEQ ID NO: 32: endo-1,3-beta-glucanase protein encoded by SEQ ID NO: 31
SEQ ID NO: 33: forward primer SE077 for amplification of endo-1,3-beta-glucanase genomic fragment
SEQ ID NO: 34: reverse primer SE078 for amplification of endo-1,3-beta-glucanase genomic fragment
SEQ ID NO: 35: forward primer SE002 for amplification of endo-1,3-beta-glucanase genomic fragment
SEQ ID NO: 36: reverse primer SE003 for amplification of endo-1,3-beta-glucanase genomic fragment
SEQ ID NO: 37: forward primer p1.3GlucaAf for amplification of endo-1,3-beta-glucanase genomic fragment, in particular for discriminating different variants of polymorphic site GLUC1.1A-SNP2
SEQ ID NO: 38: reverse primer p1.3GlucaAr for amplification of endo-1,3-beta-glucanase genomic fragment, in particular for discriminating different variants of polymorphic site GLUC1.1A-SNP2
SEQ ID NO: 39: probe TM249-GCM1 for detecting the *G. barbadense* variant of polymorphic site GLUC1.1A-SNP3
SEQ ID NO: 40: probe TM249-GCV1 for detecting the *G. hirsutum* variant of polymorphic site GLUC1.1A-SNP3
SEQ ID NO: 41: forward primer TM249-GCF for amplification of endo-1,3-beta-glucanase genomic fragment, in particular for discriminating different variants of polymorphic site GLUC1.1A-SNP3

SEQ ID NO: 42: reverse primer TM249-GCR for amplification of endo-1,3-beta-glucanase genomic fragment, in particular for discriminating different variants of polymorphic site GLUC1.1A-SNP3

SEQ ID NO: 43: AFLP primer P5 for amplification of genomic DNA fragment corresponding to marker P5M50-M126.7, in particular for discriminating different variants of marker P5M50-M126.7

SEQ ID NO: 44: AFLP primer M50 for amplification of genomic DNA fragment corresponding to marker P5M50-M126.7, in particular for discriminating different variants of marker P5M50-M126.7

SEQ ID NO: 45: forward SSR primer for amplification of genomic DNA fragment corresponding to marker NAU861, in particular for discriminating different variants of marker NAU861

SEQ ID NO: 46: reverse SSR primer for amplification of genomic DNA fragment corresponding to marker NAU861, in particular for discriminating different variants of marker NAU861

SEQ ID NO: 47: forward SSR primer for amplification of genomic DNA fragment corresponding to marker CIR401, in particular for discriminating different variants of marker CIR401

SEQ ID NO: 48: reverse SSR primer for amplification of genomic DNA fragment corresponding to marker CIR401, in particular for discriminating different variants of marker CIR401

SEQ ID NO: 49: forward SSR primer for amplification of genomic DNA fragment corresponding to marker BNL3992, in particular for discriminating different variants of marker BNL3992

SEQ ID NO: 50: reverse SSR primer for amplification of genomic DNA fragment corresponding to marker BNL3992, in particular for discriminating different variants of marker BNL3992

SEQ ID NO: 51: forward SSR primer for amplification of genomic DNA fragment corresponding to marker CIR280, in particular for discriminating different variants of marker CIR280

SEQ ID NO: 52: reverse SSR primer for amplification of genomic DNA fragment corresponding to marker CIR280, in particular for discriminating different variants of marker CIR280

SEQ ID NO: 53: DNA sequence of a 165250 bps DNA fragment spanning the GLUC1.1A gene in *G. hirsutum*

SEQ ID NO: 54: amplified cDNA fragment of endo-1,3-beta-glucanase gene from *Gossypium barbadense* cv. PimaS7, A-subgenome specific SEQ ID NO: 55: endo-1,3-beta-glucanase protein encoded by SEQ ID NO: 54

SEQ ID NO: 56: amplified genomic DNA fragment of endo-1,3-beta-glucanase gene from *Gossypium darwinii*, A-subgenome specific SEQ ID NO: 57: endo-1,3-beta-glucanase protein encoded by SEQ ID NO: 56

SEQ ID NO: 58: amplified genomic DNA fragment of endo-1,3-beta-glucanase gene from *Gossypium darwinii*, D-subgenome specific SEQ ID NO: 59: endo-1,3-beta-glucanase protein encoded by SEQ ID NO: 58

SEQ ID NO: 60: probe for detecting the *G. barbadense* variant of polymorphic site GLUC1.1A-SNP5

SEQ ID NO: 61: probe for detecting the *G. hirsutum* variant of polymorphic site GLUC1.1A-SNP5

SEQ ID NO: 62: forward primer for amplification of endo-1,3-beta-glucanase genomic fragment, in particular for discriminating different variants of polymorphic site GLUC1.1A-SNP5

SEQ ID NO: 63: reverse primer for amplification of endo-1,3-beta-glucanase genomic fragment, in particular for discriminating different variants of polymorphic site GLUC1.1A-SNP5

SEQ ID NO: 64: forward primer G1.1-SGA-F for amplification of endo-1,3-beta-glucanase genomic fragment SEQ ID NO: 65: forward primer G1.1-f1-F1 for amplification of endo-1,3-beta-glucanase genomic fragment

EXAMPLES

Example 1

Identification and Characterization of a Quantitative Trait Locus (QTL) on Cotton Chromosome A05 Linked to Fiber Strength 1.1. QTL Discovery Discovery of quantitative trait loci associated with cotton fiber properties was performed according to standard procedures. Briefly, parental cotton plant lines with fiber phenotypes of interest were selected, segregating populations were generated and the impact of the presence of specific chromosomal regions on measurable cotton fiber phenotypes was determined. The parental lines were *Gossypium hirsutum* cv. FM966 (used as female parent in the initial cross; abbreviated hereinafter as "FM"; particularly known for its high fiber yield, but lower fiber quality compared to *Gossypium barbadense* varieties) and *Gossypium barbadense* cv. PimaS7 (used as male parent in the initial cross; abbreviated hereinafter as "Pima"; particularly known for its excellent fiber quality, but lower fiber yield compared to *Gossypium hirsutum* varieties). Backcross populations with both parental lines were generated and evaluated in the greenhouse as well as in the field.

1.2. Evaluation of Plants Derived from a First Backcross to the *Gossypium barbadense* Pima S7 Parental Line ("Pima BC1F1 Population")

A QTL for fiber strength on chromosome A05 was originally detected in a BC1F1 mapping population [(FM×Pima)× Pima; recurrent parent used as male parent] of 119 individuals. The population was grown under standard growing conditions in a greenhouse. A genome-wide genetic map of about 800 markers was constructed based on amplified fragment length polymorphism PCR (AFLP-PCR or AFLP) marker data and simple sequence repeat (SSR or microsatellite) marker data from the 119 individuals using JoinMap software (map version 8 and 13; Stam, 1993, Plant J 3: 739-744). Fiber strength was measured by High-Volume Instruments (HVI) (United States Department of Agriculture, Agricultural Marketing Service) on samples from 88 of the 119 individual plants. QTL mapping was performed using MapQTL software (Van Ooijen and Maliepaard, 1996, Plant Genome IV Abstracts, World Wide Web site: intl-pag.org). Final QTL data are based on the restricted multiple QTL mapping (rMQM; Jansen, 1993, Genetics 135:205-211; Jansen and Stam, 1994, Genetics 136:1447-1455) analysis.

A clear QTL associated with fiber strength (also referred to as "Strength locus" or "Stren locus") was detected on chromosome A05. The QTL had a sharp LOD (logarithm of the odds) score peak with a maximum value of LOD 4.92 at a position of 98.61 cM from the tip of chromosome A05, with a 1-LOD support interval of 14 cM (from 91.515 cM to 105.61 cM). The 1-LOD QTL support interval was flanked by one AFLP marker, P5M50-M126.7, at 85.515 cM, and one microsatellite marker, CIR401c, at 109.13 cM. Within the QTL support interval one microsatellite marker NAU861 (94.61 cM) and a GLUC1.1 gene (94.602 cM) were located at close distance (ca 4 cM) to the position of maximum LOD value (Table 6). Primer pairs used to distinguish between the *G. hirsutum* and *G. barbadense* alleles of the markers are indicated in Table 2 above.

TABLE 6

Estimated position (according to JoinMap version 8 and 13) on chromosome A05 of markers linked to the fiber strength locus in the FM and Pima BC1F1 population

| Marker locus on chromosome A05 | Position (in cM as estimated with JoinMap version 8 or 13) on chromosome A05 of: | | | | 1-LOD support interval of Strength locus |
|---|---|---|---|---|---|
| | FM BC1F1 map | | Pima BC1F1 map | | |
| | 8 | 13 | 8 | 13 | |
| P5M50-M126.7 | 104.582 | 107.9 | 85.515 | 105.5 | |
| | | | 91.515 | | Lower limit |
| GLUC1.1A | 107.599 | 111.1 | 94.602 | 114.6 | |
| NAU861 | 106.884 | 110.5 | 94.610 | 114.6 | |
| | | | 98.610 | | LOD Peak |
| | | | 105.610 | | upper limit |
| CIR401c | — | — | 109.130 | 129.1 | |
| CIR401b | 112.813 | 115.4 | — | — | |
| BNL3992 | 117.199 | 119.5 | nd | 132.1 | |
| CIR280 | nd | 124.5 | — | — | |

As indicated above, the GLUC1.1A gene was mapped within the support interval of the Strength locus (LOD of 4.431) using SNP marker GLUC1.1A-SNP2 as indicated in Table 13 and primers p1.3GlucaAf (SEQ ID NO: 37) and p1.3GlucaAr (SEQ ID NO: 38) as described in Example 6 below. Plants homozygous for the GLUC1.1A allele of *Gossypium barbadense* Pima S7 (Pima GLUC1.1A allele or Gbgluc1.1A) had 9.7% higher fiber strength compared to plants heterozygous for Gbgluc1.1A (Ho/He ratio of 109.7%). The QTL explained 17.8% of the variation for fiber strength in the population.

1.3. Evaluation of Plants Derived from a First Backcross to the *Gossypium hirsutum* FM966 Parental Line ("FM BC1F1 Population")

QTL mapping was also performed in a complementary BC1F1 population [(FM×Pima)×FM; recurrent parent used as male parent] of 130 individuals. Fiber strength was measured on samples from 94 of the 130 individual plants. The QTL for fiber strength in the region flanked by markers P5M50-M126.7 and CIR401 was not detected in this FM BC1F1 population (max LOD=0.42, i.e. below the critical threshold value of LOD=3). However, technically, plants heterozygous for the GLUC1.1A allele of *Gossypium barbadense* Pima S7 of this population did show about 1 to about 2% higher fiber strength compared to plants homozygous for the GLUC1.1A allele of *Gossypium hirsutum* FM966 (FM GLUC1.1A allele or GhGLUC1.1A). Together with the data from the Pima BC1F1 population this suggested that the GLUC1.1A allele of *Gossypium barbadense* Pima S7 provides superior fiber strength.

1.4. Evaluation of Plants Derived from a Fourth Backcross to the *Gossypium hirsutum* FM966 Parental Line ("FM BC4F1 Population")

With the purpose of improving fiber quality in *Gossypium hirsutum*, in particular in *Gossypium hirsutum* cv. FM966, genome fragments of the *Gossypium barbadense* parental line were backcrossed into the FM BC1F1 population by single seed descent and without selection during 4 generations (FM BC4F1 population). The Pima region of chromosome A05 carrying the candidate Strength locus was expected to be present in a number of these introgression lines.

A total of 219 FM BC4F1 plants originating from 75 FM BC3F1 plants (average 3 sister plants per line) were grown under standard growing conditions in a greenhouse. All plants were genotyped for 450 SSR markers and the strength of fibers from all plants was measured by HVI (see above). In the region of the Strength locus, 14 and 23 FM BC4F1 plants were heterozygous for the NAU861 and the GLUC1.1A markers, respectively, versus 196 and 194 plants that were homozygous for the NAU861 marker and the GLUC1.1A allele of *Gossypium hirsutum* FM966.

Table 7 summarizes the impact on fiber strength of the presence of different Pima marker alleles in heterozygous state versus the equivalent FM marker alleles in homozygous state (He/Ho ratio) in FM BC1F1 and FM BC4F1 populations. Markers indicated as CIRx, NAUx, JESPRx and BNLx are publicly available markers (see Cotton Microsatellite Database on the World Wide Web at cottonmarker.org). Markers indicated as 'Primer combination X and Y-amplified fragment size' are AFLP markers (Vos et al., 1995, NAR 23:4407-4414).

A similar effect on fiber strength was observed in both the FM BC1F1 and FM BC4F1 populations for the presence of the Pima GLUC1.1A allele (i.e. plants heterozygous for the Pima GLUC1.1A allele showed about 1 to about 2% higher fiber strength compared to plants homozygous for the FM GLUC1.1A allele).

TABLE 7

Estimated position (according to JoinMap version 8 and 13) on chromosome A05 and impact on fiber strength of different allele combinations (He versus Ho FM) for markers linked to the fiber strength locus in FM BC1F1 and FM BC4F1 populations

| Position (cM) | | Marker locus on chromosome A05 | FM BC1F1 | | FM BC4F1 | |
|---|---|---|---|---|---|---|
| vers. 13 | vers. 8 | | K* | He/Ho(%) | K* | He/Ho(%) |
| 107.9 | 104.582 | P5M50-M126.7 | 1.926 | 102.52 | | |
| 110.5 | 106.884 | NAU861 | 1.334 | 102.09 | 2.189 | 102.60 |
| 111.1 | 107.599 | GLUC1.1A | 0.802 | 101.30 | 2.037 | 101.87 |
| 115.4 | 112.813 | CIR401b | 1.85 | 103.90 | 5.786 | 103.20 |
| 119.5 | 117.199 | BNL3992 | 1.329 | 103.32 | 5.786 | 103.20 |
| 124.5 | nd | CIR280 | nd | nd | nd | nd |

1.5. Evaluation of Plants Derived from the F2 Generation of a Fourth Backcross to the *Gossypium hirsutum* FM966 Parental Line ("FM BC4F2 Population")

As a next step, QTL validation in FM BC4F2 families was performed under field conditions in summer in Mississippi. FM BC4F2 plants segregate in 3 genetic classes: plants homozygous for FM marker alleles, plants homozygous for Pima marker alleles and plants heterozygous for FM and Pima marker alleles. In most cases 75-80 plants were genotyped per line and fiber samples from about 50 single plants were analyzed. This allowed testing of the effect of the FM or Pima marker alleles (and predicted linked genes) in heterozygous and homozygous condition.

The field trial included 4 FM BC4F2 families (called lines 6, 10, 20 and 94) segregating for various portions of the region of chromosome A05 carrying the Strength locus from Pima S7. Segregation was tested using 6 markers: BNL0542, BNL3995, CIR139a, NAU861, GLUC1.1A, BNL3992.

All BC4F2 plants of line 6 were homozygous for the FM allele of the markers tested. Line 94 produced only 38 FM BC4F2 plants and only 10 of those produced sufficient fiber for single plant analysis. The two remaining lines, lines 10 and 20, produced larger numbers of plants and had good marker segregation. Line 10 contained a segment of chromosome A05 of Pima carrying the Strength locus centered around the GLUC1.1 gene. The second line, line 20, contained a segment of chromosome A05 of Pima shifted to the lower end of the Strength locus support region.

In line 10 the expectation that plants homozygous for the Pima GLUC1.1A allele produce stronger fibers was confirmed. The fiber strength of plants homozygous for the Pima GLUC1.1A allele was on average 2.5 grams per tex higher than the fiber strength of plants homozygous for the FM GLUC1.1A allele (35.5 g/tex versus 33.0 g/tex or 7.5% increase in fiber strength). A similar result was observed for the two markers NAU861 and BNL3992 which are closely linked to GLUC1.1A on either side. The differences in fiber strength between homozygous FM plants, homozygous Pima plants and heterozygous plants were not significant in Anova, but they were significant in paired t-test between homozygous FM plants and the other two classes.

In line 20 the Pima alleles of markers NAU861 and BNL3992 did not provide stronger fiber. This line segregates for a lower section of the region of Pima chromosome A05, in the tail of the QTL support interval. This line also does not contain the Pima allele of the GLUC1.1A gene.

The data in Table 8 consolidate the results for line 10 in terms of "Marker Trait Performance" for fiber strength (MTP, calculated as ratio of the difference in average trait performance for two marker classes (HoFM-HoPima) and the average standard deviation for trait performance in both marker classes). It is shown that plants homozygous for the Pima allele of markers NAU861, GLUC1.1A and BNL3992 had stronger fibers than plants homozygous for the FM allele of these markers (negative MTP). However, the difference in performance was smaller than the average standard deviation (MTP value between 0 and −1).

Thus, the field trial data provide evidence in support of the idea that there is a QTL associated with fiber strength on chromosome A05, close to or coinciding with the GLUC1.1A gene, with the superior allele coming from Gossypium barbadense PimaS7.

Due to the low number of plants in the FM BC4F2 population it was not possible to fine map the QTL position. In this respect it is noted that the Pima allele of a marker (BNL3992) that was included in the introgressed Pima fragment in line 10, but resided at a position outside the original support interval on the Pima BC1F1 map also segregated with the enhanced fiber strength derived from PimaS7. This can be explained by the fact that in the original BC1 population sufficient recombinations had occurred to place this marker outside the QTL support interval, while in the (smaller) BC4F2 populations it remained linked to the QTL causal gene more frequently.

TABLE 8

Estimated position on chromosome A05 and impact on fiber strength (indicated as MTP) of different allele combinations (HH FM versus HH Pima) for markers linked to the Strength locus in FM BC4F2 plant lines

| Position (cM - vers. 8) | Marker locus on chromosome A05 | Graphical phenotype for marker of BC4F1 plants giving rise to FM BC4F2 plant line n° | | | | MTP for fiber strength in line n° 10 |
|---|---|---|---|---|---|---|
| | | 6 | 10 | 20 | 94 | |
| 78.883 | CIR139a* | h | a | a | a | |
| 79.911 | BNL3029.A | h | a | a | a | |
| 82.969 | NAU1042.A | h | a | a | a | |
| 106.884 | NAU861* | h | h | a | h | −.70 |
| 107.599 | GLUC1.1A* | h | h | a | h | −.67 |
| 112.813 | CIR401c | h | h | a | h | −.55 |
| 117.199 | BNL3992* | h | h | a | h | |
| 136.15 | BNL0542* | a | a | h | h | |
| 146.257 | E43M49-M260.0 | a | a | h | h | |
| 149.542 | E31M48-M188.5 | a | a | h | a | |
| 159.609 | E43M53-M460.0 | a | a | h | a | |
| 161.272 | CIR294.A | a | a | h | a | |
| 163.129 | BNL3995* | a | a | h | a | |

Column 2 lists markers on chromosome A05 linked to the Strength locus. Markers indicated as CIRx, NAUx and BNLx are publicly available markers (see Cotton Microsatellite Database). Markers indicated as 'Primer combination X and Y-amplified fragment size' are AFLP markers (Vos et al., 1995, NAR 23:4407-4414). Column 1 indicates their map positions on the genetic map (in cM) of the FM BC1F1 mapping population constructed using JoinMap software map version 8. Graphical genotypes for the markers are indicated for BC4F1 plants that gave rise to BC4F2 families 6, 10, 20 and 94: a=homozygous FM966, h=heterozygous. Segregation of the 'h' regions in the graphical genotypes was investigated using marker data for markers indicated with *. Average phenotypic performance for fiber strength was compared for groups of plants homozygous for FM966 markers (genotype "HH FM") and for groups of plants homozygous for Pima markers (genotype "HH Pima"). Marker Trait Performance (MTP) is expressed as ((average phenotype HH FM—average phenotype HH Pima)/0.5×(SD HH FM+SD HH Pima)). Positive MTP means performance FM is higher than performance Pima. Negative MTP means performance Pima is higher than performance FM. MTP higher than 1 and MTP lower than −1 means delta performance exceeds average standard deviation (SD). Data for fiber strength properties are based on homozygous segregates among 60 plants.

Example 2

Identification and Characterization of a Glucanase Gene Linked to the Fiber Strength Locus on Cotton Chromosome A05

2.1 Characterization of the GLUCL1A Gene Localized in the Support Interval of the Strength Locus As described in Example 1.2, a GLUC1.1 gene was mapped within the support interval of the predicted QTL for fiber strength on chromosome A05, suggesting that the GLUC1.1A candidate gene might be the causal gene for fiber strength. As further described in Example 1, the superior allele comes from the Pima parental line rather than from the FM parental line.

Based on the GhGLUC1.1A and D nucleotide sequences described in WO2008/083969 (SEQ ID NO: 1 and 7, respectively), 2 primers (forward primer SE077 (SEQ ID NO: 33) en reverse primer SE078 (SEQ ID NO: 34)) were designed to amplify genomic DNA fragments for *G. barbadense* (reaction mix and PCR conditions as described in Example 4). Two genomic DNA sequences were derived: one for GbGLUC1.1A (SEQ ID NO: 5) and one for GbGLUC1.1D (SEQ ID NO: 11).

The 2 primers (forward primer SE077 (SEQ ID NO: 33) en reverse primer SE078 (SEQ ID NO: 34)) were also used to amplify GLUC1.1A and GLUC1.1D cDNA from cDNA libraries from *G. hirsutum* and *G. barbadense* (reaction mix and PCR conditions as described in Example 4). cDNA sequences were derived for GhGLUC1.1A (SEQ ID NO: 3), for GhGLUC1.1D (SEQ ID NO: 9), and for GbGLUC1.1D (SEQ ID NO: 13). Forward primer G1.1-SGA-F (SEQ ID NO: 64) en reverse primer SE078 (SEQ ID NO: 34) were used to amplify GLUC1.1A cDNA from a cDNA libraries from *G. barbadense*. The cDNA sequence was derived for GbGLUC1.1A (SEQ ID NO: 54).

Alignment of genomic and cDNA sequences of A and D subgenome-specific GLUC1.1 genes from *Gossypium hirsutum* and *Gossypium barbadense* indicated that the GLUC1.1A gene from *Gossypium barbadense* displayed a c to t nucleotide substitution (at position 712 of SEQ ID NO: 5) that resulted in a putative premature STOP codon (cga to tga) as compared to the GLUC1.1A and D genes from *Gossypium hirsutum* and the GLUC1.1D gene from *Gossypium barbadense* (FIG. 1), that is predicted to result in the production of a truncated GLUC1.1A protein in *Gossypium barbadense* (FIG. 2). Compared to the *Gossypium hirsutum* ortholog, the *Gossypium barbadense* GLUC1.1A amino acid sequence lacks the GH17 signature (FIG. 2).

2.2. Characterization of the GLUC1.1A Protein from Different *Gossypium* sp.

Protein modeling based on an X-ray structure of a barley 1,3-1,4-beta-glucanase belonging to the GH17 family of glycosidase hydrolases (laq0 in Protein Data Bank) (FIG. 3, left), using FUGUE™ and ORCHESTRAR™ technologies from Sybyl7.3, showed that the GLUC1.1A protein of *G. barbadense* (FIG. 3b, right) is missing the active site and substrate binding cleft (located within the area indicated by the amino acids and their position numbers, displayed in the upper left part of the protein model of laq0 and described in Müller et al., 1998, Biol Chem 273: 3438-3446), which was found to be present in the GLUC1.1A and D proteins of *G. hirsutum* and in the GLUC1.1D protein of *G. barbadense* (FIG. 3a, right). The GLUC1.1A protein of *G. barbadense* is therefore predicted to be inactive.

2.3. Characterization of the Genomic Regions Spanning the GLUCL1 Alleles from Different *Gossypium* sp.

DNA sequencing of an about 165 kb and 136 kb region spanning the GLUC1.1A (SEQ ID NO: 53) and GLUC1.1D alleles (not shown), respectively, of *Gossypium hirsutum* was undertaken using 454 DNA sequencing (454 Life Sciences): Firstly BAC clones with genomic DNA spanning each GhGLUC1.1 allele were identified by hybridization using part of the GLUC1.1 gene as a probe against a FM BAC library. The BAC clones were isolated, confirmed by PCR and grouped into alleles. Selected BAC clones were sequenced to define neighboring genes facilitated by bioinformatics annotation software programs and EST searches (see FIG. 9). The BAC sequence data also identified an additional molecular marker (CIR280) located on an adjacent gene (HAT) (see Table 6 and 7 for estimated position on chromosome A05 in the FM BC1 population).

Example 3

Analysis of the Biological Role of Glucanase in Fiber Strength

3.1. Determination of Link Between Inactive GbGLUC1.1A Enzyme and Fiber Strength To determine if there is a link between the inactive GbGLUC1.1A enzyme and fiber strength, the impact of glucanase activity on fiber strength was analyzed by exogenous addition of a 1,3-beta-glucanase enzyme to fibers from *G. barbadense* (comprising a GLUC1.1A predicted to be inactive), as well as fibers from *G. hirsutum* (comprising a GLUC1.1A predicted to be active). It was expected that the strength of the *G. barbadense* fibers would significantly decrease, if there was indeed a link between the inactive GbGLUC1.1A enzyme and fiber strength.

Individual fibers were treated with a beta-1,3-D-glucanase from *Helix pomatia* (Fluka, 49103). 10 mg of fibers were incubated in 10 mM sodium acetate buffer (pH 5) and 500 µl of glucanase (1 mg/ml) was added. They were subjected to infiltration under vacuum for 10 minutes and overnight incubation at 37° C. The strength of individual cotton fibers was measured using a Favimat R device (Textechno) in a single fiber tensile test at 8 mm gauge length and a speed of 4 mm/min. The strength measure is recorded in force (cN). The results were statistically analyzed and are presented in Table 9 and FIG. 4.

TABLE 9

Callose content (as measured by the green/blue fluorescence ratio of aniline blue stained fibers (ratio green/blue)) and strength (as measured by the breaking force (cN)) of untreated fibers (no GLUC) and fibers treated with glucanase (GLUC) from different *G. hirsutum* and *G. barbadense* varieties

| *Gossypium* species | Treatment | | Ratio green/blue | Force (cN) |
|---|---|---|---|---|
| *G. hirsutum* cv. FM966 (greenhouse) | No GLUC | Mean | 0.44 | 2.92 |
| | | SD | 0.04 | 1.92 |
| | GLUC | Mean | 0.43 | 3.11 |
| | | SD | 0.06 | 1.74 |
| *G. hirsutum* cv. FM966 (field US) | No GLUC | Mean | 0.51 | 5.50 |
| | | SD | 0.09 | 2.70 |
| | GLUC | Mean | 0.55 | 4.45 |
| | | SD | 0.10 | 2.03 |
| *G. hirsutum* cv. FM966 (field AU) | No GLUC | Mean | 0.52 | 4.33 |
| | | SD | 0.09 | 1.72 |
| | GLUC | Mean | 0.51 | 3.30 |
| | | SD | 0.14 | 1.43 |
| *G. hirsutum* cv. Coker312 (greenhouse) | No GLUC | Mean | 0.47 | 4.49 |
| | | SD | 0.02 | 2.45 |

TABLE 9-continued

Callose content (as measured by the green/blue fluorescence ratio of aniline blue stained fibers (ratio green/blue)) and strength (as measured by the breaking force (cN)) of untreated fibers (no GLUC) and fibers treated with glucanase (GLUC) from different *G. hirsutum* and *G. barbadense* varieties

| *Gossypium* species | Treatment | | Ratio green/blue | Force (cN) |
|---|---|---|---|---|
| | GLUC | Mean | 0.44 | 3.08 |
| | | SD | 0.06 | 1.63 |
| *G. barbadense* cv. PimaS7 (greenhouse) | No GLUC | Mean | 0.60 | 5.31 |
| | | SD | 0.05 | 2.26 |
| | GLUC | Mean | 0.49 | 2.76 |
| | | SD | 0.15 | 1.80 |
| *G. barbadense* cv. PimaY5 (field AU) | No GLUC | Mean | 0.61 | 5.19 |
| | | SD | 0.03 | 2.57 |
| | GLUC | Mean | 0.53 | 2.13 |
| | | SD | 0.04 | 1.20 |

A pronounced drop in strength was observed for Pima fibers treated with the glucanase and a less pronounced but still noticeable reduction in strength was observed for fibers from various *G. hirsutum* lines. In this respect, it is important to note that the extent of secondary cell wall formation and cellulose content contribute to fiber strength in *G. hirsutum*, while the stronger fibers of *G. barbadense* have a lower cellulose content than those of *G. hirsutum*. The complementation experiment thus indicated that the presence of the Gbgluc1.1A allele within the fiber strength locus contributes to the renowned strength of Pima fibers.

3.2. Determination of Link Between 1,3-Beta-D-Glucan Content and Fiber Strength 1,3-beta-D-glucans, including long chain 1,3-beta-D-glucans called callose, are the substrate for 1,3-beta-glucanase enzymes. Aniline blue is a dye specific for 1,3-beta-glucans. This dye was used to determine if fibers treated with 1,3-beta-glucanase and displaying a reduced fiber strength also displayed a reduced level of the 1,3-beta-glucan substrate in the cotton fiber walls.

A 0.05% solution of aniline blue in 0.067M $K_2HPO_4$ (pH 9) was used. The fibers were incubated for 15 minutes under vacuum. Under UV, callose deposits present an intense yellow-green fluorescence. Images are analyzed and the ratio Green/Blue is used as a measure for callose. The average value of 3 images was calculated.

Figure 5:
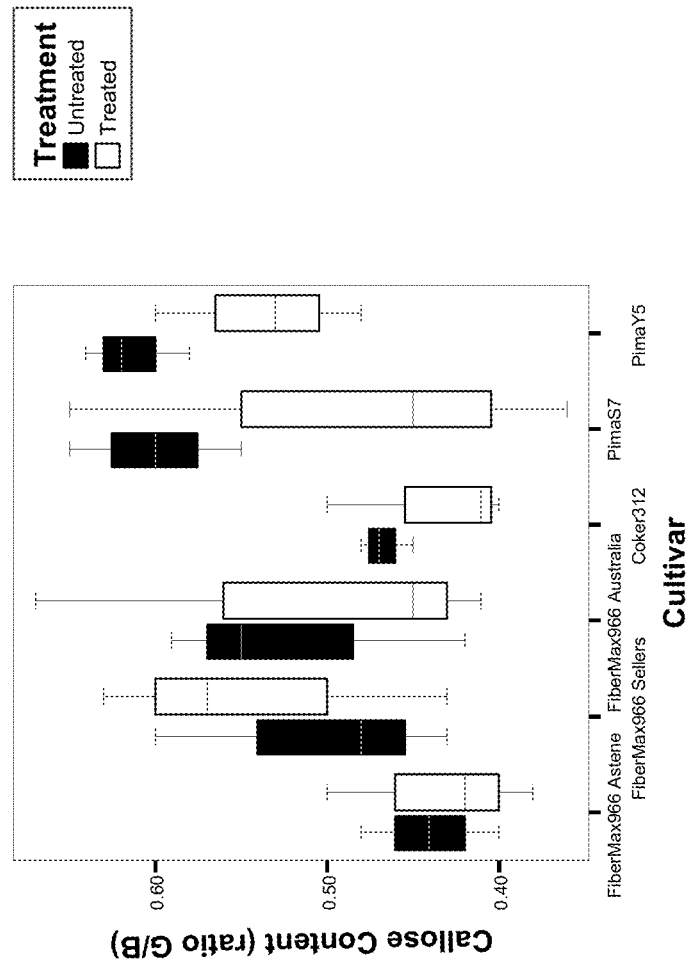
FIG. 5: Box plot indicating the difference in callose content (as determined by fluorescence measurements of aniline blue stained fibers; indicated as the ratio of green over blue fluorescence on the Y-axis) between untreated fibers ('untreated') and fibers treated with exogenous glucanase ('treated') derived from *Gossypium hirsutum* cultivar FM966 grown in a greenhouse in Europe ('FM966 Astene'), in the field in the US ('FM966 Sellers') and in the field in Australia ('FM966 Australia'), from *Gossypium hirsutum* cultivar Coker 312 grown in a greenhouse in Europe ('Coker 312'), from *Gossypium barbadense* cultivar PimaS7 grown in a greenhouse in Europe ('PimaS7'), and from *Gossypium barbadense* cultivar PimaY5 grown in the field in Australia ('PimaY5').

As indicated in Table 9 and FIG. 5, this staining technique showed that cotton fibers treated with the glucanase had a lower level of 1,3-beta-glucan and that elevated 1,3-beta-glucan levels were linked to enhanced fiber strength.

3.3. Statistical Analysis of Effect of Glucanase Treatment on Fiber Strength and Callose Content The effect of the treatment (untreated minus treated) was statistically analyzed. The results are presented in Table 10.

TABLE 10

Statistical analysis of glucanase treatment (untreated minus treated) on callose content and strength of fibers from different *G. hirsutum* and *G. barbadense* varieties

| | Callose content (ratio G/B) | | Fiber strength (Force) | |
|---|---|---|---|---|
| | difference | p-value | difference | p-value |
| *G. hirsutum* cv. FM966 (greenhouse) | 0.01 | 0.882 | −0.18 | 0.618 |
| *G. hirsutum* cv. FM966 (field US) | −0.04 | 0.634 | 1.05 | 0.041* |
| *G. hirsutum* cv. FM966 (field AU) | 0.01 | 0.922 | 1.03 | 0.003* |

TABLE 10-continued

Statistical analysis of glucanase treatment (untreated minus treated) on callose content and strength of fibers from different *G. hirsutum* and *G. barbadense* varieties

| | Callose content (ratio G/B) | | Fiber strength (Force) | |
|---|---|---|---|---|
| | difference | p-value | difference | p-value |
| *G. hirsutum* cv. Coker312 (greenhouse) | 0.03 | 0.415 | 1.41 | 0.002* |
| *G. barbadense* cv. PimaS7 (greenhouse) | 0.11 | 0.278 | 2.55 | 0.000* |
| *G. barbadense* cv. PimaY5 (field AU) | 0.08 | 0.121 | 3.07 | 0.000* |

The correlations between the treatment and callose content as well as fiber strength were statistically analyzed. The results are presented in Table 11 for *G. hirsutum* and in Table 11 for *G. barbadense*.

TABLE 11

Statistical analysis of correlations between glucanase treatment of fibers of *G. hirsutum*, their callose content and their strength

| | | Glucanase treatment | Callose content (ratio G/B) | Fiber strength (Force) |
|---|---|---|---|---|
| Glucanase treatment | Correlation | 1.00 | −0.03 | −0.48 |
| | Sig. (2-tailed) | | 0.944 | 0.233 |
| Callose content (ratio G/B) | Correlation | −0.03 | 1.00 | 0.66 |
| | Sig. (2-tailed) | 0.944 | | 0.075 |
| Fiber strength (Force) | Correlation | −0.48 | 0.66 | 1.00 |
| | Sig. (2-tailed) | 0.233 | 0.075 | |

TABLE 12

Statistical analysis of correlations between glucanase treatment of fibers of *G. barbadense*, their callose content and their strength

| | | Glucanase treatment | Callose content (ratio G/B) | Fiber strength (Force) |
|---|---|---|---|---|
| Glucanase treatment | Correlation | 1.00 | −0.96 | −0.99 |
| | Sig. (2-tailed) | | 0.044* | 0.013* |
| Callose content (ratio G/B) | Correlation | −0.96 | 1.00 | 0.90 |
| | Sig. (2-tailed) | 0.044* | | 0.103 |
| Fiber strength (Force) | Correlation | −0.99 | 0.90 | 1.00 |
| | Sig. (2-tailed) | 0.013* | 0.103 | |

In summary, cotton fibers with a higher 1,3-beta-glucan content displayed higher fiber strength and reduction in 1,3-beta-glucan content by exogenously supplied 1,3-beta-glucanase enzyme significantly reduced fiber strength and callose content in *G. barbadense*, indicating that 1,3-beta-glucan or callose has a specific role in cotton fiber strength which can be modulated by enzymes such as GLUC1.1.

Example 4

Identification of GLUCL1A Alleles in Different Cotton Species

GLUC1.1 sequences were isolated from six different *Gossypium hirsutum* varieties (Guazuncho; DP16; Cooker 312

(C312); Fiber Max 966 (FM966); Acala SJ2; Acala Maxxa), from five different *Gossypium barbadense* varieties (PimaS7; Tanguis LMW 1737-60; Tanguis CN(C.P.R.) 712-60; Sea Island Tipless; VH8), from *Gossypium herbacium, Gossypium tomentosum, Gossypium darwinii, Gossypium arboreum, Gossypium raimondii, Gossypium kirkii, Gossypium longicalyx*, and *Gossypium mustelinum*

Based on the GhGLUC1.1A and D nucleotide sequences described in WO2008/083969 (SEQ ID NO: 1 and 7, respectively), primer pairs (forward primer SE077 (SEQ ID NO: 33) and G1.1-f1-F1 (SEQ ID NO: 65) en reverse primer SE078 (SEQ ID NO: 34) or forward primer SE002 (SEQ ID NO: 35) en reverse primer SE003 (SEQ ID NO: 36)) were designed to amplify full-length or partial, respectively, genomic DNA fragments. The reaction mix used contained: DNA (200 ng/µl genomic DNA), 1 µl forward primer (10 pM), 1 µl reverse primer (10 pM), 4 µl 5× High Fidelity buffer, 0.2 µl Phusion enzyme (Finnzymes), 0.4 µl dNTP's (10 mM), 11.4 µl water (MilliQ). The PCR protocol used was as follows: 1 min at 98° C.; 30 times: 10 sec at 98° C. (denaturation), 30 sec at 56° C. (annealing), 1 min at 72° C. (elongation); 30 sec at 58° C.; 10 min at 72° C.; 4° C.

GLUC1.1A sequences from all *G. barbadense* lines tested and from *Gossypium darwinii* display a single nucleotide substitution (c to t at position 712 of SEQ ID NO: 5 and at position 470 of SEQ ID NO: 17 or at position 761 of SEQ ID NO: 56, respectively; see also GLUC1.1A-SNP5 in Table 13) resulting in a premature stop codon (cga to tga) in their sequences (FIG. 6; since the GLUC1.1 sequences from the different *Gossypium hirsutum* varieties and the different *Gossypium barbadense* varieties, respectively, were identical to each other, only the GLUC1.1 sequences of the FM966 and PimaS7 variety, respectively, were included in the alignment). The GLUC1.1A sequence from *G. arboreum* displayed a single nucleotide deletion (deletion of c nucleotide between position 327 and 328 of SEQ ID NO: 21) also resulting in a premature stop codon (tga at position 373-375 of SEQ ID NO: 21) further downstream in its sequence (FIG. 6). The premature stop codons in the GLUC1.1A sequences from *G. barbadense*, from *Gossypium darwinii* and from *G. arboreum* resulted in a predicted truncated GLUC1.1A protein sequence (FIG. 7; GLUC1.1A protein of 179 (SEQ ID NO: 6), of 179 (SEQ ID NO: 57), and of 78 (SEQ ID NO: 22) amino acids, respectively), while the GLUC1.1A sequences from all other *Gossypium* species tested did not display premature stop codons and are predicted to produce a complete GLUC1.1 protein (FIGS. 6 and 7).

As indicated above, *G. barbadense* is commercially recognized for its superior fiber quality, particularly for fiber strength, length and fineness. *G. darwinii* is the closest relative of *G. barbadense* and some even consider it as a variety of *G. barbadense* rather than a separate species. However, *G. darwinii* produces sparse, non-spinnable, khaki or brown fiber, usually less than 1.3 cm in length (see e.g. Wendel and Percy, 1990, Bioch. Systematics And Ecology 18 (7/8): 517-528). As the fibers from *G. darwinii* are not commercially used, little information is available about its commercially relevant fiber qualities, such as fiber strength.

Example 5

Genotyping of GLUCL1 Genes in Commercial Germplasm

The genotype of GLUC1.1A and GLUC1.1D genes was determined in commercially available germplasm by determining the genotype of GLUC1.1A-SNP3, 5 and 6 and GLUC1.1D-SNP1 (as indicated in FIG. 6 and Table 13) in a total of 73 *G. hirsutum* varieties, one *G. barbadense* variety, 2 *G. arboreum* varieties, one *G. herbaceum* variety, and one *G. mustilinum* variety using Illumina GoldenGate SNP Genotyping and BeadArray technology as prescribed by the manufacturer. Briefly, a GoldenGate Genotyping assay uses allele-specific extension and ligation for genotype calling using a discriminatory DNA polymerase and ligase (Illumina).

TABLE 13

Position and genotype of GLUC1.1D-SNP1 and GLUC1.1A-SNP2, 3, 5, 6, 7 and 8 in GLUC1.1D and A genes, respectively of different *Gossypium* species (*G. h.*: *G. hirsutum, G. b.*: *G. barbadense, G. t.*: *G. tomentosum; G. d.*: *G. darwinii; G. m.*: *G. mustilinum; G. a.*: *G. arboreum G. he.*: *G. herbaceum G. r.*: *G. raimondii*)

| | GLUC1.1A | | | | | | |
|---|---|---|---|---|---|---|---|
| G. sp.: | G. h. | G. b. | G. t. | G. d. | G. m. | G. a. | G. he. |
| SEQ ID: | 1 | 5 | 15 | 56/17 | 19 | 21 | 23 |
| SNP7 between | 2674-2676 | 327-329 | 85-87 | 376-378/ 85-87 | 85-87 | 327-328 | 327-329 |
| | C | C | C | C | C | — | C |
| SNP2 between | 2765-2766 | 418-428 | 176-177 | 467-477/ 176-186 | 176-177 | 417-418 | 418-419 |
| | — | CTCAT CAAA | — | CTCAT CAAA | — | — | — |
| SNP3 | 2911 | 573 | 322 | 622/331 | 322 | 563 | 564 |
| | G | C | G | C | C | C | C |
| SNP5 | 3050 | 712 | 461 | 761/470 | 461 | 702 | 703 |
| | C | T | C | T | C | C | C |
| SNP8 | 3170 | 832 | 581 | 881/590 | 581 | 821 | 823 |
| | G | C | G | G | G | G | G |
| SNP6 | 3202 | 864 | 613 | 913/622 | 613 | 854 | 855 |
| | G | A | G | A | G | G | G |

TABLE 13-continued

Position and genotype of GLUC1.1D-SNP1 and GLUC1.1A-SNP2, 3, 5, 6, 7 and 8 in GLUC1.1D and A genes, respectively of different *Gossypium* species (*G. h.*: *G. hirsutum*, *G. b.*: *G. barbadense*, *G. t.*: *G. tomentosum*; *G. d.*: *G. darwinii*; *G. m.*: *G. mustilinum*; *G. a.*: *G. arboreum* *G. he.*: *G. herbaceum* *G. r.*: *G. raimondii*)

| | GLUC1.1D | | | | | |
|---|---|---|---|---|---|---|
| G. sp.: | G. h. | G. b. | G. t. | G. d. | G. m. | G. r. |
| SEQ ID: | 7 | 11 | 25 | 58/27 | 29 | 31 |
| SNP1 | 3614 C | 304 T | 80 C | 352/80 T | 80 C | 80 C |

The results confirmed that the genotypes of GLUC1.1A-SNP3, 5 and 6 and GLUC1.1D-SNP1 in the different analysed *Gossypium* species and varieties were as indicated in FIG. 6 and Table 13. In particular, genotyping of GLUC1.1A-SNP5 in the different *Gossypium* species and varieties indicated that all analysed *Gossypium* species and varieties different from *G. barbadense* comprise the cga codon found in GLUC1.1A of *Gossypium hirsutum* instead of the tga stop codon found in gluc1.1A of *Gossypium barbadense* Pima S7.

Example 6

Detection of GLUCL1 Allele Encoding an Inactive GLUC1.1 Protein in *Gossypium* Plants and/or Transfer of GLUCL1 Allele Encoding an Inactive GLUC1.1 Protein into *Gossypium* Lines Comprising a Corresponding GLUCL1 Allele Encoding an Active GLUC1.1 Protein A GLUC1.1 allele encoding an inactive GLUC1.1 enzyme, such as a Gbgluc1.1A allele, Gdgluc1.1A allele or Gagluc1.1A allele, is transferred into cotton lines comprising a corresponding GLUC1.1 allele encoding an active GLUC1.1 enzyme, such as *Gossypium hirsutum* breeding lines, by the following method:

A plant containing a GLUC1.1 allele encoding an inactive GLUC1.1 enzyme, such as a *Gossypium barbadense* plant, a *Gossypium darwinii* plant or a *Gossypium arboreum* plant containing a GLUC1.1A allele encoding an inactive GLUC1.1A enzyme, or a mutagenized *Gossypium hirsutum* plant containing a mutant GLUC1.1 allele encoding an inactive GLUC1.1 enzyme (donor plant), is crossed with a plant containing a corresponding GLUC1.1 allele encoding an active GLUC1.1 enzyme, such as a *Gossypium hirsutum* plant containing a GLUC1.1A allele encoding an active GLUC1.1A enzyme (recurrent parent). The following introgression scheme is used (the GLUC1.1 allele encoding an inactive GLUC1.1 enzyme is abbreviated to gluc while the GLUC1.1 allele encoding an active GLUC1.1 enzyme is depicted as GLUC):

Initial cross: gluc/gluc (donor)×GLUC/GLUC (recurrent parent)
F1 plant: GLUC/gluc
BC1 cross: GLUC/gluc (F1)×GLUC/GLUC (recurrent parent)
BC1 plants: 50% GLUC/gluc and 50% GLUC/GLUC
The 50% GLUC/gluc are selected using a specific assay (e.g. PCR, TaqMan™, Invader™, and the like; see also below) for the gluc1.1 allele.

BC2 cross: GLUC/gluc (BC1)×GLUC/GLUC (recurrent parent)
BC2 plants: 50% GLUC/gluc and 50% GLUC/GLUC
The 50% GLUC/gluc are selected using a specific assay (e.g. PCR, TaqMan™, Invader™, and the like; see also below) for the gluc1.1 allele.

Backcrossing is repeated until BC4 to BC5 (e.g. if the donor plant is a *Gossypium barbadense* plant and the recurrent parent is a *Gossypium hirsutum* plant) or until BC3 (e.g. if the donor plant and the recurrent parent are *Gossypium hirsutum* plants)
BC3-5 plants: 50% GLUC/gluc and 50% GLUC/GLUC
The 50% GLUC/gluc are selected using a specific assay (e.g. PCR, TaqMan™, Invader™, and the like; see also below) for the gluc1.1 allele.

To reduce the number of backcrossings (e.g. until BC2 if the donor plant and the recurrent parent are *Gossypium hirsutum* plants, or until BC3 to BC4 if the donor plant is a *Gossypium barbadense* plant and the recurrent parent is a *Gossypium hirsutum* plant), molecular markers can be used in each generation that are specific for the genetic background of the recurrent parent.

BC3-5 S1 cross: GLUC/gluc×GLUC/gluc
BC3-5 S1 plants: 25% GLUC/GLUC and 50% GLUC/gluc and 25% gluc/gluc Plants containing the gluc1.1 allele are selected using molecular markers for the gluc1.1 allele. Individual BC3-5 S1 plants that are homozygous for the gluc1.1 allele (gluc/gluc) are selected using molecular markers for the gluc1.1 and GLUC1.1 alleles. These plants are then used for fiber production.

Molecular markers which can be used to detect a specific gluc1.1 or GLUC1.1 allele or to discriminate between a specific gluc1.1 and GLUC1.1 allele are, for example, single nucleotide polymorphisms (SNPs) or polymorphic nucleotide sequences:

As an example, SNPs and polymorphic nucleotide sequences which can be used to discriminate between the Gbgluc1.1A or Gdgluc1.1A allele and the GhGLUC1.1A allele and between the GbGLUC1.1D or Gdgluc1.1D allele and the GhGLUC1.1D allele or to detect their presence in DNA samples or plants, are SNPs indicated as GLUC1.1A-SNP3, 5 and 6 in FIG. 6 and Table 13 and the polymorphic nucleotide sequence indicated as GLUC1.1A-SNP2 in FIG. 6 and Table 13 and the SNP indicated as GLUC1.1D-SNP1 in FIG. 6 and Table 13, respectively.

In particular, a SNP which can be used to discriminate between the Gbgluc1.1A or Gdgluc1.1A allele that comprises a premature tga STOP codon and the corresponding GhGLUC1.1A allele that comprises a cga codon instead, is the SNP indicated as GLUC1.1A-SNP5 in FIG. 6 and Table 13.

The genotype of such SNPs and polymorphic nucleotide sequences can be determined, for example, using a PCR assay.

As an example, PCR assays were developed to determine the genotype of the SNP indicated as GLUC1.1D-SNP1 in FIG. 6 and Table 13 and of the polymorphic nucleotide sequence indicated as GLUC1.1A-SNP2 in FIG. 6 and Table 13 of plants of the BC1 populations described in Example 1 in order to map the GLUC1.1D and A genes of *G. hirsutum* and *barbadense*, respectively. More specifically, following PCR assay was developed to discriminate between the Gbgluc1.1A allele and the GhGLUC1.1A allele based on the genotype of the SNP indicated as GLUC1.1A-SNP2 in FIG. 6 and Table 13:

Primers:

```
Forward:    5' TAT CCC TCT CGA TGA GTA CGA C 3'
            (p1.3GlucaAf - SEQ ID NO: 37)

Reverse:    5'CCC AAT GAT GAT GAA CCT GAA TTG3'
            (p1.3GlucaAr - SEQ ID NO: 38)
```

Amplicon size: 134 bps for *G. hirsutum* and 143 bps for *G. barbadense*.

PCR conditions: 50 gDNA (20 ng/µl)+15 µl PCR mix (PCR mix: 2 µl 10×Taq PCR buffer, 1 µl labeled p1.3GlucaAf (100 pmol/µl), 0.2 µl p1.3GlucaAr (100 pmol/µl), 0.25 µl dNTPs (20 mM), 0.5 µl $MgCl_2$ (50 mM), 0.2 µl Taq polymerase, 10.85 µl MiliQ)

Labeling of forward primer: 0.1 µl 10×T4 kinase buffer, 0.2 µl p1.3GlucaAf (100 pmol/µl), 0.01 µl T4 kinase, 0.1 µl $P^{33}\gamma$ ATP, 0.59 µl MilliQ=1 µl; 1 h at 37° C. and 10 min at 65° C.

PCR profile: 5 min at 95° C.; 35 times: 45 s at 95° C., 45 s at 58° C., 1 min at 72° C.; 10 min at 72° C.

Gel analysis: PCR fragments are separated on 4.5% denaturing acrylamide gels

Overnight exposure of gel to BIOMAX MR films

Alternatively, the genotype of such SNPs can be determined, for example, using Illumina GoldenGate SNP Genotyping as indicated in Example 5 for the SNPs indicated as GLUC1.1A-SNP3, 5 and 6 and GLUC1.1D-SNP1 in FIG. 6 and Table 13.

Alternatively, the genotype of such SNPs and polymorphic nucleotide sequences can be determined by direct sequencing by standard sequencing techniques known in the art to determine the complete GLUC1.1 nucleotide sequence present in a plant followed by analysis of the obtained sequence, e.g., by alignment with the GLUC1.1 sequences described herein (see, e.g., FIGS. 6 and 7).

Alternatively, the genotype of such SNPs and polymorphic nucleotide sequences can be determined by a Taqman assay. The TaqMan assay procedure and interpretation of the data are performed as prescribed by the manufacturer (Applied Biosystems). Briefly, a probe specific for a specific variant of a polymorphic site in a GLUC1.1 gene binds the template DNA if this specific variant is present. The probe has a fluorescent reporter or fluorophore, such as 6-carboxyfluorescein (acronym: FAM) and VIC (a proprietary dye from Applied Biosystems), attached to its 5' end and a quencher (e.g., tetramethylrhodamine, acronym: TAMRA, of dihydrocyclopyrroloindole tripeptide "minor groove binder", acronym: MGB) attached to its 3' end. The close proximity between fluorophore and quencher attached to the probe inhibits fluorescence from the fluorophore. During a PCR with two primers capable of amplifying a DNA fragment comprising the polymorphic site, the 5' to 3' exonuclease activity of the Taq polymerase degrades that proportion of the probe that has annealed to the template as DNA synthesis commences. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR. The following discriminating Taqman probes and primers were thus developed to discriminate different variants of GLUC1.1A-SNP3 and GLUC1.1A-SNP5 (see FIG. 6 and Table 13):

TABLE 14a

GLUC1.1A - SNP3 of Probes

| | | |
|---|---|---|
| Gbgluc1.1A | 5' FAM- AACTCGCTCGCCTCA 3' | (SEQ ID NO: 39) |
| GhGLUC1.1A | 5' VIC-AACTCGCTGGCCTCA 3' | (SEQ ID NO: 40) |
| Forward primer | 5' CCTGGTGCCATGAACAACATAATG 3' | (SEQ ID NO: 41) |
| reverse primer | 5' CGTCGTGCCTAGCCCAAA 3' | (SEQ ID NO: 42) |

TABLE 14b

GLUC1.1A - SNP5 of Probes

| | | |
|---|---|---|
| Gbgluc1.1A | 5' FAM- ATCCTGTCAAACCAG 3' | (SEQ ID NO: 60) |
| GhGLUC1.1A | 5' VIC-ATCCTGTCAAACCAG 3' | (SEQ ID NO: 61) |
| Forward primer | 5' GCTTTTGGAAGCGATATAACATCGA 3' | (SEQ ID NO: 62) |
| reverse primer | 5' GGCATAGGCAAAATAAGGGTACACA 3' | (SEQ ID NO: 63) |

Probes specific for polymorphic sites in the Gbgluc1.1A or corresponding GhGLUC1.1A target gene, such as the probes specific for GLUC1.1A-SNP3 of Gbgluc1.1A and GhGLUC1.1A indicated as "5' FAM-AACTCGCTCGC-CTCA 3" and "5' VIC-AACTCGCTGGCCTCA 3', respectively, in Table 14a, and forward and reverse primers that are capable of amplifying a fragment comprising the polymorphic site and that can thus be used in combination with them are indicated in Table 14a. Generally, each probe set consists of two probes each specific for one variant of the polymorphic site in the GLUC1.1 target gene which comprises the variant nucleotide (e.g., the underlined nucleotide in Table 14) or variant nucleotide sequence (e.g. the probe with SEQ ID NO: 39 is specific for GLUC1.1A-SNP3 of Gbgluc1.1A and the probe with SEQ ID NO: 40 is specific for GLUC1.1A-SNP3 of GhGLUC1.1A) and a set of two primers that are capable of amplifying a fragment comprising the polymorphic site (e.g. the primer with SEQ ID NO: 41 is specific for a nucleotide sequence upstream of GLUC1.1A-SNP3 and the primer with SEQ ID NO: 42 is specific for a nucleotide sequence downstream of GLUC1.1A-SNP3, such that the use of both primers results in the amplification of a DNA fragment comprising GLUC1.1A-SNP3).

Alternatively, the genotype of such SNPs and polymorphic nucleotide sequences can be determined by Invader™ technology (Third Wave Agbio).

Example 7

Comparison of Expression of GLUCL1A and GLUCL1D During Fiber Growth and Development in *Gossypium barbadense* and in *Gossypium hirsutum*

Expression of GLUC1.1A and GLUC1.1D during fiber growth and development was analyzed for *G. barbadense* and compared with the expression of GLUC1.1A and GLUC1.1D during fiber growth and development of *G. hirsutum* as described in WO2008/083969.

DNA from a cDNA library of *G. barbadense* created from fiber cells and seed at 0 and 5 DPA and from fiber cells at 10, 15, 20, 25, 30 and 40 DPA was extracted, the concentration was equalized and a PCR amplification was performed using primers SE002 (SEQ ID NO: 35) and SE003 (SEQ ID NO: 36). The PCR reaction mix used contained: 1 µl template DNA (200 ng/µl), 5 µl 5× GreenGo-Taq buffer, 0.75 µl SE002 (10 µM), 0.75 µl SE003 (10 µM), 0.5 µl dNTP's (20 mM), 0.25 µl GoTaq polymerase, 16.75 µl MilliQ water (total of 25 µl). The PCR conditions used were as follows: 5 min at 95° C.; 5 times: 1 min at 95° C., 1 min at 58° C., 2 min at 72° C.; 25 times: 30 s at 92° C., 30 s at 58° C., 1 min at 72° C.; 10 min at 72° C., cooldown to 4° C. The expected length of the PCR product is 655 bp. After PCR amplification, the PCR fragment is digested with AlwI digest (3 h incubation at 37° C.) using 10 µl template; 1 µl AlwI enzyme; 2 µl NEB 4 restriction buffer; 7 µl MQ water. The resulting fragments are analysed on 1.5% TAE gel stained with EtBr. The expected band sizes for the A subgenome allele specific PCR fragment are: 479 bp, 118 bp and 59 bp (not visible in FIG. 8). The expected band sizes for the D subgenome allele specific PCR fragment are: 538 bp and 118 bp.

FIG. 8, lanes 2 to 9, represent GbGLUC1.1A and D expression at 0, 5, 10, 15, 20, 25, and 40 DPA. Differences in band intensities in FIG. 8 correspond to relative differences in expression. A negative (no template; NTC; FIG. 8, lane 10) and a positive control (genomic DNA from Pima S7; FIG. 8, lane 11) were included. The expression profile of the GhGLUC1.1A and D and GbGLUC1.1A and D genes can be summarized as follows:

| | Days post anthesis (DPA): | | | | | | | |
|---|---|---|---|---|---|---|---|---|
| | 0 | 5 | 10 | 15 | 20 | 25 | 30 | 40 |
| GhGLUC1.1 | — | — | — | D | D | ND | A & D | A & D |
| GbGLUC1.1 | — | — | — | A & D | A & D | A & D | A & D | A & D |

Thus while the expression of GLUC1.1A in *G. hirsutum* starts only at 30 DPA, GLUC1.1A in *G. barbadense* is expressed from 15 DPA on. However, as indicated above, the GbGLUC1.1A gene is predicted to encode a non-functional GLUC1.1A protein.

The invention claimed is:

1. A non-naturally occurring *Gossypium* plant, and parts and progeny thereof, comprising at least one fiber strength allele which is derived from *Gossypium barbadense* of a fiber strength locus on chromosome A05 wherein said plant is a *Gossypium hirsutum* plant and wherein the fiber strength allele which is derived from *Gossypium barbadense* is located on chromosome A05 of *Gossypium barbadense*:
   (a) between AFLP marker P5M50-M126.7 and SSR marker CIR280,
   (b) between AFLP marker P5M50-M126.7 and SSR marker BNL3992,
   (c) between AFLP marker P5M50-M126.7 and SSR marker CIR401c, or
   (d) between SSR marker NAU861 or the GLUC1.1 gene and SSR marker CIR401c, said *Gossypium hirsutum* plant comprising a *Gossypium hirsutum* allele of at least one marker locus on chromosome A05 selected from the group consisting of CIR139a, BNL3029.A and NAU1042.A.

2. The plant of claim 1, wherein said *Gossypium hirsutum* plant further comprises a *Gossypium hirsutum* allele of at least one marker locus on chromosome A05 selected from the group consisting of BNL0542, E43M49-M260.0, E31M48-M188.5, E43M53-M460.0, CIR294.A and BNL3995 which is derived from and specific for *Gossypium hirsutum*.

3. The plant of claim 1, wherein the LOD peak of the fiber strength allele which is derived from *Gossypium barbadense* is located:
   (a) at about 0 to 5 cM from SSR marker NAU861 or the GLUC1.1 gene, or
   (b) at about 0 to 12 cM from SSR marker CIR401c.

4. The plant of claim 1, wherein the fiber strength allele which is derived from *Gossypium barbadense* comprises a GLUC1.1 gene encoding a non-functional GLUC1.1 protein.

5. The plant of claim 1, wherein the fiber strength allele which is derived from *Gossypium barbadense* comprises a GLUC1.1 gene characterised by the presence of a T nucleotide at a nucleotide position corresponding to nucleotide position 712 of SEQ ID NO: 5.

6. The plant of claim 1, wherein the callose content of the fibers is increased compared to the callose content of the fibers of an equivalent *Gossypium* plant that does not comprise the at least one fiber strength allele which is derived from *Gossypium barbadense*.

7. The plant of claim 1, wherein the strength of the fibers is increased compared to the strength of the fibers of an equivalent *Gossypium* plant that does not comprise the at least one fiber strength allele which is derived from *Gossypium barbadense*.

8. The plant of claim 7, wherein the strength of the fibers is on average between about 1% and about 2% higher.

9. The plant of claim 7, wherein the *Gossypium hirsutum* plant is homozygous for the fiber strength allele which is derived from *Gossypium barbadense*.

10. The plant of claim 3, wherein the LOD peak of the fiber strength allele which is derived from *Gossypium barbadense* is located at about 4.008 cM from SSR marker NAU861 or the GLUC1.1 gene.

11. The plant of claim 3, wherein the LOD peak of the fiber strength allele which is derived from *Gossypium barbadense* is located at about 10 cM from SSR marker CIR401c.

12. The plant of claim 3, wherein the LOD peak of the fiber strength allele which is derived from *Gossypium barbadense* is located at about 10.52 cM from SSR marker CIR401c.

13. The plant of claim 9, wherein the strength of the fibers is on average
   (a) between about 5% and about 10% higher;
   (b) between about 1.6 g/tex and about 3.3 g/tex higher; or
   (c) between about 34.6 g/tex and about 36.3 g/tex.

* * * * *

SEQUENCE LISTING

<160> NUMBER OF SEQ ID NOS: 65

<210> SEQ ID NO 1
<211> LENGTH: 6009
<212> TYPE: DNA
<213> ORGANISM: Gossypium hirsutum
<220> FEATURE:
<221> NAME/KEY: CDS
<222> LOCATION: (2410)..(2443)
<220> FEATURE:
<221> NAME/KEY: CDS
<222> LOCATION: (2556)..(3496)

<400> SEQUENCE: 1

| | | | | | |
|---|---|---|---|---|---|
| cgcggcatat | aattttatgt | gtgtaatttg | ttgggttaat | tacttaaaat | agtatatttt | 60 |
| taattgctgt | aattaatgta | agataatttt | tattatttga | atcattgcac | aaaattaaaa | 120 |
| tagaataatt | tatttaacaa | ttcaaatata | ataataatcc | aaattataat | tatagtattt | 180 |
| ttacaatatt | caatatacaa | tatagtttta | cttcatacaa | ttaatataaa | aaaatattat | 240 |
| tcaaaataat | aactaataaa | cataattacc | atatattaat | tattttgata | tttcgaacat | 300 |
| aacgctaata | aaaaatttcc | taatcattat | taaatcattt | gtataaacta | taagaaaatt | 360 |
| gatatattgt | aaattaaact | ttattcattt | tttttcttaa | tactcaataa | attaatcata | 420 |
| ataactcata | aataatatat | aattaaaata | atcataacat | ggtagattat | ataaataggg | 480 |
| ggcgaatcta | gggagctggc | atgacccta | aaatagaatt | ttctattttg | acctatcaaa | 540 |
| atttttaaaa | ttttaaatta | gtaaaggtaa | atttgtactt | tgacctctta | aaatgataaa | 600 |
| atttactt | aatcctttaa | aatttacatt | tttactatca | taaaaattac | aatttgattt | 660 |
| tgcccctaaa | attttttct | agcttagccc | tgtatataaa | tatattattt | ataatttta | 720 |
| tatttaaaat | ataagttttt | taattataca | aataattaaa | atctgatatt | taaaactaaa | 780 |
| gtaatttctt | ttttcttttt | actttttttt | aattgcaaca | taatggttta | aatatctata | 840 |
| taacgtatga | agtaatttga | tataaatttt | attttaattt | attattatat | aaattcattt | 900 |
| agtaaaaact | tttaatagaa | tcaaaatttt | tatttgtaaa | ttcgataact | tttcttatca | 960 |
| agtatatttg | tgagaaccaa | atatttagta | aaattaatat | tcttatttat | aaatatgata | 1020 |
| aatcttataa | aaaaatattt | aaaatgaaaa | aaattgtaca | aatattataa | aaaaatattt | 1080 |
| aaaatgaaaa | acattgtaca | aaggctatat | aagaagttca | aaagtttctt | cgaccatgta | 1140 |
| ctcttataga | gattatagat | agattataaa | actatatgta | gtttctctta | acttttaaat | 1200 |
| aagaggataa | atgtattta | atgtactcaa | acttatatat | ttttatattg | acaataatat | 1260 |
| caatatcaac | ctaattaaga | ttcattctaa | cattaatgtt | gaagattttt | aataaaagaa | 1320 |
| aaggttaata | aattaattag | aacacaaaca | aacacaaatt | taagtggtat | gtaaggtcct | 1380 |
| tgacccaaag | gaaaaatttg | ttacgtcgat | taaattataa | attaatttaa | agtaaaatta | 1440 |
| cattttaacc | taaaaaaaga | gaaaagtata | tctaatttct | tcgaaaatgg | aaagaaaatt | 1500 |
| ataaatttat | ggcatttcta | aaaaaattct | gaattcgcta | ctaaaagatg | aaattataaa | 1560 |
| atccgaagca | ttaccagaag | atggatcacc | aaatcacaaa | caatcaatga | aaagtaatga | 1620 |
| taattaattg | aaagtgagca | tttaattttg | atagccatat | acttcctgct | gaatttatag | 1680 |
| gttctcatta | atgcaattaa | attatattcg | acacctttg | aatgaaataa | aatgacacaa | 1740 |
| gaggaaagac | ggttcatcta | ttttttcttt | caatcgccca | tcaaaatacc | aaaaatgtaa | 1800 |
| ctacatgcaa | aaaatcaaat | atgaaaata | ttcatttttt | gatattttaa | tatattgtgt | 1860 |
| gttcaaaacg | taaatgtatt | gaaaaattat | gatggtgttg | ttgctgtatg | tccataaaat | 1920 |

-continued

```
tcaatgtact cacatttatc aaatgtatac tttgagagaa gttattttga taatactcaa      1980 gttttttta tagatgggaa aattttttaa attattttt gattttgatg aaatgtatat        2040
ataaatttta attcgataca tataaatata tatgtaaatt ttaaatttaa atttaataat      2100
atacaattaa gaaataatt tataaatatt ttccgattaa aaataaatct ggaaagaaga      2160
aatgtcaaca cttttcatt aaatacaatt aggatgggac acgataccct catgcattga     2220
tatctcaggt ggtccaaaaa ctcggaatcc tttttgaaaa aaaacttcca gagagagtat     2280
ataaatccag cagtaggcac aagaaacgag caccagttat tgactttcct ttgtaaaaaa    2340
aaaaagtgct gagatcaaga aatatagtga aatatgggtc caagattttc tgggttttta   2400 atctaagca atg ctg ttt tta act caa ctc ctc tct cta aca g              2443
          Met Leu Phe Leu Thr Gln Leu Leu Ser Leu Thr
            1               5                  10 gtaaaacaaa cttctctaca gtgattttac agtaaatatg gctttgaaaa atatacaaca     2503
aaacatttat cttcaatcca ttttaattac tgatctacta tatatgttgc ag at   ggc   2560
                                                          Asp Gly
cgt gat att ggt gtt tgc tat ggt ttg aac ggc aac aat ctt cca tct       2608
Arg Asp Ile Gly Val Cys Tyr Gly Leu Asn Gly Asn Asn Leu Pro Ser
    15              20                  25 cca gga gat gtt att aat ctt ttc aaa act agt ggc ata aac aat atc       2656
Pro Gly Asp Val Ile Asn Leu Phe Lys Thr Ser Gly Ile Asn Asn Ile
30              35                  40                  45 agg ctc tac cag cct tac cct gaa gtg ctc gaa gca gca agg gga tcg       2704
Arg Leu Tyr Gln Pro Tyr Pro Glu Val Leu Glu Ala Ala Arg Gly Ser
        50                  55                  60 gga ata tcc ctc tcg atg agt acg aca aac gag gac ata caa agc ctc       2752
Gly Ile Ser Leu Ser Met Ser Thr Thr Asn Glu Asp Ile Gln Ser Leu
    65                  70                  75 gca acg gat caa agt gca gcc gat gca tgg gtt aac acc aac atc gtc       2800
Ala Thr Asp Gln Ser Ala Ala Asp Ala Trp Val Asn Thr Asn Ile Val
80              85                  90 cct tat aag gaa gat gtt caa ttc agg ttc atc atc att ggg aat gaa       2848
Pro Tyr Lys Glu Asp Val Gln Phe Arg Phe Ile Ile Ile Gly Asn Glu
        95                  100                 105 gcc att cca gga cag tca agc tct tac att cct ggt gcc atg aac aac       2896
Ala Ile Pro Gly Gln Ser Ser Ser Tyr Ile Pro Gly Ala Met Asn Asn
110             115                 120                 125 ata atg aac tcg ctg gcc tca ttt ggg cta ggc acg acg aag gtt acg       2944
Ile Met Asn Ser Leu Ala Ser Phe Gly Leu Gly Thr Thr Lys Val Thr
        130                 135                 140 acc gtg gtc ccg atg aat gcc cta agt acc tcg tac cct cct tca gac       2992
Thr Val Val Pro Met Asn Ala Leu Ser Thr Ser Tyr Pro Pro Ser Asp
    145                 150                 155 ggc gct ttt gga agc gat ata aca tcg atc atg act agt atc atg gcc       3040
Gly Ala Phe Gly Ser Asp Ile Thr Ser Ile Met Thr Ser Ile Met Ala
160             165                 170 att ctg gtt cga cag gat tcg ccc ctc ctg atc aat gtg tac cct tat       3088
Ile Leu Val Arg Gln Asp Ser Pro Leu Leu Ile Asn Val Tyr Pro Tyr
        175                 180                 185 ttt gcc tat gcc tca gac ccc act cat att tcc ctc aac tac gcc ttg       3136
Phe Ala Tyr Ala Ser Asp Pro Thr His Ile Ser Leu Asn Tyr Ala Leu
190             195                 200                 205 ttc acc tcg acc gca ccg gtg gtg gtc gac caa ggc ttg gaa tac tac       3184
Phe Thr Ser Thr Ala Pro Val Val Val Asp Gln Gly Leu Glu Tyr Tyr
        210                 215                 220 aac ctc ttt gac ggc atg gtc gat gct ttc aat gcc gcc cta gat aag       3232
```

```
              Asn Leu Phe Asp Gly Met Val Asp Ala Phe Asn Ala Ala Leu Asp Lys
                          225                 230                 235 atc ggc ttc ggc caa att act ctc att gta gcc gaa act gga tgg ccg           3280
Ile Gly Phe Gly Gln Ile Thr Leu Ile Val Ala Glu Thr Gly Trp Pro
            240                 245                 250 acc gcc ggt aac gag cct tac acg agt gtc gcg aac gct caa act tat           3328
Thr Ala Gly Asn Glu Pro Tyr Thr Ser Val Ala Asn Ala Gln Thr Tyr
            255                 260                 265 aac aag aac ttg ttg aat cat gtg acg cag aaa ggg act ccg aaa aga           3376
Asn Lys Asn Leu Leu Asn His Val Thr Gln Lys Gly Thr Pro Lys Arg
270                 275                 280                 285 cct gaa tat ata atg ccg acg ttt ttc ttc gag atg ttc aac gag aac           3424
Pro Glu Tyr Ile Met Pro Thr Phe Phe Phe Glu Met Phe Asn Glu Asn
                290                 295                 300 ttg aag caa ccc aca gtt gag cag aat ttc gga ttc ttc ttc ccc aat           3472
Leu Lys Gln Pro Thr Val Glu Gln Asn Phe Gly Phe Phe Phe Pro Asn
            305                 310                 315 atg aac cct gtt tat cca ttt tgg tgaacttgaa atgttattgt tggctattta         3526
Met Asn Pro Val Tyr Pro Phe Trp
            320                 325 aatcttttgc cagagacgct tcatatagtt tctgcatatt ttgaaagtgg aaaatcaatc         3586
taaatataaa taagttttat ttgttgtttt ttaattaaat aaaattttaa atattttaaa         3646
aacatcttta ttggtaatta atattaaat aaaagttta atattcaaat tttatcaatt           3706 caaaataaa ataaaatat attaaattta tttttacgaa taaattgatt ttctattaat          3766
gcagatttta ataatttga tataaattt caattcaaca atagtaattt tgatcacatc          3826
aaaggagaaa gggaaagatt taactttaat tggtgaccta atataacacg ttgaaaacgg         3886
agttcccaat aaggcaaaat gacttgtaat gacgaaagag atgtccaagt gaaatctgct         3946
ttaaagtgaa agaagcataa aaggataact aaataactca tgatctaaat tgaagttcta         4006
taaaatgcaa ctttcatcta gaaacaaggt atgtcttaaa tgatgtttta tgaatttgtc         4066
ttaattgggt tttatgcaat gaattcatgg atagcacatc tctaattata cgttgctggt         4126
ttatatgaga gtggtgcaga agttaattgt gctttaaata cttgcttagt gtttatgaaa        4186
tttgaaaagt gttatatact tataataaaa ataattcgat tcggaatcca attcagggtt        4246
cgactcaata taataaaatt ttacagatat cttgaagggg atcttcttct tctctacttc        4306
tcgagcagtg ttatatattt acaataaaga taactcaatt cgagatccga cctaatataa        4366
taaaattcta cagacatatc aaagagggag atcttcttct tccctacatc ttgaccttct        4426
tgatcaaaat gaccttcctt atatttttac atacgttgat tatatgaatc aaaagaaaga       4486
taccaaaaag tttttaaaaa taaacaacgg ggttcttatg tagagatgct tatgggccgg       4546
gccggactca actaaaaatt taggcacatt cattgggccc aggtcgggcc taacccaaaa       4606
atgggcctaa aattttgccc aagcttgact caaataaaaa tgctaaaatt cgggcctgac      4666
cccgtattaa ttttatatta ttttatataa cttttaaata tatataatat ataaaaaata       4726
ctaaaaaaat taaatataaa atttcccaac taaactaaaa ttattaagaa aaataattca      4786
tattagcgta taaattggaa attgaccaaa attaaaatta ttgtatagtt aatctatatt      4846
aaaaggacat gtaattaaaa accattaaaa ctattataca ataaattaaa tcttcattgt      4906
atacatagaa aggcattaat aattaaaaaa ctatattaag atataaacta aattcaaaat      4966
tattaaaaac aagaactaaa taaaaagca attgaaaatt acgaattaat gttaaaatca       5026
aatgttaaaa tcaagggact taaataaaaa tatcccaaaa tacaaaacat tagcttcctt       5086
```

```
tcccatccac gtgaatgcaa agtttacatg gtgtttccta gtgtttgtgc gactccaacc    5146
ttttatttac ctcttttttt ctttatttga acaattattt gataatgatt agaattttgg    5206
gattgttgct catcgtacgt gcaacactta aaatcactat gattttttcat aatttatata   5266 acctatatcg ttttggaaat taatttttatt ttttatatta ttttaataaa aataccatct   5326 accttttta atttatgatc cctttcatat ttaaaaattc aaattgacaa ttgtctaact     5386
aaacaccgtc acactccaat aagattgtaa tttcctccat cttgatatta cactcaaaag   5446
catgttgcca acaaacaaat caactagcct ttttctacca ctattcatca tcttcttaag   5506
agtgtgttta tgtcatgtgc cgagatttta ggtatggtca cgttgtggct ttaaactcaa   5566
atctattgcc catgagtcta agttagcctc cgatcctcac taaagagagg cttggcacac   5626
tttacctagc caagtacaca aggaatagag ctattagaaa gcattaaaga gttaggagaa   5686
tgtggaagtg ttttttattac tcaaagctaa cttggataca aataaaggag ggagcctctc   5746
ctttaggcaa gcttcttttg atctgatggt tacaattaat ctcgaatagg agggtcaaa    5806 cttctcactc agtttcatat tatctcttgg tgcttggttg gcctccgcct tgagacaact    5866
ttagataaca cctagtctta acactttag cttcacattg tacgcatcct tcattactca    5926
aatgccacaa agcctcctta cttaaggctc ttggtcgctc ccactacctt cggctttaga   5986
ctcatctaag atcttcccaa tcg                                           6009
```

<210> SEQ ID NO 2
<211> LENGTH: 325
<212> TYPE: PRT
<213> ORGANISM: Gossypium hirsutum

<400> SEQUENCE: 2

```
Met Leu Phe Leu Thr Gln Leu Leu Ser Leu Thr Asp Gly Arg Asp Ile
1               5                   10                  15

Gly Val Cys Tyr Gly Leu Asn Gly Asn Asn Leu Pro Ser Pro Gly Asp
            20                  25                  30

Val Ile Asn Leu Phe Lys Thr Ser Gly Ile Asn Asn Ile Arg Leu Tyr
        35                  40                  45

Gln Pro Tyr Pro Glu Val Leu Glu Ala Ala Arg Gly Ser Gly Ile Ser
    50                  55                  60

Leu Ser Met Ser Thr Thr Asn Glu Asp Ile Gln Ser Leu Ala Thr Asp
65                  70                  75                  80

Gln Ser Ala Ala Asp Ala Trp Val Asn Thr Asn Ile Val Pro Tyr Lys
                85                  90                  95

Glu Asp Val Gln Phe Arg Phe Ile Ile Ile Gly Asn Glu Ala Ile Pro
            100                 105                 110

Gly Gln Ser Ser Ser Tyr Ile Pro Gly Ala Met Asn Asn Ile Met Asn
        115                 120                 125

Ser Leu Ala Ser Phe Gly Leu Gly Thr Thr Lys Val Thr Thr Val Val
    130                 135                 140

Pro Met Asn Ala Leu Ser Thr Ser Tyr Pro Pro Ser Asp Gly Ala Phe
145                 150                 155                 160

Gly Ser Asp Ile Thr Ser Ile Met Thr Ser Ile Met Ala Ile Leu Val
                165                 170                 175

Arg Gln Asp Ser Pro Leu Leu Ile Asn Val Tyr Pro Tyr Phe Ala Tyr
            180                 185                 190

Ala Ser Asp Pro Thr His Ile Ser Leu Asn Tyr Ala Leu Phe Thr Ser
        195                 200                 205
```

```
Thr Ala Pro Val Val Asp Gln Gly Leu Glu Tyr Tyr Asn Leu Phe
    210             215                 220

Asp Gly Met Val Asp Ala Phe Asn Ala Ala Leu Asp Lys Ile Gly Phe
225             230                 235                 240

Gly Gln Ile Thr Leu Ile Val Ala Glu Thr Gly Trp Pro Thr Ala Gly
                245                 250                 255

Asn Glu Pro Tyr Thr Ser Val Ala Asn Ala Gln Thr Tyr Asn Lys Asn
                260                 265                 270

Leu Leu Asn His Val Thr Gln Lys Gly Thr Pro Lys Arg Pro Glu Tyr
            275                 280                 285

Ile Met Pro Thr Phe Phe Phe Glu Met Phe Asn Glu Asn Leu Lys Gln
            290                 295                 300

Pro Thr Val Glu Gln Asn Phe Gly Phe Phe Pro Asn Met Asn Pro
305             310                 315                 320

Val Tyr Pro Phe Trp
                325

<210> SEQ ID NO 3
<211> LENGTH: 1185
<212> TYPE: DNA
<213> ORGANISM: Gossypium hirsutum
<220> FEATURE:
<221> NAME/KEY: CDS
<222> LOCATION: (101)..(1078)

<400> SEQUENCE: 3
gcaccagtta ttgactttcc tttgtaaaaa aaaaaagtgc tgagatcaag aaatatagtg      60
aaatatgggt ccaagatttt ctgggttttt aatctaagca atg ctg ttt tta act     115
                                              Met Leu Phe Leu Thr
                                                1               5 caa ctc ctc tct cta aca gat ggc cgt gat att ggt gtt tgc tat ggt     163
Gln Leu Leu Ser Leu Thr Asp Gly Arg Asp Ile Gly Val Cys Tyr Gly
            10                  15                  20 ttg aac ggc aac aat ctt cca tct cca gga gat gtt att aat ctt ttc     211
Leu Asn Gly Asn Asn Leu Pro Ser Pro Gly Asp Val Ile Asn Leu Phe
        25                  30                  35 aaa act agt ggc ata aac aat atc agg ctc tac cag cct tac cct gaa     259
Lys Thr Ser Gly Ile Asn Asn Ile Arg Leu Tyr Gln Pro Tyr Pro Glu
    40                  45                  50 gtg ctc gaa gca gca agg gga tcg gga ata tcc ctc tcg atg agt acg     307
Val Leu Glu Ala Ala Arg Gly Ser Gly Ile Ser Leu Ser Met Ser Thr
55                  60                  65 aca aac gag gac ata caa agc ctc gca acg gat caa agt gca gcc gat     355
Thr Asn Glu Asp Ile Gln Ser Leu Ala Thr Asp Gln Ser Ala Ala Asp
70                  75                  80                  85 gca tgg gtt aac acc aac atc gtc cct tat aag gaa gat gtt caa ttc     403
Ala Trp Val Asn Thr Asn Ile Val Pro Tyr Lys Glu Asp Val Gln Phe
                90                  95                  100 agg ttc atc atc att ggg aat gaa gcc att cca gga cag tca agc tct     451
Arg Phe Ile Ile Ile Gly Asn Glu Ala Ile Pro Gly Gln Ser Ser Ser
            105                 110                 115 tac att cct ggt gcc atg aac aac ata atg aac tcg ctg gcc tca ttt     499
Tyr Ile Pro Gly Ala Met Asn Asn Ile Met Asn Ser Leu Ala Ser Phe
        120                 125                 130 ggg cta ggc acg acg aag gtt acg acc gtg gtc ccg atg aat gcc cta     547
Gly Leu Gly Thr Thr Lys Val Thr Thr Val Val Pro Met Asn Ala Leu
    135                 140                 145 agt acc tcg tac cct cct tca gac ggc gct ttt gga agc gat ata aca     595
Ser Thr Ser Tyr Pro Pro Ser Asp Gly Ala Phe Gly Ser Asp Ile Thr
```

```
            150                 155                 160                 165
tcg atc atg act agt atc atg gcc att ctg gtt cga cag gat tcg ccc         643
Ser Ile Met Thr Ser Ile Met Ala Ile Leu Val Arg Gln Asp Ser Pro
            170                 175                 180 ctc ctg atc aat gtg tac cct tat ttt gcc tat gcc tca gac ccc act         691
Leu Leu Ile Asn Val Tyr Pro Tyr Phe Ala Tyr Ala Ser Asp Pro Thr
            185                 190                 195 cat att tcc ctc aac tac gcc ttg ttc acc tcg acc gca ccg gtg gtg         739
His Ile Ser Leu Asn Tyr Ala Leu Phe Thr Ser Thr Ala Pro Val Val
            200                 205                 210 gtc gac caa ggc ttg gaa tac tac aac ctc ttt gac ggc atg gtc gat         787
Val Asp Gln Gly Leu Glu Tyr Tyr Asn Leu Phe Asp Gly Met Val Asp
            215                 220                 225 gct ttc aat gcc gcc cta gat aag atc ggc ttc ggc caa att act ctc         835
Ala Phe Asn Ala Ala Leu Asp Lys Ile Gly Phe Gly Gln Ile Thr Leu
230                 235                 240                 245 att gta gcc gaa act gga tgg ccg acc gcc ggt aac gag cct tac acg         883
Ile Val Ala Glu Thr Gly Trp Pro Thr Ala Gly Asn Glu Pro Tyr Thr
            250                 255                 260 agt gtc gcg aac gct caa act tat aac aag aac ttg ttg aat cat gtg         931
Ser Val Ala Asn Ala Gln Thr Tyr Asn Lys Asn Leu Leu Asn His Val
            265                 270                 275 acg cag aaa ggg act ccg aaa aga cct gaa tat ata atg ccg acg ttt         979
Thr Gln Lys Gly Thr Pro Lys Arg Pro Glu Tyr Ile Met Pro Thr Phe
            280                 285                 290 ttc ttc gag atg ttc aac gag aac ttg aag caa ccc aca gtt gag cag        1027
Phe Phe Glu Met Phe Asn Glu Asn Leu Lys Gln Pro Thr Val Glu Gln
            295                 300                 305 aat ttc gga ttc ttc ttc ccc aat atg aac cct gtt tat cca ttt tgg        1075
Asn Phe Gly Phe Phe Phe Pro Asn Met Asn Pro Val Tyr Pro Phe Trp
310                 315                 320                 325 tga acttgaaatg ttattgttgg ctatttaaat cttttgccag agacgcttca             1128
tatagtttct gcatattttg aaagtggaaa aaaaaaaaaa aaaaaaaaaa aaaaaaa         1185

<210> SEQ ID NO 4
<211> LENGTH: 325
<212> TYPE: PRT
<213> ORGANISM: Gossypium hirsutum

<400> SEQUENCE: 4

Met Leu Phe Leu Thr Gln Leu Leu Ser Leu Thr Asp Gly Arg Asp Ile
1               5                   10                  15

Gly Val Cys Tyr Gly Leu Asn Gly Asn Asn Leu Pro Ser Pro Gly Asp
            20                  25                  30

Val Ile Asn Leu Phe Lys Thr Ser Gly Ile Asn Asn Ile Arg Leu Tyr
            35                  40                  45

Gln Pro Tyr Pro Glu Val Leu Glu Ala Ala Arg Gly Ser Gly Ile Ser
        50                  55                  60

Leu Ser Met Ser Thr Thr Asn Glu Asp Ile Gln Ser Leu Ala Thr Asp
65                  70                  75                  80

Gln Ser Ala Ala Asp Ala Trp Val Asn Thr Asn Ile Val Pro Tyr Lys
                85                  90                  95

Glu Asp Val Gln Phe Arg Phe Ile Ile Gly Asn Glu Ala Ile Pro
            100                 105                 110

Gly Gln Ser Ser Ser Tyr Ile Pro Gly Ala Met Asn Asn Ile Met Asn
            115                 120                 125

Ser Leu Ala Ser Phe Gly Leu Gly Thr Thr Lys Val Thr Thr Val Val
```

```
                130                 135                 140
Pro Met Asn Ala Leu Ser Thr Ser Tyr Pro Pro Ser Asp Gly Ala Phe
145                 150                 155                 160

Gly Ser Asp Ile Thr Ser Ile Met Thr Ser Ile Met Ala Ile Leu Val
                165                 170                 175

Arg Gln Asp Ser Pro Leu Leu Ile Asn Val Tyr Pro Tyr Phe Ala Tyr
                180                 185                 190

Ala Ser Asp Pro Thr His Ile Ser Leu Asn Tyr Ala Leu Phe Thr Ser
                195                 200                 205

Thr Ala Pro Val Val Asp Gln Gly Leu Glu Tyr Tyr Asn Leu Phe
    210                 215                 220

Asp Gly Met Val Asp Ala Phe Asn Ala Ala Leu Asp Lys Ile Gly Phe
225                 230                 235                 240

Gly Gln Ile Thr Leu Ile Val Ala Glu Thr Gly Trp Pro Thr Ala Gly
                245                 250                 255

Asn Glu Pro Tyr Thr Ser Val Ala Asn Ala Gln Thr Tyr Asn Lys Asn
                260                 265                 270

Leu Leu Asn His Val Thr Gln Lys Gly Thr Pro Lys Arg Pro Glu Tyr
                275                 280                 285

Ile Met Pro Thr Phe Phe Glu Met Phe Asn Glu Asn Leu Lys Gln
                290                 295                 300

Pro Thr Val Glu Gln Asn Phe Gly Phe Phe Pro Asn Met Asn Pro
305                 310                 315                 320

Val Tyr Pro Phe Trp
                325

<210> SEQ ID NO 5
<211> LENGTH: 1185
<212> TYPE: DNA
<213> ORGANISM: Gossypium barbadense
<220> FEATURE:
<221> NAME/KEY: CDS
<222> LOCATION: (63)..(96)
<220> FEATURE:
<221> NAME/KEY: CDS
<222> LOCATION: (209)..(711)

<400> SEQUENCE: 5
gctgagatca agaaatatag tgaaatatgg gtccaagatt ttctgggttt ttaatctaag        60 ca atg ctg ttt tta act caa ctc ctc tct cta aca g gtaaaacaaa            106
   Met Leu Phe Leu Thr Gln Leu Leu Ser Leu Thr
   1               5                   10 cttctctaca gtgattttac agtaaatatg gctttgaaaa atatacaaca aaacatttat      166
cttcaatcca ttttaattac tgatctacta tatatgttgc ag at ggc cgt gat          219
                                                Asp Gly Arg Asp
                                                        15 att ggt gtt tgc tat ggt ttg aac ggc aac aat ctt cca tct cca gga       267
Ile Gly Val Cys Tyr Gly Leu Asn Gly Asn Asn Leu Pro Ser Pro Gly
                20                  25                  30 gat gtt att aat ctt ttc aaa act agt ggc ata aac aat atc agg ctc       315
Asp Val Ile Asn Leu Phe Lys Thr Ser Gly Ile Asn Asn Ile Arg Leu
            35                  40                  45 tac cag cct tac cct gaa gtg ctc gaa gca gca agg gga tcg gga ata       363
Tyr Gln Pro Tyr Pro Glu Val Leu Glu Ala Ala Arg Gly Ser Gly Ile
        50                  55                  60 tcc ctc tcg atg agt acg aca aac gag gac ata caa agc ctc gca acg       411
Ser Leu Ser Met Ser Thr Thr Asn Glu Asp Ile Gln Ser Leu Ala Thr
65                  70                  75
```

```
gat caa act cat caa agt gca gcc gat gca tgg gtt aac acc aac atc      459
Asp Gln Thr His Gln Ser Ala Ala Asp Ala Trp Val Asn Thr Asn Ile
 80              85                  90                  95 gtc cct tat aag gaa gat gtt caa ttc agg ttc atc atc att ggg aat      507
Val Pro Tyr Lys Glu Asp Val Gln Phe Arg Phe Ile Ile Ile Gly Asn
            100                 105                 110 gaa gcc att cca gga cag tca agc tct tac att cct ggt gcc atg aac      555
Glu Ala Ile Pro Gly Gln Ser Ser Ser Tyr Ile Pro Gly Ala Met Asn
        115                 120                 125 aac ata atg aac tcg ctc gcc tca ttt ggg cta ggc acg acg aag gtt      603
Asn Ile Met Asn Ser Leu Ala Ser Phe Gly Leu Gly Thr Thr Lys Val
    130                 135                 140 acg acc gtg gtc ccg atg aat gcc cta agt acc tcg tac cct cct tca      651
Thr Thr Val Val Pro Met Asn Ala Leu Ser Thr Ser Tyr Pro Pro Ser
145                 150                 155 gac ggc gct ttt gga agc gat ata aca tcg atc atg act agt atc atg      699
Asp Gly Ala Phe Gly Ser Asp Ile Thr Ser Ile Met Thr Ser Ile Met
160                 165                 170                 175 gcc att ctg gtt tgacaggatt cgcccctcct gatcaatgtg tacccttatt          751
Ala Ile Leu Val ttgcctatgc ctcagacccc actcatattt ccctcaacta cgccttgttc acctcgaccg    811
caccggtggt ggtcgaccaa cgcttggaat actacaacct ctttgacggc atagtcgatg    871 cttcaatgc cgcccagat aagatcggct tcggccaaat tactctcatt gtagccgaaa      931
ctggatggcc gaccgccggt aacgagcctt acacgagtgt cgcgaacgct caaacttata    991
acaagaactt gttgaatcat gtgacgcaga aagggactcc gaaaagacct gaatatataa   1051
tgccgacgtt tttcttcgag atgttcaacg agaacttgaa gcaacccaca gttgagcaga   1111
tgttcaacga gatgttcaac gagaacttga aatgttattg ttggctattt aaatcttttg   1171
ccagagacgc ttca                                                     1185

<210> SEQ ID NO 6
<211> LENGTH: 179
<212> TYPE: PRT
<213> ORGANISM: Gossypium barbadense

<400> SEQUENCE: 6

Met Leu Phe Leu Thr Gln Leu Leu Ser Leu Thr Asp Gly Arg Asp Ile
 1               5                  10                  15

Gly Val Cys Tyr Gly Leu Asn Gly Asn Asn Leu Pro Ser Pro Gly Asp
            20                  25                  30

Val Ile Asn Leu Phe Lys Thr Ser Gly Ile Asn Asn Ile Arg Leu Tyr
        35                  40                  45

Gln Pro Tyr Pro Glu Val Leu Glu Ala Ala Arg Gly Ser Gly Ile Ser
    50                  55                  60

Leu Ser Met Ser Thr Thr Asn Glu Asp Ile Gln Ser Leu Ala Thr Asp
65                  70                  75                  80

Gln Thr His Gln Ser Ala Ala Asp Ala Trp Val Asn Thr Asn Ile Val
                85                  90                  95

Pro Tyr Lys Glu Asp Val Gln Phe Arg Phe Ile Ile Ile Gly Asn Glu
            100                 105                 110

Ala Ile Pro Gly Gln Ser Ser Ser Tyr Ile Pro Gly Ala Met Asn Asn
        115                 120                 125

Ile Met Asn Ser Leu Ala Ser Phe Gly Leu Gly Thr Thr Lys Val Thr
    130                 135                 140
```

```
Thr Val Val Pro Met Asn Ala Leu Ser Thr Ser Tyr Pro Pro Ser Asp
145                 150                 155                 160

Gly Ala Phe Gly Ser Asp Ile Thr Ser Ile Met Thr Ser Ile Met Ala
                165                 170                 175

Ile Leu Val

<210> SEQ ID NO 7
<211> LENGTH: 6877
<212> TYPE: DNA
<213> ORGANISM: Gossypium hirsutum
<220> FEATURE:
<221> NAME/KEY: CDS
<222> LOCATION: (3337)..(3406)
<220> FEATURE:
<221> NAME/KEY: CDS
<222> LOCATION: (3501)..(4441)

<400> SEQUENCE: 7
ttcaaactta ctcgcttgca caaaaataat tttataaaag tatttaaaat ataaaatttt      60
tatgttgata atatttttat atacatttta tattttaaga aataataatt ttttaggaat     120
tagaaaaaaa atgtagaata atatcattga tattttaatt tttcaaaaaa ttaaaaataa     180
gttcacgtag tctaatttta tctatttttaa ttttatact ttcaaattga gataaatatc     240
aaagaacttt tggttcaata tgcaattga tacttaaatt ttaatttgat gtaattatta     300
catgaaactt ggcttgtggt ttatacgtat acatgaaatt tttattttga ttcaattgta     360
cgcatttaaa gaaatgaaaa tggttctaat tcaataatat tattagtgat ttgtgaaatt     420 taaaacttt atgcattaaa ccacacaaaa tcagagttta tgtatgatat tgcacattgg     480
actatagttc atgcatattt tttatatttt atccatgtca aattttgaaa tttcattctt     540
aacttatatg atagcagtta aatttgttaa gtcaaactct agtattagtt atatactata     600
cataacttgt agagtttagt ttaagttcac taatttgatt atttttatc tgtttatttt     660 ttcaatttca agatttaagt tttaagctta acttaaacaa tagtcattaa atttattaac     720
taaaatgtcc tggggttttt tgtaagtatt ataatatgtt tgccacgtga gattttggta     780
aaagtagagt ttaacttaac aaatttaatg gctactactt agtaaggatt agaatttcaa     840
aattaaaaaa aaaattatag aggctaaaga tgatcaaatt agaggtttaa attaagtcaa     900
attaaaatag ttctggatat taactatta aattaattaa tgtcattata aaattagagg     960
tctaaattat gtaaaattaa aatataaaaa ctaaatctcg aatgtgagta tagtataagg    1020
atcaaaagtg attttggtca tttttcttta tttacaaata ttcttagaga tgctcttta    1080 tatataatgg tttctaatgt gatatgcgcg gcatataatt ttatgtgttt aatttatttt    1140
attaattatt taataatat attttttaatt actataatta atgtaaaata ttttttatta    1200
tttgaatcac tgcacaaaat taaaatatac taacttaatt aacaattcaa atataataat    1260
aatctaaatt ataattaaag catttttaca atattcagta tataatatag ttttactta    1320 tataattaat acaaagaaat attattcaaa ataataacta atcaacataa ttactatata    1380
tcaattattt tgatatttcg aacataatgc taataaaaaa tttcctaatc attattaaat    1440
catttgtata aactataaag aaattgatat attgtaaatt aaacttttaa ctattcaatt    1500
ttttcttaat agtcaataaa ttaatcataa taattcataa ttaatatata attaacataa    1560
ccataacata gaattttta ttttggccca ttaaatttt taaaattta aattagtaaa    1620 ggaaaaatta cactttgacc ccttaaaaat gataaaattt tattttaatc ctttaaaatt    1680 gacatttta ctattgtaaa aattacaatt taattttgcc ccctaaaaa attttttctag    1740
```

-continued

| | |
|---|---|
| cttcgccctt gtgtataaat atattaatta caatttttat atttgaatta tataaataat | 1800 |
| taaattttga tatttaaaac taaagtaatc tcttttttt ttacttttt ttaattgaaa | 1860 |
| cataatggtt taaatatcta tattacgtat gaagtaattt aatataaatt ttattttaat | 1920 |
| ttattattat ataaattcat ttagtaaaaa cttttaatag aatcaaaatt tttatttgta | 1980 |
| aattcgataa cttttcttat caagtaaatt tgttgaatta aatatttagt aaaattaata | 2040 |
| tttttattta taaatatgat aaatcttata aaaataaaa aaatatttaa aatgaaaaac | 2100 |
| attgtacaaa ggctatataa gaagttcaaa agtttcttcg accctgtact ctaatagaga | 2160 |
| ttatagatag attatagaac tattcatagt ttctcttaac cttttaaataa gaattttagt | 2220 |
| gtactcaaac ttacatatt ttatattgat aataatgtca ataccagccg agttaagatt | 2280 |
| cactcgacat taatgttgaa aatttttaat aaaagaaaat gttgataagt taattagaac | 2340 |
| acaagcaagc acaaatttaa gtggtaagta aggtccttga ccctaatgga aaaattgtta | 2400 |
| tgttgattaa attataaatt aatttaaggt aaaattatat tttgacctaa aaaaatgaaa | 2460 |
| aaaatatatc tagtttcttc gaaaatgaaa agaaaataat aaattgatac attataaaat | 2520 |
| ttatggcatt tctaaaaaaa ttctgaattt gatgaaatta taataaaaaa aaagtttaaa | 2580 |
| aacatataga tttcaagaat agtgggaaaa ttatatttga caacactga agaaatccaa | 2640 |
| agcattagca gaaatggat caccaaatca caaacaatca gtgaaaagta atgataatta | 2700 |
| attgaaagtg agcatttaaa tttgatagcc atatacttcc tgctgaatt ataggttctc | 2760 |
| attaatgcaa ttaaattata tttgtcactt tttgaatgaa ataaatgaca cagttcatct | 2820 |
| atttttttc tttcaatcgc ccatcaaaat accgaaaatg taactacatt aaaaaagatc | 2880 |
| gaaaatatt catattttga tattttaata gattgtgtgt tcaaggcgta atgtactaaa | 2940 |
| aaattatgat ggtgttgtcg ctgtatgtcc ataaaattca atgtattcgc atgtatcaaa | 3000 |
| tgtaaatttt gacacaagtt attctaataa taatcaagtt attttatac atgagataca | 3060 |
| tctcaaaatt attttatat atccgaaaaa tcataacgta cgatcaaact agaaagagga | 3120 |
| agtgtcaaaa cctattcatt atatgcaaat atgatgggac acgataccct catgcattga | 3180 |
| tatctcatat tgtccaaaaa ctcagaatcc ttttgaaaa aaaaaaattc cagagagagt | 3240 |
| gtataaatcc agcagtgtgc acaagaaacg agcaccagtt attgacattc ctttgtaaaa | 3300 |
| aaaaaaagaa gctgagatca agaaatatag tgaaat atg ggt cca aca ttt tct | 3354 |
|                                                             Met Gly Pro Thr Phe Ser<br>                                                             1                 5 | |
| ggg ttt tta atc tca gca atg gtg ttt tta act caa ctc ctc tct cta<br>Gly Phe Leu Ile Ser Ala Met Val Phe Leu Thr Gln Leu Leu Ser Leu<br>          10                   15                   20 | 3402 |
| aca g gtaaaacaaa cttctctaca gtgattttac ggtaagtatg gctttgaaaa<br>Thr | 3456 |
| atatacaaca aaacatttat actgatctac catatatgtt gcag at ggc cgt gat<br>                                                                     Asp Gly Arg Asp<br>                                                                          25 | 3511 |
| att ggt gtt tgc tat ggt ttg aac ggc aac aat ctt cca tct cca gga<br>Ile Gly Val Cys Tyr Gly Leu Asn Gly Asn Asn Leu Pro Ser Pro Gly<br>        30                       35                          40 | 3559 |
| gat gtt att aat ctt tac aaa act agt ggc ata aac aat atc agg ctc<br>Asp Val Ile Asn Leu Tyr Lys Thr Ser Gly Ile Asn Asn Ile Arg Leu<br>    45                       50                      55 | 3607 |
| tac cag cct tac cct gaa gtg ctc gaa gca gca agg gga tcg gga ata<br>Tyr Gln Pro Tyr Pro Glu Val Leu Glu Ala Ala Arg Gly Ser Gly Ile<br>60                   65                      70                   75 | 3655 |

| | | |
|---|---|---|
| tcc ctc tcg atg ggt ccg aga aac gag gac ata caa agc ctc gca aaa<br>Ser Leu Ser Met Gly Pro Arg Asn Glu Asp Ile Gln Ser Leu Ala Lys<br>       80         85         90 | | 3703 |
| gat caa agt gca gcc gat gca tgg gtt aac acc aac atc gtc cct tat<br>Asp Gln Ser Ala Ala Asp Ala Trp Val Asn Thr Asn Ile Val Pro Tyr<br>    95          100         105 | | 3751 |
| aag gac gat gtt cag ttc aag ttg atc act att ggg aat gaa gcc att<br>Lys Asp Asp Val Gln Phe Lys Leu Ile Thr Ile Gly Asn Glu Ala Ile<br>      110         115        120 | | 3799 |
| tca gga caa tca agc tct tac att cct gat gcc atg aac aac ata atg<br>Ser Gly Gln Ser Ser Ser Tyr Ile Pro Asp Ala Met Asn Asn Ile Met<br>125         130         135 | | 3847 |
| aac tcg ctc gcc tta ttt ggg tta ggc acg acg aag gtt acg acc gtg<br>Asn Ser Leu Ala Leu Phe Gly Leu Gly Thr Thr Lys Val Thr Thr Val<br>140         145         150        155 | | 3895 |
| gtc ccg atg aat gcc cta agt acc tcg tac cct cct tca gac ggc gct<br>Val Pro Met Asn Ala Leu Ser Thr Ser Tyr Pro Pro Ser Asp Gly Ala<br>         160         165        170 | | 3943 |
| ttt gga agc gat ata aca tcg atc atg act agt atc atg gcc att ctg<br>Phe Gly Ser Asp Ile Thr Ser Ile Met Thr Ser Ile Met Ala Ile Leu<br>         175         180        185 | | 3991 |
| gct gta cag gat tcg ccc ctc ctg atc aat gtg tac cct tat ttt gcc<br>Ala Val Gln Asp Ser Pro Leu Leu Ile Asn Val Tyr Pro Tyr Phe Ala<br>      190         195        200 | | 4039 |
| tat gcc tca gac ccc act cat att tcc ctc gat tac gcc ttg ttc acc<br>Tyr Ala Ser Asp Pro Thr His Ile Ser Leu Asp Tyr Ala Leu Phe Thr<br>205         210         215 | | 4087 |
| tcg acc gca ccg gtg gtg gtc gac caa ggc ttg gaa tac tac aac ctc<br>Ser Thr Ala Pro Val Val Val Asp Gln Gly Leu Glu Tyr Tyr Asn Leu<br>220         225         230        235 | | 4135 |
| ttt gac ggc atg gtc gat gct ttc aat gcc gcc cta gat aag atc ggc<br>Phe Asp Gly Met Val Asp Ala Phe Asn Ala Ala Leu Asp Lys Ile Gly<br>         240         245        250 | | 4183 |
| ttc ggc caa att act ctc att gta gcc gaa act gga tgg ccg acc gcc<br>Phe Gly Gln Ile Thr Leu Ile Val Ala Glu Thr Gly Trp Pro Thr Ala<br>         255         260        265 | | 4231 |
| ggt aac gag cct tac acg agt gtc gcg aac gct caa act tat aac aag<br>Gly Asn Glu Pro Tyr Thr Ser Val Ala Asn Ala Gln Thr Tyr Asn Lys<br>    270          275         280 | | 4279 |
| aac ttg tta aat cat gtg acg cag aag ggg act ccg aaa aga cct gaa<br>Asn Leu Leu Asn His Val Thr Gln Lys Gly Thr Pro Lys Arg Pro Glu<br>285         290         295 | | 4327 |
| tat ata atg ccg acg ttt ttc ttc gag atg ttc aac gag gat ttg aag<br>Tyr Ile Met Pro Thr Phe Phe Phe Glu Met Phe Asn Glu Asp Leu Lys<br>300         305         310        315 | | 4375 |
| caa ccc aca gtt gag cag aat ttc gga ttc ttc ttc ccc aat atg aac<br>Gln Pro Thr Val Glu Gln Asn Phe Gly Phe Phe Phe Pro Asn Met Asn<br>         320         325        330 | | 4423 |
| cct gtt tat cca ttt tgg tgaagttgaa atgttgttgg ctatttaaat<br>Pro Val Tyr Pro Phe Trp<br>         335 | | 4471 |
| cttttgccag agacgcttca tatagtttct gcatattttg aaagtggaaa atcaatctaa | | 4531 |
| atattaataa gttttatgtg ttgttttta attaaataaa atttaaata ttttaaaaat | | 4591 |
| atctttattg gtaattaaat attaaataaa aagtttaata ttcaaatttt atcaattcaa | | 4651 |
| aaataaaata aaaatatatt aaatttattt ttacgaataa attgatttc tattaataca | | 4711 |
| gatttgaat aatttgatat aaattttaaa ttcaacaata gtaattttga tcacatcaaa | | 4771 |

```
ggagaaaggg aaagatttaa ctttaattgg tgacctaata taacacgttg aaaacggagc   4831
tcccaggaag gcaaaatgac ttgtaatgac gaaagagatg tccaagtaga atctgcatta   4891
aagtgaaaaa agcataaaag gataagtaaa ctcatgatct gacataaatt gaagttctat   4951
aaaatgcaac tttcatctag aaacaaggta tgtcttaaat gatgttttat gaatttgtct   5011
taactgggtt ttatgcaatg aattcatgga tagcacctca ctaattatac gttgctggtt   5071
tatatgagag tggtgcagaa gttaattgtg ctttaaatac ttgcttagtg ttcaagaaat   5131
ttgaaaagta ttatatattt ataataaaaa taattcagat ccgactcaat ctagtaaaat   5191
tttacaaaca ttctaaaggg gatcttcttt tttctctact tattgatcag tgttatatac   5251
ttataataaa gacaacctga tttgagatcc ggcctaatat aataaaattc tacagacatc   5311
tcaagggaga gatcttcttc ttccctacat cttgaccttt ttgatcaaaa tttcctcccc   5371
tctatttcca cattggttga tcatatgaat caacagaaag gtaccaaaaa gttttttaaaa  5431 ataaacaaag gggttcttat gaaattcata tgatatattg ggtctaatta ttagaatcaa   5491
ttttaagttt aaacaaattt aaaattcaaa actcaattcc attttttgttt gaacggaaag   5551 ttactaattg ttaagaaaaa taattcatat tagcgtataa attggaaatt gaccaaaact   5611
aaaattattg tatagttaat ctatattaaa aggacatgta attaaaaacc attaaaacta   5671
ttatagaata aattaaatct tcattctata catacaaagt cattaataat taaaaaacta   5731
tattaagata taaactatat tcaaaaaata ttaaaaacaa taactaaata aaaaaaacaa   5791
ttgaaaatta cgaattaatg ttaaaatcaa gggacttaaa taaaaatatc ccaaaataca   5851
aaacattagc ttcctttccc atccacgtga ttgcaaagtt tacatggtgt ttcctagtgc   5911
ttgtgcgact ccaaccttttt atttactttt tcttttctt tatttgaaca attatttgat   5971
aatgattaga atttttgggat tgttgctcat cgtacgtgca acacttaaaa tcactatgat   6031
ttttcataat ttatataacc tatatcgttt tggaaattaa tgttattatt tatattgttt   6091
taataaaaat accatctacc tcttttaatt tatgatccat ttcttatttg aaaattcaaa   6151
ttgacagttg tctaactaaa caccatcgca ctccaataaa attgtaattt tttctatcgt   6211
gaatagtaca ctcaaaagta tgttgttaac aaacaaatca attagccttt ttctacctct   6271
attcatcatc ttcttaatag cgtgtttatg tcacgtgttg agatttttagt tccggtcacg   6331 tgtggcctta aacccgaatt tcttacgcat gagtctaagt tagcctctga tcctcgctat   6391
ggagatgctt ggcacagttt acctaggtaa gtaaacaagg aatagagcta ttagaaagca   6451
tcagagagtt aggagaatgt ggaagtgttt ctattactca aagctaactt ggatacaaat   6511
aaaagaggga gcctctcctt taggcaagcc tattttgatc tgacggttgc aattaatctc   6571
gaataggagg ggtcgaactt ctcactcagt ttcacattat ctcttggtgc ttagttggcc   6631
tccgccttga gacacattca aataacaccct agtcttaaca cttttggctt cttattgtgc   6691
gtatccttca ttactcaaat gccacaaagc ctcattactt aagactctcg gtcgctccca   6751
ctaccttcga ctttagactc atctaagatc ttcccaatcg tagacaactt ggccttggtg   6811
gggaaatctt gcaccctacg gggccttaca taagaagcaa ttaaatggct ttctctcacc   6871
cacctt                                                               6877
```

<210> SEQ ID NO 8
<211> LENGTH: 337
<212> TYPE: PRT
<213> ORGANISM: Gossypium hirsutum

<400> SEQUENCE: 8

```
Met Gly Pro Thr Phe Ser Gly Phe Leu Ile Ser Ala Met Val Phe Leu
1               5                   10                  15

Thr Gln Leu Leu Ser Leu Thr Asp Gly Arg Asp Ile Gly Val Cys Tyr
            20                  25                  30

Gly Leu Asn Gly Asn Asn Leu Pro Ser Pro Gly Asp Val Ile Asn Leu
        35                  40                  45

Tyr Lys Thr Ser Gly Ile Asn Asn Ile Arg Leu Tyr Gln Pro Tyr Pro
50                  55                  60

Glu Val Leu Glu Ala Ala Arg Gly Ser Gly Ile Ser Leu Ser Met Gly
65                  70                  75                  80

Pro Arg Asn Glu Asp Ile Gln Ser Leu Ala Lys Asp Gln Ser Ala Ala
                85                  90                  95

Asp Ala Trp Val Asn Thr Asn Ile Val Pro Tyr Lys Asp Asp Val Gln
            100                 105                 110

Phe Lys Leu Ile Thr Ile Gly Asn Glu Ala Ile Ser Gly Gln Ser Ser
        115                 120                 125

Ser Tyr Ile Pro Asp Ala Met Asn Asn Ile Met Asn Ser Leu Ala Leu
130                 135                 140

Phe Gly Leu Gly Thr Thr Lys Val Thr Thr Val Val Pro Met Asn Ala
145                 150                 155                 160

Leu Ser Thr Ser Tyr Pro Pro Ser Asp Gly Ala Phe Gly Ser Asp Ile
                165                 170                 175

Thr Ser Ile Met Thr Ser Ile Met Ala Ile Leu Ala Val Gln Asp Ser
            180                 185                 190

Pro Leu Leu Ile Asn Val Tyr Pro Tyr Phe Ala Tyr Ala Ser Asp Pro
        195                 200                 205

Thr His Ile Ser Leu Asp Tyr Ala Leu Phe Thr Ser Thr Ala Pro Val
210                 215                 220

Val Val Asp Gln Gly Leu Glu Tyr Tyr Asn Leu Phe Asp Gly Met Val
225                 230                 235                 240

Asp Ala Phe Asn Ala Ala Leu Asp Lys Ile Gly Phe Gly Gln Ile Thr
                245                 250                 255

Leu Ile Val Ala Glu Thr Gly Trp Pro Thr Ala Gly Asn Glu Pro Tyr
            260                 265                 270

Thr Ser Val Ala Asn Ala Gln Thr Tyr Asn Lys Asn Leu Leu Asn His
        275                 280                 285

Val Thr Gln Lys Gly Thr Pro Lys Arg Pro Glu Tyr Ile Met Pro Thr
290                 295                 300

Phe Phe Phe Glu Met Phe Asn Glu Asp Leu Lys Gln Pro Thr Val Glu
305                 310                 315                 320

Gln Asn Phe Gly Phe Phe Pro Asn Met Asn Pro Val Tyr Pro Phe
                325                 330                 335

Trp
```

<210> SEQ ID NO 9
<211> LENGTH: 1250
<212> TYPE: DNA
<213> ORGANISM: Gossypium hirsutum
<220> FEATURE:
<221> NAME/KEY: CDS
<222> LOCATION: (66)..(1076)

<400> SEQUENCE: 9
gcaccagtta ttgacattcc tttgtaaaaa aaaaagaag ctgagatcaa gaaatatagt    60

```
gaaat atg ggt cca aca ttt tct ggg ttt tta atc tca gca atg gtg ttt    110
      Met Gly Pro Thr Phe Ser Gly Phe Leu Ile Ser Ala Met Val Phe
      1               5                   10                  15 tta act caa ctc ctc tct cta aca gat ggc cgt gat att ggt gtt tgc     158
Leu Thr Gln Leu Leu Ser Leu Thr Asp Gly Arg Asp Ile Gly Val Cys
                20                  25                  30 tat ggt ttg aac ggc aac aat ctt cca tct cca gga gat gtt att aat     206
Tyr Gly Leu Asn Gly Asn Asn Leu Pro Ser Pro Gly Asp Val Ile Asn
            35                  40                  45 ctt tac aaa act agt ggc ata aac aat atc agg ctc tac cag cct tac     254
Leu Tyr Lys Thr Ser Gly Ile Asn Asn Ile Arg Leu Tyr Gln Pro Tyr
        50                  55                  60 cct gaa gtg ctc gaa gca gca agg gga tcg gga ata tcc ctc tcg atg     302
Pro Glu Val Leu Glu Ala Ala Arg Gly Ser Gly Ile Ser Leu Ser Met
    65                  70                  75 ggt ccg aga aac gag gac ata caa agc ctc gca aaa gat caa agt gca     350
Gly Pro Arg Asn Glu Asp Ile Gln Ser Leu Ala Lys Asp Gln Ser Ala
80                  85                  90                  95 gcc gat gca tgg gtt aac acc aac atc gtc cct tat aag gac gat gtt     398
Ala Asp Ala Trp Val Asn Thr Asn Ile Val Pro Tyr Lys Asp Asp Val
                100                 105                 110 cag ttc aag ttg atc act att ggg aat gaa gcc att tca gga caa tca     446
Gln Phe Lys Leu Ile Thr Ile Gly Asn Glu Ala Ile Ser Gly Gln Ser
            115                 120                 125 agc tct tac att cct gat gcc atg aac aac ata atg aac tcg ctc gcc     494
Ser Ser Tyr Ile Pro Asp Ala Met Asn Asn Ile Met Asn Ser Leu Ala
        130                 135                 140 tta ttt ggg tta ggc acg acg aag gtt acg acc gtg gtc ccg atg aat     542
Leu Phe Gly Leu Gly Thr Thr Lys Val Thr Thr Val Val Pro Met Asn
    145                 150                 155 gcc cta agt acc tcg tac cct cct tca gac ggc gct ttt gga agc gat     590
Ala Leu Ser Thr Ser Tyr Pro Pro Ser Asp Gly Ala Phe Gly Ser Asp
160                 165                 170                 175 ata aca tcg atc atg act agt atc atg gcc att ctg gct gta cag gat     638
Ile Thr Ser Ile Met Thr Ser Ile Met Ala Ile Leu Ala Val Gln Asp
                180                 185                 190 tcg ccc ctc ctg atc aat gtg tac cct tat ttt gcc tat gcc tca gac     686
Ser Pro Leu Leu Ile Asn Val Tyr Pro Tyr Phe Ala Tyr Ala Ser Asp
            195                 200                 205 ccc act cat att tcc ctc gat tac gcc ttg ttc acc tcg acc gca ccg     734
Pro Thr His Ile Ser Leu Asp Tyr Ala Leu Phe Thr Ser Thr Ala Pro
        210                 215                 220 gtg gtg gtc gac caa ggc ttg gaa tac tac aac ctc ttt gac ggc atg     782
Val Val Val Asp Gln Gly Leu Glu Tyr Tyr Asn Leu Phe Asp Gly Met
    225                 230                 235 gtc gat gct ttc aat gcc gcc cta gat aag atc ggc ttc ggc caa att     830
Val Asp Ala Phe Asn Ala Ala Leu Asp Lys Ile Gly Phe Gly Gln Ile
240                 245                 250                 255 act ctc att gta gcc gaa act gga tgg ccg acc gcc ggt aac gag cct     878
Thr Leu Ile Val Ala Glu Thr Gly Trp Pro Thr Ala Gly Asn Glu Pro
                260                 265                 270 tac acg agt gtc gcg aac gct caa act tat aac aag aac ttg tta aat     926
Tyr Thr Ser Val Ala Asn Ala Gln Thr Tyr Asn Lys Asn Leu Leu Asn
            275                 280                 285 cat gtg acg cag aag ggg act ccg aaa aga cct gaa tat ata atg ccg     974
His Val Thr Gln Lys Gly Thr Pro Lys Arg Pro Glu Tyr Ile Met Pro
        290                 295                 300 acg ttt ttc ttc gag atg ttc aac gag gat ttg aag caa ccc aca gtt    1022
Thr Phe Phe Phe Glu Met Phe Asn Glu Asp Leu Lys Gln Pro Thr Val
    305                 310                 315
```

```
gag cag aat ttc gga ttc ttc ttc ccc aat atg aac cct gtt tat cca    1070
Glu Gln Asn Phe Gly Phe Phe Phe Pro Asn Met Asn Pro Val Tyr Pro
320                 325                 330                 335 ttt tgg tgaagttgaa atgttgttgg ctatttaaat cttttgccag agacgcttca    1126
Phe Trp tatagtttct gcatattttg aaagtggaaa atcaatctaa atattaataa gtttatgtg    1186 ttgttttta attaaataaa attttaaata ttataaaaaa aaaaaaaaaa aaaaaaaaa    1246 aaaa                                                              1250

<210> SEQ ID NO 10
<211> LENGTH: 337
<212> TYPE: PRT
<213> ORGANISM: Gossypium hirsutum

<400> SEQUENCE: 10

Met Gly Pro Thr Phe Ser Gly Phe Leu Ile Ser Ala Met Val Phe Leu
1               5                   10                  15

Thr Gln Leu Leu Ser Leu Thr Asp Gly Arg Asp Ile Gly Val Cys Tyr
                20                  25                  30

Gly Leu Asn Gly Asn Asn Leu Pro Ser Pro Gly Asp Val Ile Asn Leu
            35                  40                  45

Tyr Lys Thr Ser Gly Ile Asn Asn Ile Arg Leu Tyr Gln Pro Tyr Pro
    50                  55                  60

Glu Val Leu Glu Ala Ala Arg Gly Ser Gly Ile Ser Leu Ser Met Gly
65                  70                  75                  80

Pro Arg Asn Glu Asp Ile Gln Ser Leu Ala Lys Asp Gln Ser Ala Ala
                85                  90                  95

Asp Ala Trp Val Asn Thr Asn Ile Val Pro Tyr Lys Asp Asp Val Gln
            100                 105                 110

Phe Lys Leu Ile Thr Ile Gly Asn Glu Ala Ile Ser Gly Gln Ser Ser
        115                 120                 125

Ser Tyr Ile Pro Asp Ala Met Asn Asn Ile Met Asn Ser Leu Ala Leu
    130                 135                 140

Phe Gly Leu Gly Thr Thr Lys Val Thr Thr Val Val Pro Met Asn Ala
145                 150                 155                 160

Leu Ser Thr Ser Tyr Pro Pro Ser Asp Gly Ala Phe Gly Ser Asp Ile
                165                 170                 175

Thr Ser Ile Met Thr Ser Ile Met Ala Ile Leu Ala Val Gln Asp Ser
            180                 185                 190

Pro Leu Leu Ile Asn Val Tyr Pro Tyr Phe Ala Tyr Ala Ser Asp Pro
        195                 200                 205

Thr His Ile Ser Leu Asp Tyr Ala Leu Phe Thr Ser Thr Ala Pro Val
    210                 215                 220

Val Val Asp Gln Gly Leu Glu Tyr Tyr Asn Leu Phe Asp Gly Met Val
225                 230                 235                 240

Asp Ala Phe Asn Ala Ala Leu Asp Lys Ile Gly Phe Gly Gln Ile Thr
                245                 250                 255

Leu Ile Val Ala Glu Thr Gly Trp Pro Thr Ala Gly Asn Glu Pro Tyr
            260                 265                 270

Thr Ser Val Ala Asn Ala Gln Thr Tyr Asn Lys Asn Leu Leu Asn His
        275                 280                 285

Val Thr Gln Lys Gly Thr Pro Lys Arg Pro Glu Tyr Ile Met Pro Thr
    290                 295                 300
```

```
Phe Phe Phe Glu Met Phe Asn Glu Asp Leu Lys Gln Pro Thr Val Glu
305                 310                 315                 320

Gln Asn Phe Gly Phe Phe Pro Asn Met Asn Pro Val Tyr Pro Phe
                325                 330                 335

Trp

<210> SEQ ID NO 11
<211> LENGTH: 1186
<212> TYPE: DNA
<213> ORGANISM: Gossypium barbadense
<220> FEATURE:
<221> NAME/KEY: CDS
<222> LOCATION: (27)..(96)
<220> FEATURE:
<221> NAME/KEY: CDS
<222> LOCATION: (191)..(1131)

<400> SEQUENCE: 11
gctgagatca agaaatatag tgaaat atg ggt cca aca ttt tct ggg ttt tta       53
                            Met Gly Pro Thr Phe Ser Gly Phe Leu
                              1               5 atc tca gca atg gtg ttt tta act caa ctc ctc tct cta aca g              96
Ile Ser Ala Met Val Phe Leu Thr Gln Leu Leu Ser Leu Thr
 10              15                  20 gtaaaacaaa cttctctaca gtgattttac ggtaagtatg gctttgaaaa atatacaaca    156
aaacatttat actgatctac catatatgtt gcag at ggc cgt gat att ggt gtt    210
                                      Asp Gly Arg Asp Ile Gly Val
                                                 25              30 tgc tat ggt ttg aac ggc aac aat ctt cca tct cca gga gat gtt att     258
Cys Tyr Gly Leu Asn Gly Asn Asn Leu Pro Ser Pro Gly Asp Val Ile
                35                  40                  45 aat ctt tac aaa act agt ggc ata aac aat atc agg ctc tac cag tct     306
Asn Leu Tyr Lys Thr Ser Gly Ile Asn Asn Ile Arg Leu Tyr Gln Ser
        50                  55                  60 tac cct gaa gtg ctc gaa gca gca agg gga tcg gga ata tcc ctc tcg     354
Tyr Pro Glu Val Leu Glu Ala Ala Arg Gly Ser Gly Ile Ser Leu Ser
    65                  70                  75 atg ggt ccg aga aac gag gac ata caa agc ctc gca aaa gat caa agt     402
Met Gly Pro Arg Asn Glu Asp Ile Gln Ser Leu Ala Lys Asp Gln Ser
80                  85                  90 gca gcc gat gca tgg gtt aac acc aac atc gtc cct tat aag gac gat     450
Ala Ala Asp Ala Trp Val Asn Thr Asn Ile Val Pro Tyr Lys Asp Asp
95                  100                 105                 110 gtt cag ttc aag ttg atc act att ggg aat gaa gcc att tca gga caa     498
Val Gln Phe Lys Leu Ile Thr Ile Gly Asn Glu Ala Ile Ser Gly Gln
                115                 120                 125 tca agc tct tac att cct gat gcc atg aac aac ata atg aac tcg ctc     546
Ser Ser Ser Tyr Ile Pro Asp Ala Met Asn Asn Ile Met Asn Ser Leu
            130                 135                 140 gcc tta ttt ggg tta ggc acg acg aag gtt acg acc gtg gtc ccg atg     594
Ala Leu Phe Gly Leu Gly Thr Thr Lys Val Thr Thr Val Val Pro Met
        145                 150                 155 aat gcc cta agt acc tcg tac cct cct tca gac ggc gct ttt gga agc     642
Asn Ala Leu Ser Thr Ser Tyr Pro Pro Ser Asp Gly Ala Phe Gly Ser
    160                 165                 170 gat ata aca tcg atc atg act agt atc atg gcc att ctg gct gta cag    690
Asp Ile Thr Ser Ile Met Thr Ser Ile Met Ala Ile Leu Ala Val Gln
175                 180                 185                 190 gat tcg ccc ctc ctg atc aat gtg tac cct tat ttt gcc tat gcc tca    738
Asp Ser Pro Leu Leu Ile Asn Val Tyr Pro Tyr Phe Ala Tyr Ala Ser
                195                 200                 205
```

```
gac ccc act cat att tcc ctc gat tac gcc ttg ttc acc tcg acc gca      786
Asp Pro Thr His Ile Ser Leu Asp Tyr Ala Leu Phe Thr Ser Thr Ala
            210                 215                 220 ccg gtg gtg gtc gac caa ggc ttg gaa tac tac aac ctc ttt gac ggc      834
Pro Val Val Val Asp Gln Gly Leu Glu Tyr Tyr Asn Leu Phe Asp Gly
            225                 230                 235 atg gtc gat gct ttc aat gcc gcc cta gat aag atc ggc ttc ggc caa      882
Met Val Asp Ala Phe Asn Ala Ala Leu Asp Lys Ile Gly Phe Gly Gln
        240                 245                 250 att act ctc att gta gcc gaa act gga tgg ccg acc gcc ggt aac gag      930
Ile Thr Leu Ile Val Ala Glu Thr Gly Trp Pro Thr Ala Gly Asn Glu
255                 260                 265                 270 cct tac acg agt gtc gcg aac gct caa act tat aac aag aac ttg tta      978
Pro Tyr Thr Ser Val Ala Asn Ala Gln Thr Tyr Asn Lys Asn Leu Leu
                275                 280                 285 aat cat gtg acg cag aag ggg act ccg aaa aga cct gaa tat ata atg     1026
Asn His Val Thr Gln Lys Gly Thr Pro Lys Arg Pro Glu Tyr Ile Met
            290                 295                 300 ccg acg ttt ttc ttc gag atg ttc aac gag gat ttg aag caa ccc aca     1074
Pro Thr Phe Phe Phe Glu Met Phe Asn Glu Asp Leu Lys Gln Pro Thr
            305                 310                 315 gtt gag cag aat ttc gga ttc ttc ttc ccc aat atg aac cct gtt tat     1122
Val Glu Gln Asn Phe Gly Phe Phe Phe Pro Asn Met Asn Pro Val Tyr
        320                 325                 330 cca ttt tgg tgaagttgaa atgttgttgg ctatttaaat cttttgccag             1171
Pro Phe Trp
335 agacgcttca tatag                                                    1186

<210> SEQ ID NO 12
<211> LENGTH: 337
<212> TYPE: PRT
<213> ORGANISM: Gossypium barbadense

<400> SEQUENCE: 12

Met Gly Pro Thr Phe Ser Gly Phe Leu Ile Ser Ala Met Val Phe Leu
1               5                   10                  15

Thr Gln Leu Leu Ser Leu Thr Asp Gly Arg Asp Ile Gly Val Cys Tyr
            20                  25                  30

Gly Leu Asn Gly Asn Asn Leu Pro Ser Pro Gly Asp Val Ile Asn Leu
        35                  40                  45

Tyr Lys Thr Ser Gly Ile Asn Asn Ile Arg Leu Tyr Gln Ser Tyr Pro
    50                  55                  60

Glu Val Leu Glu Ala Ala Arg Gly Ser Gly Ile Ser Leu Ser Met Gly
65                  70                  75                  80

Pro Arg Asn Glu Asp Ile Gln Ser Leu Ala Lys Asp Gln Ser Ala Ala
                85                  90                  95

Asp Ala Trp Val Asn Thr Asn Ile Val Pro Tyr Lys Asp Asp Val Gln
            100                 105                 110

Phe Lys Leu Ile Thr Ile Gly Asn Glu Ala Ile Ser Gly Gln Ser Ser
        115                 120                 125

Ser Tyr Ile Pro Asp Ala Met Asn Asn Ile Met Asn Ser Leu Ala Leu
    130                 135                 140

Phe Gly Leu Gly Thr Thr Lys Val Thr Thr Val Pro Met Asn Ala
145                 150                 155                 160

Leu Ser Thr Ser Tyr Pro Pro Ser Asp Gly Ala Phe Gly Ser Asp Ile
                165                 170                 175
```

```
Thr Ser Ile Met Thr Ser Ile Met Ala Ile Leu Ala Val Gln Asp Ser
            180                 185                 190
Pro Leu Leu Ile Asn Val Tyr Pro Tyr Phe Ala Tyr Ala Ser Asp Pro
            195                 200                 205
Thr His Ile Ser Leu Asp Tyr Ala Leu Phe Thr Ser Thr Ala Pro Val
            210                 215                 220
Val Val Asp Gln Gly Leu Glu Tyr Tyr Asn Leu Phe Asp Gly Met Val
225                 230                 235                 240
Asp Ala Phe Asn Ala Ala Leu Asp Lys Ile Gly Phe Gly Gln Ile Thr
                245                 250                 255
Leu Ile Val Ala Glu Thr Gly Trp Pro Thr Ala Gly Asn Glu Pro Tyr
            260                 265                 270
Thr Ser Val Ala Asn Ala Gln Thr Tyr Asn Lys Asn Leu Leu Asn His
            275                 280                 285
Val Thr Gln Lys Gly Thr Pro Lys Arg Pro Glu Tyr Ile Met Pro Thr
            290                 295                 300
Phe Phe Phe Glu Met Phe Asn Glu Asp Leu Lys Gln Pro Thr Val Glu
305                 310                 315                 320
Gln Asn Phe Gly Phe Phe Pro Asn Met Asn Pro Val Tyr Pro Phe
                325                 330                 335
Trp

<210> SEQ ID NO 13
<211> LENGTH: 1211
<212> TYPE: DNA
<213> ORGANISM: Gossypium barbadense
<220> FEATURE:
<221> NAME/KEY: CDS
<222> LOCATION: (29)..(1039)

<400> SEQUENCE: 13
ttgctgagat caagaaatat agtgaaat atg ggt cca aca ttt tct ggg ttt        52
                                Met Gly Pro Thr Phe Ser Gly Phe
                                  1               5 tta atc tca gca atg gtg ttt tta act caa ctc ctc tct cta aca gat      100
Leu Ile Ser Ala Met Val Phe Leu Thr Gln Leu Leu Ser Leu Thr Asp
     10                  15                  20 ggc cgt gat att ggt gtt tgc tat ggt ttg aac ggc aac aat ctt cca      148
Gly Arg Asp Ile Gly Val Cys Tyr Gly Leu Asn Gly Asn Asn Leu Pro
 25                  30                  35                  40 tct cca gga gat gtt att aat ctt tac aaa act agt ggc ata aac aat      196
Ser Pro Gly Asp Val Ile Asn Leu Tyr Lys Thr Ser Gly Ile Asn Asn
                 45                  50                  55 atc agg ctc tac cag tct tac cct gaa gtg ctc gaa gca gca agg gga      244
Ile Arg Leu Tyr Gln Ser Tyr Pro Glu Val Leu Glu Ala Ala Arg Gly
             60                  65                  70 tcg gga ata tcc ctc tcg atg ggt ccg aga aac gag gac ata caa agc      292
Ser Gly Ile Ser Leu Ser Met Gly Pro Arg Asn Glu Asp Ile Gln Ser
         75                  80                  85 ctc gca aaa gat caa agt gca gcc gat gca tgg gtt aac acc aac atc      340
Leu Ala Lys Asp Gln Ser Ala Ala Asp Ala Trp Val Asn Thr Asn Ile
     90                  95                 100 gtc cct tat aag gac gat gtt cag ttc aag ttg atc act att ggg aat      388
Val Pro Tyr Lys Asp Asp Val Gln Phe Lys Leu Ile Thr Ile Gly Asn
105                 110                 115                 120 gaa gcc att tca gga caa tca agc tct tac att cct gat gcc atg aac      436
Glu Ala Ile Ser Gly Gln Ser Ser Ser Tyr Ile Pro Asp Ala Met Asn
                125                 130                 135
```

```
aac ata atg aac tcg ctc gcc tta ttt ggg tta ggc acg acg aag gtt      484
Asn Ile Met Asn Ser Leu Ala Leu Phe Gly Leu Gly Thr Thr Lys Val
            140                 145                 150 acg acc gtg gtc ccg atg aat gcc cta agt acc tcg tac cct cct tca      532
Thr Thr Val Val Pro Met Asn Ala Leu Ser Thr Ser Tyr Pro Pro Ser
        155                 160                 165 gac ggc gct ttt gga agc gat ata aca tcg atc atg act agt atc atg      580
Asp Gly Ala Phe Gly Ser Asp Ile Thr Ser Ile Met Thr Ser Ile Met
    170                 175                 180 gcc att ctg gct gta cag gat tcg ccc ctc ctg atc aat gtg tac cct      628
Ala Ile Leu Ala Val Gln Asp Ser Pro Leu Leu Ile Asn Val Tyr Pro
185                 190                 195                 200 tat ttt gcc tat gcc tca gac ccc act cat att tcc ctc gat tac gcc      676
Tyr Phe Ala Tyr Ala Ser Asp Pro Thr His Ile Ser Leu Asp Tyr Ala
                205                 210                 215 ttg ttc acc tcg acc gca ccg gtg gtg gtc gac caa ggc ttg gaa tac      724
Leu Phe Thr Ser Thr Ala Pro Val Val Val Asp Gln Gly Leu Glu Tyr
            220                 225                 230 tac aac ctc ttt gac ggc atg gtc gat gct ttc aat gcc gcc cta gat      772
Tyr Asn Leu Phe Asp Gly Met Val Asp Ala Phe Asn Ala Ala Leu Asp
        235                 240                 245 aag atc ggc ttc ggc caa att act ctc att gta gcc gaa act gga tgg      820
Lys Ile Gly Phe Gly Gln Ile Thr Leu Ile Val Ala Glu Thr Gly Trp
    250                 255                 260 ccg acc gcc ggt aac gag cct tac acg agt gtc gcg aac gct caa act      868
Pro Thr Ala Gly Asn Glu Pro Tyr Thr Ser Val Ala Asn Ala Gln Thr
265                 270                 275                 280 tat aac aag aac ttg tta aat cat gtg acg cag aag ggg act ccg aaa      916
Tyr Asn Lys Asn Leu Leu Asn His Val Thr Gln Lys Gly Thr Pro Lys
                285                 290                 295 aga cct gaa tat ata atg ccg acg ttt ttc ttc gag atg ttc aac gag      964
Arg Pro Glu Tyr Ile Met Pro Thr Phe Phe Phe Glu Met Phe Asn Glu
            300                 305                 310 gat ttg aag caa ccc aca gtt gag cag aat ttc gga ttc ttc ttc ccc     1012
Asp Leu Lys Gln Pro Thr Val Glu Gln Asn Phe Gly Phe Phe Phe Pro
        315                 320                 325 aat atg aac cct gtt tat cca ttt tgg tgaagttgaa atgttgttgg           1059
Asn Met Asn Pro Val Tyr Pro Phe Trp
    330                 335 ctatttaaat cttttgccag agacgctcca tatagtttct gcatattttg aaagtggaaa   1119
gtcaatctaa atattaataa gttttgtgtt gttttttaat taaataaaat tttaaatatt   1179
ttggaaaaaa aaaaaaaaaa aaaaaaaaaa aa                                 1211

<210> SEQ ID NO 14
<211> LENGTH: 337
<212> TYPE: PRT
<213> ORGANISM: Gossypium barbadense

<400> SEQUENCE: 14

Met Gly Pro Thr Phe Ser Gly Phe Leu Ile Ser Ala Met Val Phe Leu
1               5                   10                  15

Thr Gln Leu Leu Ser Leu Thr Asp Gly Arg Asp Ile Gly Val Cys Tyr
            20                  25                  30

Gly Leu Asn Gly Asn Asn Leu Pro Ser Pro Gly Asp Val Ile Asn Leu
        35                  40                  45

Tyr Lys Thr Ser Gly Ile Asn Asn Ile Arg Leu Tyr Gln Ser Tyr Pro
    50                  55                  60
```

| | | | | | | | | | | | | | | | |
|---|---|---|---|---|---|---|---|---|---|---|---|---|---|---|---|
|Glu|Val|Leu|Glu|Ala|Ala|Arg|Gly|Ser|Gly|Ile|Ser|Leu|Ser|Met|Gly|
|65| | | | |70| | | | |75| | | | |80|

| | | | | | | | | | | | | | | | |
|---|---|---|---|---|---|---|---|---|---|---|---|---|---|---|---|
|Pro|Arg|Asn|Glu|Asp|Ile|Gln|Ser|Leu|Ala|Lys|Asp|Gln|Ser|Ala|Ala|
| | | | |85| | | | |90| | | | |95| |

| | | | | | | | | | | | | | | | |
|---|---|---|---|---|---|---|---|---|---|---|---|---|---|---|---|
|Asp|Ala|Trp|Val|Asn|Thr|Asn|Ile|Val|Pro|Tyr|Lys|Asp|Asp|Val|Gln|
| | | |100| | | | |105| | | | |110| | |

| | | | | | | | | | | | | | | | |
|---|---|---|---|---|---|---|---|---|---|---|---|---|---|---|---|
|Phe|Lys|Leu|Ile|Thr|Ile|Gly|Asn|Glu|Ala|Ile|Ser|Gly|Gln|Ser|Ser|
| | |115| | | | |120| | | | |125| | | |

| | | | | | | | | | | | | | | | |
|---|---|---|---|---|---|---|---|---|---|---|---|---|---|---|---|
|Ser|Tyr|Ile|Pro|Asp|Ala|Met|Asn|Asn|Ile|Met|Asn|Ser|Leu|Ala|Leu|
| |130| | | | |135| | | | |140| | | | |

| | | | | | | | | | | | | | | | |
|---|---|---|---|---|---|---|---|---|---|---|---|---|---|---|---|
|Phe|Gly|Leu|Gly|Thr|Thr|Lys|Val|Thr|Thr|Val|Val|Pro|Met|Asn|Ala|
|145| | | | |150| | | | |155| | | | |160|

| | | | | | | | | | | | | | | | |
|---|---|---|---|---|---|---|---|---|---|---|---|---|---|---|---|
|Leu|Ser|Thr|Ser|Tyr|Pro|Pro|Ser|Asp|Gly|Ala|Phe|Gly|Ser|Asp|Ile|
| | | | |165| | | | |170| | | | |175| |

| | | | | | | | | | | | | | | | |
|---|---|---|---|---|---|---|---|---|---|---|---|---|---|---|---|
|Thr|Ser|Ile|Met|Thr|Ser|Ile|Met|Ala|Ile|Leu|Ala|Val|Gln|Asp|Ser|
| | | |180| | | | |185| | | | |190| | |

| | | | | | | | | | | | | | | | |
|---|---|---|---|---|---|---|---|---|---|---|---|---|---|---|---|
|Pro|Leu|Leu|Ile|Asn|Val|Tyr|Pro|Tyr|Phe|Ala|Tyr|Ala|Ser|Asp|Pro|
| | |195| | | | |200| | | | |205| | | |

| | | | | | | | | | | | | | | | |
|---|---|---|---|---|---|---|---|---|---|---|---|---|---|---|---|
|Thr|His|Ile|Ser|Leu|Asp|Tyr|Ala|Leu|Phe|Thr|Ser|Thr|Ala|Pro|Val|
| |210| | | | |215| | | | |220| | | | |

| | | | | | | | | | | | | | | | |
|---|---|---|---|---|---|---|---|---|---|---|---|---|---|---|---|
|Val|Val|Asp|Gln|Gly|Leu|Glu|Tyr|Tyr|Asn|Leu|Phe|Asp|Gly|Met|Val|
|225| | | | |230| | | | |235| | | | |240|

| | | | | | | | | | | | | | | | |
|---|---|---|---|---|---|---|---|---|---|---|---|---|---|---|---|
|Asp|Ala|Phe|Asn|Ala|Ala|Leu|Asp|Lys|Ile|Gly|Phe|Gly|Gln|Ile|Thr|
| | | | |245| | | | |250| | | | |255| |

| | | | | | | | | | | | | | | | |
|---|---|---|---|---|---|---|---|---|---|---|---|---|---|---|---|
|Leu|Ile|Val|Ala|Glu|Thr|Gly|Trp|Pro|Thr|Ala|Gly|Asn|Glu|Pro|Tyr|
| | | |260| | | | |265| | | | |270| | |

| | | | | | | | | | | | | | | | |
|---|---|---|---|---|---|---|---|---|---|---|---|---|---|---|---|
|Thr|Ser|Val|Ala|Asn|Ala|Gln|Thr|Tyr|Asn|Lys|Asn|Leu|Leu|Asn|His|
| | |275| | | | |280| | | | |285| | | |

| | | | | | | | | | | | | | | | |
|---|---|---|---|---|---|---|---|---|---|---|---|---|---|---|---|
|Val|Thr|Gln|Lys|Gly|Thr|Pro|Lys|Arg|Pro|Glu|Tyr|Ile|Met|Pro|Thr|
| |290| | | | |295| | | | |300| | | | |

| | | | | | | | | | | | | | | | |
|---|---|---|---|---|---|---|---|---|---|---|---|---|---|---|---|
|Phe|Phe|Phe|Glu|Met|Phe|Asn|Glu|Asp|Leu|Lys|Gln|Pro|Thr|Val|Glu|
|305| | | | |310| | | | |315| | | | |320|

| | | | | | | | | | | | | | | | |
|---|---|---|---|---|---|---|---|---|---|---|---|---|---|---|---|
|Gln|Asn|Phe|Gly|Phe|Phe|Phe|Pro|Asn|Met|Asn|Pro|Val|Tyr|Pro|Phe|
| | | | |325| | | | |330| | | | |335| |

Trp

```
<210> SEQ ID NO 15
<211> LENGTH: 656
<212> TYPE: DNA
<213> ORGANISM: Gossypium tomentosum
<220> FEATURE:
<221> NAME/KEY: CDS
<222> LOCATION: (2)..(655)

<400> SEQUENCE: 15 c ggc aac aat ctt cca tct cca gga gat gtt att gat ctt ttc aaa act    49
  Gly Asn Asn Leu Pro Ser Pro Gly Asp Val Ile Asp Leu Phe Lys Thr
   1               5                  10                  15 agt ggc ata aac aat atc agg ctc tac cag cct tac cct gaa gtg ctc      97
Ser Gly Ile Asn Asn Ile Arg Leu Tyr Gln Pro Tyr Pro Glu Val Leu
             20                  25                  30 gaa gca gca agg gga tcg gga ata tcc ctc tcg atg agt acg aca aac     145
Glu Ala Ala Arg Gly Ser Gly Ile Ser Leu Ser Met Ser Thr Thr Asn
         35                  40                  45 gag gac ata caa agc ctc gca acg gat caa agt gca gcc gat gca tgg     193
Glu Asp Ile Gln Ser Leu Ala Thr Asp Gln Ser Ala Ala Asp Ala Trp
     50                  55                  60
```

```
gtt aac acc aac atc gtc cct tat aag gaa gat gtt caa ttc agg ttc    241
Val Asn Thr Asn Ile Val Pro Tyr Lys Glu Asp Val Gln Phe Arg Phe
65              70                  75                  80 atc atc att ggg aat gaa gcc att cca gga cag tca agc tct tac att    289
Ile Ile Ile Gly Asn Glu Ala Ile Pro Gly Gln Ser Ser Ser Tyr Ile
            85                  90                  95 cct ggt gcc atg aac aac ata atg aac tcg ctg gcc tca ttt ggg cta    337
Pro Gly Ala Met Asn Asn Ile Met Asn Ser Leu Ala Ser Phe Gly Leu
        100                 105                 110 ggc acg acg aag gtt acg acc gtg gtc ccg atg aat gcc cta agt acc    385
Gly Thr Thr Lys Val Thr Thr Val Val Pro Met Asn Ala Leu Ser Thr
    115                 120                 125 tcg tac cct cct tca gac ggc gct ttt gga agc gat ata aca tcg atc    433
Ser Tyr Pro Pro Ser Asp Gly Ala Phe Gly Ser Asp Ile Thr Ser Ile
130                 135                 140 atg act agt atc atg gcc att ctg gtt cga cag gat tcg ccc ctc ctg    481
Met Thr Ser Ile Met Ala Ile Leu Val Arg Gln Asp Ser Pro Leu Leu
145                 150                 155                 160 atc aat gtg tac cct tat ttt gcc tat gcc tca gac ccc act cat att    529
Ile Asn Val Tyr Pro Tyr Phe Ala Tyr Ala Ser Asp Pro Thr His Ile
                165                 170                 175 tcc ctc aac tac gcc ttg ttc acc tcg gcc gca ccg gtg gtg gtc gac    577
Ser Leu Asn Tyr Ala Leu Phe Thr Ser Ala Ala Pro Val Val Val Asp
            180                 185                 190 caa ggc ttg gaa tac tac aac ctc ttt gac ggc atg gtc gat gct ttc    625
Gln Gly Leu Glu Tyr Tyr Asn Leu Phe Asp Gly Met Val Asp Ala Phe
        195                 200                 205 aat gcc gcc cta gat aag atc ggc ttc ggc c                          656
Asn Ala Ala Leu Asp Lys Ile Gly Phe Gly
    210                 215

<210> SEQ ID NO 16
<211> LENGTH: 218
<212> TYPE: PRT
<213> ORGANISM: Gossypium tomentosum

<400> SEQUENCE: 16

Gly Asn Asn Leu Pro Ser Pro Gly Asp Val Ile Asp Leu Phe Lys Thr
1               5                   10                  15

Ser Gly Ile Asn Asn Ile Arg Leu Tyr Gln Pro Tyr Pro Glu Val Leu
            20                  25                  30

Glu Ala Ala Arg Gly Ser Gly Ile Ser Leu Ser Met Ser Thr Thr Asn
        35                  40                  45

Glu Asp Ile Gln Ser Leu Ala Thr Asp Gln Ser Ala Ala Asp Ala Trp
    50                  55                  60

Val Asn Thr Asn Ile Val Pro Tyr Lys Glu Asp Val Gln Phe Arg Phe
65              70                  75                  80

Ile Ile Ile Gly Asn Glu Ala Ile Pro Gly Gln Ser Ser Ser Tyr Ile
            85                  90                  95

Pro Gly Ala Met Asn Asn Ile Met Asn Ser Leu Ala Ser Phe Gly Leu
        100                 105                 110

Gly Thr Thr Lys Val Thr Thr Val Val Pro Met Asn Ala Leu Ser Thr
    115                 120                 125

Ser Tyr Pro Pro Ser Asp Gly Ala Phe Gly Ser Asp Ile Thr Ser Ile
130                 135                 140

Met Thr Ser Ile Met Ala Ile Leu Val Arg Gln Asp Ser Pro Leu Leu
145                 150                 155                 160
```

```
Ile Asn Val Tyr Pro Tyr Phe Ala Tyr Ala Ser Asp Pro Thr His Ile
            165                 170                 175
Ser Leu Asn Tyr Ala Leu Phe Thr Ser Ala Ala Pro Val Val Val Asp
            180                 185                 190
Gln Gly Leu Glu Tyr Tyr Asn Leu Phe Asp Gly Met Val Asp Ala Phe
        195                 200                 205
Asn Ala Ala Leu Asp Lys Ile Gly Phe Gly
    210                 215

<210> SEQ ID NO 17
<211> LENGTH: 665
<212> TYPE: DNA
<213> ORGANISM: Gossypium darwinii
<220> FEATURE:
<221> NAME/KEY: CDS
<222> LOCATION: (2)..(472)

<400> SEQUENCE: 17 c ggc aac aat ctt cca tct cca gga gat gtt att aat ctt ttc aaa act     49
  Gly Asn Asn Leu Pro Ser Pro Gly Asp Val Ile Asn Leu Phe Lys Thr
  1               5                   10                  15 agt ggc ata aac aat atc agg ctc tac cag cct tac cct gaa gtg ctc       97
Ser Gly Ile Asn Asn Ile Arg Leu Tyr Gln Pro Tyr Pro Glu Val Leu
            20                  25                  30 gaa gca gca agg gga tcg gga ata tcc ctc tcg atg agt acg aca aac      145
Glu Ala Ala Arg Gly Ser Gly Ile Ser Leu Ser Met Ser Thr Thr Asn
        35                  40                  45 gag gac ata caa agc ctc gca acg gat caa act cat caa agt gca gcc      193
Glu Asp Ile Gln Ser Leu Ala Thr Asp Gln Thr His Gln Ser Ala Ala
50                  55                  60 gat gca tgg gtt aac acc aac atc gtc cct tat aag gaa gat gtt caa      241
Asp Ala Trp Val Asn Thr Asn Ile Val Pro Tyr Lys Glu Asp Val Gln
65                  70                  75                  80 ttc agg ttc atc atc att ggg aat gaa gcc att cca gga cag tca agc      289
Phe Arg Phe Ile Ile Ile Gly Asn Glu Ala Ile Pro Gly Gln Ser Ser
                85                  90                  95 tct tac att cct ggt gcc atg aac aac ata atg aac tcg ctc gcc tca      337
Ser Tyr Ile Pro Gly Ala Met Asn Asn Ile Met Asn Ser Leu Ala Ser
            100                 105                 110 ttt ggg cta ggc acg acg aag gtt acg acc gtg gtc ccg atg aat gcc      385
Phe Gly Leu Gly Thr Thr Lys Val Thr Thr Val Val Pro Met Asn Ala
        115                 120                 125 cta agt acc tcg tac cct cct tca gac ggc gct ttt gga agc gat ata      433
Leu Ser Thr Ser Tyr Pro Pro Ser Asp Gly Ala Phe Gly Ser Asp Ile
    130                 135                 140 aca tcg atc atg act agt atc atg gcc att ctg gtt tga caggattcgc      482
Thr Ser Ile Met Thr Ser Ile Met Ala Ile Leu Val
145                 150                 155 ccctcctgat caatgtgtac ccttattttg cctatgcctc agaccccact catatttccc   542
tcaactacgc cttgttcacc tcgaccgcac cggtggtggt cgaccaaggc ttggaatact   602
acaacctctt tgacggcata gtcgatgctt caatgccgc cctagataag atcggcttcg   662
gcc                                                                  665

<210> SEQ ID NO 18
<211> LENGTH: 156
<212> TYPE: PRT
<213> ORGANISM: Gossypium darwinii

<400> SEQUENCE: 18
```

```
Gly Asn Asn Leu Pro Ser Pro Gly Asp Val Ile Asn Leu Phe Lys Thr
1               5                   10                  15

Ser Gly Ile Asn Asn Ile Arg Leu Tyr Gln Pro Tyr Pro Glu Val Leu
            20                  25                  30

Glu Ala Ala Arg Gly Ser Gly Ile Ser Leu Ser Met Ser Thr Thr Asn
        35                  40                  45

Glu Asp Ile Gln Ser Leu Ala Thr Asp Gln Thr His Gln Ser Ala Ala
    50                  55                  60

Asp Ala Trp Val Asn Thr Asn Ile Val Pro Tyr Lys Glu Asp Val Gln
65                  70                  75                  80

Phe Arg Phe Ile Ile Ile Gly Asn Glu Ala Ile Pro Gly Gln Ser Ser
                85                  90                  95

Ser Tyr Ile Pro Gly Ala Met Asn Asn Ile Met Asn Ser Leu Ala Ser
            100                 105                 110

Phe Gly Leu Gly Thr Thr Lys Val Thr Thr Val Val Pro Met Asn Ala
        115                 120                 125

Leu Ser Thr Ser Tyr Pro Pro Ser Asp Gly Ala Phe Gly Ser Asp Ile
    130                 135                 140

Thr Ser Ile Met Thr Ser Ile Met Ala Ile Leu Val
145                 150                 155
```

<210> SEQ ID NO 19
<211> LENGTH: 656
<212> TYPE: DNA
<213> ORGANISM: Gossypium mustelinum
<220> FEATURE:
<221> NAME/KEY: CDS
<222> LOCATION: (2)..(655)

<400> SEQUENCE: 19

```
c ggc aac aat ctt cca tct cca gga gat gtt att aat ctt tac aaa act      49
  Gly Asn Asn Leu Pro Ser Pro Gly Asp Val Ile Asn Leu Tyr Lys Thr
  1               5                   10                  15 agt ggc ata aac aat atc agg ctc tac cag cct tac cct gaa gtg ctc        97
Ser Gly Ile Asn Asn Ile Arg Leu Tyr Gln Pro Tyr Pro Glu Val Leu
            20                  25                  30 gaa gca gca agg gga tcg gga ata tcc ctc tcg atg agt acg aca aac       145
Glu Ala Ala Arg Gly Ser Gly Ile Ser Leu Ser Met Ser Thr Thr Asn
        35                  40                  45 gag gac ata caa agc ctc gca acg gat caa agt gca gcc gat gca tgg       193
Glu Asp Ile Gln Ser Leu Ala Thr Asp Gln Ser Ala Ala Asp Ala Trp
    50                  55                  60 gtt aac acc aac atc gtc cct tat aag gaa gat gtt caa ttc agg ttc       241
Val Asn Thr Asn Ile Val Pro Tyr Lys Glu Asp Val Gln Phe Arg Phe
65                  70                  75                  80 atc atc att ggg aat gaa gcc att cca gga cag tca agc tct tac att       289
Ile Ile Ile Gly Asn Glu Ala Ile Pro Gly Gln Ser Ser Ser Tyr Ile
                85                  90                  95 cct ggt gcc atg aac aac ata atg aac tcg ctc gcc tca ttt ggg cta       337
Pro Gly Ala Met Asn Asn Ile Met Asn Ser Leu Ala Ser Phe Gly Leu
            100                 105                 110 ggc acg acg aag gtt acg acc gtg gtc ccg atg aat gcc cta agt acc       385
Gly Thr Thr Lys Val Thr Thr Val Val Pro Met Asn Ala Leu Ser Thr
        115                 120                 125 tcg tac cct cct tca gac ggc gct ttt gga agc gat ata aca tcg atc       433
Ser Tyr Pro Pro Ser Asp Gly Ala Phe Gly Ser Asp Ile Thr Ser Ile
    130                 135                 140 atg act agt atc atg gcc att ctg gtt cga cag gat tcg ccc ctc ctg       481
Met Thr Ser Ile Met Ala Ile Leu Val Arg Gln Asp Ser Pro Leu Leu
```

```
                145                 150                 155                 160
atc aat gtg tac cct tat ttt gcc tat gcc tca gac ccc act cat att        529
Ile Asn Val Tyr Pro Tyr Phe Ala Tyr Ala Ser Asp Pro Thr His Ile
            165                 170                 175 tcc ctc aac tac gcc ttg ttc acc tcg acc gca ccg gtg gtg gtc gac        577
Ser Leu Asn Tyr Ala Leu Phe Thr Ser Thr Ala Pro Val Val Val Asp
        180                 185                 190 caa ggc ttg gaa tac tac aac ctc ttt gac ggc atg gtc gat gct ttc        625
Gln Gly Leu Glu Tyr Tyr Asn Leu Phe Asp Gly Met Val Asp Ala Phe
    195                 200                 205 aat gcc gcc cta gat aag atc ggc ttc ggc c                              656
Asn Ala Ala Leu Asp Lys Ile Gly Phe Gly
    210                 215

<210> SEQ ID NO 20
<211> LENGTH: 218
<212> TYPE: PRT
<213> ORGANISM: Gossypium mustelinum

<400> SEQUENCE: 20

Gly Asn Asn Leu Pro Ser Pro Gly Asp Val Ile Asn Leu Tyr Lys Thr
1               5                   10                  15

Ser Gly Ile Asn Asn Ile Arg Leu Tyr Gln Pro Tyr Pro Glu Val Leu
            20                  25                  30

Glu Ala Ala Arg Gly Ser Gly Ile Ser Leu Ser Met Ser Thr Thr Asn
        35                  40                  45

Glu Asp Ile Gln Ser Leu Ala Thr Asp Gln Ser Ala Ala Asp Ala Trp
    50                  55                  60

Val Asn Thr Asn Ile Val Pro Tyr Lys Glu Asp Val Gln Phe Arg Phe
65                  70                  75                  80

Ile Ile Ile Gly Asn Glu Ala Ile Pro Gly Gln Ser Ser Ser Tyr Ile
                85                  90                  95

Pro Gly Ala Met Asn Asn Ile Met Asn Ser Leu Ala Ser Phe Gly Leu
            100                 105                 110

Gly Thr Thr Lys Val Thr Thr Val Pro Met Asn Ala Leu Ser Thr
        115                 120                 125

Ser Tyr Pro Pro Ser Asp Gly Ala Phe Gly Ser Asp Ile Thr Ser Ile
    130                 135                 140

Met Thr Ser Ile Met Ala Ile Leu Val Arg Gln Asp Ser Pro Leu Leu
145                 150                 155                 160

Ile Asn Val Tyr Pro Tyr Phe Ala Tyr Ala Ser Asp Pro Thr His Ile
                165                 170                 175

Ser Leu Asn Tyr Ala Leu Phe Thr Ser Thr Ala Pro Val Val Val Asp
            180                 185                 190

Gln Gly Leu Glu Tyr Tyr Asn Leu Phe Asp Gly Met Val Asp Ala Phe
        195                 200                 205

Asn Ala Ala Leu Asp Lys Ile Gly Phe Gly
    210                 215

<210> SEQ ID NO 21
<211> LENGTH: 1206
<212> TYPE: DNA
<213> ORGANISM: Gossypium arboreum
<220> FEATURE:
<221> NAME/KEY: CDS
<222> LOCATION: (27)..(96)
<220> FEATURE:
<221> NAME/KEY: CDS
<222> LOCATION: (209)..(372)
```

<400> SEQUENCE: 21

```
gctgagatca agaaatatag tgaaat atg ggt cca aga ttt tct ggg ttt tta        53
                             Met Gly Pro Arg Phe Ser Gly Phe Leu
                              1               5 atc tca gca atg ctg ttt tta act caa ctc ctc tct cta aca g              96
Ile Ser Ala Met Leu Phe Leu Thr Gln Leu Leu Ser Leu Thr
 10              15                  20 gtaaaacaaa cttctctaca gtgatttag agtaaatatg ctttgaaaa atatacaaca        156 aaacatttat cttcaatcca ttttaattac tgatctacta tatatgttgc ag at ggc       213
                                                         Asp Gly
                                                             25 cgt gat att ggt gtt tgc tat ggt ttg aac ggc aac aat ctt cca tct        261
Arg Asp Ile Gly Val Cys Tyr Gly Leu Asn Gly Asn Asn Leu Pro Ser
         30                  35                  40 cca gga gat gtt att aat ctt tac aaa act agt ggc ata aac aat atc        309
Pro Gly Asp Val Ile Asn Leu Tyr Lys Thr Ser Gly Ile Asn Asn Ile
     45                  50                  55 agg ctc tac cag cct tac ctg aag tgc tcg aag gag caa ggg gat cgg        357
Arg Leu Tyr Gln Pro Tyr Leu Lys Cys Ser Lys Glu Gln Gly Asp Arg
 60                  65                  70 gaa tat ccc tct cga tgagtacgac aaacgaggac atacaaagcc tcgcaacgga       412
Glu Tyr Pro Ser Arg
 75 tcaaagtgca gccgatgcat gggttaacac caacatcgtc ccttataagg acgatgttca    472 attcaggttc atcatcattg ggaatgaagc cattccagga cagtcaagct cttacattcc    532 tggtgccatg aacaacataa tgaactcgct cgcctcattt gggctaggca cgacgaaggt    592 tacgaccgtg gtcccgatga atgccctaag tacctcgtac cctccttcag acggcgcttt    652 tggaagcgat ataacatcga tcatgactag tatcatggcc attctggttc gacaggattc    712 gcccctcctg atcaatgtgt accccttattt tgcctatgcc tcagaccccca ctcatatttc   772 cctcaactac gccttgttca cctcgaccgc accggtggtg gtcgaccaag gcttggaata    832 ctacaacctc tttgacggca tggtcgatgc tttcaatgcc gccctagata agatcggctt    892 cggccaaatt actctcattg tagccgaaac tggatggccg accgccggta acgagcctta    952 cacgagtgtc gcgaacgctc aaacttataa caagaacttg ttgaatcatg tgacgcagaa   1012 agggactccg aaaagacctg aatatataat gccgacgttt tccttcgaga tgttcaacga   1072 gaacttgaag caacccacag ttgagcagaa tttcggattc ttcttcccca atatgaaccc   1132 tgtttatcca ttttggtgaa cttgaaatgt tattgttggc tatttaaatc ttttgccaga   1192 gacgcttcat atag                                                     1206
```

<210> SEQ ID NO 22
<211> LENGTH: 78
<212> TYPE: PRT
<213> ORGANISM: Gossypium arboreum

<400> SEQUENCE: 22

```
Met Gly Pro Arg Phe Ser Gly Phe Leu Ile Ser Ala Met Leu Phe Leu
 1               5                  10                  15

Thr Gln Leu Leu Ser Leu Thr Asp Gly Arg Asp Ile Gly Val Cys Tyr
             20                  25                  30

Gly Leu Asn Gly Asn Asn Leu Pro Ser Pro Gly Asp Val Ile Asn Leu
         35                  40                  45

Tyr Lys Thr Ser Gly Ile Asn Asn Ile Arg Leu Tyr Gln Pro Tyr Leu
```

```
                          50                  55                  60
Lys Cys Ser Lys Glu Gln Gly Asp Arg Glu Tyr Pro Ser Arg
 65                  70                  75

<210> SEQ ID NO 23
<211> LENGTH: 1207
<212> TYPE: DNA
<213> ORGANISM: Gossypium herbaceum
<220> FEATURE:
<221> NAME/KEY: CDS
<222> LOCATION: (27)..(96)
<220> FEATURE:
<221> NAME/KEY: CDS
<222> LOCATION: (209)..(1149)

<400> SEQUENCE: 23
gctgagatca agaaatatag tgaaat atg ggt cca aga ttt tct ggg ttt tta        53
                            Met Gly Pro Arg Phe Ser Gly Phe Leu
                              1               5 atc tca gca atg ctg ttt tta act caa ctc ctc tct cta aca g              96
Ile Ser Ala Met Leu Phe Leu Thr Gln Leu Leu Ser Leu Thr
 10              15                  20 gtaaaacaaa cttctctaca gtgattttac agtaaatatg ctttgaaaa atatacaaca      156 aaacatttat cttcaatcca ttttaattac tgatctacta tatatgttgc ag at ggc      213
                                                        Asp Gly
                                                             25 cgt gat att ggt gtt tgc tat ggt ttg aac ggc aac aat ctt cca tct       261
Arg Asp Ile Gly Val Cys Tyr Gly Leu Asn Gly Asn Asn Leu Pro Ser
                 30                  35                  40 cca gga gat gct att aat ctt tac aaa act agt ggc ata aac aat atc       309
Pro Gly Asp Ala Ile Asn Leu Tyr Lys Thr Ser Gly Ile Asn Asn Ile
             45                  50                  55 agg ctc tac cag cct tac cct gaa gtg ctc gaa gca gca agg gga tcg       357
Arg Leu Tyr Gln Pro Tyr Pro Glu Val Leu Glu Ala Ala Arg Gly Ser
         60                  65                  70 gga ata tcc ctc tcg atg agt acg aca aac gag gac ata caa agc ctc       405
Gly Ile Ser Leu Ser Met Ser Thr Thr Asn Glu Asp Ile Gln Ser Leu
 75                  80                  85 gca acg gat caa agt gca gcc gat gca tgg gtt aac acc aac atc gtc       453
Ala Thr Asp Gln Ser Ala Ala Asp Ala Trp Val Asn Thr Asn Ile Val
 90                  95                 100                 105 cct tat aag gac gat gtt caa ttc agg ttc atc atc att ggg aat gaa       501
Pro Tyr Lys Asp Asp Val Gln Phe Arg Phe Ile Ile Ile Gly Asn Glu
                110                 115                 120 gcc att cca gga cag tca agc tct tac att cct ggt gcc atg aac aac       549
Ala Ile Pro Gly Gln Ser Ser Ser Tyr Ile Pro Gly Ala Met Asn Asn
            125                 130                 135 ata atg aac tcg ctc gcc tca ttt ggg cta ggc acg acg aag gtt acg       597
Ile Met Asn Ser Leu Ala Ser Phe Gly Leu Gly Thr Thr Lys Val Thr
        140                 145                 150 acc gtg gtc ccg atg aat gcc cta agt acc tcg tac cct cct tca gac       645
Thr Val Val Pro Met Asn Ala Leu Ser Thr Ser Tyr Pro Pro Ser Asp
    155                 160                 165 ggc gct ttt gga agc gat ata aca tcg atc atg act agt atc atg gcc       693
Gly Ala Phe Gly Ser Asp Ile Thr Ser Ile Met Thr Ser Ile Met Ala
170                 175                 180                 185 att ctg gtt cga cag gat tcg ccc ctc ctg atc aat gtg tac cct tat       741
Ile Leu Val Arg Gln Asp Ser Pro Leu Leu Ile Asn Val Tyr Pro Tyr
                190                 195                 200 ttt gcc tat gcc tca gac ccc act cat att tcc ctc aac tac gcc ttg       789
Phe Ala Tyr Ala Ser Asp Pro Thr His Ile Ser Leu Asn Tyr Ala Leu
```

```
                    205                 210                 215
ttc acc tcg acc gca ccg gtg gtc gac caa ggc ttg gaa tac tac        837
Phe Thr Ser Thr Ala Pro Val Val Asp Gln Gly Leu Glu Tyr Tyr
        220                 225                 230 aac ctc ttt gac ggc atg gtc gat gct ttc aat gcc gcc cta gat aag    885
Asn Leu Phe Asp Gly Met Val Asp Ala Phe Asn Ala Ala Leu Asp Lys
235                 240                 245 atc ggc ttc ggc caa att act ctc att gta gcc gaa act gga tgg ccg    933
Ile Gly Phe Gly Gln Ile Thr Leu Ile Val Ala Glu Thr Gly Trp Pro
250                 255                 260                 265 acc gcc ggt aac gag cct tac acg agt gtc gcg aac gct caa act tat    981
Thr Ala Gly Asn Glu Pro Tyr Thr Ser Val Ala Asn Ala Gln Thr Tyr
        270                 275                 280 aac aag aac ttg ttg aat cat gtg acg cag aaa ggg act ccg aaa aga   1029
Asn Lys Asn Leu Leu Asn His Val Thr Gln Lys Gly Thr Pro Lys Arg
    285                 290                 295 cct gaa tat ata atg ccg acg ttt ttc ttc gag atg ttc aac gag aac   1077
Pro Glu Tyr Ile Met Pro Thr Phe Phe Phe Glu Met Phe Asn Glu Asn
300                 305                 310 ttg aag caa ccc aca gtt gag cag aat ttc gga ttc ttc ttc ccc aat   1125
Leu Lys Gln Pro Thr Val Glu Gln Asn Phe Gly Phe Phe Phe Pro Asn
315                 320                 325 atg aac cct gtt tat cca ttt tgg tgagcttgaa atgttattgt tggctattta  1179
Met Asn Pro Val Tyr Pro Phe Trp
330                 335 aatcttttgc cagagacgct tcatatag                                    1207

<210> SEQ ID NO 24
<211> LENGTH: 337
<212> TYPE: PRT
<213> ORGANISM: Gossypium herbaceum

<400> SEQUENCE: 24

Met Gly Pro Arg Phe Ser Gly Phe Leu Ile Ser Ala Met Leu Phe Leu
1               5                   10                  15

Thr Gln Leu Leu Ser Leu Thr Asp Gly Arg Asp Ile Gly Val Cys Tyr
            20                  25                  30

Gly Leu Asn Gly Asn Asn Leu Pro Ser Pro Gly Asp Ala Ile Asn Leu
        35                  40                  45

Tyr Lys Thr Ser Gly Ile Asn Asn Ile Arg Leu Tyr Gln Pro Tyr Pro
    50                  55                  60

Glu Val Leu Glu Ala Ala Arg Gly Ser Gly Ile Ser Leu Ser Met Ser
65                  70                  75                  80

Thr Thr Asn Glu Asp Ile Gln Ser Leu Ala Thr Asp Gln Ser Ala Ala
                85                  90                  95

Asp Ala Trp Val Asn Thr Asn Ile Val Pro Tyr Lys Asp Asp Val Gln
            100                 105                 110

Phe Arg Phe Ile Ile Gly Asn Glu Ala Ile Pro Gly Gln Ser Ser
        115                 120                 125

Ser Tyr Ile Pro Gly Ala Met Asn Asn Ile Met Asn Ser Leu Ala Ser
    130                 135                 140

Phe Gly Leu Gly Thr Thr Lys Val Thr Thr Val Val Pro Met Asn Ala
145                 150                 155                 160

Leu Ser Thr Ser Tyr Pro Pro Ser Asp Gly Ala Phe Gly Ser Asp Ile
                165                 170                 175

Thr Ser Ile Met Thr Ser Ile Met Ala Ile Leu Val Arg Gln Asp Ser
            180                 185                 190
```

```
Pro Leu Leu Ile Asn Val Tyr Pro Tyr Phe Ala Tyr Ala Ser Asp Pro
        195                 200                 205

Thr His Ile Ser Leu Asn Tyr Ala Leu Phe Thr Ser Thr Ala Pro Val
    210                 215                 220

Val Val Asp Gln Gly Leu Glu Tyr Tyr Asn Leu Phe Asp Gly Met Val
225                 230                 235                 240

Asp Ala Phe Asn Ala Ala Leu Asp Lys Ile Gly Phe Gly Gln Ile Thr
                245                 250                 255

Leu Ile Val Ala Glu Thr Gly Trp Pro Thr Ala Gly Asn Glu Pro Tyr
                260                 265                 270

Thr Ser Val Ala Asn Ala Gln Thr Tyr Asn Lys Asn Leu Leu Asn His
                275                 280                 285

Val Thr Gln Lys Gly Thr Pro Lys Arg Pro Glu Tyr Ile Met Pro Thr
    290                 295                 300

Phe Phe Phe Glu Met Phe Asn Glu Asn Leu Lys Gln Pro Thr Val Glu
305                 310                 315                 320

Gln Asn Phe Gly Phe Phe Pro Asn Met Asn Pro Val Tyr Pro Phe
                325                 330                 335

Trp

<210> SEQ ID NO 25
<211> LENGTH: 656
<212> TYPE: DNA
<213> ORGANISM: Gossypium tomentosum
<220> FEATURE:
<221> NAME/KEY: CDS
<222> LOCATION: (2)..(655)

<400> SEQUENCE: 25 c ggc aac aat ctt cca tct cca gga gat gtt att aat ctt tac aaa act      49
  Gly Asn Asn Leu Pro Ser Pro Gly Asp Val Ile Asn Leu Tyr Lys Thr
  1               5                   10                  15 agt ggc ata aac aat atc agg ctc tac cag cct tac cct gaa gtg ctc        97
Ser Gly Ile Asn Asn Ile Arg Leu Tyr Gln Pro Tyr Pro Glu Val Leu
                20                  25                  30 gaa gca gca agg gga tcg gga ata tcc ctc tcg atg ggt ccg aga aac       145
Glu Ala Ala Arg Gly Ser Gly Ile Ser Leu Ser Met Gly Pro Arg Asn
            35                  40                  45 gag gac ata caa agc ctc gca aaa gat caa agt gca gcc gat gca tgg       193
Glu Asp Ile Gln Ser Leu Ala Lys Asp Gln Ser Ala Ala Asp Ala Trp
        50                  55                  60 gtt aac acc aac atc gtc cct tat aag gac gat gtt cag ttc aag ttg       241
Val Asn Thr Asn Ile Val Pro Tyr Lys Asp Asp Val Gln Phe Lys Leu
65                  70                  75                  80 atc act att ggg aat gaa gcc att tca gga caa tca agc tct tac att       289
Ile Thr Ile Gly Asn Glu Ala Ile Ser Gly Gln Ser Ser Ser Tyr Ile
                85                  90                  95 cct gat gcc atg aac aac ata atg aac tcg ctc gcc tta ttt ggg tta       337
Pro Asp Ala Met Asn Asn Ile Met Asn Ser Leu Ala Leu Phe Gly Leu
            100                 105                 110 ggc acg acg aag gtt acg acc gtg gtc ccg atg aat gcc cta agt acc       385
Gly Thr Thr Lys Val Thr Thr Val Val Pro Met Asn Ala Leu Ser Thr
        115                 120                 125 tcg tac cct cct tca gac ggc gct ttt gga agc gat ata aca tcg atc       433
Ser Tyr Pro Pro Ser Asp Gly Ala Phe Gly Ser Asp Ile Thr Ser Ile
    130                 135                 140 atg act agt atc atg gcc att ctg gct gta cag gat tcg ccc ctc ctg       481
Met Thr Ser Ile Met Ala Ile Leu Ala Val Gln Asp Ser Pro Leu Leu
```

```
atc aat gtg tac cct tat ttt gcc tat gcc tca gac ccc act cat att    529
Ile Asn Val Tyr Pro Tyr Phe Ala Tyr Ala Ser Asp Pro Thr His Ile
            165                 170                 175 tcc ctc gat tac gcc ttg ttc acc tcg acc gca ccg gtg gtg gtc gac    577
Ser Leu Asp Tyr Ala Leu Phe Thr Ser Thr Ala Pro Val Val Val Asp
        180                 185                 190 caa ggc ttg gaa tac tac aac ctc ttt gac ggc atg gtc gat gct ttc    625
Gln Gly Leu Glu Tyr Tyr Asn Leu Phe Asp Gly Met Val Asp Ala Phe
        195                 200                 205 aat gcc gcc cta gat aag atc ggc ttc ggc c                          656
Asn Ala Ala Leu Asp Lys Ile Gly Phe Gly
        210                 215
```

<210> SEQ ID NO 26
<211> LENGTH: 218
<212> TYPE: PRT
<213> ORGANISM: Gossypium tomentosum

<400> SEQUENCE: 26

```
Gly Asn Asn Leu Pro Ser Pro Gly Asp Val Ile Asn Leu Tyr Lys Thr
1               5                   10                  15

Ser Gly Ile Asn Asn Ile Arg Leu Tyr Gln Pro Tyr Pro Glu Val Leu
            20                  25                  30

Glu Ala Ala Arg Gly Ser Gly Ile Ser Leu Ser Met Gly Pro Arg Asn
        35                  40                  45

Glu Asp Ile Gln Ser Leu Ala Lys Asp Gln Ser Ala Ala Asp Ala Trp
    50                  55                  60

Val Asn Thr Asn Ile Val Pro Tyr Lys Asp Asp Val Gln Phe Lys Leu
65                  70                  75                  80

Ile Thr Ile Gly Asn Glu Ala Ile Ser Gly Gln Ser Ser Ser Tyr Ile
                85                  90                  95

Pro Asp Ala Met Asn Asn Ile Met Asn Ser Leu Ala Leu Phe Gly Leu
            100                 105                 110

Gly Thr Thr Lys Val Thr Thr Val Val Pro Met Asn Ala Leu Ser Thr
        115                 120                 125

Ser Tyr Pro Pro Ser Asp Gly Ala Phe Gly Ser Asp Ile Thr Ser Ile
    130                 135                 140

Met Thr Ser Ile Met Ala Ile Leu Ala Val Gln Asp Ser Pro Leu Leu
145                 150                 155                 160

Ile Asn Val Tyr Pro Tyr Phe Ala Tyr Ala Ser Asp Pro Thr His Ile
                165                 170                 175

Ser Leu Asp Tyr Ala Leu Phe Thr Ser Thr Ala Pro Val Val Val Asp
            180                 185                 190

Gln Gly Leu Glu Tyr Tyr Asn Leu Phe Asp Gly Met Val Asp Ala Phe
        195                 200                 205

Asn Ala Ala Leu Asp Lys Ile Gly Phe Gly
    210                 215
```

<210> SEQ ID NO 27
<211> LENGTH: 656
<212> TYPE: DNA
<213> ORGANISM: Gossypium darwinii
<220> FEATURE:
<221> NAME/KEY: CDS
<222> LOCATION: (2)..(655)

<400> SEQUENCE: 27

```
c ggc aac aat ctt cca tct cca gga gat gtt att aat ctt tac aaa act        49
  Gly Asn Asn Leu Pro Ser Pro Gly Asp Val Ile Asn Leu Tyr Lys Thr
  1               5                   10                  15 agt ggc ata aac aat atc agg ctc tac cag tct tac cct gaa gtg ctc          97
Ser Gly Ile Asn Asn Ile Arg Leu Tyr Gln Ser Tyr Pro Glu Val Leu
            20                  25                  30 gaa gca gca agg gga tcg gga ata tcc ctc tcg atg ggt ccg aga aac         145
Glu Ala Ala Arg Gly Ser Gly Ile Ser Leu Ser Met Gly Pro Arg Asn
                35                  40                  45 gag gac ata caa agc ctc gca aaa gat caa agt gca gcc gat gca tgg         193
Glu Asp Ile Gln Ser Leu Ala Lys Asp Gln Ser Ala Ala Asp Ala Trp
 50                  55                  60 gtt aac acc aac atc gtc cct tat aag gac gat gtt cag ttc aag ttg         241
Val Asn Thr Asn Ile Val Pro Tyr Lys Asp Asp Val Gln Phe Lys Leu
 65                  70                  75                  80 atc act att ggg aat gaa gcc att tca gga caa tca agc tct tac att         289
Ile Thr Ile Gly Asn Glu Ala Ile Ser Gly Gln Ser Ser Ser Tyr Ile
                 85                  90                  95 cct gat gcc atg aac aac ata atg aac tcg ctc gcc tta ttt ggg tta         337
Pro Asp Ala Met Asn Asn Ile Met Asn Ser Leu Ala Leu Phe Gly Leu
                100                 105                 110 ggc acg acg aag gtt acg acc gtg gtc ccg atg aat gcc cta agt acc         385
Gly Thr Thr Lys Val Thr Thr Val Val Pro Met Asn Ala Leu Ser Thr
            115                 120                 125 tcg tac cct cct tca gac ggc gct ttt gga agc gat ata aca tcg atc         433
Ser Tyr Pro Pro Ser Asp Gly Ala Phe Gly Ser Asp Ile Thr Ser Ile
        130                 135                 140 atg act agt atc atg gcc att ctg gct gta cag gat tcg ccc ctc ctg         481
Met Thr Ser Ile Met Ala Ile Leu Ala Val Gln Asp Ser Pro Leu Leu
145                 150                 155                 160 atc aat gtg tac cct tat ttt gcc tat gcc tca gac ccc act cat att         529
Ile Asn Val Tyr Pro Tyr Phe Ala Tyr Ala Ser Asp Pro Thr His Ile
                165                 170                 175 tcc ctc gat tac gcc ttg ttc acc tcg acc gca ccg gtg gtg gtc gac         577
Ser Leu Asp Tyr Ala Leu Phe Thr Ser Thr Ala Pro Val Val Val Asp
            180                 185                 190 caa ggc ttg gaa tac tac aac ctc ttt gac ggc atg gtc gat gct ttc         625
Gln Gly Leu Glu Tyr Tyr Asn Leu Phe Asp Gly Met Val Asp Ala Phe
        195                 200                 205 aat gcc gcc cta gat aag atc ggc ttc ggc c                               656
Asn Ala Ala Leu Asp Lys Ile Gly Phe Gly
210                 215

<210> SEQ ID NO 28
<211> LENGTH: 218
<212> TYPE: PRT
<213> ORGANISM: Gossypium darwinii

<400> SEQUENCE: 28

Gly Asn Asn Leu Pro Ser Pro Gly Asp Val Ile Asn Leu Tyr Lys Thr
1               5                   10                  15

Ser Gly Ile Asn Asn Ile Arg Leu Tyr Gln Ser Tyr Pro Glu Val Leu
            20                  25                  30

Glu Ala Ala Arg Gly Ser Gly Ile Ser Leu Ser Met Gly Pro Arg Asn
        35                  40                  45

Glu Asp Ile Gln Ser Leu Ala Lys Asp Gln Ser Ala Ala Asp Ala Trp
    50                  55                  60

Val Asn Thr Asn Ile Val Pro Tyr Lys Asp Asp Val Gln Phe Lys Leu
65                  70                  75                  80
```

```
Ile Thr Ile Gly Asn Glu Ala Ile Ser Gly Gln Ser Ser Tyr Ile
             85                  90                  95

Pro Asp Ala Met Asn Asn Ile Met Asn Ser Leu Ala Leu Phe Gly Leu
            100                 105                 110

Gly Thr Thr Lys Val Thr Thr Val Val Pro Met Asn Ala Leu Ser Thr
            115                 120                 125

Ser Tyr Pro Pro Ser Asp Gly Ala Phe Gly Ser Asp Ile Thr Ser Ile
        130                 135                 140

Met Thr Ser Ile Met Ala Ile Leu Ala Val Gln Asp Ser Pro Leu Leu
145                 150                 155                 160

Ile Asn Val Tyr Pro Tyr Phe Ala Tyr Ala Ser Asp Pro Thr His Ile
                165                 170                 175

Ser Leu Asp Tyr Ala Leu Phe Thr Ser Thr Ala Pro Val Val Val Asp
                180                 185                 190

Gln Gly Leu Glu Tyr Tyr Asn Leu Phe Asp Gly Met Val Asp Ala Phe
                195                 200                 205

Asn Ala Ala Leu Asp Lys Ile Gly Phe Gly
        210                 215

<210> SEQ ID NO 29
<211> LENGTH: 656
<212> TYPE: DNA
<213> ORGANISM: Gossypium mustelinum
<220> FEATURE:
<221> NAME/KEY: CDS
<222> LOCATION: (2)..(655)

<400> SEQUENCE: 29 c ggc aac aat ctt cca tct cca gga gat gtt att aat ctt tac aaa act      49
  Gly Asn Asn Leu Pro Ser Pro Gly Asp Val Ile Asn Leu Tyr Lys Thr
  1               5                   10                  15 agt ggc ata aac aat atc agg ctc tac cag cct tac cct gaa gtg ctc       97
Ser Gly Ile Asn Asn Ile Arg Leu Tyr Gln Pro Tyr Pro Glu Val Leu
             20                  25                  30 gaa gca gca agg gga tcg gga ata tcc ctc tcg atg ggt ccg aga aac      145
Glu Ala Ala Arg Gly Ser Gly Ile Ser Leu Ser Met Gly Pro Arg Asn
         35                  40                  45 gag gac ata caa agc ctc gca aaa gat caa agt gca gcc gat gca tgg      193
Glu Asp Ile Gln Ser Leu Ala Lys Asp Gln Ser Ala Ala Asp Ala Trp
     50                  55                  60 gtt aac acc aac atc gtc cct tat aag gac gat gtt cag ttc aag ttg      241
Val Asn Thr Asn Ile Val Pro Tyr Lys Asp Asp Val Gln Phe Lys Leu
 65                  70                  75                  80 atc act att ggg aat gaa gcc att tca gga caa tca agc tct tac att      289
Ile Thr Ile Gly Asn Glu Ala Ile Ser Gly Gln Ser Ser Ser Tyr Ile
                 85                  90                  95 cct gat gcc atg aac aac ata atg aac tcg ctc gcc tta ttt ggg tta      337
Pro Asp Ala Met Asn Asn Ile Met Asn Ser Leu Ala Leu Phe Gly Leu
            100                 105                 110 ggc acg acg aag gtt acg acc gtg gtc ccg atg aat gcc cta aat acc      385
Gly Thr Thr Lys Val Thr Thr Val Val Pro Met Asn Ala Leu Asn Thr
        115                 120                 125 tcg tac cct cct tca gac ggc gct ttt gga agc gat ata aca tcg atc      433
Ser Tyr Pro Pro Ser Asp Gly Ala Phe Gly Ser Asp Ile Thr Ser Ile
    130                 135                 140 atg act agt atc atg gcc att ctg gct gta cag gat tcg ccc ctc ctg      481
Met Thr Ser Ile Met Ala Ile Leu Ala Val Gln Asp Ser Pro Leu Leu
145                 150                 155                 160 atc aat gtg tac cct tat ttt gcc tat gcc tca gac ccc act cat att      529
```

```
Ile Asn Val Tyr Pro Tyr Phe Ala Tyr Ala Ser Asp Pro Thr His Ile
            165                 170                 175 tcc ctc gat tac gcc ttg ttc acc tcg acc gca ccg gtg gtg gtc gac       577
Ser Leu Asp Tyr Ala Leu Phe Thr Ser Thr Ala Pro Val Val Val Asp
            180                 185                 190 caa ggc ttg gaa tac tac aac ctc ttt gac ggc atg gtc gat gct ttc       625
Gln Gly Leu Glu Tyr Tyr Asn Leu Phe Asp Gly Met Val Asp Ala Phe
            195                 200                 205 aat gcc gct cta gat aag atc ggc ttc ggc c                             656
Asn Ala Ala Leu Asp Lys Ile Gly Phe Gly
            210                 215

<210> SEQ ID NO 30
<211> LENGTH: 218
<212> TYPE: PRT
<213> ORGANISM: Gossypium mustelinum

<400> SEQUENCE: 30

Gly Asn Asn Leu Pro Ser Pro Gly Asp Val Ile Asn Leu Tyr Lys Thr
1               5                   10                  15

Ser Gly Ile Asn Asn Ile Arg Leu Tyr Gln Pro Tyr Pro Glu Val Leu
            20                  25                  30

Glu Ala Ala Arg Gly Ser Gly Ile Ser Leu Ser Met Gly Pro Arg Asn
        35                  40                  45

Glu Asp Ile Gln Ser Leu Ala Lys Asp Gln Ser Ala Ala Asp Ala Trp
    50                  55                  60

Val Asn Thr Asn Ile Val Pro Tyr Lys Asp Asp Val Gln Phe Lys Leu
65                  70                  75                  80

Ile Thr Ile Gly Asn Glu Ala Ile Ser Gly Gln Ser Ser Tyr Ile
            85                  90                  95

Pro Asp Ala Met Asn Asn Ile Met Asn Ser Leu Ala Leu Phe Gly Leu
            100                 105                 110

Gly Thr Thr Lys Val Thr Thr Val Pro Met Asn Ala Leu Asn Thr
            115                 120                 125

Ser Tyr Pro Pro Ser Asp Gly Ala Phe Gly Ser Asp Ile Thr Ser Ile
    130                 135                 140

Met Thr Ser Ile Met Ala Ile Leu Ala Val Gln Asp Ser Pro Leu Leu
145                 150                 155                 160

Ile Asn Val Tyr Pro Tyr Phe Ala Tyr Ala Ser Asp Pro Thr His Ile
            165                 170                 175

Ser Leu Asp Tyr Ala Leu Phe Thr Ser Thr Ala Pro Val Val Val Asp
            180                 185                 190

Gln Gly Leu Glu Tyr Tyr Asn Leu Phe Asp Gly Met Val Asp Ala Phe
            195                 200                 205

Asn Ala Ala Leu Asp Lys Ile Gly Phe Gly
            210                 215

<210> SEQ ID NO 31
<211> LENGTH: 656
<212> TYPE: DNA
<213> ORGANISM: Gossypium raimondii
<220> FEATURE:
<221> NAME/KEY: CDS
<222> LOCATION: (2)..(655)

<400> SEQUENCE: 31 c ggc aac aat ctt cca tct cca gga gat gtt att aat ctt tac aaa act    49
  Gly Asn Asn Leu Pro Ser Pro Gly Asp Val Ile Asn Leu Tyr Lys Thr
  1               5                   10                  15
```

```
agt ggc ata aac aat atc agg ctc tac cag cct tac cct gaa gtg ctc     97
Ser Gly Ile Asn Asn Ile Arg Leu Tyr Gln Pro Tyr Pro Glu Val Leu
         20                  25                  30 gaa gca gca agg gga tcg gga ata tcc ctc tcg atg ggt ccg aga aac    145
Glu Ala Ala Arg Gly Ser Gly Ile Ser Leu Ser Met Gly Pro Arg Asn
     35                  40                  45 gag gac ata caa agc ctc gca aaa gat caa agt gca gcc gat gca tgg    193
Glu Asp Ile Gln Ser Leu Ala Lys Asp Gln Ser Ala Ala Asp Ala Trp
 50                  55                  60 gtt aac acc aac atc gtc cct tat aag gac gat gtt cag ttc aaa ttg    241
Val Asn Thr Asn Ile Val Pro Tyr Lys Asp Asp Val Gln Phe Lys Leu
65                  70                  75                  80 atc act att ggg aat gaa gcc att tca gga caa tca agc tct tac att    289
Ile Thr Ile Gly Asn Glu Ala Ile Ser Gly Gln Ser Ser Ser Tyr Ile
             85                  90                  95 cct gat gcc atg aac aac ata atg aac tcg ctc gcc tca ttt ggg tta    337
Pro Asp Ala Met Asn Asn Ile Met Asn Ser Leu Ala Ser Phe Gly Leu
        100                 105                 110 ggc aca acg aag gtt acg acc gtg gtc ccg atg aat gcc cta agt acc    385
Gly Thr Thr Lys Val Thr Thr Val Val Pro Met Asn Ala Leu Ser Thr
    115                 120                 125 tcg tac cct cct tca gac ggc gct ttt gga agc gat ata aca tcg atc    433
Ser Tyr Pro Pro Ser Asp Gly Ala Phe Gly Ser Asp Ile Thr Ser Ile
130                 135                 140 atg act agt atc atg gcc att ctg gct gta cag gat tcg ccc ctc ctg    481
Met Thr Ser Ile Met Ala Ile Leu Ala Val Gln Asp Ser Pro Leu Leu
145                 150                 155                 160 atc aat gtg tac cct tat ttt gcc tat gcc tca gac ccc act cat att    529
Ile Asn Val Tyr Pro Tyr Phe Ala Tyr Ala Ser Asp Pro Thr His Ile
                165                 170                 175 tcc ctc gat tac gcc ttg ttc acc tcg acc gca ccg gtg gtg gtc gac    577
Ser Leu Asp Tyr Ala Leu Phe Thr Ser Thr Ala Pro Val Val Val Asp
            180                 185                 190 caa ggc ttg gaa tac tac aac ctc ttt gac ggc atg gtc gat gct ttc    625
Gln Gly Leu Glu Tyr Tyr Asn Leu Phe Asp Gly Met Val Asp Ala Phe
        195                 200                 205 aat gcc gcc cta gat aag atc ggc ttc ggc c                          656
Asn Ala Ala Leu Asp Lys Ile Gly Phe Gly
    210                 215
```

<210> SEQ ID NO 32
<211> LENGTH: 218
<212> TYPE: PRT
<213> ORGANISM: Gossypium raimondii

<400> SEQUENCE: 32

```
Gly Asn Asn Leu Pro Ser Pro Gly Asp Val Ile Asn Leu Tyr Lys Thr
1               5                   10                  15

Ser Gly Ile Asn Asn Ile Arg Leu Tyr Gln Pro Tyr Pro Glu Val Leu
            20                  25                  30

Glu Ala Ala Arg Gly Ser Gly Ile Ser Leu Ser Met Gly Pro Arg Asn
        35                  40                  45

Glu Asp Ile Gln Ser Leu Ala Lys Asp Gln Ser Ala Ala Asp Ala Trp
    50                  55                  60

Val Asn Thr Asn Ile Val Pro Tyr Lys Asp Asp Val Gln Phe Lys Leu
65                  70                  75                  80

Ile Thr Ile Gly Asn Glu Ala Ile Ser Gly Gln Ser Ser Ser Tyr Ile
                85                  90                  95
```

```
Pro Asp Ala Met Asn Asn Ile Met Asn Ser Leu Ala Ser Phe Gly Leu
             100                 105                 110
Gly Thr Thr Lys Val Thr Thr Val Pro Met Asn Ala Leu Ser Thr
        115                 120                 125
Ser Tyr Pro Pro Ser Asp Gly Ala Phe Gly Ser Asp Ile Thr Ser Ile
    130                 135                 140
Met Thr Ser Ile Met Ala Ile Leu Ala Val Gln Asp Ser Pro Leu Leu
145                 150                 155                 160
Ile Asn Val Tyr Pro Tyr Phe Ala Tyr Ser Asp Pro Thr His Ile
                165                 170                 175
Ser Leu Asp Tyr Ala Leu Phe Thr Ser Thr Ala Pro Val Val Val Asp
            180                 185                 190
Gln Gly Leu Glu Tyr Tyr Asn Leu Phe Asp Gly Met Val Asp Ala Phe
        195                 200                 205
Asn Ala Ala Leu Asp Lys Ile Gly Phe Gly
    210                 215
```

<210> SEQ ID NO 33
<211> LENGTH: 22
<212> TYPE: DNA
<213> ORGANISM: Artificial
<220> FEATURE:
<223> OTHER INFORMATION: primer SE077

<400> SEQUENCE: 33
gctgagatca agaaatatag tg                                              22

<210> SEQ ID NO 34
<211> LENGTH: 20
<212> TYPE: DNA
<213> ORGANISM: Artificial
<220> FEATURE:
<223> OTHER INFORMATION: primer SE078

<400> SEQUENCE: 34
ctatatgaag cgtctctggc                                                 20

<210> SEQ ID NO 35
<211> LENGTH: 23
<212> TYPE: DNA
<213> ORGANISM: Artificial
<220> FEATURE:
<223> OTHER INFORMATION: primer SE002

<400> SEQUENCE: 35
ggccgaagcc gatcttatct agg                                             23

<210> SEQ ID NO 36
<211> LENGTH: 23
<212> TYPE: DNA
<213> ORGANISM: Artificial
<220> FEATURE:
<223> OTHER INFORMATION: primer SE003

<400> SEQUENCE: 36
cggcaacaat cttccatctc cag                                             23

<210> SEQ ID NO 37
<211> LENGTH: 22
<212> TYPE: DNA
<213> ORGANISM: Artificial
<220> FEATURE:
<223> OTHER INFORMATION: primer p1.3GlucaAf

```
<400> SEQUENCE: 37
tatccctctc gatgagtacg ac                                             22

<210> SEQ ID NO 38
<211> LENGTH: 24
<212> TYPE: DNA
<213> ORGANISM: Artificial
<220> FEATURE:
<223> OTHER INFORMATION: p1.3GlucaAr

<400> SEQUENCE: 38
cccaatgatg atgaacctga attg                                           24

<210> SEQ ID NO 39
<211> LENGTH: 15
<212> TYPE: DNA
<213> ORGANISM: Artificial
<220> FEATURE:
<223> OTHER INFORMATION: probe TM249-GCM1

<400> SEQUENCE: 39
aactcgctcg cctca                                                     15

<210> SEQ ID NO 40
<211> LENGTH: 15
<212> TYPE: DNA
<213> ORGANISM: Artificial
<220> FEATURE:
<223> OTHER INFORMATION: probe TM249-GCV1

<400> SEQUENCE: 40
aactcgctgg cctca                                                     15

<210> SEQ ID NO 41
<211> LENGTH: 24
<212> TYPE: DNA
<213> ORGANISM: Artificial
<220> FEATURE:
<223> OTHER INFORMATION: primer TM249-GCF

<400> SEQUENCE: 41
cctggtgcca tgaacaacat aatg                                           24

<210> SEQ ID NO 42
<211> LENGTH: 18
<212> TYPE: DNA
<213> ORGANISM: Artificial
<220> FEATURE:
<223> OTHER INFORMATION: primer TM249-GCR

<400> SEQUENCE: 42
cgtcgtgcct agcccaaa                                                  18

<210> SEQ ID NO 43
<211> LENGTH: 18
<212> TYPE: DNA
<213> ORGANISM: Artificial
<220> FEATURE:
<223> OTHER INFORMATION: AFLP primer P5

<400> SEQUENCE: 43
gactgcgtac atgcagaa                                                  18

<210> SEQ ID NO 44
```

```
<211> LENGTH: 19
<212> TYPE: DNA
<213> ORGANISM: Artificial
<220> FEATURE:
<223> OTHER INFORMATION: AFLP primer M50

<400> SEQUENCE: 44
gatgagtcct gagtaacat                                                  19

<210> SEQ ID NO 45
<211> LENGTH: 20
<212> TYPE: DNA
<213> ORGANISM: Artificial
<220> FEATURE:
<223> OTHER INFORMATION: forward SSR primer NAU861

<400> SEQUENCE: 45
ccaaaacttg tcccattagc                                                 20

<210> SEQ ID NO 46
<211> LENGTH: 19
<212> TYPE: DNA
<213> ORGANISM: Artificial
<220> FEATURE:
<223> OTHER INFORMATION: reverse SSR primer NAU861

<400> SEQUENCE: 46
ttcatctgtt gccagatcc                                                  19

<210> SEQ ID NO 47
<211> LENGTH: 15
<212> TYPE: DNA
<213> ORGANISM: Artificial
<220> FEATURE:
<223> OTHER INFORMATION: forward SSR primer CIR401

<400> SEQUENCE: 47
tggcgactcc ctttt                                                      15

<210> SEQ ID NO 48
<211> LENGTH: 22
<212> TYPE: DNA
<213> ORGANISM: Artificial
<220> FEATURE:
<223> OTHER INFORMATION: reverse SSR primer CIR401

<400> SEQUENCE: 48
aaaagatgtt acacacacac ac                                              22

<210> SEQ ID NO 49
<211> LENGTH: 20
<212> TYPE: DNA
<213> ORGANISM: Artificial
<220> FEATURE:
<223> OTHER INFORMATION: forward SSR primer BNL3992

<400> SEQUENCE: 49
cagaagagga ggaggtggag                                                 20

<210> SEQ ID NO 50
<211> LENGTH: 20
<212> TYPE: DNA
<213> ORGANISM: Artificial
<220> FEATURE:
<223> OTHER INFORMATION: reverse SSR primer BNL3992

<400> SEQUENCE: 50
```

```
tgccaatgat ggaaaactca                                                      20

<210> SEQ ID NO 51
<211> LENGTH: 17
<212> TYPE: DNA
<213> ORGANISM: Artificial
<220> FEATURE:
<223> OTHER INFORMATION: forward SSR primer CIR280

<400> SEQUENCE: 51
actgcgttca ttacacc                                                         17

<210> SEQ ID NO 52
<211> LENGTH: 16
<212> TYPE: DNA
<213> ORGANISM: Artificial
<220> FEATURE:
<223> OTHER INFORMATION: reverse SSR primer CIR280

<400> SEQUENCE: 52
gcttcaccca ttcatc                                                          16

<210> SEQ ID NO 53
<211> LENGTH: 165250
<212> TYPE: DNA
<213> ORGANISM: Gossypium hirsutum
<220> FEATURE:
<221> NAME/KEY: misc_feature
<222> LOCATION: (1104)..(1379)
<223> OTHER INFORMATION: Putative microsatellite region
<220> FEATURE:
<221> NAME/KEY: misc_feature
<222> LOCATION: (1105)..(1379)
<223> OTHER INFORMATION: Region with high homology with the DQ908392-
      microsatellite region
<220> FEATURE:
<221> NAME/KEY: misc_feature
<222> LOCATION: (3053)..(4915)
<223> OTHER INFORMATION: Putative uncharacterized protein F28J12.180
      (Putative uncharacterized protein AT4g18520) (complement)
<220> FEATURE:
<221> NAME/KEY: misc_feature
<222> LOCATION: (5208)..(5364)
<223> OTHER INFORMATION: exon1 from Putative uncharacterized protein
      F7F23.4 (At1g36320/F7F23_4)
<220> FEATURE:
<221> NAME/KEY: misc_feature
<222> LOCATION: (5729)..(6147)
<223> OTHER INFORMATION: exon2 from Putative uncharacterized protein
      F7F23.4 (At1g36320/F7F23_4)
<220> FEATURE:
<221> NAME/KEY: misc_feature
<222> LOCATION: (6475)..(6643)
<223> OTHER INFORMATION: exon3 from Putative uncharacterized protein
      F7F23.4 (At1g36320/F7F23_4)
<220> FEATURE:
<221> NAME/KEY: misc_feature
<222> LOCATION: (6859)..(7103)
<223> OTHER INFORMATION: exon4 from Putative uncharacterized protein
      F7F23.4 (At1g36320/F7F23_4)
<220> FEATURE:
<221> NAME/KEY: misc_feature
<222> LOCATION: (7526)..(7713)
<223> OTHER INFORMATION: exon5 from Putative uncharacterized protein
      F7F23.4 (At1g36320/F7F23_4)
<220> FEATURE:
<221> NAME/KEY: misc_feature
<222> LOCATION: (8004)..(8163)
<223> OTHER INFORMATION: exon6 from Putative uncharacterized protein
      F7F23.4 (At1g36320/F7F23_4)
<220> FEATURE:
<221> NAME/KEY: misc_feature
<222> LOCATION: (8164)..(8565)
```

```
<223> OTHER INFORMATION: 3' Untranslated region from Putative
      uncharacterized protein F7F23.4 (At1g36320/F7F23_4)
<220> FEATURE:
<221> NAME/KEY: misc_feature
<222> LOCATION: (8636)..(9270)
<223> OTHER INFORMATION: ExonC from unknown protein (complement)
<220> FEATURE:
<221> NAME/KEY: misc_feature
<222> LOCATION: (11837)..(12002)
<223> OTHER INFORMATION: Exon B from unknown protein (complement)
<220> FEATURE:
<221> NAME/KEY: misc_feature
<222> LOCATION: (12184)..(12350)
<223> OTHER INFORMATION: Exon A from unknown protein (complement)
<220> FEATURE:
<221> NAME/KEY: misc_feature
<222> LOCATION: (20866)..(21019)
<223> OTHER INFORMATION: 5' Untranslated region
<220> FEATURE:
<221> NAME/KEY: misc_feature
<222> LOCATION: (21020)..(21376)
<223> OTHER INFORMATION: exon1 from uncharacterized protein
<220> FEATURE:
<221> NAME/KEY: misc_feature
<222> LOCATION: (21020)..(21022)
<223> OTHER INFORMATION: start codon from DT563840
<220> FEATURE:
<221> NAME/KEY: misc_feature
<222> LOCATION: (21503)..(22114)
<223> OTHER INFORMATION: exon2 from uncharacterized protein; DT563840
<220> FEATURE:
<221> NAME/KEY: misc_feature
<222> LOCATION: (22112)..(22114)
<223> OTHER INFORMATION: stop codon from the DT563840-homology region
<220> FEATURE:
<221> NAME/KEY: misc_feature
<222> LOCATION: (22115)..(22266)
<223> OTHER INFORMATION: 3' Untranslated region from the DT563840-
      homology region
<220> FEATURE:
<221> NAME/KEY: misc_feature
<222> LOCATION: (23354)..(23705)
<223> OTHER INFORMATION: 3' Untranslated region from the SHMT gene
      (complement)
<220> FEATURE:
<221> NAME/KEY: misc_feature
<222> LOCATION: (23706)..(23708)
<223> OTHER INFORMATION: TGA stop codon from SHMT (complement)
<220> FEATURE:
<221> NAME/KEY: misc_feature
<222> LOCATION: (23706)..(23929)
<223> OTHER INFORMATION: Serine hydroxymethyltransferase (EC 2.1.2.1)
      (Serine methylase) (Glycine hydroxymethyltransferase) (SHMT)
      (Glycosylation-related protein 1) (Maternal effect lethal protein
      32) (complement)
<220> FEATURE:
<221> NAME/KEY: misc_feature
<222> LOCATION: (24355)..(24456)
<223> OTHER INFORMATION: Serine hydroxymethyltransferase (EC 2.1.2.1)
      (Serine methylase) (Glycine hydroxymethyltransferase) (SHMT)
      (Glycosylation-related protein 1) (Maternal effect lethal protein
      32) (complement)
<220> FEATURE:
<221> NAME/KEY: misc_feature
<222> LOCATION: (25225)..(25633)
<223> OTHER INFORMATION: Serine hydroxymethyltransferase (EC 2.1.2.1)
      (Serine methylase) (Glycine hydroxymethyltransferase) (SHMT)
      (Glycosylation-related protein 1) (Maternal effect lethal protein
      32) (complement)
<220> FEATURE:
<221> NAME/KEY: misc_feature
<222> LOCATION: (26181)..(27176)
<223> OTHER INFORMATION: Serine hydroxymethyltransferase (EC 2.1.2.1)
      (Serine methylase) (Glycine hydroxymethyltransferase) (SHMT)
      (Glycosylation-related protein 1) (Maternal effect lethal protein
      32) (complement)
<220> FEATURE:
<221> NAME/KEY: misc_feature
<222> LOCATION: (27174)..(27176)
```

```
<223> OTHER INFORMATION: ATG start codon SHMT (complement)
<220> FEATURE:
<221> NAME/KEY: misc_feature
<222> LOCATION: (27386)..(27177)
<223> OTHER INFORMATION: 5' Untranslated region from the SHMT gene
      (complement)
<220> FEATURE:
<221> NAME/KEY: misc_feature
<222> LOCATION: (27729)..(28170)
<223> OTHER INFORMATION: Ex1-CERES41761278-homolog; also homologous to
      BE054702
<220> FEATURE:
<221> NAME/KEY: misc_feature
<222> LOCATION: (27774)..(28329)
<223> OTHER INFORMATION: region with high homology with BE054702
<220> FEATURE:
<221> NAME/KEY: misc_feature
<222> LOCATION: (29198)..(29833)
<223> OTHER INFORMATION: Ex2-CERES41761278-homology; also homologous to
      BE054702
<220> FEATURE:
<221> NAME/KEY: misc_feature
<222> LOCATION: (30911)..(31136)
<223> OTHER INFORMATION: 3'UTR_GrpE/HSP-70; 3' Untranslated region
      (complement)
<220> FEATURE:
<221> NAME/KEY: misc_feature
<222> LOCATION: (31137)..(31139)
<223> OTHER INFORMATION: TAA stop codon (complement)
<220> FEATURE:
<221> NAME/KEY: misc_feature
<222> LOCATION: (31137)..(31325)
<223> OTHER INFORMATION: ex3_GrpE/HSP-70; Protein grpE (HSP-70
      cofactor); putative heat shock protein  (complement)
<220> FEATURE:
<221> NAME/KEY: misc_feature
<222> LOCATION: (32110)..(32583)
<223> OTHER INFORMATION: ex2_GrpE/HSP-70; Protein grpE (HSP-70
      cofactor); putative heat shock protein  (complement)
<220> FEATURE:
<221> NAME/KEY: misc_feature
<222> LOCATION: (32817)..(33059)
<223> OTHER INFORMATION: ex1_GrpE/HSP-70; Protein grpE (HSP-70 cofactor)
      (complement)
<220> FEATURE:
<221> NAME/KEY: misc_feature
<222> LOCATION: (33057)..(33059)
<223> OTHER INFORMATION: ATG start codon (complement)
<220> FEATURE:
<221> NAME/KEY: misc_feature
<222> LOCATION: (33060)..(33234)
<223> OTHER INFORMATION: 5'UTR_GrpE/HSP-70; 5' Untranslated region
      (complement)
<220> FEATURE:
<221> NAME/KEY: misc_feature
<222> LOCATION: (34773)..(35119)
<223> OTHER INFORMATION: ex3-ARF17; Putative exon3 from ARF17=
      determined by EST homology (complement)
<220> FEATURE:
<221> NAME/KEY: misc_feature
<222> LOCATION: (36058)..(36815)
<223> OTHER INFORMATION: exon1 from the putative auxin response factor
      similar to At-ARF17 (At1g77850) (complement)
<220> FEATURE:
<221> NAME/KEY: misc_feature
<222> LOCATION: (36099)..(36101)
<223> OTHER INFORMATION: TGA stop codon from the ARF17 gene (complement)
<220> FEATURE:
<221> NAME/KEY: misc_feature
<222> LOCATION: (38053)..(39072)
<223> OTHER INFORMATION: exon2 from the putative auxin response factor
      similar to At-ARF17 (At1g77850) (complement)
<220> FEATURE:
<221> NAME/KEY: misc_feature
<222> LOCATION: (39070)..(39072)
<223> OTHER INFORMATION: ATG start codon (complement)
<220> FEATURE:
<221> NAME/KEY: misc_feature
<222> LOCATION: (39073)..(39113)
```

```
<223> OTHER INFORMATION: 5' Untranslated region from the ARF17 gene=
      determined by EST homology (complement)
<220> FEATURE:
<221> NAME/KEY: misc_feature
<222> LOCATION: (42998)..(43530)
<223> OTHER INFORMATION: repetitive region; similar to Gossypium
      raimondii repetitive sequences: DX405367, DX405119
<220> FEATURE:
<221> NAME/KEY: misc_feature
<222> LOCATION: (44789)..(45407)
<223> OTHER INFORMATION: EST-homology= homology with ES817816-ES801532-
      DR460504
<220> FEATURE:
<221> NAME/KEY: misc_feature
<222> LOCATION: (46515)..(46835)
<223> OTHER INFORMATION: ex4; DW507111; DW512136;uncharacterized protein
      (complement)
<220> FEATURE:
<221> NAME/KEY: misc_feature
<222> LOCATION: (47486)..(47572)
<223> OTHER INFORMATION: ex3; DW512136;uncharacterized protein
      (complement)
<220> FEATURE:
<221> NAME/KEY: misc_feature
<222> LOCATION: (51596)..(51868)
<223> OTHER INFORMATION: ex2-b; DR458828; uncharacterized protein
      (complement)
<220> FEATURE:
<221> NAME/KEY: misc_feature
<222> LOCATION: (52127)..(52198)
<223> OTHER INFORMATION: ex2; DW512136;uncharacterized protein
      (complement)
<220> FEATURE:
<221> NAME/KEY: misc_feature
<222> LOCATION: (52298)..(52711)
<223> OTHER INFORMATION: ex1; DW512136;uncharacterized protein
      (complement)
<220> FEATURE:
<221> NAME/KEY: misc_feature
<222> LOCATION: (57253)..(57590)
<223> OTHER INFORMATION: 5'UTR-(eIF-5 1); 5' Untranslated region
      (complement)
<220> FEATURE:
<221> NAME/KEY: misc_feature
<222> LOCATION: (57591)..(57593)
<223> OTHER INFORMATION: TGA stop codon  (complement)
<220> FEATURE:
<221> NAME/KEY: misc_feature
<222> LOCATION: (57591)..(58919)
<223> OTHER INFORMATION: Exon 1 from the Probable eukaryotic translation
      initiation factor 5-1 (eIF-5 1).  (complement)
<220> FEATURE:
<221> NAME/KEY: misc_feature
<222> LOCATION: (58917)..(58919)
<223> OTHER INFORMATION: ATG start codon (complement)
<220> FEATURE:
<221> NAME/KEY: misc_feature
<222> LOCATION: (58920)..(59255)
<223> OTHER INFORMATION: 3'UTR-B (eIF-5 1); second  part of the
      3'Untranslated region form Probable eukaryotic translation
      initiation factor  5-1(eIF-5 1) - At1g77840 (complement)
<220> FEATURE:
<221> NAME/KEY: misc_feature
<222> LOCATION: (60113)..(60244)
<223> OTHER INFORMATION: (complement) 3'UTR-A-(eIF-5 1); First part of
      the 3'Untranslated region form Probable eukaryotic translation
      initiation factor ? 5-1 (eIF-5 1) - At1g77840
<220> FEATURE:
<221> NAME/KEY: misc_feature
<222> LOCATION: (66909)..(89556)
<223> OTHER INFORMATION: transposon region; region with high homology
      with transposable elements
<220> FEATURE:
<221> NAME/KEY: misc_feature
<222> LOCATION: (76845)..(77564)
<223> OTHER INFORMATION: ORF-putative retrotransposon polyprotein; part
      of a retrotransposon-polyprotein (complement)
<220> FEATURE:
<221> NAME/KEY: misc_feature
```

```
<222> LOCATION: (88753)..(89556)
<223> OTHER INFORMATION: putative retrotransposon polyprotein; Putative
      polyprotein (Os05g0269800 protein)
<220> FEATURE:
<221> NAME/KEY: misc_feature
<222> LOCATION: (97467)..(97558)
<223> OTHER INFORMATION: ex1-Avr9; putative Avr9 elicitor response
      protein; galactosyltransferase family protein
<220> FEATURE:
<221> NAME/KEY: misc_feature
<222> LOCATION: (97467)..(97469)
<223> OTHER INFORMATION: putative start for the avr9 gene;
      galactosyltransferase family protein
<220> FEATURE:
<221> NAME/KEY: misc_feature
<222> LOCATION: (97716)..(97758)
<223> OTHER INFORMATION: ex2-Avr9; Putative Avr9 elicitor response
      protein; galactosyltransferase family protein
<220> FEATURE:
<221> NAME/KEY: misc_feature
<222> LOCATION: (97859)..(97917)
<223> OTHER INFORMATION: ex3-Avr9; Putative Avr9 elicitor response
      protein; galactosyltransferase family protein
<220> FEATURE:
<221> NAME/KEY: misc_feature
<222> LOCATION: (98038)..(98249)
<223> OTHER INFORMATION: ex3-b-Avr9; Putative Avr9 elicitor response
      protein; galactosyltransferase family protein
<220> FEATURE:
<221> NAME/KEY: misc_feature
<222> LOCATION: (98555)..(98627)
<223> OTHER INFORMATION: ex5-Avr9; Putative Avr9 elicitor response
      protein; galactosyltransferase family protein
<220> FEATURE:
<221> NAME/KEY: misc_feature
<222> LOCATION: (98722)..(98842)
<223> OTHER INFORMATION: ex6-Avr9; Putative Avr9 elicitor response
      protein; galactosyltransferase family protein
<220> FEATURE:
<221> NAME/KEY: misc_feature
<222> LOCATION: (98942)..(99029)
<223> OTHER INFORMATION: ex7-Avr9; Putative Avr9 elicitor response
      protein; galactosyltransferase family protein
<220> FEATURE:
<221> NAME/KEY: misc_feature
<222> LOCATION: (99143)..(99268)
<223> OTHER INFORMATION: ex8-Avr9; Putative Avr9 elicitor response
      protein; galactosyltransferase family protein
<220> FEATURE:
<221> NAME/KEY: misc_feature
<222> LOCATION: (100099)..(100101)
<223> OTHER INFORMATION: stop Avr; TAA stop codon from avr9;
      galactosyltransferase family protein
<220> FEATURE:
<221> NAME/KEY: misc_feature
<222> LOCATION: (100151)..(100517)
<223> OTHER INFORMATION: ex1-VPS9;Similarity to vacuolar protein
      sorting-associated protein VPS9 (Putative uncharacterized
      protein At3g19770).
<220> FEATURE:
<221> NAME/KEY: misc_feature
<222> LOCATION: (100879)..(101000)
<223> OTHER INFORMATION: ex2-VPS9;Similarity to vacuolar protein
      sorting-associated protein VPS9 (Putative uncharacterized protein
      At3g19770).
<220> FEATURE:
<221> NAME/KEY: misc_feature
<222> LOCATION: (101288)..(101559)
<223> OTHER INFORMATION: n is a, c, g, or t
<220> FEATURE:
<221> NAME/KEY: misc_feature
<222> LOCATION: (101736)..(105725)
<223> OTHER INFORMATION: Putative retrotransposon polyprotein;
      Retrotransposon protein, putative, Ty1-copia sub-class
<220> FEATURE:
<221> NAME/KEY: misc_feature
<222> LOCATION: (106056)..(106327)
<223> OTHER INFORMATION: n is a, c, g, or t
<220> FEATURE:
```

```
<221> NAME/KEY: misc_feature
<222> LOCATION: (108784)..(109261)
<223> OTHER INFORMATION: putative polyprotein (complement)
<220> FEATURE:
<221> NAME/KEY: misc_feature
<222> LOCATION: (108785)..(108851)
<223> OTHER INFORMATION: EX-A_EST-homology1; homology with DW504110
<220> FEATURE:
<221> NAME/KEY: misc_feature
<222> LOCATION: (108881)..(108930)
<223> OTHER INFORMATION: EX-B_EST-homology; homology with DW504110
<220> FEATURE:
<221> NAME/KEY: misc_feature
<222> LOCATION: (109095)..(109247)
<223> OTHER INFORMATION: EX-C_EST-homology; homology with DW504110
<220> FEATURE:
<221> NAME/KEY: misc_feature
<222> LOCATION: (110491)..(110765)
<223> OTHER INFORMATION: HAT-3'UTR; 3' Untranslated region from the HAT
      gene (complement)
<220> FEATURE:
<221> NAME/KEY: misc_feature
<222> LOCATION: (110766)..(110768)
<223> OTHER INFORMATION: TAA stop codon (complement)
<220> FEATURE:
<221> NAME/KEY: misc_feature
<222> LOCATION: (110766)..(110969)
<223> OTHER INFORMATION: ex9-HAT; exon9 from a putative histon acetyl
      transferase gene (complement)
<220> FEATURE:
<221> NAME/KEY: misc_feature
<222> LOCATION: (111700)..(111842)
<223> OTHER INFORMATION: ex8-HAT; exon8 from a putative histon acetyl
      transferase gene (complement)
<220> FEATURE:
<221> NAME/KEY: misc_feature
<222> LOCATION: (112068)..(112161)
<223> OTHER INFORMATION: ex7-HAT; exon7 from a putative histon acetyl
      transferase gene (complement)
<220> FEATURE:
<221> NAME/KEY: misc_feature
<222> LOCATION: (112558)..(112719)
<223> OTHER INFORMATION: ex6-HAT; exon6 from a putative histon acetyl
      transferase gene (complement)
<220> FEATURE:
<221> NAME/KEY: misc_feature
<222> LOCATION: (113115)..(113183)
<223> OTHER INFORMATION: ex5-HAT; exon5 from a putative histon acetyl
      transferase gene (complement)
<220> FEATURE:
<221> NAME/KEY: misc_feature
<222> LOCATION: (114002)..(114211)
<223> OTHER INFORMATION: ex4-HAT; exon4 from a putative histon acetyl
      transferase gene (complement)
<220> FEATURE:
<221> NAME/KEY: misc_feature
<222> LOCATION: (114334)..(114396)
<223> OTHER INFORMATION: ex3-HAT; exon3 from a putative histon acetyl
      transferase gene (complement)
<220> FEATURE:
<221> NAME/KEY: misc_feature
<222> LOCATION: (114499)..(114587)
<223> OTHER INFORMATION: ex2-HAT; exon2 from a putative histon acetyl
      transferase gene (complement)
<220> FEATURE:
<221> NAME/KEY: misc_feature
<222> LOCATION: (114551)..(115026)
<223> OTHER INFORMATION: CIR280-AJ567224; CIR280 homology region:
      AJ567224 (complement)
<220> FEATURE:
<221> NAME/KEY: misc_feature
<222> LOCATION: (114741)..(115026)
<223> OTHER INFORMATION: ex1-HAT; exon1 from a putative histon acetyl
      transferase gene (complement)
<220> FEATURE:
<221> NAME/KEY: misc_feature
<222> LOCATION: (115024)..(115026)
<223> OTHER INFORMATION: ATG start codon (complement)
<220> FEATURE:
```

```
<221> NAME/KEY: misc_feature
<222> LOCATION: (115027)..(115106)
<223> OTHER INFORMATION: HAT 5'UTR; 5' Untranslaterd region from the
      HAT gene (complement)
<220> FEATURE:
<221> NAME/KEY: misc_feature
<222> LOCATION: (118613)..(118711)
<223> OTHER INFORMATION: 5'UTR-gluc1.1; 5' Untranslated region from the
      gluc1.1 gene
<220> FEATURE:
<221> NAME/KEY: misc_feature
<222> LOCATION: (118712)..(118745)
<223> OTHER INFORMATION: ex1_gluc1.1-GhA; Exon1 from the gluc1.1-GhA
      gene
<220> FEATURE:
<221> NAME/KEY: misc_feature
<222> LOCATION: (118712)..(118714)
<223> OTHER INFORMATION: start-gluc1.1
<220> FEATURE:
<221> NAME/KEY: misc_feature
<222> LOCATION: (118858)..(119801)
<223> OTHER INFORMATION: ex2-gluc1.1-GhA; Exon2 from the gluc1.1-GhA
      gene
<220> FEATURE:
<221> NAME/KEY: misc_feature
<222> LOCATION: (119799)..(119801)
<223> OTHER INFORMATION: TGA stop codon from the gluc1.1 gene
<220> FEATURE:
<221> NAME/KEY: misc_feature
<222> LOCATION: (119802)..(119882)
<223> OTHER INFORMATION: 3'UTR-gluc1.1; 3' Untranslated region from the
      gluc1.1 gene
<220> FEATURE:
<221> NAME/KEY: misc_feature
<222> LOCATION: (125857)..(126250)
<223> OTHER INFORMATION: repeat region-EF457753; mobile_element=
      "retrotransposon:putative gypsy (complement)
<220> FEATURE:
<221> NAME/KEY: misc_feature
<222> LOCATION: (126686)..(127281)
<223> OTHER INFORMATION: DW508475; DW508475-EST-homology: Protein
      transport protein SEC61 subunit alpha (complement)
<220> FEATURE:
<221> NAME/KEY: misc_feature
<222> LOCATION: (127723)..(128016)
<223> OTHER INFORMATION: ES798478; ES798478-EST homology (complement)
<220> FEATURE:
<221> NAME/KEY: misc_feature
<222> LOCATION: (127846)..(127930)
<223> OTHER INFORMATION: DW508475; DW508475-EST-homology: Protein
      transport protein SEC61 subunit alpha (complement)
<220> FEATURE:
<221> NAME/KEY: misc_feature
<222> LOCATION: (131142)..(131351)
<223> OTHER INFORMATION: 5'UTR-MEKK1; 5' Untranslated region from a
      putative Mitogen-activated protein kinase kinase kinase 1
<220> FEATURE:
<221> NAME/KEY: misc_feature
<222> LOCATION: (131352)..(132364)
<223> OTHER INFORMATION: ex1-MEKK1; Exon1 from a  putative Mitogen-
      activated protein kinase kinase kinase 1
<220> FEATURE:
<221> NAME/KEY: misc_feature
<222> LOCATION: (131352)..(131354)
<223> OTHER INFORMATION: MEKK1-start; ATG start codon
<220> FEATURE:
<221> NAME/KEY: misc_feature
<222> LOCATION: (133541)..(133625)
<223> OTHER INFORMATION: ex2-MEKK1; Exon2 from a  putative Mitogen-
      activated protein kinase kinase kinase 1
<220> FEATURE:
<221> NAME/KEY: misc_feature
<222> LOCATION: (133733)..(133795)
<223> OTHER INFORMATION: ex3-MEKK1; Exon3 from a  putative Mitogen-
      activated protein kinase kinase kinase 1
<220> FEATURE:
<221> NAME/KEY: misc_feature
<222> LOCATION: (133895)..(134052)
<223> OTHER INFORMATION: ex4-MEKK1; Exon4 from a  putative Mitogen-
``` activated protein kinase kinase kinase 1
<220> FEATURE:
<221> NAME/KEY: misc_feature
<222> LOCATION: (134538)..(134610)
<223> OTHER INFORMATION: ex5-MEKK1; Exon5 from a putative Mitogen-
      activated protein kinase kinase kinase 1
<220> FEATURE:
<221> NAME/KEY: misc_feature
<222> LOCATION: (134704)..(134763)
<223> OTHER INFORMATION: ex6-MEKK1; Exon6 from a putative Mitogen-
      activated protein kinase kinase kinase 1
<220> FEATURE:
<221> NAME/KEY: misc_feature
<222> LOCATION: (135417)..(135527)
<223> OTHER INFORMATION: ex7-MEKK1; Exon7 from a putative Mitogen-
      activated protein kinase kinase kinase 1
<220> FEATURE:
<221> NAME/KEY: misc_feature
<222> LOCATION: (135827)..(136036)
<223> OTHER INFORMATION: ex8-MEKK1; Exon8 from a putative Mitogen-
      activated protein kinase kinase kinase 1
<220> FEATURE:
<221> NAME/KEY: misc_feature
<222> LOCATION: (136034)..(136036)
<223> OTHER INFORMATION: MEKK1-stop; TGA stop codon
<220> FEATURE:
<221> NAME/KEY: misc_feature
<222> LOCATION: (136037)..(136074)
<223> OTHER INFORMATION: 3'UTR-MEKK1-part1; first part of the 3'
      untranslated region from a putative Mitogen-activated protein
      kinase kinase kinase 1
<220> FEATURE:
<221> NAME/KEY: misc_feature
<222> LOCATION: (136279)..(136761)
<223> OTHER INFORMATION: 3'UTR-MEKK1-part2; second part of the 3'
      Untranslated region from a putative Mitogen-activated protein
      kinase kinase kinase 1
<220> FEATURE:
<221> NAME/KEY: misc_feature
<222> LOCATION: (141152)..(141888)
<223> OTHER INFORMATION: ES809331; EST homology regions (complement)
<220> FEATURE:
<221> NAME/KEY: misc_feature
<222> LOCATION: (143913)..(146679)
<223> OTHER INFORMATION: retro-transposon region; region with high
      homology with Gorge3 gypsy-like retrotransposon
<220> FEATURE:
<221> NAME/KEY: misc_feature
<222> LOCATION: (163794)..(164082)
<223> OTHER INFORMATION: ex8-PIP5K1; Phosphatidylinositol-4-phosphate
      5-kinase 1 (EC 2.7.1.68) (AtPIP5K1) (1-phosphatidylinositol-4-
      phosphate kinase 1) (PtdIns(4)P-5-kinase 1) (Diphosphoinositide
      kinase 1) (complement)
<220> FEATURE:
<221> NAME/KEY: misc_feature
<222> LOCATION: (164725)..(164818)
<223> OTHER INFORMATION: ex7-PIP5K1; Phosphatidylinositol-4-phosphate
      5-kinase 1 (EC 2.7.1.68) (AtPIP5K1) (1-phosphatidylinositol-4-
      phosphate kinase 1) (PtdIns(4)P-5-kinase 1) (Diphosphoinositide
      kinase 1) (complement)
<220> FEATURE:
<221> NAME/KEY: misc_feature
<222> LOCATION: (164916)..(165046)
<223> OTHER INFORMATION: ex6-PIP5K1; Phosphatidylinositol-4-phosphate
      5-kinase 1 (EC 2.7.1.68) (AtPIP5K1) (1-phosphatidylinositol-4-
      phosphate kinase 1) (PtdIns(4)P-5-kinase 1) (Diphosphoinositide
      kinase 1) (complement)
<220> FEATURE:
<221> NAME/KEY: misc_feature
<222> LOCATION: (165127)..(165250)
<223> OTHER INFORMATION: ex5-PIP5K1; Phosphatidylinositol-4-phosphate
      5-kinase 1 (EC 2.7.1.68) (AtPIP5K1) (1-phosphatidylinositol-4-
      phosphate kinase 1) (PtdIns(4)P-5-kinase 1) (Diphosphoinositide
      kinase 1) (complement)

<400> SEQUENCE: 53
caaggaacga gttgatgaac aacgattagc ctgcatccca ggaacctctg ttccatcgaa        60

```
gaccggttct tgttcctcct cagcaagatc ttctcttgta gtttcgttca cttcttcttg    120
agctttggaa tccaaatccc catccttatt catcctgtca ccttgttcag catgtttgtc    180
atctttgtct tctttattac cctcctctaa cttattaaca tcgtccttgc tgatgttcag    240
actatgcatc tcctccacct ccacaggttt tccctgatct tctttgtgaa taccatcagt    300
atgtccctct ggttttcat ccatgggagg atctgttata ttttgtaac tggagttacc    360 ctcttcccta atgtcagaaa aacataaata ttgtcattca acttgtgaaa acatggccct    420 taaactttt catcgaggat ctcttcccag gttcctgcaa ggacatttca tatagacaaa    480
ttcaacagaa gaccaattcc actacggatg aaaaatgaat ataagactct tatacttcca    540
taaacagagt catatttgaa agcagacatc catttcaaaa ctgcctaaca aacaatagga    600
tctccatttt tcactctttg gctatttaaa caggaaaaat gtaacaaaaa agggaacaaa    660
ataatctgtt gtatataggc tcttattcat tgattttcag aaatatgaac ataatccagt    720
atattaaacc aaaacactag atgaaatcca taataagaaa ttgtttcaaa gcactagatg    780
tgatccggca agtcaagccc tgaagcttta gttttcgacc attcctagtc aaaagaaccg    840
gtcaacctaa atcctccatg atggaagaag tagtaatatt atgaacaatg aaagtcaaag    900 aaaaaatag cagagaaatg aatctgtgac caaaattaaa taacaaaaaa gattaaatct    960
ttaagtcctt aacacttgat caagttttca tttaattacc acacaactta atctccaaaa   1020
agaaataata ataataaacc ctgaaatttt atcgatagga ttttttgcaag ttaatcataa   1080 cgggaagtat gaaaactgaa aataagagag agagagagct cttacagatc cagagagagt   1140
gaagaaaaaa cagtgaatat aaaagaaaag aaaaaaagat ctggagagag ttacagaacc   1200
aaaaaagaaa gattaagtt aatatatata tcaactttgg agttacaaat ttggtgtatt   1260
aatgttttga aaggaaactt ataattgaaa attgaaaagg aaagaatagt caattaatgg   1320
agggtggatg attttcagaa gcagaggcgg gcggtcggga caagcgggaa atccgtgggc   1380
ctatcttttt tttgtctttt tagacttaag gaccccctta tcctatttct ttattttgga   1440
cacccaatac ttttgattc tttccaatcc atcccttatt gtttccattt tttaaaattg   1500
aggaagaatt aagatgacta aattgctaaa tcgaatataa tttaattcga aggactcaag   1560
ggaagccaag gtccttgctt gactctctca agtctaagct atatataaga ttagaaaact   1620 aatttactt ttcgattact taactttaaa attttataaa attaaaccat ttaaaaattt   1680
tcgttcaaat cactagactg ttaaaatggt cactatatag ctttctttat tcacattgct   1740
tgcataattg taaactctca ttaatattct cttttacagt ttagtttttt acagaccaaa   1800
tttcaagtag cttttttctt ctatatctta aattaattgt cttcttctac ttgccgaaga   1860
gtattgatcc actataccaa tcatcaaatt gtagcttgaa gttcgctagc tgaacttaaa   1920
aaaaaaacct taatagctca gtaacttgaa taaaaatttt cgaatagttg agtgacgtaa   1980
atgagaagtt tgaatagct caataaccat tttaaaaaat tttaaattta agtaaccaaa   2040
atgtaaattt actaatagtt tagcgacagt gggtataatt taccctttcat tcaattgcgc   2100 agacataata aaatttattt aatgtaatag gatcctaaat atgaaattgt acatatatta   2160
aatgttttaa taaaaattc aaatgtaaaa cactatcaat ggatttagta aactataaaa   2220
tactaatact aatcgttatt caactcgttg aaaactacag cacaactttt gattttgagt   2280
tgttgcgtat tttactgctt tcatgttgtg gaagctttca aggacaacga cacatatcat   2340
gcaaacgttt taagttatta acacgtcttc tttggattac acgaacagat tggatttacc   2400
aagcaatatg aagctgtaga ttgtaaatat cttatcaaac acgttgactg caatggctgc   2460
```

```
atgacatgtt cctatccgtt ttccaggcat tgcatgtgac gattacatga aaaagcagac    2520
tgcttaacat tggcccttga agaggtatcc aatgcagtaa tgttataaac gaaggagaac    2580
atatacttga tttctactcg tatataattc aaaattcgta cgaaaacgaa ggaagatgca    2640
cgggttcgcc caggggaaaa gttatttaac atgacaaata agagcagcac agaaaataag    2700
gataagtaag acatcatctt tcttttttctt tttttttaaag tttgtgagta tgaactagat    2760
ttacatggtg tttacaaaga acataactac ctatatgtac ctgttgccgg agtgatattc    2820
agtgctcagc acagcatgat agaaaagctt gtgacatttt ttgaagctcg gaaggaaaca    2880
gcaccggcat gcctttctta atacaatagg ggcaggcaat ggcgtaactg cataacagca    2940
tagcgatttt cgttttaact gttattttt ccttgtccat cgcatatatg atacatacac    3000
gctgcagtga aaagaaataa ttttgacaat tgcaactcca tgcctaagac aattaggtca    3060
ccactaatat ttccgatgaa ggaccttcat ccaattcaat atctccgcat gcactaagaa    3120
ccgtagcgag gatgtaatca tccacctcaa aaccttctgc ttccatccga tacatgagtt    3180
gcaaagcttc tcgacatagc ccgtttcttg cataacccat gatcatggcc ttccacgaaa    3240
ccaaattcct ttctggcatg ctgtcaaaaa cacgagaagc ctccgctaca aaaccgcatt    3300
tcgcatacat atggatcaat gcactgccca cgaagacatt agaaaaggca ggagttttat    3360
ttgcgaagga gtgaattaac ttcccttttg taacagctcc aagcttagca catgctttca    3420
aagctgaaga ataggtaaaa gagttaggtt ctacaccctc ctccatcatt tctttcaaaa    3480
aatcaagagc ctcagcctca tgccctacgc ttgcacagcc agaaatcatg gcagtccacg    3540
agacaacatc cctcagcggc atctgttgaa ggactttgga ggcaacatcg tactccccac    3600
atttacaata gaaccatact agagtgcttc ctatgtacat attcctttgg atagattttt    3660
ttactatttg tgcgtggact tccttgccca taagtaaatc cacaactgaa ccacaagccc    3720
taagtatgct tacgatggtc aagttattag caataatatt tcgactcttc attactcgaa    3780
aaagactaat ggcatcctca ccaagaccct tcctagcata ccctgctata atagaagtcc    3840
aggtaaccgt atttctacta ctcatcccgt taaacacaat cctagcatct actacctccc    3900
cgcattttgc atacatgtcc acaagagaag accctaagaa aacatcattt ttgaacatct    3960
tttttattat ggcaccatgt aattgtctac ctggtctcaa tgccttttgc tctccacaag    4020
ccttcaaaac actgcaaacg gtgaactcat taggccaaaa accatcactt agcattctcg    4080
aaaacaacga gaaagcctcc tccgcatatc cttgttggga gcaagcagtt atcatagctg    4140
tccaacaaac cacatccttt tctgccatcc catgaaaaca ttgaaaagcc cttgacaact    4200
ccccacattg tgcataaaaa taagtaacag cactatccac aatcaagttc ctacaattcg    4260
ctttcaggaa acaccatgaa atttgtctgc ctaactcaaa atccgcccgc ctactacaca    4320
aattcatcaa acaaacaagc atcttcctgt tcccttgaac cccacatgat atcgaatccc    4380
aaaacaacct caaagcttca tcatcaaaac ccaatttgga gtaccattaa atcattgctg    4440
tccaactgac gacatttctt tcagccatat tatcaaacac ctttcgagct tccactagct    4500
tcccaaattt taaatacgaa cttatcaaat tattctcaac ataggtcact gggttcccta    4560
aacgcttcaa aacaaccgca tggactctcc taacttgtct gccattgcta caagattgaa    4620
gcaaagctgc cagctcatca gaaccgacat ttcgactaac caacggtcgg gttctatccc    4680
taaaaccagc atctgggtct tcatggtaag ttgaaatact ggttaaatca tcgaattcgg    4740
gtagaaaaca tgaatctttg gaagaaaaac aagaaaattg gggtgggttt ttggtgattc    4800
```

```
ttggtctgga ctcgtttttg gaattcgaat aatgaaatga tggactttga atagtgaaaa   4860
aggaaggcca ttgaaagtgc gccacttggg gtgaaatcac cgttaacgaa agcatcagct   4920
atatctttgg atttcttcaa aactcccggc ggaaaacaga acccagtttc ccgaagttta   4980
agctcttgtt tttgttaaat cccgaggctt tcaaaaactc catcggataa aagaccattt   5040
tgccactaag ccagcaaaac gacatcgtct tgcaggttgc aacctctgca caatatcact   5100
tctttgccgg tcgctaaaac cttattctag aaccccctgc caaaaacctt cttaaattgg   5160
ttcctgctat aaacttacaa agttaaaaat ttaatctttt tctttccatg gaattggctt   5220
gtgcaagttt tcaagtttgt tctatatttc cagtaagatt aaaatcttct aaagccacaa   5280
aatttgaatc ttctttagct ttacttcctt cctgtaaaag ttcaaattca cctgggattc   5340
gttgtttgtc ttcaaagttc ttaagtaagt tactctttt tacctaataa tttgcagcta   5400
aaggttatta atttagcgtt ttattcactg tatttatctc tctttcccgc gctgccttcc   5460
tgcgtaaata atggttcaac ctggaattga atacgttaat aataattaag tgctatagct   5520
gaagtattct atgatgatta gctttatctt ttctttttct ttttttttt tgttttaagt   5580
tcttttcgtt tgaagtaaga aaattgggaa cttcttctag catgattatt tgggaaagca   5640
ttgtttgtta ggagcttctt tggtgcttgc agagatgcat atattatttt taggccattt   5700
gtctttaaca gatagttctc atgggcaggt tattctgcat tgggtgttaa tcgggtaagc   5760
gggcagcagc ggttttctct tgcggctgtt gttggtgata aaactgcggt gccaaataat   5820
tgtgatgaag agaagatttc agattcagat tctgccggtt cctcggtaat taatgatgag   5880
gtgaccggag atggggaaaa tgatggtgat aaaggtaatg ttgaggggtt ggatagcggt   5940
aaaatgatca gagtgtgtga caagttaatt gaggttttct tggttgacaa gcctacgcca   6000
actgattgga gaagattact tgctttcagt aaggaatgga acaacatccg acctcatttc   6060
tttcagcgtt gtcaggaacg agctgatgtt gaaggtgatc ctggaatgaa gcataagctt   6120
cttcgacttg gaaggaaatt gaaagaggta tgttatttga ttataattat aatcttttgc   6180
aatcaatatc agttttttgt atgagatatt tgaatctgga gaattgtcta gctgctcatg   6240
attaattcta gattgattat aaagagagta cgaacaaggg agagaaatct acctgctttt   6300
atgatgctga catgctgaac agatccatgt gcagtgaaga ttcctaggaa tcgaatttct   6360
tattctcttt ggatggcatg ttagtcatat ggctttaata gttgaggcat gtctgatgca   6420
tactgttctt attttcaagt tcatgctgat gtcatggtga ttcttgttat acagattgat   6480
gacgatgttc aaagacacaa cgaacttctt gaagtgatca agggttcacc atctgagatt   6540
agtgaaattg ttgctagacg tcgtaaagat tttacaaaag aattctttgt gcatatccat   6600
actgtagcag aatcatatta tgacaatcca actgaacaaa atggtaaggc agtatgattg   6660
aataatttaa ttatcaaaac cttattgata attattagta tgaatgttta gtatcgtgtg   6720
ccagttttaaa ctatatgcct aacaaaataa gctgtgtggt gagttgcatg gcttgagatc   6780
agaacttta gttcatatac ttgttaacca tatgccttcc cgaccttatt ccttcattta   6840
tttgtttata cttgacagct ctgtcaaagc ttgggaatac ttgcttggct gctgtacaag   6900
cttatgatac tgctgctgaa aacgttgagg cacttaatgc agcagagttg aaattccaag   6960
atatcatcaa ttcaccctct ctagatgttg cttgccggaa gattgatagt ttggctgaga   7020
aaaaccaact tgactcagca ttggtgctaa tgatcactaa agcttggtca gctgccaagg   7080
aatctaacat gacgaaagat gaggtactgt tgctgacttc agggaggaaa aagcccctcca   7140
cctgctctat aaatcgtatg atgcgatggt caactagatg tagttcttgt tttgtgactc   7200
```

```
agggtgactg cacctagaag aaccctatga tgatattctt ataaattaat ggaatgatta    7260
ctaggttggg gatgaaggga aaagggatta ttcattttgg cattctagta aagagcggaa    7320
ctaattttag aagtacaacc atatagtcat ttgtggggaa gccaactgat gtgttccttt    7380
tgataagcat taaaattttc agtaggattg ctaatttaag catcatcagc cgatggtttt    7440
agaaaaaaaa ttaactttac gataaattcc tatgttttgg agtgctgctg taagatgtct    7500
taccaagtta tcatctcaat tgcaggtaaa agatatattg taccacttgt atatgactgc    7560
tagaggtaat ctacagaggc tccttccaaa agagattaga attgtgaagt accttcttac    7620
aattgaggat cctgaggagc gactgtgtgc cctaaacgat gccttttcac ctggagaaga    7680
acttgaaggg agcgatatgg acaaccttta cacgtatgtc ttttgctctg acttgatttt    7740
tatcagaatt tagtaccatc taggaattag gcttacaatg cattggctta atctttcaag    7800
tcaatcgtcc agccttccgg gtcctgcttt ttatagtttc aggtgcaaat gatgagttag    7860
gttggtagtt atcccaggaa aggatttgat agttactctg gtgtcctgct atttgcctaa    7920
accaaacatc gtttaaattt tgtgtcatcc tcttttgcgc gtaagtttgt tccttcattt    7980
aactcattgt aatgaaattt taggactccg gagaagcttc ataccatgat gagagctgtg    8040
gtggatgctt ataatttcag ccatgaaggc actctcttaa gggaagctag agatttgatg    8100
aatccgaaga taattgaaaa gctggaggag ttgataaaga ttgtggagaa aaacttcatg    8160
tgacgtggag ctaagtcgta cttgaatag ctttacgtat atttcttggt ccagaaatca    8220
taatctttaa tctctacctt gattgagaat ctgaatatat ataggtgtga taactctaaa    8280
tttcgggttg gttcatagct caagcagtaa tactgcccgt acccgaaagc atcaaagtag    8340
agttacttca caacaaaaat tggcaataga agaagaatag tctttaggtg tgaatgttca    8400
aacatacaag gtgccaatga tctcctgcag agattgatct tgttgtggtc ccataatttt    8460
cttttctttt tcttaatatt agaacttgtt aatcagatgt tacatgaatt actggcaaat    8520
ataccttgat ttcatattaa atattaattt aacaatattt caataaaatt aattgccata    8580
atgcgatttc attttttctc aataaagtaa cacaaaatta taaggttcaa agttctctg    8640 taaagagcat ttatgaacta aattagaagc cattaactct tgtgacttgt cccacatgtt    8700
ataagtttag gtaaaaactg tggtcagctc ttaattctta agaaacttag gcttgaatta    8760
ttgaagttga acaccaaaaa aaaaggtctt agaatctgta aatgattact tcttcctctt    8820
ctttggtggc tgaatcgatt cttcttcatc ttcgtcttca ttttcaggct cttcatcttc    8880 tacagttct ttttcttcct catcatcatt gccttcattg tcgtcaccat caccatcgtc    8940
ctcatcctcg tcttccggct catcatccac attttcacct tcttcttcct ctccgttctc    9000
ttcttcccct gctccatcag cctctccacc accaatttcc ttgttggagt tgccattttg    9060
gtcattggaa ttgttcccat gatcttcacc atcagaaggg tctccttctt cattgtcttc    9120
tccgggtcca tcattatcaa tgtcttcatc ttcgtcttca tctccatctt cctcagcatc    9180
aactatcgct tcatatctat gtccacccaa atcactttct tgcttttcac cttctgggtt    9240
taccatcaac agttcaacca gattctgaaa ctattacaac aatctaagct aattatcacg    9300
tatgcttgac aattgcacca tgaaaatata ttgaaaccaa caaattacaa accccacaaa    9360
acgaaatact cccattgtaa aatgactaaa acgggaatta gcttttcacc catggtcatg    9420
cagaacccaa cccaagtttc ttcttacatg catattaatt tatgacaaat tattgaatct    9480
actacattga aatatgaaac tccacaaaca gaaagatgaa tacttctcaa tatacaataa    9540
```

```
caaatagtag attagaaaat taaaaccact gaatactaat ttttaaatta attctataaa     9600
gcaattgaat tcaatgtgaa gttaacattt tctatataca cgaataaaat attagtaaaa     9660
aagatgtcgt ttttggcgtc aaaatgattt tagttgcttt aaatagaaat tgggagtttt     9720
tttcttatat cggtactcga ctaaccaatt tttcttacat ttaatcttca acttagcaat     9780
ttttcttgaa attcttttca tattagttta aaatttttgt aactttttt actttagtct     9840 ctaaatttag attacgaaaa aatttcagtt tcaataaaag attaggggtc aattttttta     9900
aaaaaaatct tataaatgct agattttaat aggtcgctgt tgttatttat taataaaaaa     9960
attataattt aaacttttt tataaatttt gtttataatt tttatatttt taatttttt    10020 taatttaaa agggttcaat tgatttttta aaaaattgtt actaagattt ttttttatcc    10080
tctggcatta ttagtttcga aacattctaa tatacttcaa ataaaagagt atggatcaaa    10140
ttgaataaat gtgtaaaggt tgagggctaa atttactatt atacctaaac actaaaacaa    10200
acatttaaca gtacaaaaat tttaacgggt ggattgtttt cctcactcat ctaacataca    10260
atagctaatt tgctcatttt ttaatagaga cgctaaaatg caatcattat atagtacagg    10320
gagttttgtg ttacttttac aaattgaaaa attactatga tagcaattag accctcacgt    10380
aattataagg aattctagtt ccctatacat gtttggctca aagagtataa ttatgtcata    10440
attctctata tcatgtttgg taatataaat tataattaca aatttacata atttttaaatt    10500 ctaaatgaaa aaagaatatt agttattatc aaaaattatga ataatactta agaaaaaaaa    10560
ctactataca aataacaaaa cttaaaatca aatcataata tataatatgt tattccaaga    10620
aaatatttca taatacaatt attaataaaa ttaataataa taattaaaca ttctacacaa    10680
atttatctaa ttactctaga atttcatatt tgttgagcta tactttgaca ctaagcatat    10740
acttgttata atcaaatggt ctttgcccaa atattaataa ttaataataa atattatgca    10800
attagttaaa attagtataa atattttata ataaatacta tgtaatttag ttaattattt    10860
agtatatcaa aatatatgat aaattatctt ttgtcaataa attttttaaaa ttattaacaa    10920 gattagaaaa ataacatata attatagata ttttttaaaa ttaaaatact attattatat    10980
aaaaagtaac ttttttaaact taaaaaaatat aggacataat tgaaaagtta taaaataatt    11040
agattatagt atggttgttt gtaattaccc gcataagtac tccaatactc ccctttttctt    11100 aagaattgga gtgcatgatt gaggtgttct agttacatt aatttagtaa tggttatcta    11160
aacataccac acatgcgtaa ttacaaataa ttaaactcaa actgaatcac taggcaattt    11220
ttcaaaggca aatctataaa taaacccctta ataaataagg attaatatat ttttaatgaa    11280
agcctttatg acttacaaac catttctagc cataggttta attttgtttt agaatggaag    11340
gttaggattt agcttttta ggtttaaagt tggtatagac ttttaggatt caagatttat    11400
agtttataat tttataaaaa tataaattta ttttttagat ttaatattta gtatttaaaa    11460
tttaagggtt atcctagtca aggtttaaat tttattttt aaaatatatat taataattac    11520 taattataca aatttaaaat aagaaataat atagtaactc actgtccgtg agtccaatag    11580
gaattgagga actgtgagca tggtactacc cattttttat tggggggaggt ttgaacgctt    11640 tattaatat ttatatatat tggtgggccg acaaggaatc aaatcccggg aactcaacat    11700
aattttacgt aaaacagaat ctatgttttc tatttcagtt ccgcacattg tgcgcttcac    11760
ccacaccagc agcgcaagtt agcaatcacc aaaaataaaa aataaaaata gaaacctaaa    11820
aagaaccaac ccttacttga ggtggaaaag caagagcttg aaacgtagct gaggaggcga    11880
gtagggtgag tacggttccc caccacgcgc acattagcaa accatggtta aacttaacca    11940
```

```
tcaattcgct ataaccttct ttggtctcca tttgtacggc acaagggaag aaaaaattaa    12000
acctagggac aaaaaacaat aacatcaatc aaccatacta ccgttagatc tgatacctgt    12060
catctcagcc gtcagatcta cagagattgg ttcgaaatta tgtaaataag acaagagata    12120
gaggatagca tattaaacag ttaacgttaa ttaaaagaaa acgacaaaaa aaaagcttca    12180
tacctgagaa attctaggga gctcggaaaa attttccagg aaatgggagg aaatgtaag     12240 aaagaaaaca agacaaagtt aagagtggga aggggcggtt gaaagtatag gaaaggaaaa    12300
gtttctaaaa agagaaagac acttgtttgt ttagatccaa cacttgtttt ttgctacaaa    12360
aacattagtg ttttttgagt caatgtttaa gggtgatgaa acacatggga gaaaaaaaa     12420 ggagaaaaaa taccttcaaa attcaaaaca ggagaaatga acaagttttt gttcatttat    12480
tactattttc tttgggtggt tcgtattttg gaattggatt ccattaatag tctattattg    12540 atgcctttt catcctattt ggggctgctt cttttttttt tctttttttga gaatattgta    12600 gtaatagtta agttttttat tcatttattt taagtaattt atgaagaaaa ggtaaattaa    12660
ttattatata aattcattta tttgtttctc atgatggaga attgattcaa gttgtggtgg    12720
ccgctttgaa gaacaagtcg aaatcctcgt gaagagctgc ggtatccatt ttaattcccc    12780
gaacataaaa tgctgagctt ctccatgtga cacacaggca gcgcaaaatt acgatacttt    12840
cattgctcag ttaacatagg ccggtgcaga attgaaatgt ggtacgggag ccgttgggct    12900
gggcccaata gctaagttgt cggaccagaa ttatgattta cggaatgcca tcgagcgtgc    12960
tttcgaacat gttttagttt ttactgctaa catagccgac aagtctgctc catactctct    13020 cttttaaaact gaagtaccat atgaaataaa tgatccatcc gcattatcat attaaaattt    13080
attttaataa aacaaacaag aaataagaaa cgaaatcata ctaattatca cccaaaaatg    13140
gaccttaaat ccataaagtt tgatcatatc aatacagcat gagatattca aaatcactga    13200
acatgattac atgcagctat gaactacaat ggccgccccc ctaagcttcc cctaaccctg    13260
ctgttagact tccttatttta ctccaatcta tagctttgcc tttgtaattc tgcacaagtt    13320
tttaactgta aagatcaccc taccccctaa gccaataaaa attattctct gccttctct     13380 ttctttgctt tgctccccccc cccttccat gataaaagtg ccccacttttt cttggttatt    13440 gatggaattt cagcttagaa ttcatggctt tacagccttt gctggaccat ggcaggtggg    13500
caatgacagc ataactcccc aaaccataaa atcttggaca atggtccctc tccaacttag    13560
accataatca atattcagac aagtgttaaa ccgtaatcaa cattaagtac aataaaaaga    13620
atcaaaacta atccttatag tttaattaat gccactaatt tttttttccct tcctttaatt    13680 gtgtgtacct aaaacagctg gcgaactttg aagggtattg tcaggcatga aagaacattc    13740
atggaggcca tttatcacat aacagctcaa gaaaaggaca aaatccaaat aaagataata    13800
taaatggaaa tgggtgtcca ttaaagtcaa tgggctgttt caatgatcta accgttccca    13860
tttcatgatc tgtagaagaa tggctttgcc tgacaaaagg gttacttttt ccacaaaagg    13920
gacttagttg agttggtgaa ttgcatgcat tcaacatact ttaaacatca aaacgaaaga    13980
ttgcagctat actatagctg tgtatatcaa ttagttatct atcaatgcac atgattcact    14040
cgaactggat taaatttgaa tcaatttatt taacaaaatg aactttgaaa attggtattc    14100
tttggaatta gttcaacttg attcatagta ttattagatt tacaacatgt ggcatgctcc    14160
cacttggcac atgatgagct aaggtcctta atcaaattgg caatgcaaaa aggaaagaaa    14220
agaaaagaaa ttctactaaa tcaaaaccat aatcatgaaa agagagagta tgccccctaa    14280
```

```
atagctttca attgattcct ttattttat ttttatcatt ctaaagccta aggcctagaa    14340
agcactagta ctagcattac attactataa atgctaagtt gatgtggttt tgaggaagat    14400
agtaagttta tttattata gaactttaaa atgctccctc ttttagggga tgagaaggag    14460
ctaaaagcta ctctatagtg ggaaggaatc ccaaagtgga gttttttatt tattaaaata    14520
attaactttg gatagttgga tgaaaaggct aagggaagca aagcaatctc ttccccattt    14580
tttctcacca tcaatgttag tcaaagaggg taactaggct ataggatcta tctccctaaa    14640
cgaatttgag cctctattgt ccttatatat atatataaat ttcgggtcca cgttgatacg    14700
ggagaatggg gagggaatag tgaaatctat atattcgtag ctttgagttg atcggattgt    14760
tagatattaa tttaaatttt agttatcaat attaaattag gattttagtg tgcttttatt    14820
caagattatt taattgttaa atttatttaa tgaattatat ttaatagctt ggaaattttg    14880
gtgaataaaa tttcttcatg aataaagttt tttggtgacc aaggaatggt ttagcacttt    14940
agcggttaga attaagaagt taataaagtg gtattttatt gttttgagat tgcgtatttg    15000
tatttccatt tcgttaccca taattttac ttcattttaa gtaaactgtt tatacatgga     15060
cggtaatttc cacatgtgta gtatatttca gtttattaa tattaaaaaa aatttaaacca    15120
caaattgatt aactaatctt ttttttaaaa gaaaactaat acgatctttc taactttcca    15180
atttagaata tggtaagcag agattaacaa atattttta acattaaatt attttttct     15240
ttttatttac ctcataaccc aaaaattaat catgtaaaac acaattcaat cgaaccccca    15300
agattttcac tttggaaact acttttttga aactcgtctt ttgaatccac cattccttt     15360
caaaacgtt aatttttagt cgagatttct cattttagct ttcacataaa atccaaattc    15420
aaaacccaat taaagtggac gaaaatgtt ggtgtgttgg ggataaaaaa atttataaaa     15480
aattaatgaa agtttccagg cgtgtatcaa tatcaatttc tttaaaattt tattttatctt    15540
cacctatatt atgatgtaca aaagagttac tgataaataa acctcgagga tacaataaaa    15600
ctcaatgatt gtctatgttt tacactaacg gaaacagtcc actgagcact aagcggagct    15660
taataaggat atcaatttct ataaatattt ttttttcttta tagaacaacc taaaaatata    15720
aaagatgccg agataataga aataaattttt attttatatg tttttgagt gtcatacaaa     15780
taaattttta ctcttattta tcgaatatct catgtctctt tatagtgaca taactactca    15840
aacggataac aatatatta gcaataaata taattattta atagatatct acttaaataa    15900
ttacgattaa ttgtaataat taattgatat aacttttgaa tttagaagat ataaagatta    15960
ataaaatagt actataagaa aagaatattc catcagccgt tggcccatgt atactcttaa    16020
cctagactgg aagagaataa cttacaaaa aaaaatcata aattctttca aagagaaaat     16080
atcatgagaa ttcgtaggtt attacaaata tacaacaggg aagaatacta atcatgaaa     16140
aagaaataat aatgattaat aaaattatta aagtcctgtt tgatgaatct tatttactta    16200
tttatttaaa tttaaaaatt ttaaaaaata taaatattat atcaatacat taattattaa    16260
aatatatgaa acaacagtta taaacatgtt aatattggta taaatatata ctagaaattt    16320
aggtgcagtt tcaattttac aagtaaaatt aagaggtttt tatgttttat gtgtatttaa    16380
ttggtattta aaaaatgagt aattatatca ataagtgtta ggtgcagtaa taagacatat    16440
tacacgttta aagagagatg tatgttcaaa ccttggcgat aactttgttc gaaggaggag    16500
ctacaaatcc caaatataaa ccgtaaaata aaaatcgaga ataccaaaaa aagaaaaggg    16560
gtaatcattt tgtccaacac ctgtgggtaa aagaaaaccc acaagctcat ttatgatggt    16620
gtcaagtgta cttttttaatt attttattgt tgttttatta caccctaaaa acaaatggtt    16680
```

```
tcatcctaaa cttgcttatt gaattttttt tttacttcac caattgtgta tgaaataata    16740
atccttaaga aaaatttaga actaaataaa taagagacat aatgattttt taatccatgg    16800
tgttaaaaaa gttccaccac tgagaatata ctaaataata atatattatt tggataacca    16860
ttctatacat actagattat gtcacaccta aaaaatttta tgtaaaaaaa tattttttctt   16920 ttgaaattaa ttcattaatg attataggtg gaatggtcaa taatttatat aaaaatcaca    16980
ttaaatatgt gttcgattct tggatatatg tgatttttag ttgtttcatt taaagattat   17040
ttaaaagaaa tcaataaata ttaggcaaaa gggtctgaaa aatccttagt aaaaaaataa    17100
aagaaatcaa ttgagctctt agaaaaaaaa tgcactcaaa ccctcaaaga aaaaaaaatc   17160
aattacactc ttccattaat agaatggaac catcgttaac cagattgatc attaacatga    17220
catgattgat agaagcaacg agaaattgac acgtgacatt ttatgtggat aaatatgacg    17280
tcaacatatc tatggtatat atacaatagc agttagtaaa tcagttgata tcaacattaa    17340
caattttata ttagttgatt caactaattc aataacaaaa ataactatct tcttaacata    17400
ttaactatta actatttaac tgtcataact gttaagctga tttattccac aatagttact    17460
catccggttt atatgatcaa agtgttgaat aacgacttca taaattttg ccatcccaaa     17520 ttactattta ataatatttt ttggtgacag aactatttat attagtgtaa atttaaaata    17580
attttacatc attctgtaac ttttatacaa attaatattt taataatcaa atcgttgaat    17640
ttttcaagat atatgtactt gttatacata tacatttta agtcaattcg atattctatt     17700
atatcaattt gaaatattgc ttgtattact atatatttac cggttgcttt ttttatacat    17760
aaaacgaata attagaaatt tttaattat gaaaaatttg gcatgcatga tatatacgta      17820
aatagaacat gaaatatgat agttaaatta taaaatatt aatcatataa aaactataca     17880
aatatttaaa aatactttaa ttttacatag gtgtaaatta acgaattcct ccccacaaaa    17940
ttttatttaa aattaattat aaaattatat aaatggtaaa atatatttat taatatttat    18000
gattttaata gtttcaaact taaaaaaaaa tccaaacttg accccaaaca aatatggaat    18060
aaaaaaattt agatcactat tttgaaaatg tttggtggta aaaaaaaaat taaggatata    18120
tttgaatgag tagtaagatt gatttagata agactaaaaa tagtcttaga gagatttatg    18180
gtatcaacca cattgaatat ggcaatggtt aaattaaaat tatttgtaag atatgtgttc    18240
gaatttaaat atactagtat taatgtacag agagataata aaaaaaaatc atcttaattt    18300
aaaacataaa cagtaaaaga aacatttatc aaatgaataa ataattataa ttgatgtagt    18360
tatatttatg tcaaatagta gtttaattaa taaataatta aaagtagcat aaaaaagtaa    18420
aagtattaat aaaaatatgg ttaaggcctt ttgttgttgt tgacacttta gtgtctcgtg    18480
ttcaagcttt gttgatataa ttccccctta atttataatt cgattcagta aaaaaatatt    18540
ataatatatc aaataatatt tatttattta tttattactc tagtagttat taaaatatttt   18600 tatttaaatg aaaaattaag tgatcaatat gttttcatc tatatcaatt ttcttataaa     18660 tttaaaagt tagttcaaaa taatattgaa ccattatttt atttaaaata attacatgaa     18720 tttactttt aaatattatt tttattagaa aaatgcaaat gatataatta taaatgaaag     18780
gagaggaacc cgttgtaaaa ctaaagtggt gtttcattat tttataattt tttatacgat    18840
taatatttta acaaattgac cgttaaattt atcaatatat atttacccctt catgcatgta   18900 atttttttgaa tcgatccaat atattttatta tattaattta aaatattatc tatattaata  18960
tatatattaa cagttgaaac tttttttatat aacacgaata gttaaacatt tttattttttt  19020
```

```
tctcaaaact taacaaacat gatttacatg aaaaaaacat attattaaaa tattaattgt    19080
ataaaaatta taaaaattaa ttttatacca atataaatag attctcccct acataaaata    19140
tttttttaaa tatgctgaaa accttgtat aaaaaaatcc ttttaaacat aaaaagaatt     19200
aagataaaaa gtacaatcga atatctttt aagaaaaaaa atataaaaaa gtattagtgt     19260
tgcggtgagg tgactacaca ttcccttcca tgtgaaaagt ttttttacgt agcttttatt    19320
acattatata tttttgaat attaatttta ttataaaatt ttgtcattta ttttttataa     19380
actatttata ttttattaat aatagttaaa taaaagata atgcgcttca acacatttga     19440
aactcatcta tactaacaac aattctaatg tcgatcaaac taaaactaaa ttaattacaa    19500
tattacatga tatatatata tatatagaac gcattagaaa caatcactga tcattgtcat    19560
taatttgttt agagggcatt ggaccatcca gttgtatcca tctaacatca ttaagaagaa    19620
aatgaaacat tccctcccta tttattacgc catttcctgg ctatttttaa tacccctttt    19680
aatttaatat ctataattct aaacttaaaa cacttttct attttcatgt cccattataa     19740
tctacaacta ttatattagg caatgcatat aagtataact atctcagact tttcttttga    19800
caacaataat aatatccttt gaacaacata aatacaccaa caaaaagggg ggaaaaccat    19860
gaaatatgaa aactaaaaaa gatataaaaa agaccaacat cctttgaaca agtgaacatg    19920
tcccattccc caaaacccca cgaccccaat ttcttttaat ttattaatta aaacacagcc    19980
agaataaaaa gtaagagtac tggtcccacc cgcacctcct atcaacaaat taaaaattaa    20040
aagacaacat tcatatcatt aagaaaatta agtatggatt gtaaagaaaa ttatgataag    20100
ggaatatgta tatataaata tcatccactt cagcattcta ttgcctttga ttaacaaata    20160
ggaagggttt aatcattagg gatttgtttg gtcaaatgta accacaaatt tgggtcccaa    20220
aacattgtat aatccataat caatgtaaac aattccacat cttttttttc cctttgttg    20280
tttaagatcc accgtttgat gggtccttaa gctcgtgaaa gcaacggttt tgattaattt    20340
aagacgcatc gaattgaaaa ttgataatat catccatttt gtatgaaatt tattgctggc    20400
aggcaaagga agagtacttt gattcaagca tctggaattc taaaatgaag gaagaaataa    20460
ttgcaagtta aaaaaggaga aacgtagctg aatctcagtt gttaatgcct aacttgatta    20520
attctaagca aagcattttt tttaaaaaat tattctttaa attacaaaaa aaaaaaaaac    20580
taacttgtca tcttctctct cattctcttt atttataaat aaaaatatat aaacttcagc    20640
tacacagaat ctgggggtga aaacaaaggg aagaaatcag aagttcacga aaatttcatt    20700
tctttaagaa aggcgttaag ccccatcttt tctttctctt tctttttttct tgaactgttt   20760
tccagattgg taattttctt ttttcttttt aaatatatat ttttcattt ctgccaatta     20820
aacaatgaaa atggcatatt accaatcatc ctttcccctc tataggaaac acccatcatt    20880
gctgccaaca atccttttca tttcaacctt agaaacctga gcttctaaga tattccttcc    20940
ccttcctttc ctttctattt cttcttctct ccctctcttt caaccttctt ctccactttc    21000
ctttgttgct ttttcaacaa tggatgcatc ttctacaagc tcagtcaatg ggttctatac    21060
cttcttgact cgtggcatag atgatcttga acgtgtttat ctctctaata acttcatgtc    21120
catccaattc cttcaagggg ttctttccct tctccgatct ttccactccc agctactcct    21180
cctcatccaa aaactccacc ttcccgtcgg tgataagtgg ctcgatgaat acatggatga    21240
aagttcgaag ctctgggaag cttgtcatgt tatcaaatca ggcatctccg gcatcgaaaa    21300
ttattactcg gctggcttta atatcatttc ttcttttgat aatcatcgcc atcttactca    21360
ccagcttct agacaggtcc ttctttaaat tcccaaacct tacaacaatt tcgttatatg    21420
```

```
tatattctttt ctcgagttttt tagcattgaa ttcatgatct gatatggctt tttatttttt    21480
ctaaaaaact atatggaaac aggtaatccg ggcaatttcg gcgtgccgca gggaagctgt     21540
gggattggaa gaagaaaaca gggcgttgat ggaaacgaga atccaaccgc tttcgttaag    21600
gtttgacgag aaagtttcga tcgaatcaaa gctgaacgga ttcaatggtt tccgaggagt    21660
tttatacgca atgaggaatg taagctcgtt gctcctaatg atcttgctgt acggattagt    21720
ttattgtcga acggaatcca gtttcctacg aggaggatat gaagggtgtc taattttcgg    21780
atcagctttc atgatctcaa cagggagatt gcagcaaaga gtggcggcag agatcaacca    21840
aatgaatggg aggccgggga tattgcttta tgagttcagg agatcgaagt tggcaatgga    21900
ggagctgaga ggggagctgg agcggagggg cggcggaggg gtggaggagt gggaaacgga    21960
ggtaggggga taagggaaa gggttgagaa cttgaaaggg tggtttgggg tgttgagatc      22020
tggtgctgac aacattgttg tgcaacttga tgatttcttt gatgagattg ttgaagggag    22080
gaagaagctt ttggactttt gcagtcatag gtagagaaga aaagaagatt aaattataaa    22140
aaaaaaatgt aggatggttg aaaaaaaaag ttacaaaaat acttgataga agaaggttgt    22200
tgttgtacct tttgacccctt ctcttctttt cttttctttt tttcagaaaa aaaaagattc    22260
tctttttatt tttcacttca tgcatttgtt gttgtttcta ccgcagttga aacatggaaa     22320
tagtggtttg ttttccccaa aaatccagaa ggaaaatata tgcagggaa ggggaaacag     22380 agtaattcag gggtctcaac tatcttaaca atgtaaacag ttaaaataaa aaaaaataaa    22440
ataatggtta ggactattt tcatgcaggg aaggggatgg aatcttctat atatataata     22500
ataactagaa agtgtctatg ttagagctac atatataaat attttgtagg ttattaatta    22560
attttatatg tgttttgaa agtgacttcc ctcttgacct ggtaatttat atatacagtt     22620 gtcaattta gagatgaaaa gagaggaaaa atcaggggta gaggatgctt taagatgata    22680
tattagaggg ggagggagtg cacgagagag gttttcctgg gtagcttaa atgtttaaag   22740 cacaagtaat gggttcgttg ccgctgggga tgcgtctgat ttagggtttt tcaactttgg   22800
aagcaatgga gttttaatg atgaaagctt caaagttcta atcactatca ccccctttct    22860
tcctgacatg tccccatcta tgggtagcag aaagttttg cagaacagta tgaaatcgac    22920
cctgctctat gcataggcta ccgttgcctg tttcaccaac agatccagca aagccccctc    22980
aattatcaac ccaaatcatt ttcttcactt gctttatttg ttatttaaaa gagaaaaaga    23040
aaagggtttt ccagcttttg tttcctcttt acgcactagt tactgaaatt agacaacaat    23100
tattatatat gattccaaga acagaagcta ttgcaagtaa aatgcagaaa caatttaatg    23160
gcaggctata agaacaaaca tcaaaagcaa caggtagata taatgcatgt ctgtggtagt    23220
atatatacac tagagatcaa acatctcccg aatatcacat attcagcttc gacgaagtag    23280
cataaatatg aacttaaata aatggagctc cgcaatccac caaggaacat agtagtacta    23340
tgctctgtca actaattcaa taggctgctg catataaatg taggagttgt tgccaaggtt    23400
tcttcacatg tggatacatg tatagttcta taaaccatga ttgtatcaaa aatattttaa    23460
taccgttttg aaagaactga ctataacttt ttacaaacaa cacacatgga agacaactga    23520
ttcagcaaag tgattttgag gaaaagaac cagaagtgta tacctatgct atataattta     23580
caagagtaga atgggaaaaa catagacggc caaaaatata cttaaattac caggaaaaag    23640
tgagggtatg ctagagataa aacaaaatga tgtcaagtaa tatgcaggcc atcttttata    23700
actgttcaat catcgaatcc gggcattgca aactgagcag caaatgcttc aactcgattc    23760
```

```
cgaagatcaa tgatatcttt gttattctga agacccttga gaaactcttt ctgcaatttt   23820
ccgtgatctc tctgtacagc acttgtaatc tgagctgctc tgtaaagaaa gtcagccatt   23880
gtctcaaaat cagaatctga acagcctctt gatgtcatag caggcgtacc tgagagaaaa   23940
ttagggaagt taaagacatt aatggaaaaa gatgggttgt aagccaatac ttaggtgaca   24000
aagaagcaca aaccaaaaac acaagatgtg ctcttttaa caccttcgta tcctcaaatg   24060
atctttgatt gctataatac tctctagcta tgacacgaat tagtcacttc taaatatgtt   24120
attagtgtaa taaacatat tagtgcactt gaaagaactg attaatagta gtccataaca   24180
ttattttacc aattggctaa tttcaacgac tcaaaaacaa tctgcaaaca aacctagaaa   24240
atgtgcttgt ctaacaataa taaaggcacg atctactttg acctttaatg aagctctatt   24300
tattcccgca accccccccc cccaaaaaaa aagaaaaca agaatactcc ttaccaattc   24360
taactcctcc aggagaaata gcaccatttt caccaaatat agcggtttta ttcagggtga   24420
tgtggcacat ctcacacgct ttctcatagc atttacctgg ggaacagaat aagagaatta   24480
tttatagaag gaagcgttca aggaagcata tgttatgata tgaaggaaat gcactgtgta   24540
tgactaattg cgcatatagg tcattttca tggtaataaa ttttttgaat tatcaaacag   24600
gttaaactcc aaattcccat caacaaatag atgggctggg atgtagacag aagaaaaact   24660
tgtagagaat atagtctaga agcaattctt ccttctctta agattctcaa gaaaataggc   24720 agtgttaaa ctgaactata aacgttatt ttcacttctc agaatatttt atttcagttg   24780
ctttattagc ttttccagtt gaatttataa aaactaacct atccatactc cttggagtaa   24840
aacacagtca taagctttcc ccttttaaaa catagccaag aaatggttat caaagaaaa   24900 aaaagccttg aacaagacta gtaagattta ttacaatgaa ttgcaagttg atgttcacaa   24960
ggggcttatg ataaatcaag aatctatgtc atgttctcca acaaggatga agaaaagaat   25020 agaaaaatt tattgataaa gccattaaga agttttaag tgaaaactgg ttgcaaaaat   25080
ctacaatgct tacataatca aaggaaacta catggagaaa tagcttaatt ccaaccagaa   25140
acaatttaaa tatattagca tatatgctt cagcatgtaa atgcaccaaa aatctatcat   25200
attgagcagg caagatcaac gaacctgtca agcctagagt agtgagatcc caaagcaaca   25260
aatggttgtc agtgcccca gtaaccaact tgcatttct tctcagcaga gcagatgcta   25320
atgcctgagc attttctc acctgttgca tatatgcttt gtattctggt gttgccactt   25380
gcttcaaggt tatggcaaga gcagcaatat gattattatg aggcccccct tgtaatgatg   25440
gaaaaacagc aaagtttatc ttttcctcaa aatcatactg gccactacaa tcaccactgt   25500
taccgagaca catgccttgc tttcttgatt ttgcacccct cctataaaaa attataccct   25560
cccttgggcc acgtagactt ttgtgagttg ttgaagtaac aatatcacag tagtcaaatg   25620
gactggaaca ttcctgcaat ggaaaaagt gaacatgctg gtaagggaa agaagaacac   25680 aaatttgcct ttgcatgaaa ggaaatactg atttcatcaa aatgaagtaa cattacaaat   25740
actgattcca ttcaacttca ataagccata agttccaaat attgctagga aatacagatt   25800
aaaagggtga tatttggttt cttccaacta aagtttaacc tttctctcta aatggtaggt   25860
atagtatggg gcatctttgg tcttccttaa atgcaaatgt tagcatgtat gtttaggttg   25920
agttcagtag caagaactcc atgcatatcc agcagtcaaa cagtaattct aattgacaat   25980
ttaccaagag caatgctact tgtaagttaa cctaagtgat accaaggaaa tggacacttt   26040
tatggtttag ataactaact taactcgggc ctattaatat ccaaatgaat tgcaagacac   26100
ctctactcag ggcacaaaaa tctttataat agaatcagaa catcaaacca ataattactc   26160
```

```
aaaacaagaa aatttcgaac cttagctgcc acaagaccac taatttgagc catatcacac    26220
atcaaaaccg ctccacacct atctgcaatc tgcctaaacc tggcatagtc ccactctcta    26280
ggataggaac tcccgccaca aataagaatc ttgggccggt aatcaagcgc cttttcctcg    26340
agcttatcat aatcaatata ccctgtttga ggattcaact tataaggaaa actctcaaaa    26400
aatatagacg cagcagatac tttcttccca cccggcatat accatccatg actcatatgc    26460
cctccagacg gcggatccaa ccccattatc ctatcgcctg gcaacaagag tccggtataa    26520
acagcgaaat tagcggaagt acacgaataa ggctgcacgt taacaccca tttctcggaa     26580 tcaagattaa aagctgtcaa tgcacgctcg tggcataggg tttcaatttg atctataaag    26640
tggttgcccg tatagtacct ggcgccaggc atcccttcgg agtacttgtt cgttaaatgg    26700
cttcccaatg cttccatcgc agctcggcac acaaagtttt cggaagcaat aagctcaatt    26760
cccaagaact gcctttgttt ttccttattc atgatttcat tcaattctgg atccgcctct    26820
tctagcggtt ggtttcccca tgaccggaca gcggctcgtc tttggtcaaa acttggctcg    26880
gaacataaca gtttacaagg gttcgaaaca ggtttaggat cccttgtct tttcacgcac     26940 atagatcgcc ctagaatcct aatttcttca tcttcgttgt tgtggtcttt gtgcttgccg    27000
ttctccaaac gaggggcacc gtcgtctttt tcctcgaaga actgtaaagg aacgggccgc    27060
accgggttcg acgagcagcg aaagctggta tcgatttgaa gcgaaatcga atcgtctgca    27120
atggaatttt tagcaaaacc caaaggcaaa cccgattgag cctgagataa atccattcaa    27180
acccttaaaa aggcaactat taaaattaaa ataaaaaaat gaagtgtttg ggagaaactc    27240
tttgagggag taggggaata acagcttacg gcccttaagg gtaagcgtaa aagcaacaaa    27300
aacaatggct gcacttccta aagcaattac aacggaaata acgaagcatt gcctgattct    27360
ttgaagcaaa aacagagcaa aaatttgagt aacttttttt ttttcaattc atgtacaaat    27420
tggaattatt aatacatata gatataatgt tgaaagggaa aggttctaat gtagacggaa    27480
tcacgactag gttcaagctt gtcaggggc aaaaaaattt gaagcccggc ccagaaccag     27540
aataaaaggg ggaaaaatgg aaaaggtgtg atctttttt cttttcaatt catatattat     27600
aatgcataaa aggaaaagtt aactcatgta gactgaatca ccgctaggtt caagcttgtc    27660
agaggcccaa aataatttga agcccggccc agatccagaa taaaagaggg ttcgtggatt    27720
ctaatacaat gcttcttttc aacctttttt gtcgtcgtcg cgtcgtccat ggagtcgcct    27780
tcatcgtcga cttccttgaa ttttctttcg tactggaatt atctcaattt tctactattc    27840
cgtccggctc tcgctgtgct tttcgttctc tcttttatta ttctctgtaa ttcttatttt    27900
tttcctttca aaacttatcc tttacttttt cgtaatttaa gggttttgct ggctgaaaat    27960
tgtcttctct tttttttttt gcttgaattt atttataaaa attttaaatt tatagggtgg    28020
ctgttggcgt ggaagttggt tctggttcat gttccactgg ttcaagaaat tttcggtctg    28080
aggaaaaaac cggttaaacc aaagccgccg actcgtcgat tatcaagata ttataacagc    28140
atcaactctc atagttctac ttctcaatag gtaatttatt tatttatttt taatttgttg    28200
cattatgttg tgttagcatg aaaaagagat tgaattttt agttatagct tgggtgtgtg     28260
ctagtttatt aatgaaagaa cataaatttga ttagagaatg ttaattaagg tgaaattgaa   28320
gtgataaatt gcatcattta gcactaagaa cccttaatgt agtagctgct aagatattga    28380
ttcagtgatg tgatatgct acatcacttg aactggacct agtgagtgtt taatacgagt     28440
atgcgtctag acatgagttt acttattcta aattttttgg tatattttga ggatattatt    28500
```

```
tcgtactcat gtctgaatcc aaatgacttc ttattccaca ccaaaccaag gtcaggttag    28560
ctcatgattt ggccttagac cttggaagat acaatttggt gaatgggatt tattgctata    28620
cactattcac ctgcctttgg gatttgcatt agaaaaggaa ttttctcaaa agaaagggca    28680
attaaccaat gtttaattta tgaagggaag aatcagtgtt caatattctt gtatgtgttc    28740
atatgcagtt tgttcgacgt tggttagtta aaaaaatctt gtataacgat tggaattgtg    28800
ttcccttgca ttagccatta ggttgttttt gatggttttc ttgctgttca ttgggttgtt    28860
ttacgattct tagtttcagt atttcccttg gatactctct atctatgtta tctgaacgtt    28920
ttatttaact tcaagtatgt gttagatacc tctgtggaac atattcaggc gtgttggtta    28980
tatttgtcaa agtaacctgc agttcagtct gttctttctt atttttatttg cctgtaattt    29040 agcactttag cagtgccagt ggcatatcta aactgtatgg ttggtgttga aagcagaaaa    29100
aaaaaaaaaa aaagaacttt attgatagct tgtaaaatac aatgtttata taattttcat    29160
ccccaatctg agtgcaactt tgtgtggatg atagcagcca caaagctctg tttccagatg    29220
gtcgaaacct aaagcagtgc tggcagcttg aaatacattg gagaagattg agatgattca    29280
atttgtttca tacttttgtg gacagaaagt tgtcaaacag caaaaggtaa acttgttcat    29340
tatttgatct aaatgaagga aatgacattc gagatgacta gagaatgtag tgttttgttt    29400
atcacttctg taaatatatt ttcaactgtt gtaaaaaact ccattactga aaatatatga    29460
tgatcattaa aagtttccat ttcttgttcc attagaattg gagtcatgag tacttccaat    29520
tatagtatag gtgtcattga aattatctta accgtgcaag tgaataataa atgatttggc    29580
aaccagaaat ggcctttatta tgaaagtaca ttacatatga aaattttaat ccgaatttgg    29640
aagtgaatgt caaatgtaag tggccttact ataaagagat gacagaaatg taaatgtgag    29700
tatgtaaatg tacattatc ctacacaggt gtggatatat atacatctct ctccaaatta    29760
ctgtacgagg agtttatgta tataaataat tttaaaattt ttaatcattg tttatatatt    29820
ttttataatt cttaattaat tttagatttt tttatagttt tttaagaaat aatgaactcg    29880
gtaaactatt tgccctaaat cattctagat gcctttagta attttaaaaa aactatgctt    29940
ttttctgtat ttaataattt taaataatac taaacatttt tataatgttt taaaaaatat    30000
atgtcccaga tgaaatgaat cagtacaatt atttgttcag gctcatcatg gatgggattt    30060
tttaaataat tataaaaaaa ttatttattt ttaaattttt ttaaaatatt ttcaccttaa    30120
catgaggtac atatctaatt cctccatcag ctacatcaac attcaacagt agaaatggat    30180
gtaatttaaa taaaatgatc aatttgtttt ttacctaaca tataaaaatt aatttattta    30240 ttttaacta aaaatgaata taattttaaa caaaattatt attttttat ttacatacga    30300 gaattaattt atccattttc taagtaaaga tggatgcgat tttaaacaaa atgacgagtt    30360
taccttttaa ttttatagag attaatttac tcatttctaa gtagaaaggg taaaatataa    30420
tttaactctt aatatgaatg tcttcgtgca cttttaccta atcatactca ttctttaatt    30480
tcatattata taaaaaaatt gaaaaagtca aattattact taataacaac acagataaaa    30540
tttgaataaa aaatattaat ttatataatt tttaataata tatatagact aatttacccca    30600 ttttttaaat aaaagactat actctttcca actccattat ttgaaagatc atattcctga    30660
tcgcatatgt tagacatggg ttttaacaat gtgctcaaat gtagccatga gaacgttact    30720
attagggacg tccgaaggat tatggacgga agaaatattc agaatggaaa tttacaaaaa    30780
tctgccggtt gagttgcatg gtgaaaaacg atggttgctt ttcagctaat aatgagttga    30840
tattcaccaa aaccaaagcc catccaagct caggcagcta tcaacaaaag aaaaggaatg    30900
```

```
ggaaaatatg ttgctttgag aaataaataa atctgaatat tctttagttg tacaagtgtt   30960
tgccccsttt ccgagaaaag aaacattaaa taaaatgtgg cccatgaaaa ccaaaatgtg   31020
ataatgttac ataggcaaaa atagcaaatg aaatatgaaa aagagaaaaa gccttcacgt   31080
actaatgaga tttgtcaaga ggaccaattg tatgtagcag caatgcccat ttagatttac   31140
tgatcatctc ccgaagattc atgagtgacc acagttgctt tcttactact acctggccct   31200
gaagaaactt taaccatcgc tggtcttagt agccgatccc aaggaggaa tccacgacga   31260 aattcttgga tgataatccc ttccttgaac tcttgcgact cttcgcgtgc tattgcttcg   31320
tgtagctgta acatacaagt tggaaccaag tgaatcaata acaaaaatga ctaggaatgt   31380
actgattctt gtgacaagtc actccaaagc ctatacaatt tgttcaacca aatttatgga   31440
tgggtatatt tctctttttgg gctcaaaaca ggaatattca atcagatata ccccgaagaa   31500
taaacttatg tcaaccagat gagatgatct aaacatgaaa actaaaccga acaggtatat   31560
gcaccgagct ttgtaatctt ctgtttaaga tttagaatga tccctagtat ggacacaagc   31620
tctcaatcta aagaagtatg cttttgctgc tggactagca tggcatccaa ctttggagat   31680
caaaagaaga ttttcatcgt atgtacctag cagtagcaca aacttgcaat atagtttctg   31740
aatggatatc actcacttag cacccccata aagtgcacag cttgaagata atcaggctag   31800
ctcatagagt ttgaaactga aacacaaact gaaccaagag aatccctaaa cagacgaaac   31860
taacaattaa accaaagtgt ttactagact gaaggtttgg ttcctacgct acatattcta   31920
accttttgca aaaatttaag cagataggaa actaactgaa ccatgtgtgt gcctgtgggt   31980
ataaatgtat acaaagtatc ctacacttgc aatatgttct ctaatgtgac tgaaccaaac   32040
aaaaccctat tgaaggctag caacaaataa agtaacaaac agacattact tgtagcattt   32100
aaaacttaca gagggatcaa agggctttcc aactgtaggg acaacagcca cttgcaaact   32160
cctcatgatc tccacaaatt gcttgtatat accctgataa ctcatatcta tcttcttttc   32220
tttctccgtt tcgggtttaa tttgttgctt ggctctctca aaactgtcaa ccatgggcaa   32280
cagactctcc atcacttctc ctttagcatc agaccttgcc gtaagtctct ccttctcaga   32340
tcttttccga taattatcaa aatcagcttg caaacggata tacttctctt tcccagaggt   32400
tatctctgcc gacaattcca aaacttgttt ttccaatcca ttcttctcgt tttctaaaat   32460
gctaattcta ctctcaattt cagatacaat cctatcatct ccattgagaa gcgcctcccg   32520
gtaaactcca atcatggcct ttaaaccggg aaaatcttct ccagctgatg cttttacatt   32580
ttcctgttaa aattccttaa tgaaattaat actaattaca aacaattaaa caataataag   32640
catctattat cgattgatat gattcaattt tcatcttcag ccaattttt tctactgtga   32700 tataataaag gagggaaatt ctacatatcc ttctctcaat ctaatgctac aacttataat   32760
agatacaaga aaagaaaata aagaacccag gaggaaggga gaaaaaaaga acttacagtg   32820
cgagcagatt cctgggctga aagagaagcc ttgaaagtcc acctttgggg atagtttttg   32880
cggttcagag ggaaggaaag gttagatgga gaaacccag aaagggtttt tgaaaagcta   32940
ggtctttggt aaagaaattg gaccggcgat gaagctatat gggtgtgttt tgagggtttt   33000
aaagaagaag cagagaagtg agaaggaaag agagagtggt tagagaatga agcagccatc   33060
tagaatggtg aacgatgaaa ctgggattag tagattgtgc aatagattgg cgtgtaaaaa   33120
tttaaccaaa ttaagcctg ggaaaagagt ccttggtggc agccactagc cagcccgccc   33180
tttggccttc ttgcctttgc cggacaccgt gactgagtgg aggatttctc tggagaaagg   33240
```

```
agattgaatt gaagcgattt cgcttactaa ctttctcttt gggctgtgct tatgggcctg    33300
gctttgtttt ggataaagcc ccccaaaaaa cccaattgga atgctctctt ctccaatatt    33360 ctcaacttt  cttgttttct cagaagtgaa taatcaataa taatatcttc caaaaataat    33420
aatagtagta tataatacag ttgaataaaa taatgagaaa ttggattttt ttataatttt    33480
ttgttttata aataataatt aatattaata ataaacatt ttaattttt aagactatga      33540 gtataatttt aacatactaa attaataaat tatttttaa ttccacttc aaataattaa      33600 caaatttcat tcaaacattt tttttagtat aactaacatt acaatccaac caacaagtgt    33660
taaatatagt gtcaaaatac attgcactcc caagagaaga acgaacaaag tgtaaatctt    33720
ggatataaca ttgtagaaag gggcaatcat gaaccttaaa tataaaccgt acaataaaca    33780
taaaaagtaa aaaaaaaaag gaaaaccaat cttacaatca ataaaaattt caaaactcct    33840
actaatagta taccttacca ttcaacactt cttgttgtcg tttatgcaaa cataatgttt    33900
tataacttct aacaaattta acaactattt tagattttc aggacttgaa aacttctaaa     33960
gaaagaaatt tccagttctc tcatgcatct ctggattctc tttgttttg taagaaacaa     34020 aagctagatc tcattaccat ggcattcatt agaggttcat ttacttttgc attgtgtcac    34080
ttaagctagt catcttttta gcttattatc tagctttata tatacttgca attctggcat    34140
tggtaatcct gaaagcttat aaataagtat ttgcattgtt agacaatagg ttttaacaaa    34200
ttagtataat gagtttagc attgttaaac agacatattc ggcctctagc gcatgtccca     34260
ttaatcatca aaatgaaaga atatagaagt tacctccgct atcaatgatg gccacttgtc    34320
ctcttcttct tcgtgctctt tgctttgcat gtgtcggact cgagtcgaga atttacatat    34380
gttacgaaga aacccgacaa cgcaactacg tcaaacaaa ccactaatct ccaattcatc     34440
cgtgtggaaa gagataataa gcccttttct tgttcttgtt tttgcggaat tgaggttggt    34500
aagtagatat tttagtcttg aaaaagattt cattaggcga gtaatatttt ttcaaaatag    34560
taccaccttc aggtttggag ttaaaattaa aaataaagag aataaatctc aaatttgata    34620
aaagaataaa attttctaaa ttcataattt caataaaatc agcctcatat tggctaaatt    34680
tttaacacta ttatcgattt aaactataat tagttcctca cattaagtga acaaaaaaat    34740
tgtcaaacta aactatcaac attaaatttc aattttggtg atagtcaaaa gaccaaaatc    34800
aaaatttgac cataatcata ttagcaagaa aaagagccca gaaaagataa tgtaacacgg    34860
aaatggcaga gtcaactaat ttgctctaac tccaattcca atctaagcat ccgtccacac    34920
acacgaaaaa aattccactg tcgtttagta ccaagaagaa aaagggggaa aaaccgaga    34980 ttgtgtcaaa tatcaacatc ttttaacaca gactagaatc aaaacctaag cacgtattta    35040
tatgagcaag taaacaacta gagataaaat catatcaggt gtcaacctcc tgactgcctg    35100
cctgcctgcc taaaattacc tgcaaaacaa aatattttag cgaacaacat atcaatatat    35160
gggtcagaca gaaaacaata gcacctcaag cccgtattga aatgcgtctg tgcgggtaag    35220
tatataaagc tatgcatcag aatataacag tacgatacta ttttacacca aaattatgga    35280
gctcatattc aataaatgat gtttaggaat taatatatac atgtgtgtgt gtgtgtgtgt    35340
gtgtgtgtgt gtgtgtgtgt gtgtgtgtgt gcgcgtttaa caggtataac taggcttaga    35400
ccaaaataga tcaccattat gcattttctt acatacccct tgattttgtt ttcttattat    35460
taagccaacc ttattccaac cccagaaaaa cactcacaaa gcaaactggt tttctcaaaa    35520
tcctgaacga aagtcttttt ggaccagacc ccttggagac caaggctttt gggtgtacca    35580
caaaaccatg agaaattgga caaactgttt ttatgactct aagcaaagcc tgcttcaagt    35640
```

```
cttcaaccat ttcctggctc aactcttcta tttccttta atactgtcgc tcaaagaaaa   35700
ttaatggcag gcaaatacat cctttggaaa tagggaaatt attagtttgg gtgcacgctc   35760
attcttgaca agcagtcagc tccggccagc aacaactaaa atatttatgt attccagtgt   35820
tcttttttga gaaatgtagg tacaactcta tagacgacat tggtcacaac ttttccccca   35880
accttcctaa tactaaaata cacaggcaag cagatgaata tggaaaagga aaacagatca   35940
tttctagaac aacaggatga aaaatagata aagctttata acatccaggc tcatgtaag    36000 catcaaatag cagtagcagc atgataaaat tgtaaaatcc aataacagaa accatacccta  36060 aacagttact catctgcatg atctggacaa caattcattc acaaggagaa gccttcaaaa   36120
gttgaggctc gttggcattg gacatctagc ctgtcaagca gcttcgaaca gccataagtc   36180
aatgaaagat ctaaggagtt cttttcactc acagcttcat catgcctttt acctccaaca   36240
tcatccatgc aaccaacatc atcaaatctg cttctgacag gctctttcaa agcaattatc   36300
ttgccaaaca atcgaaacga accaacacct actttgcttg agttgcaacc cccatgttca   36360
ataagttccg tgccaaagga aaccatgctg ctctgactat caggtgacaa gttgtcagac   36420
tgtgaactgc caatattgag ctcagtggat attctagttg gcttgggtac cacatagttg   36480
ccagagaagt tatcagtgga catcactggg gtattctcac tcacatcgtt ggttaaactt   36540
tgcaagtgaa aatgatattg cctggctccc tgcatgccag caggaaaaga attgtaattc   36600
aacagtgatg gattcaaata ccccattgtt gaattagtta accctgacac aggaaatatt   36660
tcaccctctg catcagccag ccctgaatcc tgagaaaact tcagcctctt ttccgagggg   36720
aacgaggaat gaagcggtga ggaggaagaa atttgaactt gccatgggtt cactttcctt   36780
gcatcctgga gaacttcagg ttcatcccaa gcaacctaat gatataaata taatgcaata   36840
gtgagtcaca aaagatagag gagaaaaaaa attctataag tagcaacatt gatgaaatta   36900
aaaagttaga ctcaattacc atcaaaaact ttaataaaga ttaaacaaac accatcctac   36960
cacaaaccca cccccaaaat gctgccttgg aaatgtttca aaatatgaat aaacttttct   37020
atcattagta ccagtcatag aacatgagta aggaaaagaa aaagagagag cgagagagat   37080
taaaccaagc cttgatcata gaaccaaaag cttacctatt atatgttatg aagatagtat   37140
ggcatacaaa tatccacaaga tacatctcac ctaagcatca aatttaaaac ttaggaaaca   37200
tgatttgatg gggctgaagt taactcaaca tgactaaact catttctttt gttagtcagg   37260
tggctcaaaa ttgaatgaat cctttattcc tttcataaat ataagttat agaaattcag    37320 aattacccac aatcaatatc aagtcaaata tttaatgatt ttacaaatac cttgccaaaa   37380
tgcaacaaac agaaaaaata agaacaccca tcttactttg agagagaaaa cactacctaa   37440
caaggcacac aaaatccaaa cacaacctag aagaaaagaa aagaaactgg tacaaaatca   37500
tttctgatct gaatgagatt ctaaggaaat tctacaagtc taatctgatt ggcaccaccc   37560
atccttggtc aaattcctaa gaagagtaac tctaaaattt gttgacttt ttccacttc    37620 tgtttcttaa gtctcattaa aatgttaata atgatttgaa gcctaatata gggcactgat   37680
ttttattctt tattttttt ttgggggtg ggggggtgat gcaaaacag atatacaaga     37740 agtaaaatgc agcctactcg tagagctgta gaacattcca acctcaattc ctaagtaaaa   37800
caccataact tacgttatat aagcattttg tactctttca cttttaagtg cacttaattt   37860
aaatactgtt gaaagtatag tgcataattc tggattatta ctgattaaat tgttcattga   37920
aaatagatca acagtaaacc acattcaatt taaacttcat ttggatgacc ggtctaccac   37980
```

```
ccgccatata aatgaagctc taatcacaat gaataaccac aattcaaaca attgagcccg   38040
aagcactttt acctgaagca ttcgccaagg cgagccaatc caggggccag aatccggtac   38100
agcagcagac ataactgtcc cttgaaacca agccaatcgc gaggagtcct ccgtctcaac   38160
tgccatcttc actctggtcc ccgcagccca gtaagtactg attccagcct ccaccaacac   38220
cgccctcgcc acgaaatcag tccaaccggc ccgaggataa tacacaacct cgaacgggaa   38280 cccctcgct gccttctccg ccgcttcagc cactgcctcc gccgtcatcc tccccttcc    38340 ttccctttc attgctcctc catcactcgg ctctctccac ctccccgaat cccctccgcc    38400
ttctcccgcc ttcattgctc gccggactcc aataaacatt ttccaattac agtccctcat   38460
gaaaacaaca gaatcgccgg cgataagctt cttttgatta acgaacttgc tccatcccgt   38520
agtgagcaga tgcctacgtg gcgtccctcg ataaatgtga cgaaactccc aaacaccgcc   38580
gcgaacgtcg gtgacggaga gagtctgaac cggcggatca gcattgtagt cgagcggcgg   38640
gaaaacagaa tcggcacaaa accgcgggac ggagaatcca ccgccgttgt tggcatcaga   38700
gggcgttaaa accttagcaa atgacacgat cttattccta tcagaatcct caacttcacc   38760
attcacattt agaaattgat taggaagcct agaagtttca acaggggtga gtaaaagctt   38820
agcgaagacc tcatcggttt tcggatcggc aagataatga acgtcggaga taacgcaatt   38880
aatgagaggc ctagacagta cgagagagga cagtttgggc gtggaaccgc aaacttgttc   38940
aaggtggcct tgagggaagt aataaaccct agaattaacg gtggggatct gaacggaaga   39000
gccggcacaa gctcgccaga tccttggatc aacatgacga agctccggag gactagaccg   39060
tgaaggcggc attgggccgc ttagggttta ataaacgag gagagaattc aaaagggtta    39120
aaaagaaaag gggcagcgag tctaagagtg agtgatgttc gttagatttt tacttgagag   39180
atttatattt ttaatttgtt tttatgtttt tatagtattt tatggtctgt ctgactctga   39240
cgcagactct aagaggtgag gtaggaaaga gagagagttc cgtctcaagg tcggagaagc   39300
gggcaaggac gggcagatgg gcaatcacga aacccaaatg ctgttatgtt agcgtttgtt   39360 ttttcctt tccttttcgg ggagaaaaaa gggcagaata tatggtcggt tagaaattta     39420
cataaccgtc tcaacgtcgt cgttgtggac gctctacctt ccaaaacgta gagtacaatc   39480
gctctggaaa tgaagatgaa gtttgttctg aagtaaagta cgaaagtaac cttttgatgg   39540
taagaggaag tcaccaatc aaatggtcgt gaatacttta catttggaaa aaggtcgacg     39600
gagacatatt gagtgaatcc ctgtttggtt ggggtgtgtt tgtggggggg gggggtggg    39660 ggggaggtt gtgatttgtg agagaaaaaa accgagggaa ttttgcaacg accggatttg    39720
gattccctct ctctgcctag ctgtcgcaat ttacattcac taccgacatt ggaattttt    39780 taatttaatt ttctcttgtt ttttgggtcg tatttaaaca caataattac tggcaatagc   39840
catgacatgg taataatctg gactctcaat tttttacaa aagatatcaa tggtttaatc    39900
tgacactgaa attttgttta aaaccttttcc ctgcttaatg aaaaattgag gataatttca   39960
acttaatttc cttctaatct aacaaaaata aataatatta ttaaacatga ggaagtagat   40020
gctatttatc atggtatacg gatcttcttt attatagtcc ttatctatca tttcatgttt   40080 tttttatat attaaatcca acattctcca tcttttcatt ccaattgctc cccctatgcc    40140
taataataga ggatgggtt tagagtacat ggtggaccaa cctattggaa gaacttttgt    40200
tcccgaatta tcatattcga aaatgtgggg gtcaaactta gattaaacct ttagaagtct   40260
agtccaaggc gaatttctag acattttactt aaagcacctc ctcttttgat ttttataatt   40320
atttatatat ttttaattaa aatttaatt ttttatacat atttgattaa tagattataa    40380
```

-continued ttatatagta atttttttata ttttgataat ataaattata attaaacaat taattaattt 40440
taaattttaa aaaatattaa ttattataaa aattatcaat aatacttaaa atctcttaac 40500
aaacagtgat tcatgaaaaa tatattctac aatatcatta ctaatataat taacaaggaa 40560
cctactatat attctatagt aaagttttta actaaaaagg gaaacattca gttgtggtgt 40620
agtctttttg cttgataagt ggcacacctt atgaattagc atgtggacaa tagacattaa 40680
aaaggtgatt aggtcttaat ttaattagta actgtattgt tgctaatgca agaatacata 40740
ggttcgaatg tgttaaaatg aattattatt ctatttaaga gttggagaag ggttatagat 40800
agttataaat cttatatata ataataacct ataatgaaat taatgttaaa gaaaagtcat 40860
caatttatct cccatattaa ttattcaact tttttggaaa tatatactaa ataataataa 40920
ttctacaaag catttaatta taattttttt ccctatattt tagaaaagat atatttaaca 40980
ctatatataa aataatttta gtaaaataac aattaccgta attagaattt atagagagcc 41040
tataaataaa ttgtctgcaa taaacaacac agaataaata atattttgag ttatcgttca 41100
agaaaatttt gaaggtatca ttttaaattt aaactttgat ttatattcta ttatttagtt 41160
tttgtaaatt atgtataata tatattttta catttttttaa agcttaaaaa aaattctcaa 41220
actttaaaaa aaaagcaatt aatttttttt ctcaattaag cacttaaact ttcaaaatat 41280
atcaaaaagg ccattaaagt ttttcaaaaa aaggaattaa gcctctactc tctttttttca 41340
ctcaaatggg tactttaact ttcaaaatgc attaaaaaga cttttaaaat taaaaaaaata 41400
agcaattaag ctcctactct tattaaaaat tagaaaaaga ttataaataa taataaataa 41460
taaattttag aaaaaatatt aaattttaat aaaaatttta aattttatta aaaattagaa 41520
ttttttttaca aaaatcgtaa caaataaaaa attgtaaaat tatataaaaa tcacaaaaaa 41580
aaaatttaac gacccctagt ttaaatcaat taaagtcatc acgtgtagca atacagcatg 41640
acatatggtg aaaaatgata aaataaaaat aaaaattata gaaaaattta taaaatgttt 41700
cttttggtac gataattttt tataaatttt ttacaaaatt tatatttttt tacattttgt 41760
ataattttct tacgacttta taaaatttta taattgttta tattttattt ctatttttat 41820
atttttaata gtttttaata gttgaatttt tttatttaaa atttaataat atttatagct 41880
tttaatttta atttttaaaa tttttaataa aagcaatggt ttttttttaa aaaaaaagct 41940
ttttgcacca ttaacactat tttttgggt aacccttaag cgtattttga atcttctgtt 42000
tttattgaca ataactcccc tattgtaatc aaatgtggtg tgtttttatt aagctgtacg 42060
tggaagagtt ttcatcgcag tagataaaaa caaatatcga ctggttatca gaaaattgca 42120
tcccataaaa gtcaggtaat agcttttcaa tttatccttt tgaattattt tcctttacat 42180
tcaaattttt attaagtgtt attacaaatt acacttacaa ttttcaatat tgattttttt 42240
taaataataa taaattccag gatcgaaggt tcaaattcat caaaaagaat tagatttgaa 42300
ttcatacaag aaaaatgatt atgaagattt atttcatgtt tctatttgat ttatttatgt 42360
aatcaatttt ccatctaatt taatatggtt ttccttattc tttattgaca tgtaaatgat 42420
gccaaatttg tgtaaatttg atttttttttc aattacttga ttatttgtat ttagggtaaa 42480
ctatacttga tcactcaatt atgcttatgt ttttgctttg gtcacctaac tttaataaat 42540
ttaacatttc tcatttacaa attctatcaa tttaatcttc aaacttccta atcaaaattt 42600
taatttttaa aactgaaaca ttccacatct ataaatttat aaaatctcaa aaaaaaaaac 42660
cttcttcaat taaaagccgt tttccaagtc aattcctgat actaatgagt ttatcttaaa 42720

```
tcttttatttt cttttctttt tcttttttca ttagttttct tctaaatata atattttata   42780
acccttttcat tgataaaatt ttggctaaag aaaatgaaaa caaacccctt taaaaaaaaa   42840
cacttcagac ttactcttat tgttatcagt atgataatta tttcaaggta caaagaaaaa   42900
gtcttcaaag ttggtcattg aaattagaaa ttaaatctag agttaaaaaa catagctttg   42960
aaaaatccaa tggttcaatc aataattatg taagagaaaa tatatataaa ctgattaaga   43020
aattattatg tgttatattt atttttaatt attaaatcca taataagtaa tatgtatcac   43080
taataatcta atttagcgtc aaatcattcg ccaagttaaa ctaaaactaa atttatgtta   43140
gttagagtga aaaaaaaata tttataaaaa tataaattat ttatataaat ttattatatt   43200
ttttatttt taaaattttc tattattttt aatagtgttt agttaatttc taacactgac   43260
ttattaaaaa ataaacaaaa agggttatat atactaaatt gaataatttc aaccataaat   43320
aaaacaattt agaggtgtga aatgcttta ttttaaaact tggaagcttt agttaggaag   43380
ttttaggatc aaattgatag aatttataaa tatgaatggt taaatttatt gaattattta   43440
gaattaggat caaattgaca gaataagtaa gtattgagga ctaaatatgt tattttacta   43500
gttagaaaaa cacttttcgt tatcaattta ccggtgccta aattaaattt ttttaaagtt   43560
aagtgatcaa aacatgaacg taagtataat taggtgacta tttatatggt ttacccttat   43620
atttaatgtg ttgtataatt aaaatttatt ttccaatgcc ttgattattt gtacttaata   43680
gaaattaata aaaatgttaa cttttgatat caaaataaaa taaaacttct gagataaaag   43740
caaatgtaaa aatacagcaa tagatcatat catattggca tgaaactaat gcaaattta   43800
gtactataat tctaatttat taaaataata ttactttgtc aaattaattt atccatatta   43860
atgcaacaat taaaaatatc atattagcat gaaatagttg cattgttatt aaagttttgt   43920
cttcttattg taattcacca aaaaaataaa tattttaat tattaaatta gacatttaat   43980
atgttttacg taattatatg tttattatat aaaataagct aaataatttt ttttaaatca   44040
tataagtaga agcttttatt gcttactacg ccatctacta taatcttaat taatatgtaa   44100
tactcgctat aatgttaata tgagagtctt aattaatata tactacttct tttaatttaa   44160
gattgaattt aaaatacttt taatatttaga atcactttta aattgaattt ttttctatta   44220
aaaaattatg ctgagttatt tttaaaggaa attttataat ttaaattaac tccacttttt   44280
taattaacta aaaacatatt tcttataata atttaatttg acatattatt tttaaaattt   44340
taaattaaaa tatcttaaat tgaagtaatt taatatgttt taattattaa atataatcaa   44400
ttcatgcatc gcatggaaga aaagctagtt ttatttaatt acattaacat tccatattaa   44460
tcaagccttg gttcttatgt ttatacaatc aaacgcatca gtttagtgca aattttctgg   44520
aaagaaaatg agcactttg gccgaattga gtgagatagc aaataattaa tatgacttta   44580
tccagattat ataagtgaaa tgttaacaag gaaataacga caagacagaa aatgatagtc   44640
tgccgctttg gcacgtttca cttttgccgtt ttggcacgat tttgagggtt ttcttttctc   44700
tttcttttttc tttactgttt ttgcgttttc tgttgcagtt ttgcttctgg ttatgtggtg   44760
tggagaggtt ttgatttgct atgtgagtga tggaacgtgg tattgcggat ctgaatctag   44820
aggatgcaga ggatgaggct ttctcttttgc cggaggaatc agaagaaaaa aattctgcgt   44880
atagttttg cttggtggga tgtttcctga cagcgtggtc catttccag ccttgatgaa   44940
tactttggca aacatttagc atccattgga aggggtacaa atatcagatc tggggggaaa   45000
acgattatt ttcaattttt tcaatgagat agatatttct cgtgttatta catgtgctcc   45060
ttggactttt aataaccacc tcttgatttt tcatcggatt cagtagaatg aagacccgat   45120
```

```
gtctatccca ttggtgtatt cagattggtg ggttcaagtc catgacttgc ctccgggttt    45180
ttttagagat tcaatggcgg ttttgttttg aaatttttgtt ggcagatttc tagaatatga    45240
tacaaagtag gttcttaatg gatataggaa tttcatgcgt atatgtgttc agattgatgt    45300
gcgaaaacct ttgaaacgaa gaaagaaaat tatgattgct gagtcaaagt tctcttatgc    45360 aaatttttaaa tatgaaaaat taacattgtt ttgtttttta tgtggctgtc ttagacatgg    45420
tgagaacttt tgtctggtga gattacgtat tggagcacaa gaaatggagt ttgggtggga    45480
tctatcgttg agggctcaag cgaggaaggc tttcacgatc aacagcatct ggctaaggga    45540
taatggggac agttgtcatt ttggaaagtc ttagtttgag cagcaatata gccataattc    45600
aagtcaaaat caaggatgtg aattatgggg taattttaat aatatccttg ggataaattt    45660
ggaaggttcc aaatctattg aagagatgaa tgaagaccaa gaaggggga aatttcgtca    45720 tattgatgga aagagtgtga ggcatgggaa aattcaaatg gtgggacctg ctctaaatga    45780
tgatgtttta aggaatgttc cggggcggaa tctaacatcc ctatctcgta accgtcgcca    45840
gaataggtaa gaggtattac cacagacaga acatcacaga tccatacaga attacggata    45900
tcacataata ttaatgcata agcaattcaa caattcatcc cttatggatg tctccaagac    45960
ctgagacata cttttagaaa atgtcgggac taaaccaaac atgttcagaa ttttcagaac    46020
ttaaaaaaaa attcaattct attgaagtta cacacccgtg tgatcaggcc gtgtgcctta    46080
cacgggtacc agacaagccc atgaggtcca gccgtgccaa acaaagtat acatattgac    46140 ttttacacac ggcagtgtga tacttaattg gctactgact tgagcccacg gccatatgac    46200
acgcccatgt gtcttaaccg tgtaatctta agaggttact gctttgcata cacggccaca    46260
aggcacgccc atgttccctg cccatgtggc acaatgcagg cttggtttaa gccaacttgc    46320 caccctttt tgggtcattc ctaccagcaa tattaaacaa catttatacc aaaatattta    46380
gctaaaacca tgctcaaaac atgtttcatt ataactaaat catcatcatt caataaccta    46440
ttcaaatcca taccaaaaca tattaaaaat cttattacaa catgccaaaa tgctcatttc    46500
ataactcact tatggcatct tctaactcat ggtaaaactt accatttcct caacttggca    46560
tatttcaaaa tgaccaccac atacaaggcc atataaccat tacaagcata cacaatttag    46620
catcacaaac catttaccaa aactaagcac aaacatacca tttgctagcc aactctcatg    46680
gcataacata tatacatatc aaaacttaaa tacatagaca ttctatccta tacatgctat    46740
acttaaaaat atttacactt tcaaagtac caaaatgaat tcgatagtat ggtgacaatc    46800
ctcgactatc cccgagcctt cagtagctaa gataactgta aaatagacaa aaatcacaca    46860
gagtaagcta caaagagctt agtaagccaa atacaattgg tctaactatt aaagcatata    46920
aagtacaaat caacagcaag aattcatagc catttcacag aatagttcat gagcctaact    46980
atgctcattt gcttgtatac atgtcatgtt ttatttccat gatttcatac atactacgca    47040
ttcattattt cacagaaaca atctttcata ttcaaaaatt tactactata cgaatgtatc    47100
tatagagatt atacatttca tatattcatt cccatatgtc gtactctatc atcagatggt    47160
tcagaaaaga tacagatact cataaacggg tacaatgcca acgtctcaga catggtatta    47220
catgtaattc agtatcgatg cctctgtccc agacagggtc ttacatgaat tcagatacga    47280
tatcgatgtc ccagacacga ttttacacaa tatttaagat cgatgacaac gttccttttaa    47340 aaacatacag agcttttcaa atactaacat attatcgaaa tttactcgga attcattcat    47400
caggctctca tagccgtcca atacagatta taactagtat atacaacatt caatcaattt    47460
```

```
aacacgtaat tgtattttga cttacctcgt acgaatttca gatggaaacg agtcgactat    47520
tcaattattt tggacttccc tcgatctaag ttcgattttc tttgttcttg atctaataca    47580
atttaaattc aaccattcaa tcattcattt catgcaaaat aatccatgaa cacatattta    47640
gggcacttta cattttaacc cttacatttt cacactttga caatttagtc tattttccac    47700
aaaatcacaa atatgaaaaa ttcaccaaga ctatagcttg gccgaatata catatcctcc    47760
atacaagccc aaataacata tttaattcac aattcagtcc ttcaaaacct catttttcaca   47820 aattagccca aatagctcta ttccataaaa aatttaaaaa caaagcatga taatctcacc    47880
tatatctttc ataatccata taaaaacatt acaaagctca tataatcatc aatggcacat    47940
ttcataatct tcaacagaaa cagaaattca gacatggatt ttgaagaaca agaagcaacg    48000
atcacagaaa cgtaaaaatt ttcaaaaaca gacgaaaatt cataccttaa tcaaggatta    48060
agccgaaacc taaaatggct ttcaacacat tcatgcaatt tgttttcttt atttcatgtt    48120
aaagcacgaa ttaccattgt atccctcata aataaacata tcaattacat aaaacaaggt    48180
catttatgac cactcataaa ttcaatggag taattgccac ataaggccat aataatccaa    48240
agcaatgcca attaaacaca ttgaatatat ggcatgcaaa ttttatcatt tatgcgagta    48300
aatcattttt cataattaag catagaaaca gacaaattaa atcacagaaa cttcgaagat    48360
ataaattcac atatcataga cagagaaaat aatattaaaa tattttttca aaatcgatta    48420
cgtggtctca aaactactgt tccgactagg gtctaaatca gactgttaca cggaaggggc    48480
ttttgactaa aatggagttg tcaaatatgg aatgcaaatt agaggacgct caaataatta    48540
atgaggaagg aaaaaaaaag acaaaggtct gatttttttaa tctctaatgt ttctaatgga    48600
caagattcgt tagaggtttg tggtgggtgt ttcgctcaaa atcaacaagt atcagcggct    48660
gccattaggt aagccgaccc acagcaatga agttattttg ttggaatatt cgtggattgg    48720
ggagtctgcg agcagttaga agacttcagc acatgctgaa aatttatcat cttcaaattg    48780
tcttattcat tgagactaaa ttgaatgcta atagaatgga aagggttagg aaacggtgtg    48840
gattttttaa tggtattgac gttccggctg aaggttctcg aggaggatta agtctagggt    48900
ggaatgaggg acacttggtc aatttgaaga gtctctcaaa aaatcacatt gatgtggaaa    48960
ttcaagatga taaaggaaaa catcgacggc tgtttacagg ttttttatggg gctccagatg    49020 ttagaaataa agtagagacg tgggatttac ttagacgatt ggggagaaat aattcattgc    49080
cttggttggt tgggggagat tttaatgata ttctcttgtc acatgaaaag caataaggta    49140
taccaaggga aaaggctaaa actgaggcat ttcgtagaac gttaaaggat tgtcttttgg    49200
aggacattgg ttttttctagt ccctggttta cttaggaaaa aggggcgaat tttggagtgg    49260
aacattaggg aaagaattga cagaggagtt gctacggata cttggcttta aacttttcca    49320
acttattctc tggggcatct cccgcactct ttctcagatc attgtccttt gttctttgag    49380
acgaaggttg gtaagaaggg gaaaagtctt attattcaat tttatttttaa atcttggtgg    49440 gtccttgagg agtcgtgtga agaagaaatc aaaaagcttt gggaagaaag ttctggatct    49500 tatttttaatc gcatgtcaac tcttgtaaac ggtttgaaag tttgggcagg caaaattcaa    49560
gccaaacaaa ggtacgaggt gaaacggtta aatagaagac ttgaggaatt gaatggtgat    49620
aagagatcag atgggacttt ggcggaactt atggaggtta aaattcactt gaatatggaa    49680
atgaataagg aggagagata ttgggaacaa cgtgcaagag tgaactggtt gcgaatgggt    49740
gataaaaaca cttcgttata aatgtgcctc gcagagaagg cgtactaatc gagttagtgg    49800
gctttagaga attgatgggt cttttgcaac caatgagaga gagattgggg atattgctta    49860
```

```
ggcatatttt ttcgacttat ttgaatctag aggagttcaa gatgtgaagc acatactctt   49920
agagatcaaa tcgtgcatat cagatagtat gaatcaatgt ctgatggccc cttacacaga   49980
ggctgaaatt gctgatgcat tgaaaggaat gaggcctaca aaggcttctg gttctgatgg   50040
ttttccggcg atttttatc agaaattcta gcatatcatt ggtaaggata ctagtgaatt   50100
ttgtttggat gtgttaaatc atggtcactc gttggatgaa ataaacagaa ctcacttggt   50160
gttgattcca aaacctgcca atcctattaa tctgaaaaac tttcgcccta tcagtttgta   50220
tatagtgatc tataaaatta tcgctaagtc cgttgccaat catttacaaa aggtgttgga   50280
tggttgtatc gatgactctc agagcgcgtt tgttcctgga aggctcatta ctgataatgt   50340
gttgttggca tacgaggtac ttcattcttt taagaacaaa agatcagagc gaaaatgttt   50400
tatggcctta aaacttgata tgagtaaagt atatgataga gtgaagtggc cttttattaa   50460
aggcctaatg tctaagttgg gttttgcaaa tgggtttatt gatttcgtta ttcgctgtct   50520
taattttgtt caatacttta tcttaattaa tggagaagaa ggattgagct ttaggtctat   50580
gaggggttta tgtcaagggg acctactaag cccttactta ttcttatttt gtagagaagg   50640
tctgtcagcg ttaataagac tgacttgtca ggagggaaag atttgtagag ccaaggtgta   50700
cagaacttct tcatcaatca cccacctcgc attctgtttg gggaagtttc gataggggg   50760 ataagtatgc ttcaagagat ccttagggaa tatgaggttt gcttgggta atgtgttaat   50820 tttgaaaaat ccatgatttt tttcaattcg aatgtaaatg atcatgatag gaacttgggg   50880
tttcaggttc ttaacgttcg gtgttcaatt gaccttgaga aatatctagg acttccaaac   50940
atggtgagac gaaaaagaa atttgctttt caatgtttga agatatacg aaacaaagga    51000 ttaccagtta gagcattagg catatttcac aaggaggtag agaggttttt ataaagtcg    51060 ttttgcaagc aattcccaca tatacgatgg cttattttct tttgctaaaa tctttgtgca   51120
cggagttgga aaacataatg agctcttttt ggtggaataa aagtaatagg aagagaggca   51180
tgcattggtg tgattggaag tccttaagcc cactcaagga agaaggtggg atgggttttc   51240
gtgatttaaa ttttttttaat attgtatttt tggccaaaca gggttggcgt tgttacgta   51300 accctaagaa atattataag gattctgatt ttttaaaatc caaattgggt aatttacctt   51360
cctttaccta gcagagtttg tgggtgacaa aatgcctcct tttgaaagga ctgggttgga   51420
ggattggtga tgggcagaag gtctctattt gggatgatgt gtgggttcct ggaaatgatg   51480
tgcttaatgg tcagaattca acttctaatt cgaggctatt agaagtcgca gatttgattg   51540
atactagtac aaggaaatgg aatgctgagt tgatttctaa taactttacg gagacggatg   51600
ctgagaggat tttatgtatc cctttgtctt tgagttcaca tgaggatctt atcatctggc   51660
gagatgaacc tactggagag tattcggttc gaagtggcca caaagttctc tcacatgttg   51720
ggcagactca agtacatgac acttacgaac ttttttacaa gagactatga aatttagatt   51780
taccctctaa aattaagatt acagtttgcc acctattgaa gatgtcaaaa gggagcaaaa   51840
acaagggagc acttgttcaa aaattgtcct gttgcaaagg aaacatggga gaggttagat   51900
attgtttggc ctgtctcaga agaaagtacc gaattcattg aatggttaaa aaattttttt   51960
gaatctaatt ctttgggcat gtgtaagagg tttgcgtgcg cattatgagg gatttggacg   52020
tccagaaata gatttattca taagggaaaa atgcgattga ggatccaaat tgaagatttt   52080
gttacaaact acctaaagga acttgatggg gtgaagcagg ttttacctga caaaagaatc   52140
catacaacca gatgggttgc tccatcaggg ctatgactga ggataaattt tgacgcggct   52200
```

```
ttcaatagtc aaagaaagga attgtgttct gggttagtgg ttagaaatgg aaagaataa    52260
gttatttgtt caaaaatat cataaataat aatataccgt ctgcttttgc ggccgaggtg    52320
ttggtgtgtt atcaggcact agatctggga ttccaactcg gcctgaaggg cgtggaagtt    52380
gagggagact ctaggtcagt gattcacaag ctgcaagaga agaaagaaga tagatctgaa    52440
attgctgtgt atattgaaga ttcaaaaaaa atgagtttga gttgcagata ttgtgctttt    52500
cgctttctca atagggaagc taacatggtt gctcatctta ttgctactga agacattaag    52560
aatggggaaa atacttatct gttgcagagg atttcttctg gtgctgaagc gacggtgatg    52620
gacgatcgca gatggacaaa aaacgtgcag gtgacaaagg tttggcaagc tgaagaggag    52680
tctggagggg gttatataag gatatctgat cgtttttttt ggtggttttt gttttgtcaa    52740
aaggattgcg tataagagaa ggttttgtt tttcggggtg atatttgttg gatttgacgg    52800
gtggtaataa tgattctgat aactttccct ttcagttttg ctattttcaa gagggggttt    52860
atttgttggc tacagctggg acgaagtctc tagagctccc ccgtcgattc tgctgctagt    52920
cttaattgtt gttgggccgt ttttttattt tgttagtttt ggttttttc gtttttttgg    52980
accttttcat gtttggggtc tacttcggtt ctgttttgga ttttatgttt ggtcttgatt    53040
tctacgaata tccggtattt tctcaagaaa aaaaaacatt ccatattgat tgggtcattc    53100
cttctttaac attaaacata taatctttat tatcattaat tggtcattaa caaagtataa    53160
ataattaata ataaatatta tgtaatttag ttatatttag tataaataat ttatagtaat    53220
ttagtttatt atttagtagt tcaaaattat taagaaatta tctataatta tatttaaaaa    53280
tctgtcctaa aattaaaata ccatctttat ataaagtgt ttaaaaaac ttaaatcgaa    53340
cattttttgga aagataatta gatttgaatt taattatttc taattaccta taagaattta    53400
ggagggtcca attatattta atttaataaa atatactaat tatagtagtt atctaaatat    53460
gccacaaatg tataattata aatatttata cataaatctg actttctaaa catgactaaa    53520
ttttattata tgtatatata ttaaacatta aataatttct taaagaaagc attaattatt    53580
tttaatagat attatagata attatttgat atatttttaa tagaatttat ggagtttcaa    53640
ataagatgaa tttcgaatat aagtttatgt atgtaattaa accttaaata atgagttttt    53700
taattaggta aataaggtta aaaaattatt atgtattttt aattaatagt taaaaaatta    53760
aaaataatat aaataatata ttttttggta caccaataat ttgaaaataa actattttaa    53820
agaaagtgaa tacataatta atattgaaca acttaaaatt ctcaaatatc tttattttat    53880
gtgtggaatg aaaaacttta ctatcaatat atcaaatcaa taattttgat ataactaact    53940
atccacaaaa tcttagatta ttttattggg taaactatac aattagtcac aaagttatta    54000
atgtgttatt gttttaacca tcgaactaca aaaatttttca atttcatcac gttatcattc    54060
atttctgttt tgatcaccca ttgattaaat tactaataga aatggtaagg tgacctttt    54120
ttacttggta tgataacata tttagttctc agcatttaca catttgatca aattaaccct    54180
aatttaaaat aatttaacaa agttaacctt ccatatttat aaattcaatc aatttgatcc    54240
tcaaatacat cttcatcatg catctcgcct cacctcgttc cattgccttt tatattgttt    54300
ttttttata aatatttgt ttacataatg ttttattcac ccatatttgt cataatctag    54360
taaacatagt agaactaaag agatgtgcca aaaatatata taaaaaggc ataatgattt    54420
atttgatctt ttaactttac aagaaaaaag ttattttaac ttcttattca aattttcacc    54480
ttttaaccg ttgaaattgt gtactttgat aaaccatctc aaaatggatg gaaaagttaa    54540
tgtttgttaa cttagttgac tagcatacac gtggatgcca catcaacaat taattattat    54600
```

```
tttcaattta aaaaattcaa aaaaatataa tgttttaaaa aaattataaa aatattttttt  54660 aatttaaaaa ttaattaact gctgatgtgg catacagcta gactattatg ttagcgaagt  54720
taacaaacat tgactttttt catctatttt gggtgatttg aaaaataacg taagtttaag  54780
ggataaaaaa aacgaaaaat taaataaata actaaaataa ttttttttatg agattagaca  54840 gttaaataaa ttattattcc ttctttatac atatattggc acatttctgt agttgtatca  54900
cgtttacaag attatgacgc aaatgggtga ataaaacatt atgtaaagaa tatatttata  54960
aaatcattat ataaaagtca aaccgagagt attaagttca aatcctccta caataataat  55020
ttataaaaat attcttgaat atctgtaaag gctgtacttg gctctcacga tgcatatatt  55080
tttgatacaa atattattag ttgtaaaata cattttatat ataagtatta gcttgatata  55140
tatttatggt tttgcggcta ataaaggctt atggaaagaa tttcagagat attccttaat  55200
gctgagcaca taaattgtgt caggtgtata catacaaatt ttaagtctaa accattccac  55260
cgaagaaaag tattgaaaga tattttgtgg aagtctacaa gagcaaccta tgtgaaggag  55320
tttgagaaca caatattctt acaaatggtt ctattggatt gatactaagt agtggtcaaa  55380
atctcacttc tcaaccgaaa gcatgagtga tatgatgttg aagaatgttt taataaggtg  55440
ataattgtaa ctttaaatca tatatattta ctcaaaattc tcaaatttat gtgaatggtt  55500
actaatagct tgtttcttgc ttgtaaatac cgtactaatt cattatatta tttttttattg  55560 atgtcgtgag atttattgac ttacgctacc taaataaaca aaaatcgaat gacaagcacg  55620
atgctattcc aacttttacg tgttaaaatc acatcatctt gctttgccct tcaaatgtta  55680
atcatagaaa tgaattcttg cgaaatgcac ttgtacaact ttctttcacc ggcctggggt  55740
tactcatttt tctgttcttt actcttttt gcactgtttt agatatatat tgatttgtat  55800
ttgttgtgaa ttaaactcaa tggacgctgc ttcaatgatc atatcatatg agaagagaaa  55860
aacggagcaa ggctgcaacc ttttcaagcc aagctgcaat aaacacttttt atggaggccg  55920 ttggtgggaa acatatccga gaataccca aataacttgt gggacaagat tttacaaatg  55980
ctcaaaacat taaggtggtt tcataattaa tgcatacatt gtctctctga catttccaaa  56040
ttttgttaat ttctatctat tcaaatgtaa tgcctaaggt ctgtatccaa atacgaagat  56100
ttttttgatg aatccatttt tggtggtaca ggagtttaca tatatcatgg agcactcgtt  56160
gatgaaaatt gcgacttcta gcatctccac gaggattatt tagaatgtgt tgcaatttgt  56220
atttcttact tcatcatgtt atgttttagc tgtcaacaac gatttcaaaa tgggattcca  56280 atctttttata atcatcagta tacaattatg aaggaagagg tgaataaaat ctgattcaat  56340
tcaaaaaatt aaattttaaa ttttgaatta aatagtttga gttatttgag ttaatcaagt  56400
tattcggatc aatcagataa aaaattaatt tttcggttta acttgaatta tgaatatcta  56460
aaaattcgaa taagaaaaaa taaaactaca tcgttataat aaatgtttag ttaaaattca  56520
aaactattaa gataaaagtt aaaattacgt cgttttgata aatgtttact aaatttaaag  56580
acaaaatcat tatattatgt atgtagttaa gtaatcttat acttcatcta ctagttaaat  56640
aatcagttca tgtaaacaca acattgagta tgataagatt cgtcaacttg atttgactca  56700 aaaaatttt actcggtcca attcaattgg aaaaaaattc aaattgagtt ctgttgctaa  56760
aataagattc gtcaacttaa ctaactcgaa aattttttac tcaactcgat aaaatactca  56820
cccctacaac tagatacttt cctaaaatcg actcgataaa atactcatcc agcaattaga  56880
taccttctca agaagagcac taacgatatc atgttgttga tttgtctgaa aaactacagc  56940
```

```
caaaaacgac ttctcttgta aactgcgatc ttgtgaatgt ttttagatta gcaccgcatg    57000
tgatgttgat attttcttgt atatattatc aaagctcaag ttttttatgg agttgaaaat    57060 catattttt  gaagaacttg atatttttat ttattaaaaa caaagattga gctaaaagcc    57120
ctaaacttga attacactta aaaaacagaa tgttttcaaa aatatatat  tttggacagt    57180 caatttcat  caaatcaaac atacctaaat gttgttttgt tcaaatttaa tacttcccat    57240
tatacttgtt taatagtcag gtaaagccag gccaacccaa ataggagctt tgcttttaat    57300
tcgacgaaaa caaagaagc  gcacaaaaca aagtgaattc aaatcatcgt taagcacaac    57360
cagaaaaaat tccaaccccg gaaaccgaac tcaatacaga caacaaaaac catagaaagc    57420
acaacaaaac agcgagcatg tacgccaggc gtagctcact attttattta aagaacacga    57480
ccaagtccca cacactgaaa actatagcca cggtagagaa aattattgca ctataaatag    57540
cacgtctgcc ataaaaggca caataaacga ctataccaag agcttcagaa tcactcctct    57600
tctgtctcag actcggcatt ctggagccat tcgatgaagg gcttggagtt cttccatatc    57660
tgagaactct tattaccacc ggctacaccc ttctgatacc attccatgat gaactcttct    57720
tccaagatgt cattgtcata tagtgcttta agaaccaaag ccacctcctt agctgcctcg    57780
aggtttgcct tgccacagaa agactcgata gaattgagga gcatcatctg ccatccctct    57840
tctctggctg ctgctacaag gtagttcttc ttttagtta  cttcctccgc aaacccctc     57900 ccaacattat gaaagagtgc agtaaaaagg gcgtccatga tttcttggga cgttccagag    57960
agtgaaccca ggaaggattt aagctgagct gcagatgacc ccttcttgag gtatttcttt    58020
atctcatcaa caagtttctc atgggcagtg ccaccattct cttgtgcctt aacctcacgc    58080
tctggcgact tcttcagtga cttctttttct tcttcagtag aaagcattac catatcagct    58140
gtaacagcac tcaactgctc ttgtatacgc tgttgagcag cctccagtga agtatccgtt    58200
tgccactgca cattatcatc atcatcatca tccacctctt cgttctcatc agcctggctg    58260
tgagttgggg agtgatcctc atcagaatgt ttgcttttct tcttggttac tgcaccttg     58320 gcagcagtag cctttgaagt agtagtggta gaggaacctt tcttttttgc ctcttttta     58380 atcttcttaa gctcttcatc agcggcctca ccctccttga gtctttcctt tcagccctc     58440 ctcattgcct tcttgtcttt tgaagacttc ttagcctcag gtgggttttt aagaatgaaa    58500
gttgtaagct tatctctcat gtcaacatca gaaacaaacc cacacgcggc acatttcagg    58560
gtaagcatct gtgtcttagt aataactatc tcagtttcag ggttcccaca gccataacac    58620
tgaacatact tcttaatgaa gttctcaaga agccctgcaa gcttggcagt gtcatgggcc    58680
ccatttacaa gagaagttcc agtcttctca tcaaacttgg attgggctcc cagttcacaa    58740
ccaaaatatt ttgtggtgta agaagcaggt ctagccaagg cctttgcaat ttctaccatg    58800
ttaaccacgt tagtcttgat gccatttcct ctcccttcaa tcttggttat cattttaggc    58860
atcttatacc tataaaaggc atcatcactg ttcgaagcac caatattttg caaagccatc    58920
ttgatcaaac tgagggagac cgttaatcag aaaggagata tcagatactg gttatcaaaa    58980
tcgtggggag aaatctgtta ccaagctgcc tccttgcact tggaagatgt tgcataaaac    59040
ggaaacccaa actgtgtctc tgattggcct caatatgcat gcagctaatt ccagaacagg    59100
aacttctatt ctttttctg  tacgtgggac agtactctcc aagcaatcca attgatgaca    59160
aaaagaaaga ggcccgttca gacataaaag aagactcaca agtaacagac tccactttgg    59220
caatctgcag cagagcagat taatctgcag acttcctgaa agacaatgat ggagtttatt    59280
caggcaaagg tcagagcaca gaatatcaat aactggcata aaaccataac atgaaaattg    59340
```

```
ctacatcagc gaaacttgaa cattactagc aaaaccataa cactacaatt ttcaaaattg   59400
catctatagt tatgcatgaa gaaatacccca tactaaacat cgtcaacttt tgtaatccaa   59460
taaagcatag catattccag tattataaca tcaaaactcg ggatatctat caaaaccaag   59520
attaaattat ttcttcataa gtttctctat accaataaaa agtttagatt gtaaagaaaa   59580
taaaaaatga tttattaagg actgattgaa gcaacgaaac tagacagatc aagacttaaa   59640
agaaaaacct aaatccgcag ttctaaatct cctataatac aaaaaatatc ttattagaaa   59700
atactgaaaa taaggtaatt aaaacgaaaa tttaagtact acgatcttgg tattaaaaaa   59760
cctaagcctt ccgtccaacg ttaaataatg aaatattaag caaatataaa tatgaaagaa   59820
tatctgcatt gcgataatct aaattcgaaa aaaaggaaa cagaaaacaa accctctggt   59880
ttcgatctga tcatctaaaa taatacaaat acaaagctaa attaaacaat aagctcttac   59940
aacataaaca gctcaacaac gatcgaacaa aagaaaagga aaaaaaaat ctagctatcg   60000 gtcaaaaaat gagagataca atgaacgata gacaaataaa aagaaaaaaa aaagcaaaca   60060
gatcaataga aaatgaaaat aataaaaaaa tatgaaacaa aagaactaa acctttgatg   60120 agatgaggaa aatgatggta ggagataaat tgtgaatctg aggcaggaga atttggaagg   60180
aaaatagata ttagggattt ttcttgtgga gaagaattga gaagctctca actttataca   60240
cgccaacgaa gggaaatgtg aaacgctagg gcaaacgcag catcttgaat tttctagtat   60300
tgattattct cgaataaact tatttttatta ttaccatatt gcccttaatt ccctttttcta   60360 ttaaggattc ttttgggtag ataataaaaa attttaatta cgaaattagc cggattattt   60420
agcagaataa tttatcttat aaaataaaat taggtgtcgt taatgtgtta agtggtacca   60480
acttaaaaaa tatactctca tttgacaatc attccaggtg aaaaatattt ttaaatggtg   60540
ttattacttt gtcgagcaac acaaaataaa tactgtacaa gtaaaaaaat tatattttaa   60600
aacggtgcca cctaacaatg tggtggcacc aaaatttgta tttatatccc attcccagcc   60660
taaaaaataa atcgttgttg tttatcaatt ctaatgacac atattaggat cttttcctcat   60720 tataaactac ttatgcaggt tgatggaacc tgactgtggg aaatatttac aaacccttct   60780
tattgcagtt gtagaagatg ataatcgaaa cgtactacta atagccatta ccattatgga   60840
gagtgagaac atgtaattgt gacaattttt ttgacgaact tgcggagtca tattgttaaa   60900
caagacattt acattatttt ttatcgatca aaggggttaa ttgcggtgat taggtgtttt   60960
gaagttccgt ggagattgtc caagcaactg atagtaaagc gacgcatgct gtaacagccc   61020
gttttcagtg aaaatggaac agtggtttcg agaccacaaa tctgagtccg gaagaaaaat   61080
aattttaata ttatttgtaa cacccccctac ccgtatccgt caccggaata ggatacgaag   61140
cattatcagt gttacaaatt tatttatcag acatttatt tcatctagca ttcatattg   61200 ggaccaatca aaatcaaaga tattgccgcc tgaacatact taatttcctt gtatcaacgt   61260
atcaaagata atcacatatt tacatgtcat gataaatatc attctcttat cgtttcttca   61320
taaacataaa tcagttaatt tgttatatca atatttcatg taccatcaac tcatattcct   61380
tatatcacat aattaggttt cacgaactta tctggctgaa ttgcaaaaat accaagattc   61440
aagggtattt cggtaatttt ctattttcct cgattttttca accatcttg atttaaatta   61500 ataatttcat tcaatttatt aatttagaca ataaataatt catttactc aatttggtca   61560 tttttgatat atttataaaa ttgccccctaa agttttactt ttattcaatt tagtcttcga   61620
gcctaaaata tgcaaagtaa ccactttaat gtaacccatg ctaactaaat attcatatat   61680
```

```
attttccttc actaatatat caagaacata gaaccttata taagaaaact ctaccttaac    61740
atcattttca tgcttttgat attagcttac atgagaaact ctacttaaaa tatattgaag    61800
tcttaaagtt cttaccttgc cctattgatt tcaatcttta actgattttt ctctctcctc    61860
cagcttctat ttcttgaatc caacttgata ttataactcc ccttagtctc cttaacattt    61920
ttctcttttg gtagctatgg aaattctttt gatttctaat ggtgcgtttg tttgctagga    61980
aaatatttta cggaaaatat tttcttggtt ttccagtgtt tgtttgcctg aaaacatttt    62040
ccatttggaa aatgatttcc aagacacggg taaaatgtct tacgttttag ggaaattgcc    62100
ttacgaattt catttctgta agacattttc cagtccctcc ttcatctagg taaaagtctc    62160
tccttcttcc tttcttcatt tcttttcttt cttctgttct tcatttttcta gtccatcgca    62220 tatatcattt tctcaagctg ctgtttcatt tcctctcttt ctctctttct caggattatt    62280
ccatccctct tcactaggtc ttggcttaag gtatggcata aagctctttt ttttcttatt    62340
gttccttact tctccataga ttttatgact gaaattttat gctttccttt gtttcttttag   62400 ctagggaaga aacttgaatg atttagggat tcccaaactc aaattttaa aaaagagaaa    62460 taccgaaaac aagcttgaaa ttgaaatcgt tcggtttcaa aaatctctaa cctttgttct    62520
tttagttgtt gataaaaata aaattatgga ggtttggttt ggtacctagg agccctaacc    62580
aataacacca atcttgaaat cgagagatat gtgggtttga aagccatag ctgagttgca    62640 gcaattatga gtagtcagtg tggttggttt gagaggactc aaaggatctt gaaatggtcg    62700
tcaagaaacc tagattaaag ttttttgagga acttgagaga gagggagtag tgaagtaagt    62760
aacctagatt ttaattactg gatattttg tggatgaatg tacttgtttc ggttatgaat    62820
gcttgtgatc tgttttgtaa ttgcctttgt atatcaaaca taaatatttt tgctcacagt    62880
aatgtagact aaatcacata aaagattcaa tattttgctc acaaatctga taaactagca    62940
gctagaattg gagtttcttc catgttggat taccttttt tgaaaccatt gattacccca    63000
taattacatt agcattctaa aatagaattt attccatata ttgtaatcag aaatttaaga    63060
gaaagaaata agacatgata atatcttaat ccaaatttaa tggttgcatg atattcgtaa    63120 catgtttta agatttataa atgactcgtt cttaagacta acttattatc acgattaagg    63180
caagtgtacc tatcgaacag tagtatagtt cagcaagacc ggattgttga acccaaagga    63240
aatacgagta ctagtattta cttccttttt attatctagc ctaaaaatta agaggtttgg    63300
ttatctaaac tacttactaa ctaagaatgc acagaaagaa aacttgggaa aatactttg    63360 ggaaaattcg attgattgag acaataccta aggaaaaatc tgtaacgacc caaatttaa    63420 ggtcatcgaa aaattaaatt ttcgggtcat tattttcgca aaataaattc gtaaacattt    63480
attagaaata tttatgaagc tagtagtgta gttgattaga ttttggttaa gtgaattagc    63540
ttgaattaag gctaatttag tgaaaggact agattgaatg aagagtgaaa gtttaattgt    63600
agaacaaaga aaattgaggg gactaaatag gcaattaagc ctattctaaa gaatgaggcg    63660
gcaaaacata aaaatctttt attttttatgt tgtttaaatt ataaatatat tattgttatt    63720
attgttattg tattacaaat taaattaatt atattattat attatgaaat aaattaagaa    63780
aagacaaatg tatggtgcat atggtgacat gtgtaatact aatatacata caattgtaaa    63840
atacatgtat atttatttat tatataagta tattattaaa ttatatatta gtattaagta    63900
aaagatattt atataataaa tagattaaag aaagacaaat gtaataatat aggtgtatgc    63960
aaatgtaaaa tagatattgg atattaaata gatatttat tatagttatt attaagttat    64020
tataatatat atatatatat agtaaaagga ataaaaagaa aaagaataga aaagaaaga    64080
```

```
aaggatgaaa cgaaacagag agcaagggaa agaaagaagg aaggaagaaa gaaagaagga   64140
aaaagggaaa attggatttc aaggcttgaa agttaaatag gtatgtcaat ttagccattt   64200
ttacttgatt ttgatgtttt agaaactttta gaacaaggtt ttgatgaagt taagttgata   64260
tattgtaaga tagttgatta taagacattg ttccttgttga acaaaaagat gaattaaggg   64320
ctaaattgat agaaattcaa gttagaaatg aaataaggat tgaattgtaa agtgattcat   64380
aagttttgaa tagtagggac taaattgaag aattttgaaa tcatagttta tggtgaaatt   64440
agagagctga aataagtttg aagtgaaaat gaaatgaaaa tattgagtta aatatgaaaa   64500
ataaaagtta gtctcggttt agggactaaa ttagaattaa ggtaaaagtt ggatagaaat   64560
tgaaatattc aatgtgaaaa atttaatgat agtgtattaa taatatttaa ttaattcccg   64620
tagctaatga tgtctcggaa aatctttgtt aagcgaggat aaggcaaaga caacgggatt   64680
tagctcggaa actacggttt gtatttctat aaactgaact taatagttaa ttgttatgtt   64740
aatattcgaa ttgcttgaga atggaaatgc taaggtaaga attataatgt tttataattt   64800
attgaatttg attattaatt gttgtatcat gattgatatg tgacaagtaa ttaaagtatg   64860
aaatatttga atgtgtgatt attggaaaat gaattaaaag gcatgttata ttaaaattga   64920
aatatgtata ttgtattgaa attgaattgc atgtgaattg atatggaaaa gtgtattgaa   64980
atgaaactga aaatttgaaa gtttactaaa atccctatta acaatatcgg gctagtcgga   65040
aataattggc atgccatagg attggaagtg ttcagggata tttcgactgt gtgtcgataa   65100
gacactatat gtgtcgacta ctgtgactgt ttcggattca ttctgaagag gtactctata   65160
cctgactgtt actgttattg tttcagattt gttccgatga ggtactttgt gtaccgttac   65220
gttactgtta ctattaccgt tacgatgtat ttcggcttca gccaatgaaa cactgtatac   65280
tatccccggt gtgtgggttg gatccgtgta tccgtctagg tccaagtcat gttaataagg   65340
gtaattaaaa gtattaaagg ttgactgcta cggaataatt gactgttatt gataaataat   65400
tgttactgca taactgactg ctatagagtg ccggaatgtt actgtataaa accgataaat   65460
tgattgatac tataaatgtt tattgatact gaatcaagga ctgaagtatg agtaaaacat   65520
gcgaatggaa agtattaatg tttagatgat ttatgaattc atttgaaaag ctaatcgagt   65580
taataaatga taaaaattaa gtgaattatg aagagtttat ttatgaattg aatgattaaa   65640
taattatgat cgttatatga ttttatgtat atattatatt ttaagtatta gtttatagaa   65700
attgtaatac cctaacccgt atccatctcc gaaacagggt tacaaagtgt taccaataca   65760
tacagaacat ttacagatta atcgaaacat tactattcac tttctgagat catatatata   65820
taacgacctt tatttaggcc cttgaagccc aacatgaaca ttaaaatcaa gtcggagctc   65880
aactgatttc tcgtaaaatt ttccgcttaa ttaatttttt ttaaaagtt tacttgtgaa   65940 cagtacccac acgcccgtgt gattaggccg tgtggattcc acacgcctgt gtggcttggg   66000
acacgcccgt gtcccttgtc cgtggagctt tctgtttatg acatcatcat caatttaggg   66060
gcacacggcc acatcgcacg cccgtgtcct aaagtcttgt ttcatatacg gctgagacac   66120
acggccgtgt ctctgcctat gtggtcaata tctaagctat tttccaagcc ttggtcgacc   66180
ttaatctctt acacacttat acaaaatcaa aagcatataa catggtattc atttaatgat   66240
taaacattct caattaaact acaaacatag catttgtatg tcatcataca tgtgtctctc   66300
atactcattt taccttgtct attatggtac cacttataat tttataccat gattatcatc   66360
ttaccaaata ttttcagctt aatcatcaag catatatatt taaagctaga tcatatcttt   66420
```

```
ataaaatacc acatttcaga tgcgcggaat aaaatacttg ccttagacat ttcaatccaa    66480
cttcataccc aacaagcatc atattgaaac tagtcacata tatacatgtc atgatatgta    66540
tcattctcat actgttttct tataaacata tatcatttgt tttcctcctc ctcctctcca    66600
ttccacatcc ttaatgtata taacattctt gtaagtgcaa tttcacaatt tacttattaa    66660
tgcttacatc aagctgttta cacgagtcat agtcactcaa tcatttataa ttcaagctac    66720
agagctcgaa attaagatcc gtaaatttcc cctgaaacta gactcacata tcattccaca    66780 taaaatttt agaattttg gtttagccaa ttagtacagt ttattcattt aattttcccc    66840
tgtttcacta tcctacggtt ctgacctctc ttcactaaaa attaattata tcatagtaca    66900
aatctcggat aatgttccca ttgatttcta ttgaaaatag actcattaag gattctaagc    66960
atataaattt gagcctctaa ttaattttat ctaattttg gtgattttcc aaagtcaaaa    67020
caggggaacc cgaattcgtt ctaaccttgt ctcacaaaat tcattatatc tcataattta    67080
caattcaatt gcttacaccg tttctctata agaaactaga ctcaataagc tttaattaca    67140
tattttattc atcctctaat tcaatttata caatttatgg tgattttca aagtcaacct    67200 actgctgctg tccaaaactg ttttagttca agatgtttat taccatttt cctctaaatt    67260 tcacagctca tacaattcag tccttgctca attagcccat ctattaagct aattttctc    67320 aattaacatt ttattccatc attctaaact attacacaac ctttgaaaat cataatttta    67380
acacgaaacc ttaattcaca acttttcac aattaggtcc taaaatcaat ttctattcaa    67440
attacttgat aaaatcatca aacaacaaaa tcaaagcttc aaattcattt tatatcatca    67500
taaacagcca acacttatca attatagctt ttaattttgt tcataaaatc aaaaactaat    67560
gaattaaaca cttggaccta attgtaaaag tcacaaaaac ataaaaatat caaagaaaag    67620
ggcaagaatt gaactcacat atgtcaaagt atgaaaaacc agcagctttc agacctccca    67680
tggcgttttt gctgaagaaa aatgatgata tctctagatt tttctaattt gtcttgtttt    67740
atatgtttaa tttacaaaat ttcccatttt gcccttgttt ctccttgtct ttttgttga    67800 ttttcttgcc caaccgtcca gcccatacaa tttgggtcca attgccttt aaatccctcc    67860 tttttgatca cttaaactat ttaatcacaa tttaataaat ttggcactat tttcaattta    67920
gtctttttta attcattgac taaccaaacg ttaaaatttt ctaacgaaac tttaatacta    67980
acttaataac actccataaa tatttataaa aatatttatg gctcggttta tgaattcgag    68040
gtctcgatac ctcgttttca ccctaatttc ttgattaatt cttttaaagt cgcaaaattc    68100
actaattaaa aaataattct tttaagttcg cgcttggcct ataattatta tttgttaaaa    68160
tttctaaaat tactcgtcag atttagtgat ctcgaatcac tgtttccgac accactgaat    68220
aatttgactg ttacagaaat aacactgagt tcctactcag cgtacaattt gtttccgtgc    68280
gcaggttaag gtaaagtcag attgttgagt cagcattcca ggccgatccc gaactcaata    68340
aggtaaagta tgttaattga tgataatggc atgtacctag gatgtcttaa gtgtgtcata    68400
ttggattgtg attgtaatag tgaaataagt aaattgataa ttgataatga tacgtgataa    68460
gtgtttaaag taagtattgg atagtacata aaatgtgttt gaaattgttt aatttaagac    68520
attattaagt atatgtgtta aattatgata tgatggttta atgagtatta agtgtgttta    68580
accatatttg gactaattga atggagaaat tttgaaatgc ttgttgtcta caatttgcag    68640
gattggtaaa tttaaaaata caaggttcat tttgagacca cgtgattgt cacacgggcg    68700 tgtgccttgg ttgccacgac cgtgtcttaa agtcagttta gtacacgggt aggccacacg    68760
gacgtgtgtc atggccgtgt ttaaaagtca gtgttgtaca cgggttaagg acacgggcgt    68820
```

```
gtcccaagcc gcacgggtat gttaaattta gccacacggg cgtgtggtac tgtctaaaat   68880
aagaaaattt aaaattgtac gaaaaatttt ctaagcttcc gatcgagccc cagtttgttt   68940
aattattctt attaagtatt gtggacccac taaagctaca taaagaaatg tataattctg   69000
tatttattct tgttttacat ataaatatac tgtattgacc ggtaatactc cgtaatcctg   69060
ttccggcgac gggacgggtt tagaggtgtt acaaaatcca cctagacttc acttgttatt   69120
taactttgaa tcagacgatt tattcatttg acttgatccg tagaaatccc taagttatat   69180
tattatctct ctcgagacaa ataatgtcta accctaggtt gaataattga aatctttttc   69240
taattaacac tctagaattg cattaactcg atttatggat tcccttatta gttttcaccc   69300
taatccggca aaatcttatc accctatctc taggcgtgca atgaactctg cttaattata   69360
acaaatttac tcttagacag ggtctattcc tcctctgaat aagagcttaa cttgaatcaa   69420
tatcctggaa tattaaaaaa agaattaaga acacataatt aagaacaagt caaatattta   69480
ccatataatt cagataataa taacaagatt cgttttaggt ttcattcccc ttaggtattt   69540
aagggggttt agttcatact tatgaaagaa aacctctcag aagcataaag ataacaaaac   69600
ataagaaaac ccaaaactcc tgaaggaact tgaaggagaa tcttcagtct tgatgatgaa   69660
tccggcttct gagatggatc aatcggcttc ccttgagtaa ttccttgctt cctactttgc   69720 gtccccttc taagtgcatc ctcaggtgtt taaataggct ttggaatgcc tatgagccct   69780
caaaattggc cttttccgaa ttggactaaa cttgggctcc gcaggacac gctcgtgtac    69840 gattacttaa ggctgtggtc aaggctgtta aatgggcacg agcgtttgat ccacccgtgt   69900
aagtcatgct tcaatcctgc caaagggaca cggccgtggg acacgcccgt gtgagaaagg   69960
ccaggccgtg ttgatttccc gagtgggttc attttctcca ttttcggccc gtttcccgct   70020 tttttactc tcctatgctc acctaagtat aaaatatgaa attaaaggat taggagcatc   70080
gaattcacca attctaaaga gaaccatcc ataaatgcgc taggcatggg ataaaaatat    70140
gtataaatta tggtttatca aatgccccca cacttaagca tttgcttgtc cttaagcaaa   70200
atcctcaact cacaatcaaa ataaattatt ctcactttat aatctctatc aataatatct   70260
caaaataatc tatatgtact catatattga aaattcaact aaaagtacat caaagtttca   70320
aacattccaa gttgagcatt ttatcatgaa aacataggtg tctcccctca tctaagtgat   70380
tacctttaat caaaatatca cagagtttaa catcctcact aaagattcac tcaaatcact   70440
caaggtgttt aaggacatca ataaaagcac tcattagtca atatgaaaag ttattaccat   70500
aggcttgctt gaaaatcaaa tctccaccac tataaattga gttgatacat caatcaaaaa   70560
ggtcttttag agggttgtaa tcgtggcttt ggttaggggt gtggtcacaa gttgaaagaa   70620
gatgttagaa tcgagattga attaaaaaat tatctagcta gaaaaaataa ctagtcatca   70680
gttgactacg agtgagcttc ttctcagaag atggaattta aatactgcgg ctcaataata   70740
ccgaattact accaatatgt aagtatgaat gttttttta aaaaacaac tcaaaataca    70800 aaatagaata aaacatagtt aagcaactat tccaactcaa atctcgacaa aaataggat    70860 caaattaatt taggggattt caataataat gagtttatggg ttaatattag gggtaaatca   70920
atgaatggtt tgttaggctc aagggggttc actaaggggt aattgtgaat gtaggctttt   70980
atggagtgag tgggttaaac ctaagtgcct ttatcatttt gacatatcaa atcaaacggt   71040
gtggtcttga catgcataat caagcaagtt ctagaataac aattcaatac tgacgcactc   71100
ataatgaaag tgagcatgaa agaaataata gatgctctta aaggctcaag atctcacaaa   71160
```

```
aattatagct ttttgatgtt caaacttgtg aatttcaact caagacaata cctaaactta    71220
gggaaacaac ctaaatgttt tttaattcta caaaaatcaa cttattatgc ttgattccct    71280
aatgtcctaa agtttaaaca atcaatgcat aaatacctat gttttaattc aagacatatc    71340
aataaaaatc ataaattaat caaaattcat tctaatagtg gtatgagtga ttcacgtgag    71400
aataagataa aattcaggga tttctaatga tgatatgaaa gaactcccca cacttaagat    71460
gtacattgcc ttcaatgtac aaagatagat atattgacaa agatagatat ataatcataa    71520
gatagggaga gaagtgaaat ttcctgaatg atgcatggac tccttgaatt ggagtcatgg    71580
agaatgaacg gcgaaagcaa tgatgagggt ggaggaggat actctggtag tggtagaggt    71640
tgggttccac aaatgctgcg ccaaaagaat attatatctc aagttggcta tggtcgtggt    71700
cgagcagggc atggcagtca tggagaacct ttcccagtgg agtttcaagt tcctgagtaa    71760
tagtgagatt tggagctctt tataactgtg atagaatcaa aaactttttt aggaaatata    71820
taaggaagaa taattactcg taattaatta cccagaaata aaaattgtaa ataataatt    71880 ataaaaccta ataaaaataa gcttaaagaa aaataaaaag tagtcttaaa ataaaataaa    71940
aggaataaca gaaaataata aataaaagtt tttaaacatc ttcatcgcta gatggttcgc    72000
gaggtggggg tggcaatgag atgtggaatt gctaacaaat ctgctgtaga gtagcatcaa    72060
tgctatcgaa gcgccgaaaa cactactgct cgaatcaagt aaggcgctca gagatgtcaa    72120
cgtatgaagc taccgcatga actggacgat gagaaggtgg tggctgagtc ggtggatcct    72180
cgtaacgtgg agggacatca tcagtaatat cctctggtcc tcttcatcgg tggactgggt    72240
gaggcagtat tgagaagggt atatgccacg tcatttctcg atcatcctca tacttagcat    72300
gctcgagatg ccctgcgggg acatttggct gattagagtg agggagaatg attgggcttg    72360
taacaccctg aaaatttcta cagtaagata ttatccttaa tatagtaaaa taaggaaata    72420
aagtgataag aagaggaaaa attgagttat gtcactggga agtatattat gacatattga    72480
ttaaagaagg actaaattgt aaaagtgaga aaagttttgt agcctaagag taaatactaa    72540
aaatttgagg gattaaagcg taaatatgaa aagttgaagg actaatagtg cgaatatttt    72600
aagggttgaa tgatctagaa accaaggaaa attgatgaat taggaccaaa ttgaataggt    72660
aaagaattat gagggactaa attgtaattt taccaaatta agtgataact caagaataga    72720 atttttaaaag atcactaagg gcaaaatggt caattggaag agagagaaat ctagagacaa    72780
tgatgatgtt ggagatattt tagataaaat aaataaataa atattagttt attaatactt    72840
taaattgatt tttaaatgat attttttttat tattttatta ttttatttag tatacataag    72900
gaaagaaaga tgaagaatca tcatcttttc tttcccatgc aaaccaacgt gagagaggaa    72960
gaagaaaaga agttttcttt ctttacaatt tagtcctttc accaaaaatt cattattttc    73020
acctaaaaat taaaagaatt tccatagcca tcaagagaga aagatagcaa ggagatgatg    73080
gggagcaaga atatcaaatt ggattcaaga aatagaagct ggaggagaga gaaaaatcaa    73140
gttaaagatt gaagtcaata agaaaaggta agaacatcaa gatttcaata tatttttaag    73200
tttaatattg ttgaaaaagc atggaattga tgttgattca gagttttctt atatatggtc    73260
ttatgttctt tgtcatgtta gtgaagagaa aataagagaa agtaatgaaa aatagcgtag    73320
agaaagaaaa taagggtgtt ataaacatgg taaataatac cttgcactaa aatagtttta    73380
gacaacaaca atagtctaaa tttgaaaaat caccaaaaat tgtgggaacc aaattatagg    73440 ttaaatataaa tatgaaatta aatctcattg agtttagttt cttataaaat aaacggtcta    73500
agaaataaaa ttgtaatttg tgagatatag taaattttgt tagataaggt cagaataatt    73560
```

```
tcgggttcct ctattctgac tttggaaaat cataaaaaat tttagaaaaa taattatggg   73620
cttaaattta tatgattaga attctgaatg agtctatttt caagagaaat aacgggaaca   73680
tcatttcaat tctgtacaat gagataatta acttttagtt aagaagggtt ggaattgtca   73740
gacaacagaa taagggtgac tttaaagaat aaactatact tattggctaa accaaaaatt   73800
ctaaaatttt tatggtaaga cgatacataa gtctagtttc atggaaaatt atcagatctt   73860
aatttcaagt tctgtagttc aagatataaa taatttagtg actatgacgc aaatggacag   73920
ttttgaatat acatataagt aaatagtgaa attattgata ttgttatttg aagcatgtta   73980
tataaattaa ggatgtggaa tggagaggag gaggaggagg aggagtaaaa tatgtatgaa   74040
tactcatcta gcatggctaa tttgcatgtt ttaggctcag ggactaaatt gaataaaagt   74100
aaaactttat agataatttt gtaaaaatat tagaaatgac caatttacat gaaatggatc   74160
attttattat ttaaaattat aaaattgaat gaaattatta atttagctca agattgggga   74220
aaaacatgtt ttaaggatta aattgaaaat tgttgaaatt atggaaaatt ctgatatttt   74280
atagaattca tgggttgtta tcaatttttt tgagaataac ggctggaaat aaggattaaa   74340
ttgtaagaat tttatttttt ttagcttaag gatgaaattg tcattaatta aaagtttag    74400 gggtaaaatg gtaattttgt ttagagcatc aatttaatgt attagaacat gaaataaatg   74460
aaaacgacga tcaaatttct ttataaagat ctggatgact cgagaatacg agacttgaat   74520
gtggaaaaga aaagatatca gattaatgaa attataaaca tgaacaagta acgaggtaag   74580
ttagtgtaac ttgaattgta tttttaaatg catgaaatat tgatataatg aattacctga   74640
tttatgttta tgaagaaatg gcaagagaat gatatttatc gtgacttgta attaggcgat   74700
tatctttgat acgttgatac aaggaaatta attaaattaa gacgagtaat aaattcaagt   74760
acaacatatc aagaaaaata agtacgttaa gggacaatat gtttgatttt aattggttcc   74820
aaatatgaac tttagatgaa ataaaatatc tgataaataa atcggtaact ccggtaatgc   74880
tctgtaactc tattccgctg acggattcgg gttggggggcg ttacagggct gttgtgttga   74940
ggagcccaaa gtgccgagcc agtcagtcac atagggccca atagagatga cccctctcct   75000
gtgtcactcc gtctggtggc gaatggccaa ggcaataaag taggcgaggt cgatgacgtg   75060
cccattcacc atactttata agaaataggc gtcgtgggtg gtgatgacgc cggtgctctc   75120
tcgtctctct atcagagtgt gagccaagat ggcatgtaga tacctcaagg atggaggag   75180 agccgatacc ttggagcggc tgggatcgta ggtggccaag gtaggacaa agttcctcca    75240 acattttgag agggagtagt ggatgtggcg gtggaggggtg ttgagttcat tgtcatccat   75300
gaactcctct gtgtatagac ctagtgcaat cccgaacttc ggtacgctca actggcgtac   75360
tagaccacca aggcggaact agaccgttcc aggatcgtcg aagttggtca tgacggtctg   75420
aagatggaac gtcgagcaga gctccaatgt aaactcgaga tacgttggct tgacggtctc   75480
aaagaagagc ccccacgggt cagttattag gagggttcgg acagcgtcag ccaattgaat   75540
ctgttcgagt gcgacccagt caatgcagcg gcctacacct aggggtcggg cccgtaatat   75600
ttgatataat tcctcttagg gtcccggggg aacctaaaag aacgggtgcc taatctccgt   75660
ggtaggactc gaggataatg ctgctcattt tcgattcttc gaggcgggaa caacagtctt   75720
cttaccacgt gatgatgaca ttatacctgc gttgaaaaat taaagtttaa ccaatacgtt   75780
ccaaaaatag cacagaagca caaaactaaa tagaaaattt catgagactt acgtagtgga   75840
tgaagtaaac aaaactacta aatatatcaa gttatagtat tatgggaata atgtaacaag   75900
```

```
aatatgaatg aatgcatgtg ggaagcataa atttcatgaa actaggaaaa aggaaaaagt    75960
agagcataat ggagtaacta aaatgacaaa attttttataa acaagcatga gtgttttaat   76020
attctaacta tgaatattct ttcaaaatag ttcaatagag cagagagatc atgaaataag    76080
caacatattt agagaaaata gagggaaaag agtaaacaaa cgcaaaaaag aatgacttgg    76140
ggcgtcgaaa ttggtgttgt aggcggcgca cgagcgtggg aggaaggcgt gtgaagttgc    76200
agcggctagg gttagaaatt tttggggagg gatatgatga atagtgaggg gtttatatag    76260
attttgaggc atacggccat ggggcacgcc cgtgtgccct aattttttacc cgtatgtttc   76320 gtatttttt gaatttgagc acgtctgaca ttcggcccac gcctgtgttc cttgggcgtg     76380
tgggtgcaca cgaccgtgtc acatggccat atgtcgcttc attcgtttct tccacgccct    76440
tgtatgaagg tccacgcccg tgttaatttg gcaggttcac tcacgggtgc tgggcacggg    76500
cgtgcggtat gttcatgcta atttgacagg ttcacccacg gtttcgaggc acgggcgtgt    76560
ctcacgccag tgttgttttg gaaggttcac ccacggctat gtcgcacggc cgcagcaatt    76620
tatcgcttcc cgtgttagaa aaattttgcc ctgttttcac acagcctaag gcacactcgg    76680
gtgcctggcc gtgtgggttt tagaaagcct gcgttccatg atttggttag tacgttagat    76740
gttaaaaact aaaatttaaa taaattaata ctattagtgc tcgggttgcc tcccgagaag    76800
cgcttatgta tagtctaagc tcgacttacc tctctggtat atgatcatgg tggatcaagg    76860
agtttacact cctcatccct gctatcaatt ttatcaacat aaggtttaag acgagtacta    76920
tttaccttaa acgtgccaaa tttgaggtga tttaactcga ccatatcgta tggaaaaatg    76980
ctaattatcg taagagaggt tttttcattc ggttcagaaa tggtgattcg aagatctgct    77040
gtatctagta gtactttgtc tcgaacttga agttgatttt cggaagaatt aagcttatca    77100
tggcgtggtt ttggtttatc gtgttttctc ggtttatgta tccgccattc atctagctcc    77160
tcgatttgta accttcgttc ttcatggatg ggttctttat tgttgcttgg cttatgtatg    77220
ttcttcgaac ctatttcctg caaagaaggt tgcaccatat ggttagtttt agccgaatga    77280
tttgtaaagt caccttcaat tattgatgtg ttattcaaat tacgggtttg aagggtgatt    77340
gtttcatctc ctacacgaag tgtgagttca tctgtgccaa cgtcaataat tgttccggta    77400
gttgctaaaa agggtcttcc taaaattaaa tggacgttgt tatcctcctc tatgtctaga    77460
acaatgaaat caactgggaa tataaattta tcgattttaa tgagtacatc ttcaataata    77520
cccctaggaa atctgatagt tttatctgct aattgaatgc tcatcctagt ttgtttaggt    77580
ttccctagac ctagttactt aaacaatttg taaggcataa cattgatact agcccctaaa    77640
tcaaccaacg cattattaac atctaagcta ccaattaaac aaggaattgt aaaattctct    77700
ggatctttta gtttgttgga ccgcttattc tatagaatgg ctgagtagac cgcatctagc    77760
tctacatgcg atgcttcatc taacttccgt ttatttgcta gaagctcctt taaaaacttg    77820
actgtgtttg gcatctacga aaaggcttca ataaacggta agttaatatg tagtttcttt    77880
aaaagtttaa ggaatttacc aaattgtttg tctgagcggt ctttctttat cacattgggg    77940
tatggcacac gaggtttata ttctgtaatt actggctttg ccttatttg gcctacctca     78000 tctttacctt tacttaccac catttttggc cttagtctg caactagccc ttcctaatct     78060
tgaatggcaa ccgcgttgag ttgctccctt gggttagatt cagtgttgct tggtaggctg    78120
ccttgtggtc gttcagaaat caacttggcg agctgtccaa tctgagtttc aagcctctgg    78180
attaatgctt gttgattttt gagtgctgtc tcggtattct aaaaatgagt ttctgacact    78240
gagatgaatt ttgttagctt cttctcaagg ttcggctttt tctcttgttg gtaaggtggt    78300
```

```
tgttggaagc ctggagatgg tggtctctga ttcccttggc ctccccatga aaaatttggg    78360
tggttcttcc aacctgcatt gtaagtattg ctataaggat tgtttgaga tcaaggattg    78420 ttacccatgt aatttaactg ttcgttctcc atgttgtggc cataaggtgg gtattctgaa    78480
ctgcttgatc cacctccgct cgcttcgcac tgcattactg ggtgaaccta tgaaaaacta    78540
agaaaaccat caattttctt attcaagagt tctacctaaa tagagagcat ggtgaccgta    78600
tcgatgttat aaatgccagc tattttcatt ggctttgtcc tcgtgacttg ccattaatag    78660
ttattcagtg acatctcctc tataaattca taggagtctt catctatctt attattgatg    78720
gttccgccag tagctgcgtc aaccatttgt cgagtcgaat gattcaggcc attatgaaag    78780
gtttgaaatt gtagccagag tggtaaccca tggtgagggc atcttctcaa gaggtctttg    78840
tatctctccc atgcattgta gagtgtttct aaatctattt gtacaaaaga agagatatca    78900
ttacgtaatt tagccgtttt aaccggtgaa aaatatttta ataaaaactt ttcggtcatg    78960
tgttcccaag tagtgattga ccccgtggca atgagttcaa ccactgttta gctttgtttt    79020
tcaatgaaaa ggggaataac cgaaggcaaa tggcgtcatt agaaacgcca ttaattttaa    79080
atgtatcaca tagttccaaa aagtttgcca agtgagcatt gggatactcg tcctacaaac    79140
catcaaactg aacaaactgt tgtatcattt gaattgtgtt aggtttcagt tcaaaagtat    79200
ttgcggctac agcaggtcta actatgctcg attcagttcc tgttaaagaa ggtttagcat    79260
aatcatacat aatgcgcgga gtaggattct gattaacagc aatcgtagga ggtagcggat    79320
gttcttggtt ttcagtcatc tccttggttg tggttgaatt attgtcctct tgctcttcct    79380
ctatgtatcg agcttcgcct tatttctctt cggttttgc aaactgtgcg atcgatctaa    79440
ctgttaaaaa gtagtggttc tggccgtaaa ctagaaaaat ctgtcagaag aaaatgaatg    79500
aagaattaga aaagaaagta aaaacttaaa ttgcaataaa agtaaaacgg ctaaagtaat    79560
aaaaatcgag tattcctaat atcctagttc ctcggcaaca atgccaaaaa cttggttgcg    79620
tgatattcgt aacaggtttt aaatatttat aaatgactcg ttcctgagac taacttatta    79680
tcacgattaa gacaagtgta cctatcgaac agtagtatag tttagcaaga ccggattgtc    79740
aaacccaaat gaactatgag tactagtatt tacttctttt ttattatcta gcctaaaaat    79800
taagaggttt ggttatctaa actaattact aactaagaat gcacagaaag aaaacttggg    79860
aaaatacttt tgggaaaatt cgattgattg agacaatacc taagaaaaaa ttcacctaga    79920
cttcacttgt tatttaactc tgaatcagac gatttattca tttgacttga ttcatagaaa    79980
tcctaagtta tattattatc tttctcaaga ctaacaacgt ctaaccctag gttgaataat    80040
tgaaatctct ttctaattaa catcctagaa ttgcattaac tcgatctatg gattcccttá    80100 ttaggtttca ccctaatccg gcaaaatctt atcaccctat ctctaggcat acaatcaact    80160
ccgcttaatt atgacaaatt tactcttagg cagggtctat tcctcctctg aataagagct    80220
taacttgaat caatatcttg gaatatcaaa acaagaatta agaacacata attaagaaca    80280
agtcaaatat ttatcataca attcagataa taataacaag atctttctta ggtttcattc    80340
cccttaggta tttaaggagg tttagtccat acttatgaaa gcaaacatct caaaagcata    80400
aagataacaa acataagaa aacccaaaac tcttgaagga acttgaagcg agatctcag    80460 tcttaatgat gaatccggct tttgagatgg atcaatcggc ttcccttaag taattccttg    80520
cttcctaccc tgcctccctc ttctaagtgt gtcctcaggt gtttaaatag gctttggaat    80580
gcctaagagc cctcaaaatt ggccttttc gaattggact aaactagggc tcggtaggga    80640
```

```
cacgccagtg tgacacgtcc gtgtgtgtaa cacccctaa ccccgaactg ttaccggaac    80700
gaggttatga ggcattactg gacatatcag acaacttact aataatttgc aattaatata    80760
actttcatag tataatacaa taattaagtc cctatcttga actctcgaag ttcaaacacg    80820
tattaaaagt agaacgggac ttgttcgagt attccaattt ttttttttata aaaatttcgg    80880 cagcatttct gcttattttt acctaaacct cctgcaattt caaccaaaa caaccaacac      80940 caatatttca cattcatata actattattt atatcactaa caaaatttta acttaataac    81000
tatcatagca tcattcaaaa ttgattaaaa acttcattca tttaacaact taatgttcat    81060
gtatcaaaat atcatgtact ttccttacta tttcatttaa ccatctaaat tttataattc    81120
atcctttact acccaaagta atatacatat tcaagtgact aaacaacacc tatgtacatg    81180 ccactttac ccaaaagaaa aatatacatc accaaatttg tgttggagtc gggattgttc     81240
tggatgctga gccgggacac ttgacttcta ctaacctgca cacggaaaca accgtacgct    81300
gagtatggat atactcagtg gtattactat aaatcaaatt atatcaacaa tagtaaaaac    81360
ataaatatta aaatacctaa caattaatgt catatgtact aattcataaa tcaatgtatt    81420
ttctcaaact taaatttata tcacttatga atatacattt catactttc tcttattatc    81480 acaattccaa tttcaattcg taattcttct catttcaatg cctcaaattc acatttcaat    81540
ttttcaccct attaacgtaa ctcggacttt ggcggataca cggatccaac caaacacacc    81600
aatatggaac tcagtgcctc atcggatagt tcgaagtaat agttgacacc cagtgtctca    81660
tcggcctagc cgaagtaaag ttggtaccca gtacctcatc gaatctatcc gaagaaatat    81720
agtgacaccc agtgtctcat cgactcgagg tcgaagtatc ccttccaatc ctatggcatg    81780
ccaactatat ccgactcagc ccgactagtt aatagggtat tcaattcact ttctcaatcc    81840
tatatcactt tcaattcacg attcaaatca ccaatcattt ttcaatcaat acgcttttca    81900
aataattaca tattccatca ttcacttatt caattcaatt tgattcaatt tgcatcactt    81960
tcattttcac tcaatattca tatcaatttc acatacttac ctcaagtctt acttaccata    82020
cataacaata aaaaaattca gcaatcaata ataattaaaa ttcgaattat agtaatacac    82080
accgtaactc tcccgttcct cgatgacttt ctcctttcct ttcgatgctg atgcttcaag    82140
ttctttgttg gctattaaac ttccaagctt taaaatccct atttccccta tttcctttct    82200 ttccttttctt tttctccttc tttctcccct gtttcgtttc ttctctgttt cttttgttat    82260
gtttcttcaa ttcttttatg ttatatttta tatttaatta atttaataaa tatctatttt    82320
aataacaaat actaatatta caattggata catatttaat tttacatttg tatcaataat    82380
tttattacaa ttgtcattat tttatttgtt tcttaaacaa aaaatctcat aatttaataa    82440
tttaattatt taattaacaa acatctttt acttaaatta taagtaattt agtatttaaa     82500
ttacaaatgt accaatacaa ttcttacaca tgtatatttt attaccatac aattgtcttc    82560
tatttaattt atttataata tattatcaat taagtaatca taataattta atataaaact    82620
ataataataa tcattataat atatatataa tttaatatat aaaacctaaa taaaatcttt    82680 gatttattt caatatgccg cctcaattta tgtaaatggc ttaattgcca ttttgatcct     82740 ttttatttc tattactta gaattaaact tttacccttt ttcaatttag ttcttttgc       82800 taattattct aaattaagct aatttcacct aattaaatct taattagaca caccactagg    82860
ctcataaata tttttaataa ttattttga acttatttca ctaagacgga ggccctataa    82920 ctcactttc cggtgcccgt gaatttcagg tcattacagt gtgtgattac ttaaagccgt    82980
ggtcaaggct attaaatggg catgggcgtg tggtccactc gtgtaactcg tgcttcaatc    83040
```

```
ctgccaaagg gacacggcca tgggacacgt ccgtaggaga aagtctaggt cgtattgatt    83100
tcccgagtga gtccattttc tctgttttcg gcccgtttcc cgctcttttt actctcctat    83160
gctcacctaa atataaaata tgaaattaaa ggattaggag catcaaattc accaattcta    83220
aggagaaacc atccataaat gtgttaagca tgagataaaa atatgtataa attatggttt    83280
atcatttaaa caaaataaac ataatttgtt ccatctattg ggaatgctag aatctcttca    83340
ttacttactc gttcactctc tgtttcttct tcatctgttt ctacttcttt gttttcatct    83400
ctaggtgccc aaccatccct tttctcttgg ttttgattt aacatagtag ttttctgttt    83460
agttgctgag aaagtgaaag aaaataaagg aaactgttgg ttttgtttt tttgaaaggt    83520 tcaagcttga taagcttcca aaagaatatt tgtttctcat ggtcgttctt cagctgcaaa    83580
taagcaggtc taatgacttg ttcgcgaatt tgaaagtgtt gttttattaa aataagaaaa    83640
aaaaagtaat tagtaagtga attaaatcaa acatgtaaat attctagttg atttctttga    83700
gttttggctt ttgtcattgc aaaatcaaat cttgcgtaat atatctatca ttttagtcca    83760
acctttattg ttgcttagtt tagcatcatg gctgcagttg taaaaagttt ggtctgaaaa    83820
aaaagtgcat ttggaaaatg ttgctttgaa aaattatggt ttgggaattt taatcttta    83880 gcattgctgt taactactac tatgaaaagt taaaatgtca atttaaaaa catgatctta    83940 gaagataggc gagacaaatg atgtttttt gcatttttct ttttcaaaat catatttca    84000 aacagcaaaa ccatcaaagt gcattttcct tgtttaggtc aaaaagtatt tgtcgaaaa    84060 gctttggtta ctaaaatcat tttagcaatg atttgaccat caaaaagtaa ttttttgtta    84120
acatccctta cccgagaccg ttgcagagtc gagcacaagg cactactaaa cttatttgag    84180
cacttaacca aattcagata atttatatca tactttcag ataagttgtc caactgcgtc    84240
atagttgcta ataattcat atctcgagtt ataaaactca aaatccaaat ctgtaaattt    84300
tccccgaatt tatactcata tatatactta caaatttttt tctagaattt ttggtgaagc    84360
caattagtac aatttattag ttaaaatctc ccctatttca ggatttgact actctgacct    84420
ttgtgtatta cgaatcagat atctctctgt acagagcttc gataactatg ccgttttgtct   84480 ctaataaaac tagactcaat aaggaatctg taaatataa ctatgacttc taattatctt    84540
tgtaaaattt atggtgaatt tccaaagtca gaacagggga tccagaaatc gctctggccc    84600
tgtttcacaa aaatttaaac atctcataaa atatagctca tatcctgtt tcgcttcttc    84660 catatgaaaa tagactcatc aagattcgat tccataactt attcattatt taattccatt    84720
tatactattt ttagtgattt ttcaaattca aactactgct acttaccaaa aactgtttta    84780
gtacaaatat tgttaactag tttataacat ctttacttca attcattcaa actctataca    84840
tgccatataa atctttaaac ataaaacaaa aactaccgga attgatctga atagtgtgcc    84900
ctgttgtgtt gatccgatct accaacttct ctttaattca atctacaaaa gaaattatca    84960
aacacacaca agtaagctta ttgaagctta gtaagctcat aggcataaaa acacaaatca    85020
tatcaaatat tgtacacaat catatatcta ttagtttaac tatttcatcc tccaaatcac    85080
aatttcatta ataactcatt ggaataattt ccatatggct actcacaatt taactcccttt    85140 aggcccattt ctcatttact tcattgtcaa attagggaac aataagggaa ttgagtgctt    85200
cattatcaca ttgccatact aaattatgga ctttcacatt gttacgcatc acacactgaa    85260
gccatagcct tgccatggtc ttacatggtt cacatatcat accgaagcca tatcccagac    85320
atggtcttat acggaatcac attatcacat tataccgatg ccatagccca gctatggtct    85380
```

-continued

| | |
|---|---|
| tatacagagt cacattatca cattgcaccg atgccatagc ccagctatgg tcttaaacgg | 85440 |
| gcgcacttat cacatatttt tcgtcaattc atcagggtca cagaatagaa acactcaaat | 85500 |
| ccattgttcc tactaatttg tacttttagt tacacattat ttattagtta atgcaaattg | 85560 |
| atagtattca tcaacaataa aatactttaa caatcataag actttcataa caaaacattg | 85620 |
| aactttgcca tatgaactta cctggactaa tttgcaaaag tcgtagaaat taagggacta | 85680 |
| ttcttgaatt ttctcctttc cacgattcag ttcgttttct tgatctataa ttataaaatc | 85740 |
| attccttcat tagaatccat tccaattcta tttcacttca caatttatgc tgttcaaatt | 85800 |
| tcgaaattac acttttaccc caaaatttac agttttcaca atttagtccc tgctcaattc | 85860 |
| acccatcaat tgaactaatt tttctcaatt aacactttat tttatcatta taaactatt | 85920 |
| caaaaccttt tatattctta atttcaacag caaccttcaa ttcacaactt tttcacaatt | 85980 |
| aggtcctaaa tatcatttcc tatcaaaatc acttaataaa accaccttaa tataaaatta | 86040 |
| gaacttaaat ttcataataa ttcatcataa acttccctta tccatctagg gtaacttcta | 86100 |
| atttcacccca taaaatcaaa aactaatgaa ttctataagt ggacctaatt gtaaaagtca | 86160 |
| taaaaacata aaaattatca agaaaaagca agaattaaac tcacatgatg taaaatatga | 86220 |
| aaaaccagct ttctccagac cttctatggc attttagctg ataaaatatg aagagatctc | 86280 |
| tagattcttc aattttattc ttattttata tgttaaagtt ataaaatttc caattttgcc | 86340 |
| cttatttccc ttattttttct gctgatttttc ttgcctttgc cgtccagcct attcactttt | 86400 |
| aggcttaatt tcccttttaaa tcttccttct tttaacactt gagctattta tcccttttag | 86460 |
| caaaatttat ttttattaca atttagtcct ttttatttaa ttgactacct aatcgttaaa | 86520 |
| atttctcaac caaactttaa tactagctaa atgaaacttc ataaatattt ataaaaatat | 86580 |
| ttatagcttg attttcaaat tcgaggtctc gatacctcgt ttttgtcccg tttgacctaa | 86640 |
| taaattcttt taattcacta atttcaccat ttcacgaatt cttctaaatt cttacttgac | 86700 |
| tcataaaatat taaattacta tcttgttcaa tcttatttgt cggatttagt gatctcaaat | 86760 |
| caccatttcc gacaccactg aaaattaggc cgttacattt tgatagcttg aagcattact | 86820 |
| aaacaagaac ttgttttcct tccaaagtgc gtcaatgaag aagcattaga gtttagagat | 86880 |
| gttagtggga aattataaag gaagatttaa gagcagaatt cccaatgtac ataaaaattt | 86940 |
| tgttccaatc gatgggtagt agagtattga gtgacaagtc tttttccttt ggaaacagtt | 87000 |
| acccaaagag ctaatgaaat caaatttgga gagccttact ggagaagacg aatcactaaa | 87060 |
| gaaaaagaat caatccttaa aagtgattaa tgcttccatg aaccaaacct tgacggatca | 87120 |
| agcaaaaaag attgatcagt tgaggagtga tcttttgcag ctgaagaacg accatgagaa | 87180 |
| gcaaaatatg aaacaactga agggcttgtt tttgaaacag cagcatacat tagtcagatc | 87240 |
| gattttagtt ttaacatcat ctcaagctta gtatgagaac tattttgggg ggttttgata | 87300 |
| cttttagaaa tagttgttat tttggtagga ttacaaatat tgcttttatt aagttggagg | 87360 |
| gtcatgatta tgctgataat caactccttg aaagaatata tttgaaagaa tatataaaga | 87420 |
| atgttgaagg gtttatttta attgcatgtt catgatgggt ataataagat ccaaaagatt | 87480 |
| atgattttttt gttcaatcat aaataagtga tggtatatga tttctttttt tttctaagaa | 87540 |
| aagaatagat aatgcatgga catctccctc taggattaaa actttagcag ccaaaaagaa | 87600 |
| atgttcaatt tgtgtatata taaaaaataa ttaaaaatat agagtgacaa aaatgaatat | 87660 |
| taataaccat taattacact aaaagcaatg tatcatataa aatgttattg caataaagaa | 87720 |
| tatataaaga tgattacttt aagtaatagt aaatgtgttc gtagcaaatt acacttacca | 87780 |

```
cactcttttta aggttagtta acgtatcgtt atgataataa taataatatg attgtttatg   87840
tttccatagg gtgtttatta aaaaatccac agtattttac ttactattaa acaatgcctt   87900
ataatatata tttcaataat cattaatcct tacataatat aatatcactg ctataaatga   87960
atcaattaat attgaaaaaa gacaaataaa taataataat aaaaggaagc aaaaagagaa   88020
gtgcatggaa aacatgttga actttcccgg tcagtgcaaa tacttatatc gttgttttat   88080
taaaaattat aaatgaatat cagatatctt catgagctac tagtgtatca aatatcagtt   88140
ttcatatatg tatgtatgca ctttagtcat ggtaacttta ttcatatatg tgatcttatg   88200
aacaacttgc atcttttttg tagtgatcaa atatttgtgt ggcattattt tgtgtagatg   88260
gatcgtagtc aagatcaaaa tgcaattgtc ggagtcgtgg cttcagtttt agcttttggg   88320
gttctttgga ttaaaaaatt aaaaactaga aagaaaattg cttctcactc tcgtgtgaat   88380
cgagattatg aaagagaaaa ttatattaat agtattttat atagtggtga ccaacattgt   88440
attaatgtga taaggatgag accgattgcc ttttttaatt tgtgtgatat tcttagtagg   88500 aataaatttgt tacaatcaac taaatctgtg aatattatgg agcaagtagt tatatttta   88560 catataattg gtcataatgt aaggtttcga gtgattagat ctagatatta tagatcaact   88620
gagacaattc accgttactt tagggttgta ttgagagctt ttttgaaatt gtataaacta   88680
gttattagat tacctgatga gtcaactcct agtgaaatta gaaacaatcc aaggttttat   88740
ccttatttta aagattgtat tggggcaata gatggaactc atgttcgtgc atccgttcca   88800
cttagcattc aaggaagatt tcgtagccgt aaagggggga cgacacaaaa tgtattggct   88860
gccgttacat ttaatttgaa attttcctat gttctagctg gttgggaagg tagtgcacat   88920
gactctcgta ttttaagtga tgcactttca cgcccaagag gattaagaat tccggaaggt   88980
aataattatc attcaatatc aaatagttct agtaagctca taatttatta gtagtaatta   89040
tgttttgtaa aattgtaggt aaatattatt ttgctgatgc tggatatggc gtccgaaatg   89100
gatatattac cccatattgt ggtgttcgat atcatttaaa agagtttagt gctcaagggg   89160
ctgaaaatgc aaaaaaattc tttaatcttc gacattcatc attgtgaatc actattgaac   89220 gtgttttgg gattttgaag aaacggtttc atgtattaga tgctgaacca ttttggaatt   89280
ttcaaactca agtagatata gttttggctt gttgtatcat tcataatcat ataatgggag   89340
ttgatcctag taatttactt aatcaatgat tatacgagga gcctgagtct aatttgataa   89400
tatcaactct tacagagcga gaagaaagag aataagtaag agaatggtct gctaagagag   89460
atgaaattgc acaaactatg tggactgatt atatggctag aaatattagg taggtttagg   89520
gcttagggtt gttgtttcta tgttatgtat gttttagttt ttttttgtta atattggttg   89580
agtaatgata ttgaaatttt agtttgttgg attgaaatta ttatgtcttg aatttgttgg   89640
atattgattt ttatttcctc aaaacttcga caaacaattt ttttctcctc ttacttactt   89700
cagctaatct ttgtgcatag aaagggacca aatgtaatat atacgggtaa ggaaaaaaaa   89760
gagatgaggt gttggataag ttgtcatgac cgattagtca tgtcagcagt taggtgatac   89820
caacctgacg cattgtaatt aatgtgatca atcggtcacg atagcctatt taacacatcc   89880
tactcttttt tttctagttt tttttaattt ccaattggtg tcgccaatat atcaggcacc   89940
actttaaaaa ataaattttt taatcgtacg atatttgttg tatatttaaa gaaaagacct   90000
gtattgttct gtgttgcttg acaaagtaac aacactactt aaaaaatatt tttttatcta   90060
gaataattat caaatgatga ggtgtttttt tttaaattgg tgtcgcctag catattgaca   90120
```

```
gcacctaatc ttattgtaaa aaacatacta ttctcgtaaa taatctacaa catgtctcat    90180
tttcgtaatt attatttttt gtattatata agtaaaaaaa ccagatttt tattatttat    90240 ttcaagtaaa aattttgaat atattgtttc caaacaaaag aaattgtgcc aacttcccga    90300
tctaaatatg atatataaga aaattgatct ataaccttat tccctactta ataaaaagcc    90360
gaaatttaaa tttcttcaca actaagcaat gaatttcctt cgtcatagtg agggtaatta    90420
agtaatttca ttgttaaaag aggttaatag ataaaggaaa aaaagaaagt agagaagata    90480
attatgatat ttattcctat aaaatgtaat tatttaattt aaaaaattaa atttaaaatt    90540
atatcattat aatagattat ataaaatacg aaaccaacta aagttcaaga caacataaaa    90600
taagtaaaac atgacagaat atgaaaataa tgcaaatata aaaaatgtgt taaatttaca    90660
tttaacgaat tattaacata taaaattta taaaatattc attcatttt aaatacaaga    90720 aaaacacaac atgatatgaa tatatatttt tatttaaatt catattaaaa attatgtata    90780
tgacaaaaat taaatacaac ataacatgag tatacaaatt atcctataag ttaagtcact    90840
attataatat atgtacaact tattataata ataaaaata taaatatgac ttgcactaaa    90900
aaaaaagtca aaaatcaata tcaaaatatg atatgaaaaa taacatgaat gtaacatgaa    90960
aaataataca aatataaaca tgatacgaaa aaaaacatga atgtaacatg aaatacaata    91020
acataacaaa attgacacta taataactcc atttttaca cgtattttca tgttgttttc    91080 ttttttttt tcaatattct aagacatgtt taatatatat tatactttat agaaattctg    91140
acacattaaa atattttgtc aatttaaaaa atatatttat ttatattatt ttttgtattc    91200
atttcatatt ttagtcattt ttaatttgta ttataaaatt aaaattaatg tgttcgaaat    91260
tcatcataac cagattgttc attaaaaatt taatcatatt taaatcatat attatataat    91320
aaatgaattt attaagcatc taaattgtct cataaaaatat gataatatgc ttgcagctga    91380
gcggacattg atcacattta tttgattta taaattattt tggcaattga ttttattgta    91440
aaatttaagg ttttatatc cagaattttt atacgtggat ggtttagaat aataaaagaa    91500
tggtgtttaa atttttttta gttggtttca gtttcgattt caaataatct ttttatatcc    91560
ttttataaaa tatttaaata tttttattta ttaatttatt ttttataata aaaataactc    91620
cttaaagcaa taccaaattt atagtacaaa ataaaagaat tatgtaacaa atatatttat    91680
taaaatcaat taaaccttaa ttctgttaat acatgtatat tctaatacac ttaaacacgt    91740
gaattgtact taaaattaat tgttaaaagg tattatttag aatactatag tagttgtact    91800
gcacctaaga tgagatgtta tttattttga ggtaaaaatc attttcgtaa ttttatcatt    91860
taaaaaatta ttaaaaaaat atgttcgtta ttattatatg tagttatagt ataatcttta    91920
ataagtatgt aattgttttt tcctcatcac catccctaaa caatagtttg cattatgttt    91980
atgtcaaatg attgataata gattcttata atattcttta tctgatctta ttgttaaaat    92040
tgagttacaa gatgctacag tataaaacaa aacagttata aacaatgatc agtaaaaaat    92100
ataaatattt taattagttc aatatgttgt gtaacttttt gaagtcatat agaccaaaat    92160 gtaaatttc atcaaaagtc acacgatcat gtaacaaact gagaccgtgt gaaaaactaa    92220
ctgaccaaat ctacaatatt cacacggtac gtgtggccag cccatgtgac aatcgagaac    92280
catgtgcttc aattcttttt attttttaat agacacatgg tcatgtcacc aactcatata    92340
taaaacataa ctgtgtggta caaatatatg tcatttggtg ccaatttcat accaaactac    92400
atcaacgcct actaattaca caaggcatac aagtaaacct gcataaaacc caaccggcat    92460
accattttaa actaaccaat cactttctca atcaataatt tacaaaccta actcaattcg    92520
```

```
cgtgcaaaca ttccaccatc aaatgtgcct ttaataccaa accatacata tagttcaaca    92580
attatgccaa cttgtcttat ttagtattca attttttcaca tttaaactta tacatttcca   92640
tcacttcaat tataactagt tacatgccat aatgcacact tatatgcata acacataaac    92700
atccaagatt caaacatcat ttaaagttca atttcataat gcatgaaaaa taaactcata   92760
tataaataca atacaacttc tatatacatg ccacaaaacc gagcccagaa caaataaagg    92820
actaccgatt taaaaattgg atagtgtgag cttcgagata attcgaccaa cgcattccgc    92880
aaaatgacta caactgaaac aagaaacaaa atagggcaaa tatttcataa gcttagtaag    92940
ctcatatgaa attgtttagc ttaccttgac attcagataa tttaagcaat ttaaaaaata    93000
ttaaaactaa gcacgaaaat cctttgacat cctattactt ttacatgtac attaacaaat    93060
atttggagat tagtacatta cttaccatga acttataaca tatccataca gaacataaca    93120
gattgtcata tagcatatac taattcaatc acacttcaac cgtaacatgt ataattccat    93180
tcatgccaat ctttcaatca tttacaacca cataatgtca tttcctttc tgtcctttgc    93240 tcgaaggcta cagtaaatta aactcaattg cacggaattg atttacttac atatatagat    93300
gtatttggcc tgctaacact aatttcggat caagattgct aacactagct tggtttgatg    93360
ttgctaacac tagctttaga gaatctgcaa catatgttgg atctcaagcc atcaagttaa    93420
ttcctgatca caactcccat ttattcatac agactgatat acttgagccg ctaactttag    93480
cttcagatca aggttgctaa cactagcttg gttcgatgtt gctaacacta gctttaaaga    93540
attcacaaca tatgttggat ctgaagccat caaattaatt cctaattaca gcacccattt    93600
attcatacag actgatatac ttgggctact aacactagct tcatatcaat gttgctaaca    93660
ctagctttaa agaatccgca acatatgcaa gatctcaagc catcgaatga cccctgatca    93720
taattaaatg tgctcatcgg tcgggtcagg cctaagcata atattaacat actttatgct    93780
tacctaataa gtgtggcccg actcgaaaca tgggcctaaa attttgtcca aatccatcca    93840
tatttacaaa agattaaccc aagcccattt tatgcccatc catattattt tttaaatatt    93900
taaaaaatta tttatattat attattttaa tatttaataa aatttatat attttatttt    93960 attgaaagtt tttatatagt catcttaaca ttatttttaat gtttatatta aagtagtatt    94020
atatattttg tataagttta ttttttttaat gtgttctaaa ttacattata tataagaata   94080
acataatata aagtattatt aacttaaaaa tgggttgggt ggggccaagc tcgggcctta    94140
aatcttcaag ctcgagtccg tctcatattt taaacgggcc taattttttt gcccaagcca    94200
attttttagg cctaatttt ttgcccaaat cttctaaaat ttcaggtgga ccttcgagtt    94260
tggacgggta acctaaccca tgaacaggtc taatcataat gcacattttc attttttggga    94320 atttaatagc atgccatttg catctcaata gtttactaaa ttcacacggc ttgttatcga    94380
atttctatca tttctatttt tgtaactgta tacattttc atatttcaaa taacaatcca    94440 tataccttt aaacattata gcatcatcct gtacatataa ttcgttcata taataatttc    94500
acatctagtc tattttgcat atctatacgt atttagcata tatttcatat atttcaattt    94560
agtcttttag ctgccgaaaa cattatactc aacaatccaa actaaaagaa gaaaataaaa    94620
tacaaacata tacatatcat aaaattaataa agtaaatttc atatgaactt atcagacaaa    94680
atctacaatg agcgaaaagt ccaagactaa tatgcatttt cccttttca cgatttccta    94740 tcgattgatc cgaatctcga tctatacggt aattcatttc aatttatcaa ttctaaatac    94800
cctataacat cttatttcat gtatatgacc tcttactttc agttttcaca attaccctaa    94860
```

-continued

```
aattttgcat tgtattcaat ttagatctta aaaccgaaac tatatatctt tcacatttaa    94920
actcaaattt tcaatccttt ttcaatttca tccttgaata atcctaaaga aacaatattt    94980
acaaaaaaat ataacaaatt tgacgtaatt tcattttagt ccatataatc aaaactataa    95040
attttctttt acaaactagt acctttcatt tccttataaa ctaagatatt aacaccaaaa    95100
atttcaaaat cattaatgac aacttttaca aactttaacg cttttaaaaa cagagatatg    95160
ttttagctaa atcgagttat aatgatctaa aaaaaataca atttacgaaa aatggacatt    95220
taatacccta aatgcaatgg acgattcttg aaggaatttt gaatcttttt ctcccctctt    95280
caatggttta tattctgtgg aggaagatga gaatgaaaat tctctttcca tctaagtttt    95340
attttacaat tcattaattt taattaaaag aaaattaata aaaccaaacc aaattcatgc    95400
actaaccgtc caagcgaact tattatggtc caattactat ttaaatccat tcaataatac    95460
catttgaccc atttagctat taagatttaa tagtgattaa ttttttttact attttttacaa   95520 tttagtcctt ataccttaat taaccatcca atcactaaaa ttttcggatc aaaattcaat    95580
tcatctatat aacatctccg taaatatttta aatatttacg agctcagttt actaaaacga    95640
gatcctgata ccttattttc taaaatcact gactttaagg tcgaaccact tgtactttaa    95700
ctaatgtcta attaacaaat ttatcagatc aaaattcaat ataactttac gatagacttg    95760
tatatattat taaataatat ttactcacta gatcattaaa atataaaatt ctaaatttt     95820 acccatatta ctttggcagg ttatttccac gttaacatac aaggttaagt ggttttaaat    95880
ggggacaaat cttagaatta tacgtgaact ttgatttaat gtgtaattta gtatattaac    95940
tttagttttg tgtaattata cacatgaaac tttgattgtg aatcaactat acacatttaa    96000
agaaataaat acaacacttt ctttttatat tatataaata aattatttg tatatgcaat     96060 atgtaaatgt aaaatagtgc tatatgaata attatttaa taattccata aaaattaaat     96120
taaatcaaat caaatcaaaa tctcatttat aaaattatat aaaattataa ttaatgtata    96180
atattacaca tttaactaaa aattatatat aattttgaga tttatctttt tagaaatatt    96240
aatatttcaa ttaaagtcaa gagttttcat taataaaaaa aagggtctta tatgtgaggg    96300
cttatttaag ggttttttttt agtatattag cctacaataa tataaaggtc aaattttggt    96360
atttgtcctt ttacaaggtt caaatttata tttaattttt acactttgat agtatatttt    96420
tataatatta ttagttaatt caaataatta cattagtaat tattttgatt aaaatggaga    96480
tgttagcttt ttaggttaaa gtttactaca agtactgtac catattataa atttcatttg    96540 aatacccctac tattaaaagg aatattttaa ttcttatata tttgaaaagc taacattcta   96600
gcccttgcag atttaacttt aatgttaaca gaatgacatg tttaatgatg atcgactgtg    96660
atattaaatt aaattaaaaa gttaaacaat aattttaaaa atgagaagcg ataagaaact    96720
gaatttgctt ttacccaaaa ttgttttcaa ttttttttca taattattgg tttaaattaa    96780
ttttagttta gttcacatta ctcaccatta aaccacatca ttctatctat ttttttagatc   96840 aataaatttt tttaaatttt attgaaaaat taacttaatg ccaagttaac cattgttaag    96900
ccatgttatt ccattaacaa taaaattagc atgtaagaac taaaatgtta acttttcaaa    96960
tgtacataag ttaaaatatt attttgaata atagagggat aaaaacaaat ttttgatatg    97020
atagaagact tgtagtaaac tttatgctga ttttttcctt ttaactaaat caattaattg    97080
tattaattat ttgaattaat taatcaatga gattgtaaaa ataaaaggat tacattagaa    97140
gaggtatcaa aattagaatt tgatccaaaa taaaagagcc aagtcgggta accaaaccgg    97200
ccgtataggg tgtttggttc atggtacaag tcacgacatg acatgcggca taaatggcga    97260
```

```
gggcgtgaga gcgagcccaa atcaggacag aaaaactcca acatttaat gcggcaattc    97320 ctttgttgcc taactgttct cattttctgt tatttcgtcg ctcccgctcc tgcgcgccta    97380
atgtttcatc caaaattacc acaacaattc caatactctt tgttcacaat ctccacctcc    97440
gcttcgctcc tcctcttctc tcgcccatga agcaacgtag ttcgacgaaa atctccctta    97500
aatggatccc atttctctgc atctccttct tcatcctcgg aactgtcttc tctaacaggt    97560 ctcccttct gtttgttctt tcttttatta atttatgaaa tggtgtcaat gcctttcctt    97620
ttgctttttc ttttctcttt ttttgggttt gggtctttga ttgttggggt ggagttattt    97680 atttattat ttatattatt ggattttggt tacaggctat ggattccaac tatattcaac    97740
gattgtgaca ctaagaaagt atgttcctat tatgttcaca atgacagttt ttttaacttt    97800
agtttttggt tttcttcaac ttttttcttt aaaaacaaag ctttattgtg ttttgcagaa    97860
gcctgcaaca gataatgatg agaacggtga agttttgaaa acccacgaag caattgagtg    97920
agtgcgaaac tgggttctta ttcttttagc taaagttcat gttttgctt tgggaagtct    97980 tcacttttca ctattaattt ctttgcaatt tttatttt gatgagggcc taactagatc    98040
tctagacaag tcatttgcaa tgctccagat taagttagct cccccaggta gttctcagaa    98100
aatgaagaac tcggatgcca ccggtgctgt ctcgaccttg gctggtatcg actcgccgag    98160
gaagaaagca ttcatggtca ttgggattaa cactgctttt agtagtagga gacggcgtga    98220
ttccatcaga gaaacttgga tgccacaagg tctttatag agcatttgat tcgtttcttc    98280
tttgtatttc attatccgaa atgaattctt atgtttatgt ttgagcaggg gaaaagcttg    98340
ttcggttgga gcgtgaaaag gggattatta tccgtttcat aatcggccat aggtaaaatc    98400
atttttcagt tccttttca agtgcatgca tatggagatc aaatcttgag cgtgaatggt    98460
aatgtttaaa gtgtgatgaa aatgggagaa atgtacttgc ttcagtatga aattcaaact    98520
gacgtacgtt tatatctgca tttattaact ccagtgcaac atccgacagc attttagata    98580
gagccattga ttcagaggat gctcaacata aggacttcct tagactggtt agacaagtct    98640
tcccgtgata atgtcgaaaa ctcttactga catattatcc ccatttcata cctttaaact    98700
gttaccaacc ttctaataca ggagcatgtt gaaggatatc atgaattatc tgcaaaaaca    98760
aaaacttata tttgtactgc agttgcaaat tgggatgccg agttctacgt caaggtggac    98820
gatgatgtcc atgttaatct tggtgggttt gccatctcta atgttagaaa catatagaac    98880
ttaacaaaag cttttgattg tttcattagt gaatttgttt atgcatattt ttttctgata    98940
ggtaagctag ctgcacttct tggccgttac cgttccaagc ccatggccta tagggtgc    99000 atgaaatccg gaccggttct ttctaaaaag taattagttc tggtattttt tttttcaatg    99060
ataatactac tctccaattt gctttgtttt gtcctgcaaa gtttgttata tccttttct    99120 tgaattcctc tatgtcctta aggtctgtca agtaccatga accggagtac tggaaattcg    99180
gagaagaggg gaacaagtac tttcgacatg caactggtca gatatatgca atttcaaagg    99240
atctcgcaaa ctacgttgcc gcaaaccagt gagatcatct atttttatat gaaagtcact    99300
tttttttttt tttggctttg cctaattgag gatcttggtt tcatctttag agcccttgta    99360
tgtgtgtgca tttggcagtg tcaccttcat ccccttcctt cccttggtt ttcttttttgt    99420 tttttaccag ttagatcatg tagcagtttc ttttttactta aagcatgtca tcaaaacatt    99480
gaagatcggt tattaccctg cataaattct gttatatttt atatcgtaga gctaaatggc    99540
agtctcagac tgttgaattt gcattttgtt ttgatgtagt gactttgcac ctttgatcct    99600
```

```
cggcactgat aatattctac cttaaaaaga caggcatggt taataacatt cagggtgatt    99660
ctgactgaat tgcaggcata tattgcacaa gtatgctaat gaagatgtgt ccctcggttc    99720
atggtttatc ggcctcgagg ttcagcactt gaatattaag agcatgtgct gtggtactcc    99780
accaggtaaa gttcttcaag aacacaagta gtttaatcaa aggaaggtcg aaacaaggat    99840
ggattcatgt gaaacgcacg caaaccataa ccataggcat tctaaattag aatgaggtgg    99900
gtaaattagt gtttgcttaa tggagattct gttttggaaa tgcatggtgc agattgtgag    99960
ctgaaggcaa aagcaggcaa tgcgtgtgcc gcatcatttg attggagttg cagtggaatc   100020
tgcagatcag tggagaagat caaaatcgtt catcaaaggt gcggggaagg ggatgctgta   100080
atttggagtg ccttatttta aaccgatata aggttttctt ttgggggagg aaggggggggg   100140 ggtttcgtgg ttgatcaatg gtggaggaaa cttctgcttt caatgcatat cctcgaccgt   100200
ttactttcag aaatggaaaa caaaaaaaag gcggcgttga gttgttagat agtatgtatt   100260
tatacacaca aaattttgtt ttttctttct catagaaatt atattcattc aagaatgagc   100320
ggaattttaa ttggttctca aaagtataat actcaactca aattacaagc tatattcagt   100380
ctaagcccag aaaattgtca ataatctgt tggttataag ccgaaatgga taatcccgac   100440
gttttcttaa gattgcaaga ttttctagag cgtaatgcgc cagccttcct ctactgattt   100500
cgttaaatcc atcaaaagtt ccctctgtct tcaattattt acttttttct tttcattata   100560
gttctcatgt ttaagtgtat ataagagctt aagatagaac gtgatttgtg cttaaccaga   100620
attgattaat gattgtttat ttggtaataa tcaacaattt cttttttggta atgaggctgc   100680 taaaattcaa aattttggag gaactagatt ttaattgttt attgcttcga attcaagtaa   100740
aattctcgac acgcaagctc ttctgtttgt aaatccgttg ccaaacagaa cttaatttca   100800
ctatgagaag gatcgggatg tttaattcta gaaaatcatt tctgggtttt taaccgtcgc   100860
tatattgcat cttcgtagtt ttgttctcca acaatgctcc tcatcccgcg caggagttct   100920
tcaccaacat ggaagctgct gttcgagctc atccgctttg gggcggatgc tcagaggagg   100980
acctccacag tgctggtgaa gtaagccatc gatacttgca tatatcatgg gatttgggtc   101040
taaattactt gcttttatta tttttaagca atttggatac taagcctgtt gaaaagtcaa   101100
caaaggtagg aagcaacttg ttaaaaaggt tgagcaagtt gcaccgaatg ttgaaaagtt   101160
gaatgggata attacaattt tggtccctaa ttttttaggc catttgcaag ttagtccctg   101220
aacctcaact ataaataggc ttttcattt ttcatttcaa ccatcccaac caatctttct   101280
ctcttagnnn nnnnnnnnn nnnnnnnnnn nnnnnnnnnn nnnnnnnnnn nnnnnnnnnn   101340
nnnnnnnnnn nnnnnnnnnn nnnnnnnnnn nnnnnnnnnn nnnnnnnnnn nnnnnnnnnn   101400
nnnnnnnnnn nnnnnnnnnn nnnnnnnnnn nnnnnnnnnn nnnnnnnnnn nnnnnnnnnn   101460
nnnnnnnnnn nnnnnnnnnn nnnnnnnnnn nnnnnnnnnn nnnnnnnnnn nnnnnnnnnn   101520
nnnnnnnnnn nnnnnnnnnn nnnnnnnnnn nnnnnnnnnc ttccctggga attgaacttt   101580
gtgtgatttt ttagtacaat aatttacacg cttccgaccc tattggaaca acaagtggta   101640
tcaagagccg aaggttaatc gtagtatgct ttgtggttgc agtttaaact gatcttccac   101700
atcagaaaag atttccttag gtatattgaa agattatgga gaaacggtc ggtgtaggag   101760 cttcaacatc gtccatatgg acaagaccga caattgcaaa tgcaagattg gccgtggaga   101820
tctttgatgg cacgggccat tttggtatgt ggcaaagtga ggttctagat gccctttttc   101880
agcagggtct agacattgcc attgatgaag agaaaccaga tgatgtacag gagaaagatt   101940
ggaaggcgat caatcggttg gcatgtggca caattcgatc atgccttcct cgagagcaga   102000
```

```
ggtatgcttt ttcaaaggag acttctgcaa ataagttgtg ggtggcactt gaagaaaaat   102060
ttttgaagaa aaacagtcaa aataagctcc acttgaagaa aagactgttt cgcttcacat   102120
acgtcccaag taccacaatg aatgatcaca tcactaaatt taatcagtta gtcactgatt   102180
tgctgaatat ggatgagaca ttcaaagatg aagatttggc tttgatgctg ttggggtcac   102240
ttcctgagga gtttgagttc ctagaaacta ctctacttca tggcaggagt gatatatctc   102300
tgagcgaagt ctgtgcggcc ttatacagtt atgaacagaa aagaaggac aaacagaaaa   102360 actcaatcag agatacagaa gctttagtag tccgaggtcg ttcatacact cggaagaaaa   102420
ctcaaagggg gagatcaaag tcaaagtcca gactcgtgaa agatgaatgt gcttttttgtc   102480 atgagaaagg ccactggaag aaaaattgtc caaagctgaa gaataaggga aaagctgctg   102540
tagatgcttg tgttgcaaag catgatacta gtgactctga actatcactg gttgcatcat   102600
catcgtcgtt ccattcagat gagtggatat tggattcggg ttgtacctat catatgtccc   102660
ctaaccggga gtggttctct gatttagtag aactaaatgg aggagttgtt tatatggca   102720 atgacaatgc ctgtaaaact gttgggatag gttcaatcca attaaagaat aaagatggat   102780
caaccagagt tctgactgat gttcggtacg tgcccagttt gaagaaaaat ctcatctcat   102840
tgggagcctt ggaatccaat ggttcagttg ttactatgag agatggggtt ttgaaagtga   102900
catctggcgc acttgtgata ttgaagggca tcaggaaaaa taacttgtat tactaccaag   102960
gtagtacagt tattggagca gtcgctgcag cttccggtaa caaagacttg gactcaatgc   103020
agttgtggca tatgaagttg ggacatgcca gcgaaaaatc cttgcaaatt ctggcaaagc   103080
aaggattgct gaaaggtgca aaggcttgca aattaaaatt ttgtgagcat tgtgttctgg   103140
gaaagcaaaa gagagtgaaa ttcggcactg ctatccataa tacaaaaggt attttggaat   103200
atattcactc agatgtgtgg gggccttcca aaacaccttc gttgggagga aaacactact   103260
ttgttacttt tgttgatgac ttttccagaa gagtttgggt gtataccatg aaaactaaag   103320
atgaagtgct tggagttttt cttaaatgga aaactatgat cgaaaaccag actggcaaga   103380
aaatcaagcg gcttaggacg gacaatggag gggaatataa aagtgatccg ttcttcgatg   103440
tgtgccaaga gtatggtatt gttcgacact tcacagttag ggatacacca caacagaatg   103500
gagtggcaga gcgtatgaat cgaacattgc tggagaaagt tcgatgtatg ttgtccaatg   103560
ctgggttggg caagcaattt tgggctgagg ctgtgacata cgctggccat cttgttaatc   103620
gtttgccatc atctgcatta gaaagaaaaa ctcctatgga ggtatggtct ggaaaaccgg   103680
ctacagatta tgattcctta catgtgtttg gatccactgc atattaccat ttgaaggagt   103740
caaagttaga tccgagggca aagaaagctc tctttatggg aatcacttct ggagtgaagg   103800
gatttcgtct ttggtgctta agcacaaaga aaatgatctg tagcagagat gttacctttg   103860
atgaatctgc cacattgaaa aaggtagcag ataaagatat tcaaacgagc aatactccac   103920
agcaggtgga gtgtactcca aaacaggtgg agtttgagca gatggggatt tgcccagtta   103980
ataagtctaa ttctccagcc acaatggagg aattagaggt tgaagagatt ctgacccaag   104040
aaccactaag tacaccagaa ccagttgcag ttgcaaggcc acggagagaa attcgtaaac   104100
ctgctcgatt tactgatatg gtggcctacg cccttcccgt tgttgatgat attcctatca   104160
cttatcaaga agcaatgcaa agcttagaaa gtgataaatg gaaaagcgcc atggatgaag   104220
aaatgcagtc tctccggaag aacaatactc gggagttggc gcaattacca aaaggtaaaa   104280
gggcaatcgg atgcaagtgg gtattcgcaa agaaagatgg atctcctagc aagaaggata   104340
```

```
ttcgctacaa ggcaagattg gtagctaaag gctacgctca gaaggaggga attgactaca    104400
atgatgtatt ttcccctgtt gtgaagcatt cctccattag aattttgttg gccttggtag    104460
cacagttgaa tttggagcta gctcaacttg atgttaagac agctttcttg catggtgagt    104520
tagaagagga gatctatatg actcagcccg aaggatacac agatgctggt ggtagaaact    104580
gggtttgtaa gctgaacaaa tcgctatatg gattgaagca atccccgagg cagtggtaca    104640
agcgatttga tagcttttatg agaaggcaga agtacacaag aagcaaatat gacaattgtg    104700
tatatttgca gaagctgcat gacggatctt tcatttatct actcttgtat gttgatgata    104760
tgttaatcgc ttcgaagagc caaaatgaga tagataagct gaaggctcag ttgaatcaag    104820
agttcgagat gaaagatcta ggtgaggcca agaagattct cggcatggag ataagtagag    104880
atagaccgag aggcaagctc tgtttaaatc agaagcaata tctgaaaaag gtattacaat    104940
gttttggtgt aaatgaaaac acaaacatg taagtacccc acttgcttct catttgaaac     105000
ttagtgctca attatctccg aaaactgaag aagaaagaga atatatggca aaagtcccat    105060
atgctaatgc agttgggagt ttgatgtatg cgatggtgtg tacgaggcct gacatttcac    105120
aagctgttgg agttgtgagc aggtatatgc atgatcctgg aaaaggacat tggcaagctg    105180
tgaaatggat tctacggtat cttcgaaaaa ccgtagatgt tggtttaatt tttgaacagg    105240
atgaagcact tggtcagttt gtagttggat atgttgattc cgactttgct ggtgatttag    105300
ataaacgtcg ttcaactacg gggtatctgt ttactcttgc gaaagcccca gtgagttgga    105360
agtctacctt acagtctaca gtagctgtgt ctactacaga ggcagaatat atggcagtta    105420
cagaagctgt taaggaggct atttggctta atggattatt gaaagacttg ggagttgttc    105480
aaagtcacat tagtctatat tgtgacagtc agagtgctat tcatttagcg aaaaatcaag    105540
tctatcattc aagaaccaag catatcgacg taagatatca ctttgtgcgg gaagtctttg    105600
aaaaaggaaa aattctactt cagaagattc cgacagcaga taatcccgca gatatgatga    105660
ccaaggtggt aacaacaatc aagtttaatc attgttgaa cttgattaac atcctgaaaa      105720
tttgagcacc tttaggtgta tggcgctcga gagcgcattt ggaggcacta caaaagatag    105780
ctttatcgaa tttgaggagt tgaaggaagt atgtgaagat gtgattatcc taatcaaatc    105840
ttcaaggtgg agattgttga aaagtcaaca aaggtaggaa gcaacttgtt aaaaaggttg    105900
agcaagttgc accgaatgtt gaaaagttga atgggataat tgcaattttg gtccctaatt    105960
ttttaggcca tttgcaagtt agtccctgaa cctcaactat aaataggcct tttcatttt     106020
catttcaacc atcccaacca atctttctct cttaannnnn nnnnnnnnnn nnnnnnnnnn    106080
nnnnnnnnnn nnnnnnnnnn nnnnnnnnnn nnnnnnnnnn nnnnnnnnnn nnnnnnnnnn    106140
nnnnnnnnnn nnnnnnnnnn nnnnnnnnnn nnnnnnnnnn nnnnnnnnnn nnnnnnnnnn    106200
nnnnnnnnnn nnnnnnnnnn nnnnnnnnnn nnnnnnnnnn nnnnnnnnnn nnnnnnnnnn    106260
nnnnnnnnnn nnnnnnnnnn nnnnnnnnnn nnnnnnnnnn nnnnnnnnnn nnnnnnnnnn    106320
nnnnnnnttt ccctgggaat tgaactttgt gtgatttttt agtacaataa tttacacgct    106380
tccgacccta ttggaacaac aaagccgacc tttcaaaatg agacatcatg gctggtaagt    106440
ggtcggattt gtgtttctgg tgatttcctt tttgctatat gcagtaaaat taaagacatt    106500
gctgcatcaa tcttttcgca taaggccact gatctgtttt atgctctatt gaacatactc    106560
tgatttagat tttagatatt ttacagaaac aatagcatga ccattgatgc atatatgtag    106620
ccattttgct tcatgctata taatatattc ccttttggcg ggcttgatgc cttattaatt    106680
ttcagttcta taagctctat atctgatgaa ggatagtctt aatgacagta aacctatttg    106740
```

```
atcatgtagc ttactttgag acagtacgca gctccggcag gttgttatgg ctaatatttt   106800
gttgtactga gaagttattg aacccagaca aagagaactt tgcgatctga accaaatctt   106860
ctgaaataaa acctttaagt agagaagatc tgtcatcaat tactaaagtt ccatcaatct   106920
caaagctgga gaatcaaggg gcaaccatgc ttctgcagga ggatcagaca aggaaagtgt   106980
tcgagagtgc ccatatatgt ttgttcattt tagtgacctg aaaatcaatg atgttgagga   107040
cctgaataac tataaacaac ttgtcttcaa gtatgtttgc ttttgaaagg actgggtagc   107100
gtttctgcaa ctattccttc ttccagttca ccagctctag ctccagaaca tgttggaaca   107160
gtgaaggaat ctgaagataa tagagtgatg gaactaaata ttggactgca aaagatact   107220 gacagggtgg atgatatccc aagttcagtc tctaaacaag aaaatagagt atccaatttc   107280
ccaaggatga ggcagttgca cccccaggag acaaccatga tgacacctct gaacaatagc   107340
tgactgggtt gatgttaatt tttttggaat atcatggcct ttcattgttc tggtaacctt   107400
gccactagga cttttttctt ccctctttta tgcagcaaat gactactgct gcagctgcaa   107460
atgaaaagac aatgtaagac caagttctta atttgaactt tgaaatgatt tggtttggaa   107520
attcataatg ccctgtagat gcaagttttg ctgtaacact gtgggttcaa ctcggcaaag   107580
cccttatttc agcacatata ggtacaattc tttgcttcat cctcgtacac agtatcgtgg   107640
ttcgttacga atggtaggaa agctgtaaac ttggaacttc tgttttgaag taagatgtgg   107700
caaccttttg gatcataaac caacattgac atgccaggtt aaacatgtag ataccttgat   107760
cattattgaa ttattggatt gatttattta ttttcaaacg ttttttgttg gattgagtag   107820 cttttcttgtt ccttcatacg catcatcatc ccatccccaa gattgagaga tggtgcatta   107880
tgtcatgcca tagatatttt gtccaaataa aatatcgtat tatgcctgat atttcttctt   107940
tttttccttg gggaagtgaa tatccgatca agaggccaca acttggaatt tgcttgatat   108000 ttcttttttag atcttaggct aaatgcaccc ggaatttgat tcaataatag atgcatagat   108060
cttctctgaa aggcatgctc caatcacttg atggagaata cgaaggcaac tgattttccc   108120
agtaagtgag tgatacaacc aaatagatat gacaaaacaa gtaatagttt atttaaaatt   108180
tagacaaaaa ttttctcggt attttgacag tatttatt ataattgtat acaggttgga   108240
gggtaaggag agagaagagg caacagtgac agataagcat atctttgatt ttctaggcaa   108300
tctctggcaa tgcaatattg atgacactga tcaggtacta acataaaaat taaaacagtt   108360
gcttatattt aatcctttct ccatcctact ctttaaatta gacttctcca tgtgcttgga   108420
ccggccaacg actcaatta ttatttaaaa cataacatta ttttgtatta atttttatatg   108480 ttttatactt atatttaatg ctttgacatg acttggattg aagaaatcaa atcaatttga   108540
ttatatgaat aatccgattt ttggacagat cccgttgttt acataaaaag catatttat   108600 acttatagta ccccttgaaa aagccttcat cttcctcctt tactcctaat ctctttcttt   108660
cctttattcc tttgttttct tttcagattt gttaaaagaa aagcaaagga ggggccaacg   108720
cagcatggga aatagatata attgccatca gaatctacgt ttgaatcata caaagagaag   108780 catcttttg ccgatgttgt gttcgaaggt atccattaat aaagatgtga tgaagcttcc   108840
caaatggaaa gacaagttac cggatgacga ccctttgtct ccaaagatcg gttgcatggg   108900
acaagtgaag aggaacaaca ggattgttgg cttccctgca ctcgatatca ccaccaagat   108960
caacaacagc tgcaatgcta ataataatac caatgataat ggcatcaagt atttcaagct   109020
caagaagttg ttttccggca aaagaaaaca agggtttgta gaacatggtg ggaaagagaa   109080
```

```
cagtggttcg cgttcaatca acatcgaaaa catggatccc cctttgcctg tgatcaagag 109140
agtgccgaaa caaggtgata aaggagaagg agacactctt tggcagagga gatctcgtgg 109200
ggtttcattg gaaagcttac agcttctaca gattcaactt aacagacgtc gagaaccgac 109260
cactgtttaa taactagggg gaacactaca aggttagata cgtgtatatg atttgttctt 109320
aaaatttcca tgtttttta tgattgtggt gttgaagaga ggcatcgaat tatggtgatg 109380
ctagttaaga gatgtatatg aattattcat caaagattta ggaatttta tctctcaaaa 109440 ttattgatgg aaacaccatc attatatttt cttgatgatt gttatgtcaa tgtggaaatc 109500
aagtgagtat gcattgtggt gttagatcaa gtgtctattt caaataaatt tcacatctgt 109560
gataagctcc agttgaactt taaactaaat aaagggttta aaacttatga caaacgtaat 109620 ttttcttgt attatattat atatctacta accagatcat gtcataagat aaaaaaggat 109680
gggataaaaa atttaatttt gcctttcacg acaagctttc tttaagccca attttttttt 109740
tgtctgcaat atttgaactc aaaatttat tcttgttttt tgatgaatga attaatttac 109800
accagtctta taactagaca aacaataata aacattgacc aaatgccaaa agatatgaat 109860
aaatttatgg tcggcagcac agcaaacagg atccacttta aagtttaaat aagtcaaata 109920
atttcagcat tcaactccta cgagtgcaag gagtgtttag tcttcaattc agaatctagg 109980
tagtctgata ggtttaggat gcctaacttc gataattgat ggtggatatt gaagtttgct 110040
taaaccctaa atgattttt tttctagaca ataatgttg cctttgtat aagatttgat 110100 aattcaccaa aaacatatac tgctttcttt cacatccatt gtcaaattaa ggggcagaca 110160
aacataaaaa attaagggac aagacatgaa cgatttatat aatttaaaga cttgagtttc 110220
gaatgtcaaa ccaaatctaa agggtgggta caagaaagtg aaagtctcgc agtgaatatt 110280
tcaatcaatg ccatttcttc aataagttta atacctgatt tttaaaatgg taaactttgc 110340 ttcttttta acgtctaaac cacacacttc gagatttcat tcagtttcag catagtattt 110400
gcctgtagct agaagcggtc ataaagacta attcttgtta ttttattatc tacaaaataa 110460
catctatccg cgggatatga aacatactta aacatggaaa catggtagat atcctctcta 110520
taaaacctaa ataagcgtat gatgtcgcac aagagtgtca ttacgttgta tctcatggtt 110580
aaataaggga atttacaggt tagcttgtga aatgatgata ggagaatcta attcaatctt 110640
tttaagtttc ttattctctc ctatttttta tacaaacaca agttacaatt tcctagtaaa 110700
acagctacta actaaacaaa ctggttagtg ttaaacctct tctttataca agaagctatg 110760
tagcattaac tctgttcttt atatggtgtc cagattaact tgctaacatc aacctcaagc 110820
ccaccacgcc cagcggcttt tagatgacga tccaacacct tgggatccgc acatataaca 110880
tgctgcccct tcctgtattg aatcagttct agactctgca gagtggtcaa tatatcctcc 110940
gcctttatag ctgtcatgtc actgagctcc tggacagaat aggttcacgt accaaacagt 111000
aataacaatt cagtgaccat tgacccaaat ttctcagaga atggtaaata cagctattca 111060
gcaataccta cttaactaaa aaacaataat aataatttat cacacaagct acataaaatc 111120
tatcaattca ggaatgtttt taacatgttt tcattttttc aaaatgggaa gatgaactga 111180
acctcgagtg ttattttact attctgggat gctcatttat atttcctagg cgaggatact 111240
cttgctcacc attttaaaat aaaagccacc atgactacta gcaagctact caagcttgac 111300
tgcaaagata cccagattag atctgttgcc cacaggacaa actgaagagg ttcaagtaat 111360
ctcagaaaat tttaatttc aactccaata tcctaagaac ccattcaaag cttttctttg 111420
tatttgttat ttaataggta attaagtctg tctaatcaaa tttgaatata actttatgat 111480
```

```
agatgggtcc agtttagttg aacttgagcg ttgtcacaat gtaggcttga ctccagtaaa   111540
ttaccctcaa atgcaggcac aaattctcat ggaaaggtta ccttaccaac tgctaaccaa   111600
gtttctaaag tccaatatcg ggtttaccag gtcacacaag cagatgcaat tgcataaatc   111660 acacccccc taggacttaa gatattcagg taatgatacc ttgatggaaa tatttccttt   111720 atgcttttc aggatgtcta aaagaaccct tgtccagtac cctctgtagc tcaacagccc   111780
tagatcggaa agtggtcttt caggtgtgcc aactttacct tctttctttg agagttcata   111840
tgctggtcca taacgatgac aaaataagca ataaagctca attaataaat aacaactagg   111900
atgaaatgca aaagacaata taagagagg catttatatt caatatctag aaggctctag   111960
catctagcta tttatttaa gacataagaa gggaagtctt tttttctgaa ccattgataa    112020
agtaaggcaa aaaaattata aaataaagta gcaggcacag agcttacaaa aggcaattaa   112080
aaacttccca tagcctttcc tttgatatgg aggaagggtg aggatacatg ccaaattata   112140
ggattcctct gaatgctttt cctgcatgat cagatgcaaa atgctaagat atttgttgtg   112200
acggataaga cagtctaaaa gactaagaca cggtgcagat aacaatgaaa taataataag   112260
gattggcaac attctaagca ttccaggtgt aacgactaca aaatttta ccgaacatgc    112320 tatggggttg aataagaaac ttaaagtccc aaaatacaca agagaataaa ttttactact   112380
tgaaaacttc taatatgatg acaataaggt caagaaatgt tgtatgcact ccatgccacc   112440
agagttggaa cattgcaact acaaaatatt agaacagcct tagacataaa aagatctgtt   112500
gtaacctcca cacagtgtca aattataagc aacaaaaatg cagtagaaat taattacctt   112560
ggaaaagtat ccaaccatgt ggcaaccacg atcatcacat tcacacaaaa catagaatag   112620
aaacaggtca acatcgtaat aaagggtctt gtggtcaagg aacaacttcg ccaaataaca   112680
aagattctgc ccataaactt tgttcttttt gccatcaacc tgtctcaaaa tatttgaaca   112740
taggaagatg aatgtcaaca aaggctaaag atctgcagca ttctacaaca tgacattttg   112800
tagcaggagc tagaaaaaaa gaaaaatggt gaaaattatt tctacactag taagccaaag   112860
ttgaaaatta attgtctcaa cacaacattt ttcaaagtat catttaaaaa gatctcaaga   112920
ttattggatt ttacatacaa agaaagatgt gtgaaaattg aatttacaaa agcaaaaaca   112980
atagggtagg gtcgaagaaa gccacaacaa tatagatttt acttaactag atcaaggaaa   113040
ggctatttcc ttttttttctt tttgtgaact ttggcacaga aagtagtagc agtaaaagct   113100
attcaagaat atacctcaaa cattgacagg gtaccacttc gatatatttc gtccccaggg   113160
ggatgcttca aatcacactt cctctacaga gtagcatgaa aacagaaagt tagtattgat   113220
tctgctccat ttgtaacttg aggcaatcgg attaagaggc aaaactcaaa gacaattttt   113280
cactacaaaa atccaaaagc aattttttaa ggcagcaata tcctacatct gtaccacatt   113340
ccatcctatc cctggcatga taaagaaagt acataacaaa ataaatgaag gcataagata   113400
ggaaattaca ctagggaatg caatttaaga tgagttaaca tcaagggaaa atattactgc   113460
tgcaatacct tgatcttaaa acacaatggc cataaaacca ttgataatca atcatgcata   113520
ataacagata cttccagctt ggcaagcaaa ttacatatct cataattgtt ttatcttaat   113580
caattaggtc aagaatgaag ggaaaaaaat gataagagga aaacctaaac ctcaacttac   113640
aggtctacat ctacataatc tgcatagtac tagatgatga atagaaagat aactcttaac   113700
aaaccaaggt tacacaaagg aaaaaaaaaa tgtcaagtgt cacttaacaa accaaaggtc   113760
acttaagtta cttcaaccaa aagcatgcag aaggaaaaca tgtggcaagc aaaaattata   113820
```

```
ttcatgacaa atgaagcaaa cttgcattac aatgttcaag gttgctatgg ttcacacaag    113880
gttcttacaa tgctagaaaa aaaaaactag tacatagaga acatttaaaa tactataaag    113940
taatgcaacc ccaagcattg cagaggggaa aagactattg ctacactgag gcaaagctca    114000
ccatatgcct ttgaagttgc tctttccttt tcatgaagtt gaggcaaaac tcacaaaagt    114060
acaacttcaa cgaatcatta tattctggtg gaaagggga gaagtaccat gtctcaattt    114120
catatcttcc aagttctata gtcgcaatat ttttcacctt cgtgaattcc tcatgttcac    114180
gcaagctggc agcatccagc tcctcatgac cctgaagaaa ataaaatgat agacgattac    114240
aaataatata atttcacaaa agcaacatgc agaaatttca aatgatcctc tgatatttac    114300
acatcaccga gcaaaaggtc tacgtttact tacaacctca acgtgtgtct catcaatctt    114360
acgtttctgg tggcgtgtca ttttaagct tgctacctga gaaccccatg agcaaatttg    114420
ttcaaatcag aacaccctca aatgataaac aaagagtaaa cataagtgca aggttctaca    114480
ttgtaaaaga atgtttacct tatcttcgac cttttcatca acaaccgttt cgacagaatc    114540
aagatcaagt tgttcaagct tcacccattc atcaagcctc ctattaacta tcatttcaat    114600
atcattatta taaaaaaat atacatcaat ttccaaaatt ttctaacata ataattctaa    114660
aattatcaat tgaatcacaa aaaagaacc tgaaataatt aaattaaagc aaaaaaccct    114720
aggaagaaca caaatcttac actcggtgta atgaacgtaa tattcataat cactgggctc    114780
agcggactgc agctttcggc gttcgatgac tttgacagga tgatacttgc cgtctctcca    114840
gcggcacatg acgcgagtac ccacctctag ggggtgtata cccgtcctcc tcttttcgt    114900 agcctcagac tcctgcgctc cgtttgagga ggccaaaggc ctctggttgt cgtcggccgg    114960
agcagcggcg gcgtaggatt gtgttgaacc attctccgta atcgtcggcg tgtctatgga    115020
acccatgggg tggtgtcgt ctgagagggt ttcagacttc gagtgggctc aacaatacaa    115080
aagagggggt agaagaaaat attttggg cttcagccca tcgagttcct tctcgggtaa    115140
attaatatct tcgtctttgg gtcctacaaa ctttagtcac atccacaaaa atattttata    115200
aagtatttaa tatataaaat tttatattga taatatttt atataaattt tatatttaa    115260 gaaataatag ttttttaaa ttataaaaaa taataataat atcattgagc attttaattt    115320
ttcaaaaaat aaaaaaag ttcatgtagt ttaatttgat ccattttaat ttttatactt    115380
tcaaattggg ataaatatca aagaacttg ggttcaatat gtaatttgat acataaattt    115440
taatttgata taattatata catgaaactt gaattatggt tatacgtata cataaaactt    115500 ttatttgat tcaattgtac acatttaaag aaataaaaaa ttcaattatt ttcatatcaa    115560
attaatataa ttgtttgagt atgcaacatg ccaacatgaa atggttctaa ttcaataata    115620
ttattagtga tttgtgaaat ttgaatcaaa ttaaactttt atgcacaaaa tcagagttta    115680
tgtatgattt gcacgttgga ttaaagttca tccgcatttt ttatatttat cctttttcaat    115740 ttttgaaatt tcagtcttaa ctttcatgat aacaattggg ttagttacat accatacata    115800
aattgtagag tttagtttat gttcactaat ttgattattt tttatttgtt tgcttttcg    115860 atttcaagat ttaagtttta agcttaactt aaacaatagt cgttaaattt attaactaaa    115920
atgtacgggg tttattgtga gtattataat atgtttgccg tgtgagattt tggtaatagt    115980
agaatttaac ttaacaaatt taatggctac tacttagtaa ggattagaat ttcaaaatta    116040
aaaaaaaata tatagaggct aaagatgatc aatttagagg tctaaattaa atcaaattaa    116100
aacaattctg catattaact atttagacta actaatgtga ttataaaatt agaggttcaa    116160
attatgtaaa attaaaatat aaaaactaaa tctcgaatgt gagtataata aaggataaa    116220
```

```
aagtgatttt ggtcattttc ttttatatac aaatatttt  agagatgttc ttttatatat  116280
aatggtttct aatgtcatat gcgcggcata taatttatg  tgtttaattt gttttattaa  116340
ttacttaaat aatatatttt taattactgt aattaatgta aaataatttt tattatttga  116400
atcattgcac aaaattaaaa tatactaatt tatttaacaa ttcaaatata ataataatcc  116460
aaattataat tatagtattt ttacaatatt caatatacaa tatagtttta cttcatacaa  116520
ttaatataaa aaaatattat tcaaaataat aactaataaa cataattacc atatattaat  116580
tattttgata tttcgaacat aacgctaata aaaaatttcc taatcattat taaatcattt  116640
gtataaacta taagaaatt  gatatattgt aaattaaact ttattcattt tttttcttaa  116700
tactcaataa attaatcata ataactcata aataatatat aattaaaata atcataacat  116760
attagattat ataaataggg ggcgaatcta gggagctggc atgacccta  aaatagaatt  116820
ttctatttg  acctatcaaa attttaaaa  ttttaaatta gtaaaggtaa atttgtactt  116880
taacctctta aaatgataaa attttacttt aatcctttaa aatttacatt tttactatca  116940
taaaaattac aatttgattt taccccctaaa attttttcct agcttagccc tgtatataaa  117000
tatattattt ataatttta  tatttaaaat ataaagtttt taattataca aataattaaa  117060
atctgatatt taaaactaaa gtaatttctt ttttctttt  actttttttt aattgcaaca  117120
taatggttta aatatctata taacgtatga agtaatttga tataaattt  atttaattt   117180
attattatat aaattcattt agtaaaaact tttaatagaa tcaaaattt  tatttgtaaa  117240
ttcgataact tttcttatca agtatatttg tgagaaccaa atattagta  aaattaatat  117300
tcttattat  aaatatgata aatcttataa aaaaatattt aaaatgaaaa aaattgtaca  117360
aatattataa aaaaatatt  aaaatgaaaa acattgtaca aaggctatat aagaagttca  117420
aaagtttctt cgaccatgta ctcttataga gattatagat agattataaa actatatgta  117480
gtttctctta acttttaaat aagaggataa atgtatttta atgtactcaa acttatatat  117540
ttttatattg acaataatat caatatcaac ctaattaaga ttcattctaa cattaatgtt  117600
gaagattttt aataaaagaa aaggttaata aattaattag aacacaaaca aacacaaatt  117660
taagtggtat gtaaggtcct tgacccaaag gaaaaatttg ttacgtcgat taaattataa  117720
attaatttaa agtaaaatta cattttaacc taaaaaaga  gaaaagtata tctaatttct  117780
tcgaaaatgg aaagaaaatt ataaaatttat ggcattccta aaaaaattct gaattcgcta  117840
ctaaaagatg aaattataaa atccgaagca ttaccagaag atggatcacc aaatcacaaa  117900
caatcaatga aaagtaatga taattaattg aaagtgagca tttaattttg atagccatat  117960
acttcctgct gaatttatag gttctcatta atgcaattaa attatattcg acaccttttg  118020
aatgaaataa aatgacacaa gaggaaagac ggttcatcta ttttttcttt caatcgccca  118080
tcaaaatacc aaaaatgtaa ctacatgcaa aaaatcaaat atgaaaaata ttcatatttt  118140
gatattttaa tatattgtgt gttcaaaacg taaatgtatt gaaaaattat gatggtgttg  118200
ttgctgtatg tccataaaat tcaatgtact cacatttatc aaatgtatac tttgagagaa  118260
gttattttga taatactcaa gttttttta  tagatgggaa aattttttaa attattttt   118320
gattttgatg aaatgtatat ataaatttta attcgataca tataaatata tatgtaaatt  118380
ttaaatttaa atttaataat atacaattaa gaaaataatt tacataaata tatatcctaa  118440
taaaaataaa aytagaaaga ggaaatgtca aaacctcttc attatataca attatgatgg  118500
gacacgatac cctcatgcat tgatatctca tgttgtccaa aaactcggaa tccttttga   118560
```

```
aaaaaaactt ccagagagag tatataaatc cagcagtagg cacaagaaac gagcaccagt    118620
tattgacttt cctttgtaaa aaaaaaagtg ctgagatcaa gaaatatagt gaaatatggg    118680
tccaagattt tctgggtttt taatctaagc aatgctgttt ttaactcaac tcctctctct    118740
aacaggtaaa acaaacttct ctacagtgat tttacagtaa atatggcttt gaaaaatata    118800
caacaaaaca tttatcttca atccatttta attactgatc tactatatat gttgcagatg    118860
gccgtgatat tggtgtttgc tatggtttga acggcaacaa tcttccatct ccaggagatg    118920
ttattaatct tttcaaaact agtggcataa acaatatcag gctctaccag ccttaccctg    118980
aagtgctcga agcagcaagg ggatcgggaa tatccctctc gatgagtacg acaaacgagg    119040
acatacaaag cctcgcaacg gatcaaagtg cagccgatgc atgggttaac accaacatcg    119100
tcccttataa ggaagatgtt caattcaggt tcatcatcat tgggaatgaa gccattccag    119160
gacagtcaag ctcttacatt cctggtgcca tgaacaacat aatgaactcg ctggcctcat    119220
ttgggctagg cacgacgaag gttacgaccg tggtcccgat gaatgcccta agtacctcgt    119280
accctccttc agacggcgct tttggaagcg atataacatc gatcatgact agtatcatgg    119340
ccattctggt tcgacaggat tcgcccctcc tgatcaatgt gtaccttat tttgcctatg     119400 cctcagaccc cactcatatt tccctcaact acgccttgtt cacctcgacc gcaccggtgg    119460
tggtcgacca aggcttggaa tactacaacc tctttgacgg catggtcgat gctttcaatg    119520
ccgccctaga taagatcggc ttcggccaaa ttactctcat tgtagccgaa actggatggc    119580
cgaccgccgg taacgagcct tacacgagtg tcgcgaacgc tcaaacttat aacaagaact    119640
tgttgaatca tgtgacgcag aaagggactc cgaaaagacc tgaatatata atgccgacgt    119700
ttttcttcga gatgttcaac gagaacttga agcaacccac agttgagcag aatttcggat    119760
tcttcttccc caatatgaac cctgtttatc catttttggtg aacttgaaat gttattgttg    119820
gctatttaaa tcttttgcca gagacgcttc atatagtttc tgcatatttt gaaagtggaa    119880
aatcaatcta aatataaata agttttattt gttgttttt aattaaataa aatttttaaat    119940 attttaaaaa catctttatt ggtaattaaa tattaaataa aaagtttaat attcaaattt    120000
tatcaattca aaaataaaat aaaaatatat taaatttatt tttacgaata aattgatttt    120060
ctattaatgc agatttaaa taatttgata taaattttca attcaacaat agtaattttg     120120
atcacatcaa aggagaaagg gaaagattta actttaattg gtgacctaat ataacacgtt    120180
gaaaacggag ttcccaataa ggcaaaatga cttgtaatga cgaaagagat gtccaagtga    120240
aatctgcttt aaagtgaaag aagcataaaa ggataactaa ataactcatg atctaaattg    120300
aagttctata aaatgcaact ttcatctaga aacaaggtat gtcttaaatg atgttttatg    120360
aatttgtctt aattgggttt tatgcaatga attcatggat agcacatctc taattatacg    120420
ttgctggttt atatgagagt ggtgcagaag ttaattgtgc tttaaatact tgcttagtgt    120480
tcatgaaatt tgaaagtgt tatatactta taataaaaat aattcgattc ggaatccaat    120540
tcagggttcg actcaatata ataaaatttt acagatatct tgaaggggat cttcttcttc    120600
tctacttctc gagcagtgtt atatatttac aataaagata actcaattcg agatccgacc    120660
taatataata aaattctaca gacatatcaa agagggagat cttcttcttc cctacatctt    120720
gaccttcttg atcaaaatga ccttccttat attttttacat acgttgatta tatgaatcaa    120780
aagaaagata ccaaaaagtt tttaaaaata acaacgggg ttcttatgta gagatgctta     120840
tgggccgggc cggactcaac taaaaattta ggcacattca ttgggcccag gtcgggccta    120900
acccaaaaat gggcctaaaa ttttgcccaa gcttgactca aataaaaatg ctaaaattcg    120960
```

```
ggcctgaccc cgtattaatt ttatattatt ttatataact tttaaatata tataatatat   121020
aaaaaatact aaaaaattaa aataaatatt tcccaactaa actaaaatta ttaagaaaaa   121080
taattcatat tagcgtataa attggaaatt gaccaaaatt aaaattattg tatagttaat   121140
ctatattaaa aggacatgta attaaaaacc attaaaacta ttatacaata aattaaatct   121200
tcattgtata catagaaagg cattaataat taaaaaacta tattaagata taaactaaat   121260
tcaaaattat taaaaacaag aactaaataa aaaagcaatt gaaaattacg aattaatgtt   121320
aaaatcaaat gttaaaatca agggacttaa ataaaaatat cccaaaatac aaaacattag   121380
cttcctttcc catccacgtg aatgcaaagt ttacatggtg tttcctagtg tttgtgcgac   121440
tccaaccttt tatttacctc ttttttttctt tatttgaaca attatttgat aatgattaga   121500
attttgggat tgttgctcat cgtacgtgca acacttaaaa tcactatgat tttcataatt   121560
tatataacct atatcgtttt ggaaattaat tttatttttt atattatttt aataaaaata   121620
ccatctacct tttttaattt atgatcccctt tcatatttaa aaattcaaat tgacaattgt   121680
ctaactaaac accgtcacac tccaataaga ttgtaatttc ctccatcttg atattacact   121740
caaaagcatg ttgccaacaa acaaatcaac tagcctttttt ctaccactat tcatcatctt   121800
cttaagagtg tgtttatgtc atgtgccgag attttaggta tggtcacgtt gtggctttaa   121860
actcaaatct attgcccatg agtctaagtt agcctccgat cctcactaaa gagaggcttg   121920
gcacacttta cctagccaag tacacaagga atagagctat tagaaagcat taaagagtta   121980
ggagaatgtg gaagtgtttt tattactcaa agctaacttg gatacaaata aaggagggag   122040
cctctccttt aggcaagctt cttttgatct gatggttaca attaatctcg aataggaggg   122100
gtcaaacttc tcactcagtt tcatattatc tcttggtgct tggttggcct ccgccttgag   122160
acaactttag ataacaccta gtcttaacac ttttagcttc acattgtacg catccttcat   122220
tactcaaatg ccacaaagcc tccttactta aggctcttgg tcgctcccac taccttcggc   122280
tttagactca tctaagatct tcccaatcgc agacaacttg gccttgatga ggaaatcttg   122340
caccctaagg ggccttacat aagaagcaat taagtggctt tctctcaccc acttcattta   122400
cggttgcctt gaggcaccct ttatctcgtc agggcttagc tcaccttgtc tcctcattcg   122460
actaatggtt gttattggct cccctactct tttccttacc acgattctta aggaattcaa   122520
ctcattcact agggtaatca actaaggact ctggtactgt cataactcgc ataaggttta   122580
aacacccttc gttgaactct attccatcaa gaaagctgaa taaggcctca ctctcgctca   122640
tattcgacat ctaaagtatc aactccgaaa acttgtgcac atggttatac accgtatcac   122700
tttgggtaag ccacctaaac ttcgatcaag cctcctaatt ggcatacttg aggtagaatt   122760
gtagcttaaa ctccctttaa aaggcttcaa aagtatcaac ggttccacct tcacgccttg   122820
catcatcgct cttacggtgc caccaaagta aggcaacatc aaagtaaatt gaagcagtgc   122880
ttaccttgag ggcatcttcc tcaatcccga tcaaataaaa ttattgctcg atgctctaga   122940
gaaagttatc cacctctttg gcattactcg tgcctttgaa ctcttttggc ttcaatacat   123000
ctactcaata actcgaccac attggcatgc cgccactttt ggttgccttg acacttaaaa   123060 gctcacccctt aaacttcttg atttctctac tcatcacccc caccaatgct tagagggcct   123120
cattctttct agcaagctca cctaaggcat cccttatagc cccattcaac tcctccataa   123180 gttttttcctt tagctcatct cgagactgcc tcatctcaga tttgatctca taagggaat   123240 ctttggtgtc ctccacctttt ataaggacat cgctcataac caacttgatt ttggccatcc   123300
```

```
gggtctccat aatgttcaca aagcccattg acgaaacctt cttgcccttc atggcacctc   123360
gattctcaac catgttgtcc tcttgctcac ttaacttctc gatcacatta gccatcgttc   123420
caaccacaat gttagaaatg caaggtttga tatcacttgt cacgtgctaa gactttagct   123480
ttggtcgctt gcagccttag actctgattt ctcactaacg agtctaacac ttataggctt   123540
ggcacacatc acctaggcaa ataaacaagg aagagagcac ttagacaaca ctagagagtt   123600
gggagaatat ggaagtgttt ctattacaca aagctagctt ggatactgac tggttacatg   123660
cgtgcgcatt aaaacaacta atttatgaaa caatttttaa agtccaattg tactgtaagt   123720
atacatgtca gttgtaatat ttatagtgtt acaatgaaat actggaatat tctaaggatc   123780
gaacccaaag gaagaggcga ttgggcaata actagcatac acaatagagg ctaagtgatt   123840
attgatacga ttttatatta cgacgattca taaaagataa gtttgcaaaa aagattaaat   123900
attcttctct agagactaat ttgcaagaaa tgtaaactag atgaactatc tattaaatga   123960
ctaatggggg ttggttggct tcatccaaca cgtgactagc tagtatttta ggaggcgaca   124020
tgtagctagg gaggtcgacc cgtattatat cgtccctcgt gcccttaggc aaaggacgag   124080
gatatacaca taaacatact ctccttcaag ctccaacttc atcccttcat tctctcaagc   124140
cctttgctcc tctttctttt ctgcttaact cctttatcct aacctctgag cttcctaaat   124200
tgggtaaatt gactctgatc tccttgccaa ttttctagta tcaacaaatt ttgcctcttt   124260
tcttttctta aatatatatt ttttttaca tactaacttg ctttgataat tttttgctta    124320
tatttatatc ggataagcaa catttagtct cgaaacttga taacttttcc taattttggt   124380
gacgaagtgg cataatttca aaatatcata tcatcgtata gactaaaatt taaaaaaatt   124440
atcaagttca ataattaagt tgaaatcttt ttccaaattc aaagaataaa tattaaataa   124500
ttccatatat atatggtatg tgcggttctt ttgtctacag tactgttctt tttatgaaac   124560
tataatttat tgatcaatta aatcaattaa cgctatattg attaatcttc gaataaaatc   124620
tcacatggcc atttggagct tatattaaac tatgcttcca gaaattttgt agcaatcaag   124680
tttggtagga catttatttt ttcttttctc tctctcatta cgctaaatat aaatttacgt   124740 tatatttttaa cattaatttc gagttttaat ttgattaaaa taatcgttat taatggaaat   124800
gcatttaaat atataatatc tccgtattaa aaaaaattaa aattaaaatt catttttatt   124860
gcatttccat ataaaagtaa ttatacgaat gaactaagtt aagttttgtt actaaaattt   124920
aattttttat ggaatattat tacatgttta attcttatat ttgcttagag tttacatata   124980
taaaataaaa ctttgcgtga actattataa tagttatttt tgtttgtctt atgttatatt   125040
ttggtcactt atgtctaaaa tattatgttt taatcactta cgttatcgtg ttgtaacatt   125100
ttagtcactg aaccactaat tatcgttaag taacggtaag gttgtaacac tcctaacccg   125160
tatccgttgt cggaataagg ttatgaggta ttacttgact gaacaaaact tctataaggt   125220
caaagatact taccagacat aaattatcat caatgcaaac ctatctcatt gattttccat   125280
aagagctctt ataaattttc aaaatgactc actatcaaaa cataaccgaa tatctaataa   125340 caattaact actatcaagt tataactaaa acatttcaac atattagttc aattataagg    125400
cttctctaaa caaatgagc aagccatctt cgcatggcta taagtatac aaagtcgaaa     125460 tatcattcta cctatagtct atcctataca tgccttaaac catgatgata tacaatcttc   125520
tcaactcaca taatgactcg atagtgtgat gatatctccg gctcttccaa ctcgagctaa   125580
agtgtaaacc tataagaaat ggaaaagaga acatggagta agcttcaatg cttagtaagt   125640
tttaagcaat gcaaacaatt aatttactta tagatcgatt atttcaaatt ttcaagaaat   125700
```

```
cattcctaga taattgccat tttggccaag tatccatgaa cataatgcat ttttagcaaa  125760
ttcacctcac ttgaatctga actcaattaa aaccaaatat tgaaatcaca aaaaagatca  125820
taagaactcg aaaagcatct cattaactag ttttaaccat gtttgcaaca aaatcacaaa  125880
ttcactacaa gctgtcttcc tgagcaacag tcactaaatt atttatagct ggagctaaga  125940
aactccaaat caagtaccgt taattttctc taaaaatagg ctcatatatc ttccatccat  126000 caaatttta gaattttgg tttgaccaat caataccaga ttttattga agtttcccct  126060 gtttcactgt ttgactaatc tgaccactct tcactacgaa tcaatttct cattatacag  126120 aattcaaaat atgttatcgt ttatttcatt tgaaactaga ctcattaagg agtctaagaa  126180
tataaatttt atcttataat catcattata caatttacaa taattttcta aaaacaaaat  126240 agggatttc aaagtcattt tgactctatc tcacgccact tcaaatatct cattatctac  126300
aattcttttg tttacacggt ttcttttata agaaaataga ctaattaatc tttaattaca  126360
taatttattt agcttctaat tcaatttcca caatttatgg tgattttca aaatcacgct  126420 actattgttg tcccaatcag atttattaca aatttactct ttcacacatt ccttgcattc  126480
aaattatcta acatgtata tcatgtcatt caagatcgaa ctcatataac ataagcatta  126540
aaatgcttca ctatcagctt tagttcaatt gaaacgaata aaatacaata tcatattcac  126600 atttaattt tcataatcgt aatcacctaa aaataaaatc atatacttcc acaacctt  126660 ccacaaggac caagtgttta tatttgaata taaacataga atcacttcac ataacttcac  126720
acatttactg aatatatcac gatcacattt atagtcataa cacttattca cagatgcatc  126780
actttatcta tttataattt aattcaaatc aaaatcgcat acgagtacat gatacatacc  126840
tggccaactt aatatgtaat gcactttcaa tttgtcaact tagtgtagga tcttgtaatt  126900
gtatactttt atcaaattca tcggcacttg gcctgctagg tataaaaccc gaaattatat  126960
taccagcaca aagcctacgg gactttagct cggatacatt tccagcacga agcctgcggg  127020
actttagccc agatacattt ccagcacgaa gcctgtggga ctttagcccg gatacatttc  127080
caacatgaag cctgcgggac tttagcccgg atacatttcc agcacgaagc ctgcggact  127140 ttagcccgga tacatttcca gcacgaagct gcgggactt tagcccggat tcattttcaa  127200
cgtgaagcct gcaggacttt agcccgaata catttccagc acgaagcctg tgggacttta  127260
gcctggatac atttctagtg tcttgcatat ttattcacat gtaaacacat ttcacataac  127320
atatcacatt agcaattcaa ttgcttcatt cgaatataag cacaaaatgt acacctaccc  127380
tttaactttc ggttcaataa tcatacacaa ggaacacata atcttttcac tatcccagtt  127440
tcacttttaa taaccattcg gctataggcc atattcacaa attatttcac acacaacctc  127500
gatcaagcag gaacaatagt cacaattcat ctattataca aatatcccat tctttgactt  127560
tgtttcataa tagctattcg gtcaccacat atataccatt caattcacat tcgaatttat  127620
acaaacaagt acaataaaag tgtatacata ttacacactt gcacatcatc acttaatagt  127680
cattcggcca cattatatac ataaatcatc catttcatat tcggctttat agcctaaata  127740
caatatactt attgcaaatc gaacttgtaa aggtcaaata attacttatc attttatata  127800
atcttaagcg cgtaacaaat caaatttaat tacttaagga cttacctcgg caacgataat  127860
cggaacgaga cgactaatcg accactttga tttccccccc gatccaaatc cgaattccac  127920
ttttgccaat ctaattaata tcaaaattaa ctcacttatt caacatttca ttaaatttta  127980
tctaaaggca cataatttgg gcattttgca ttttatcccc taacatttta catttttaca  128040
```

```
atttaatccc tatttcaaaa taacacaaat tactcaaaat ttcatcaaac ccctgttagg   128100
ccgaatttac cttaggtctc tagtaaccca tatcttttat ttatttcacg ttttgaccca   128160
tcaatttaca aatttctaaa tttagtcctt aatacacatt tttatcaaaa aaaatcactt   128220
aattaaacat gaaaatcaaa catcaaagat ttattaatca tcatcaaaca acaatttcat   128280
cacataataa acaatggaaa atctcaaatt cttcattaaa tccaaaaatt aaggcatgag   128340
tttactagta ctcgaagcaa cgatctcaaa aaagtaaaaa ttataaaaaa ccgagtaaaa   128400
cacatacccg aaataagctt tcaaagtgcc aaatattcaa agcttccaaa ctcatctttt   128460
ttcttttcac attcagctat ggagaaagat gatagcataa aaagacaaaa acacatggct   128520
tttgatttat ttaattaaac tttttttttaa catttttacca ttttaccatt aaaataaatt   128580
catatataca caaatgccaa accaaatatc atccactatc ttataaatgg gctatttacc   128640
atttaaggcc atcatattaa aaagccaagg ccaattgaca cctttaacta atagcatgca   128700
acttttacgt tttacgcgat ttagtccttt ttattaaatc aagcacacaa cgataaaatt   128760
ttcgtacgaa aatttcacac atatcaattc acatacttta aacacagaaa ataatattaa   128820 aatattttt tactcggatt cgtggtcctg aaaccattgt tcttactagg gtctaaacta   128880
gactgttaca aaggtgacgt ggtacgttaa attatcattt caaacaaaaa aattaaggta   128940
aattatataa ttggtcctta tattttttgt tttgagtgat ctaattattt tcttttatgt   129000 tatttaact ttattttttc tttaatttcc attatcttca gttctcccct tttccatatc   129060
ttttaatata gttttttta tattttttat ttgttaaaat tagtcctata ttttattt   129120 ggtacttgaa cttgacactt tttagtccaa tttaatactt gaacttaaca ctttttccta   129180
atttggtacc tgaacttgat attttttta tttggtactt catctttttt ttatacaact   129240
tgatacataa acatgattgt ttttattaat ttgatacta atcttttttt attaattttg   129300
acatttgaac ttaacagtta agtagtttga aatgaaagca aatcaatgtt agaatggcat   129360
ttataaataa aataatactg acatggtttt taggtgggat ttctaaagta aaaaataaaa   129420
ataaaaatct aaaaaaagta acaatgttct tcatcttctt cttacacttt ccaccattca   129480
atcgaataca atgtctctcg tctataccaa tgaactttca caaatttcga ttaaggtaaa   129540
gggcctataa attggggatt tcgtcgattt gaggttccta atggaatttg ggtttcacag   129600
ttagggattt agtgggtcct aagtggaatt ggaaatgagt tagggattta aaaaaaaaaa   129660
cataaaaatc atattattga aatcaaggtt tcaaatttca tgggagacct gtagtagata   129720
aggagtaaag acgacgcaat tttttagtt aatttgtata acatttaata attttatgta   129780
ctaaatagaa tctaaaaata atttagacat caaattaaga aaaagtctc tataagcgct   129840 ttcgagtgtt cacaatatat gctttcagat accgctatat aattataact cgtatttact   129900
caatggatac aaaacaccca tagatttgag gtactcaatg tgatcttaag ccctttttcca   129960 attaatatat gagtccgctt ccacatcgtt taatttcaag ttttttaagtg catgtatttt   130020 aaacttggga aatatgtgta atgagcccct acttgaatag attcgaaaac attaggccct   130080
tatttgaatg ttttaaaacg tttggccttt attcaaacaa ctttgaaaag gttaggtctt   130140
atttgagtat ttagccataa aaatatgctt aggatgagat ttgaaaccat accaattgta   130200
ttagtaaaac ttaaaattta ccacttaaag ttttatttta aaatatgatt aattaatttc   130260
aaatcttacg ttatattatt tttaaacata tatctgtatt ttttcacatg tgcatgcaag   130320
tgataggatt tttaattttt attataaaat aattgatatt taagatttag atttatctat   130380 atatattta aaagaattat ccatatctt acatagatat acatagtaat atattatttt   130440
```

```
tataaagttt ttcttaatct ttttatttga tatatattaa acctaagaga aaagaaaagg    130500
aggatttatt taaaggttca catccttgcc tatcatgcca cgtggcgttc aacggtttgc    130560
ggcgtgtaaa attttgaaag attttaccat cgtcaatccg gataccaaaa gattagacgg    130620
aagaaaaatt gaggtgtgaa attggagaaa attaaaaata aaatgatgag aaatgaatta    130680
ccatttatcc cttcaaaaac ccaaaaaatt gacttcaaaa aaaggatccg atattcctct    130740
tgaagcttca ttaaaatatt atgtattgaa ttttgttgtc agacttcaat attctcaaat    130800
tgaaataata aagaaaagca acttatattg aaaacgtagc ttcctttcat taccttaaaa    130860
aataatgatg tacggatcat tgagaacaga atttaactca actcgctcaa ataaaataat    130920
catgaaataa aagtatttgt tgttataatt tttttaaaa tatcaaataa ataataaaaa    130980
catggttatg ttatgttgga agaagatgca gaggtggaat aatggtccca ccactccgga    131040
agccaaacaa tataatcttt caaaatgaca tttctcattt tccacgtggc accgcgtata    131100
ctctgattta ttatctttct cactcgctcc cgacggcgtt taccagtctt ttctatctcc    131160
tctttcagct ttttctctt tctcccctc ttcgactcgc ctcttttccg ctcccatatt    131220
cttctcacct gaattttccc tgaaagttgg ccaagaagat aaaaagtttc gtttcccttc    131280
tgaattgata tttttggaaa ccctagctta cctcgattgt agacctttt tttaaatgga    131340 tttggctgca tatgcattac ctacctcgat tctttagtcg tagaagcgcg atgtattcga    131400
agaggagccg gagtaagccg agactcgagc gccgcaatgc agcgaagcac atcgactacg    131460
atgcagcgtc gttttcttcg tctctcgatg atacctcttc atcttcttct ctaatcacgc    131520
gatcgctcga tttgtccgat aaaaccagct tccgtatcca aggaacagag ggagagttcg    131580
accttatttg tcggaccttg ggcctttctg gtcctgaaga ttttcccatt ccagccgccg    131640
cttgggagtc ccgtaaaatt cgatcctcgt cggatcttct gcctcggtcc agattgaacc    131700
ggctggatag tcctgaggaa gagacaggca agataatttt agaagacggc actgaagtaa    131760
cagtctctga attaactgat agggttttgg cttctgcttt gaccgaagat gactcgcccg    131820
agttgaagtt aaacgagtgc tgctgtgatg atagaaactt ggtcgatgtt gctacttcaa    131880
ctgaattgaa gtcaaacgca tgctgggttt cgaatgttgt cgatggagga gggaattatg    131940
gaattaaagg gattaggcca ccgggtttaa agccgccgcc ggtgatgaag ctaccggtag    132000
tcgatagcgc ttgctcaact tgggatctgt ttagggattt cgcccccgaa gatgatagag    132060
ggtgtatagt tcaggttcac ttacattcat cttccgatga agaagaagtt aaaggagaga    132120
aggatagggg taatgaagaa aatgctaagg aggaggataa ttcaatgaga atgggagaga    132180
ctgcagtgct ttctgagtcg tgctcgttta aacttcaaa tgatgacgat tcttcgagtt    132240
ctacctcaga acctatgtca aacatttccc ctaacggtag gttcaaaaga acaattactt    132300
attgggagaa aggtgagctt ctggggcgtg gatcatttgg atcagttttc gaagggattt    132360
ctgagtaagt gatgaaattc tgtcccaact ttatttccag cttgattaaa tgcttatagc    132420
tagttctttt taatcaagat aatttatcta tcttttgata tgcgcaaatt agtttgggaa    132480
ctgccttatg cctaattgtc ataattttgt cgctttgggc ggcactcttt tagaggtcag    132540
aaagcatcta gggtcaaaag ctgttcttgg tgttggttaa gcatccagag aaaggcattt    132600
ttgtatttgt ttttattttc tttggtcatc ctagtttcca tcgcccattc ccttagttct    132660
ttggggagca ctgtattaca tgtttcaggg ttgcatccaa agattgctag atatcattaa    132720
ttccgttaat accaataaat acctaatatt tggacatctt gtgttttttc tacctcgaac    132780
```

```
tttaaggcgt tgacgcattt tagccttaag gttcattagc ctttaagtgt tactttgttt    132840
gctgcttgaa gttttgcgta gttgatacac tcatgtagcc attttttgtgg gcaaaattatg  132900 gatgattatg aacccccttcc tctatggtga gtacaggtaa agtccattat tgacttatga   132960
agggttctgc ttgttgattc cggtctatgg cttccgatga tcctatgtgg ttagaaactg    133020
gttaactgga gatatcctgt tctatagctg attttaagat gataaattta gttgttttct    133080
ccaagctcct aatctacttt taaccttccc aatcattatg taattaactc acatcaaaag    133140
gacattacgt gcctaaggcc tctcgaaccc acaacctcca ggagtctgtc agcagcatgc    133200
ataccatctg agctagcact tagtcggtat gaatttagtt gttacctatt gttcaagagt    133260
tgaaaaataa acctagggaa gctcattgca ctgcgacctt tgagatgtga agctaattgt    133320
tgatattttg gaaagctatg gaatgacatc atcttggagt gactgaatga agtactgtta    133380
gaaatacttt caaaattgca aggaaaagcc cattttatct tattagctat taattggtta    133440
tctacttgtc caatagatta cgtattactt ttatttagga agagatgtt tttcttttac     133500 tcatgcttta ctaattattt atttattcat gtccttgtag cgatggattc ttttttgccg    133560
tgaaggaagt ttcattgctt gatcaaggaa gtcaggggaa acaaagtatt atccaacttg    133620
aacatgtaag acagattttc tcttctactt ttttaattgt tcgttttcat gaaatacccca    133680 tcttctactt gtttctgtct gatataattt ctttatttcc tttcgttttc aggagattgc    133740
tcttttaagc cagtttgaac atgaaaacat agttcagtat tatggcacag ataaggttct    133800 attttttga cactcagctt aataggataa cctcataaat gttcttcttc ctagttgtct     133860
aatttttttt cttttaattt tatggtcttt gcaggatcag tcaaaattat acatctttct    133920
tgagcttgta accaaaggat cccttttaaa tctatatcag aggtatcatc tcagagattc    133980
tcaagtctct gcatatacaa gacagatttt gcatggattg aagtatcttc atgaccaaaa    134040
tgtggttcac aggtaagtaa agggaccttta tgttgctgct taattatttta tgtaccactt   134100 aaaaaacttt tgtttgtttt ctctagccaa atctgagttt ttatttgtac ttcttttagg    134160
tgtatttgct aacagcaaat tgcttcatat gagaaataaa ataaaaattt cttcacttta    134220
acagattgaa gttttcagtc cttatctcta ttgggatctg ttgtaatgaa tcataatctg    134280
tatgcatatg tcatattccc tctcggaaga cttttgaagt cgagaatatg aatcataatc    134340
tgtatgcata aagatttttt tcagcatttt acttgctatt attttgtatt attttttccct   134400 taaggttaga tgcctgcgca tttgttattg ttatgatatt gaaagtaaaa ttgtgttctt    134460
tttctatgct ctacctaagt ttccatgcac ttagaatatt cttctctcaa ggctcattta    134520
cttgtatgtt gatacaggga tatcaagtgt gcaaacatat tggtggatgc aagtgggtca    134580
gtgaagcttt cagattttgg gttggcaaag gttttatcc gaaacctaag actttaattg     134640
tctttcttgt tttattatct ttaagcaggt cgaactcatg ttggtgctga tgcttgtttc    134700
caggcaacca agtttaatga tgttaaatca tgcaaaggga cagcattctg gatggccccc    134760
gaggtgtgct tctattcttt cctttcagaa atgataatct gtaatagctg ctgtttgatt    134820
tgtgtagaat atcagtttct tttgtattgg ggatcctgct tgagatattt agcttcatag    134880
tatactgaat attaggaaat gatgacatgc attcttggta aatatttctc ctgtactaga    134940
gatatacagc ttatgagaat actcaattat gaaaaggatg ataacataat tcttttcaga    135000 tatttatccta tagtgtacaa aaggtgtgaa tcactctttg ctgatccatc ataaattttct   135060 caggcttcac tcaattggct ggatcttaac atttagttta cagtgaacac ttctttttatc   135120 ttttagctca ctagtaattt cctaagtagt atttggttag acaattttca ttgacggata    135180
```

```
attgctaatg ttttggtgat ggcagctttc cttttctgaa acactgctgg ccctttttta 135240
aatcatacct gaacggtgtc ttcagtttct agttggatgg gtttcagtac ttttttttctt 135300 ctagaaacac accattcttg ttgtcttttc tacgtagtag ttatttgttt ttgtgacaca 135360
gactactggt gatgattagt cctcccgaat tctgattatc agctgttgaa ttacaggttg 135420
tcaataggaa gggtcaaggg tatggacttc ctgctgatat atggagcctt ggttgtactg 135480
tgttggagat gttaacacgt cagattccat actattattt ggaacatgta tgtacctcgt 135540
cttcctgata tgaacattag tttacttgac aattaagttt atgtaaaatc caaataaaga 135600
agaaaaaagg atctggaaat ttctatgctg tcatctccaa atttcaaaaa ggcttatagg 135660
gttttaaagc atgaaatttg gttcctacca tgaagctttg tccagaaagg tgtggacgaa 135720
tattatattt gtttcaaata atttccttct acaagagcta ttgagttaaa ttttttataat 135780 ctcctttatt gtgcaataat gtcatcgttt gtgtaattca aaacagatgc aagcattgtt 135840
tagaattggc agaggtgagc cacctgcagt tcctgattca ttgtcgaaag atgcacggga 135900
ttttatcttg caatgcctac aagtaaatcc ggatgctcgt ccaactgctg ctaaactctt 135960
gcagcatcca tttgtgaaga ggtcttttcc cacacactca ggctcagcat ctcctcatct 136020
tggtcgtcgg atatgaatgt ttagccatga aactaaattg caacaagtaa tcaggtaaac 136080
attttctgct gatcataaat ccgttggcaa catgctcctt tggtcaggtt tcagaagaaa 136140
cattgtcctg gaaccttcat tatcacaaca tgttagctat ccatatccta agataccttga 136200 atattatccg gtaacaatgg tacattttttg gtatcagttt agcttcattc agagctttgt 136260
tcttgtattt gtgtgcagaa agttacacat tcacggagtc tagttattgc atgcagctcc 136320
gtccttcatg aggaagaaga caagtttgcc ttctcgggct ctgatgttgc taccttttagt 136380 tttgctccta gagactcaaa gagtctcaaa cctggtaggc agaaagcaat tctgaagctt 136440
tggctatggt ctaatggcat tgacattaga tttaactatc catgaccatg aacccacgat 136500
gaagctgtag agagctgagc tgctcttaat gttaaaatta tttgttatag ttttgtcagg 136560 tctgggatttt gatttagccc ttattttatg tagatttttt ttttttgggga tttgggtgaa 136620 acattagctg taggagaaat tatttgtata tatgtatctc attattgatg caaaaaataa 136680
atactagttt gctctatgta tcgactatat ctaatattga gattacgaga attacgtcgc 136740
tttatgattg ttattaccat aaataatata tttatttgca tttagacctg cagttggagg 136800
tttggcttaa aaatagaggg tttggattta aggttagaaa aatgaatttg gataaaaatt 136860
atgggttaga tttttaggcaa gatttttttt gggctcaagt ttgacctggc ctgaatatta 136920
tattataaaa taatatatta attatatata ttaaataatt atatatattt atatttttat 136980
taaattatta ttttaataat aattaaattt attaattaaa acttttaaaaa acgtacccaa 137040 ctaaataact taactcaaaa tataaattttt aaaatttata tttaatacaa taaaatatttt 137100 attatattta tttgtgtttt taatataata aaacatttat tatatttatg gtagtgtttt 137160
ttaatataaa tattttttaat gtattagaaa atttttatttt tagccttttttt tttaagtgta 137220 tttagtttat tatatttaaa aaatatttttt aagtaaaaat taatctaaaaa aaatcaaata 137280 tgaatggatc aggttaaact tgagtttaac tttattaaat taaattaaat tattaaaaaa 137340
ataaatctat ttttttaaacc gactagactc aaatttaaaa cttttaattta atggactcaa 137400 cctacctgcc caaccatgag tacctctatt tgcattatga ttatctaatt ttgcgatgtt 137460
aattctcttt acagccagtg tactggaaat tagtataaat gggtaatggt tgattataat 137520
```

```
aaaatgcacc atcatgattc ctgaactaat ttatcagact caatttattt ttatcgttta  137580
taaataaaaa tcatagtgct atgaaattat ttatagaata attagaaaaa ggaaatttat  137640
gattacaatc acaatctctg tattttatag ttaactgtgt aatgtttaaa agaataaaaa  137700
aaaatcgata acattttatt gtaacttttta tcgtataaat aaaatccgga cattgtataa  137760
attttttgtt tgcttgatta agaaaagagt aaccatagat ctcaggtatt ctgtactaag  137820
ccagattaca ttaaaaaaaa aaaacaaaca aacttgaaaa caatatcttc cttaaaagtt  137880
tgacatcaat ctcctctcaa cgactttata aaatagacat ttggattgag ttagatttgt  137940
ttaaacttga aaataggtca tccaactaat ttttatagga cataaattac atataaaata  138000
acattataaa attaaaatta aaacgactt gagccaaact caattttta aatattaaag  138060 tttgaatttg actcatattt ttaaaatatt taattttta tgaacttatt ttttaaattt  138120
aatattttta tttaaattct tacaaataag taaacttttg agtttaaaca aataattgag  138180
ataaagtgga atattcttga actcatacaa gaggtgttaa aagtttaata gtttcgtata  138240
tcctatatca taaacatcat catgaagaat tctcaattag tatgatataa aaacaggttg  138300
attcgatgta catgatggca taattatatg actaaattga atggtgaatt tattaaaatt  138360
ttaattgtat aaaaattatt aaattacaat atattcacaa tgttggtaaa tatatatata  138420
caacaaatat atttattaga aatttatgca ataatcaaat aacatttgat tgaaatagta  138480
aagttgaagg tttcaaattt atatatcaac cgagattcaa atttcatctt atgtgatatt  138540
ttattaattt tacatagaca aaacaccta ataataatga tagtaacaac aacaacaaca  138600
acaatctatt ttattttatt ttataaagga atgctcattt taataatttt tcaattgaat  138660
tggtgttgat taactcatga catcgactca attaagaatt ttaagtataa tgtagatgga  138720
agtaaataat tttttttaat tttgtactaa taatatatat aaataaataa taaaaactac  138780
tctttcagaa attaatatat atattaagtg tgtttggttc acggaatcta aagattatct  138840
ctggtaatta catcaacaac acgtaagatt acttgacaca ttactgaata tgttacatta  138900
ctttatttgg tttatttagt tgaaatgtaa aatttattta tttagttgat agaatataag  138960
accatttaaa aactaatttt acttaattat ctttataat ttttctcttt tttattcttt  139020
actacaaaaa gattgaagtt tttttatatt ttattgtatt gataaatgaa tgaatttctt  139080 aaaataaatta atttcatgtc tactttctca aataaataaa ataaatatga ggaagagtaa  139140
tacatagtta gggcttatct tttgattaaa gtgacgagaa aagaaagaa ataaaaatat  139200 attttttac taaacatgt tatttttat gatttaaggt taaatttaat taaaataata  139260
gaattgataa aattgttaag tttcttcatc taaaaataac aatagttgaa atgtttgtat  139320
agacaaaaat cttaattttc ctcaactgaa ataataatat atagtaaaaa aatattatta  139380
ttttattttg gtttaagtaa aatagtaaat ttttttttca aaagtgtgta attgtagaaa  139440
agtttacatt acaaaataat aattttgaa aaagaaagc aagataatga atgattaatt  139500
aagaaagagg tggttttaa gataattgat ttaagatcat ttttgaaatt cgaataaaaa  139560 aattactca tacaaatata aatttagttg agtcaaagt ttcttgtaga gaatataaag  139620
aggatattgt aatcaatgta ggaagatttg aattcgagcg tgttgaagtt cattatcctt  139680
ctctttatat attagggagg ggttatgaat agttctaaac attatatcaa aaattaaata  139740
taatcaaaat ttataataaa attatttaaa aatatatata tatatgtcat aatgtgggag  139800
atgaagctaa gccattgtca tcattacgca ccaggaagag tggttttgtt gactacgaca  139860
agcttgctgt gcccataact aacaaaccat gttgaaggct tacctttgct ttcttttcgt  139920
```

```
tttcgcatta catccatccc ctagttttta tttttccgag attgagtggt atggtcaaat    139980
cctacattaa actacaagct tttatgctta ctcttcttca ttaatggtaa aggatgatat    140040 tttactttg tattatttac tgctggatct ttcgctgccc tctattttt ttagttaaaa      140100 tgtaaattta ttaccatatt aaaaattgtg attatatttt attttgattg atatttgtca    140160
ttataatttg agaatatgat taaatttgac ccacaatttg atcaaatttc gccattgaat    140220 tttaatttt tattgaattt tattattaat ttttaattaa attttagaaa ttaataagtt     140280
attattggtt tttatggttt aaaataaaa tattatttaa atatttatt ttaacaataa      140340 gttaatttat aaataataa aggttaaaag aataactaac attttgtagt taatgataga     140400
aagacttgaa aaaatatatt caataaatta agtttacttt ttataaaata aaattatttt    140460 tattaattt taatgttgta ttaattaatt tattgtttgt aagtgttaaa ttaaaatatt     140520
gaaatttgtt ttcattaaaa ttaagtagtg aagttcaata aagaatcaaa ctttaacgac    140580
acaattcaat cccaaagacc ctaacaattt aggcccatac ccaaacaata tatctggcgc    140640
agaagaaact actccaatcc ctcatgttat gatcaaggcc caatccttca ccaggatctt    140700
gtgctgctgt gttaagggtt tcaatgttgg caaatttatt agttttcctg gaatttgaac    140760
ccggtaacca atgggtcttt ttttcttttc ttttttttggc tattttctcc caaagagaaa   140820
agataaccat tacttgtaca aaggaatgtt aattggcatc taccttatct agaatcctaa    140880
aaagtaacaa gtgtttacac ctgaattgta gtcaccttca tatcaggcat cttttctttg    140940
ccaagttgat atatatatac acatatatat gatcaacatg cagtaaacca aaaggtttgc    141000
aggatgtagg ataattatct atataagcat aagaatctgg cattattttc acttcaactt    141060
tatgtcgaca taaggtgcc accttgcccc aaaacagaat aactccaccg gttatttata    141120
ggaagggatg agcaagggag cttaggcaaa ggtaagttaa atacccaagt atctataaat    141180
ttaaatatat aaattaataa gcaccaatct atggctcaac tagggtcgtc tctgtcagca    141240
gaaaccgaga cactgagcaa tgtcctaagc ctggtggagg ccttcagagc atttgattca    141300
gacaacgatg gcgcaatcaa tgctgcagag ctaggggga tcctgagttc gctgggtac    141360 aacgctagcg agcaagacgt gagggccatg atgcgagaag gggacgccaa caaggacgga    141420
ttactgagca tggaagagtt cctagagatg aacaccaagg acatggagct tggggagctt    141480
gccaatttcc tcaggaccgc tttccaagct tttgaagtcg aaggggatga tgctttgact    141540
gctgccgact tgtatgaggt tatggggaac cttggcatcg atcagctttc cttggaggat    141600
tgccagagtg ttattgcctc catggatgct gatggtgatg gagctgttag cttggaggac    141660
ttcagactca taattaattc cttatttttag attattaaac ttaagttttc tctatatatg    141720
cgccttgggt gctgcggtat ttccatgcat gggaataaag atcagtcaag aaacattaat    141780
attactagca gaagtactgc atgtttgtgt ttctgttctc ttactatgaa tagaaagcga    141840
atacaaagtg gtctcccatt ctctaatcaa tggaagtttt catttaattt tctttttgaa   141900
aatatatcgg gaaattgaaa tttcacattt tccttacaaa ccacaaacaa aaatttatag    141960
aaaaatattc ttggcaaaag ctgagttttt aacatcttta taagaggctt gaatcccacc    142020
acttaaaaat atatatatat gtgagtttct gatattattc taaatttaag taccactaaa    142080
taagtagttt ttaaatttat tctaatctaa aattagatat aaagaagtga atgataaaat    142140
ctaagtagca atattttttc tcatgaaatg ggattaaaag gtttgggggct gcgaaaagca    142200 agacctaata atcttgctat gcttgccaaa ttaggtttgt aattattcat gaataagaaa    142260
```

```
tctttaaggt gttgtgtttt tcaaaataaa tatctccata atgaatcgtt ttcaatggca    142320
aaattgaagg aaaatgcctc atttacatgg agagcattgc taacaataac tagggaggtg    142380
actcttaaga gttgtaaatg ggcaattggt gggatgatag cattcgtttt ttgcttgatt    142440
ggtggttcgg tacagaaata ttgagtcaac aagtaatggt tcaaggggta tgtacaggcc    142500
aattttgggc caccccaaaa cccaactaac ctaccctaac ctaaacagcc caatacccat    142560
aagcccaact aatacatcag ccaacccaaa attcaaaccc catttacaac caaaacccaa    142620
taatacaata cccaaaccca atttacaaac cctaacaacc caagcccact atctaaaaaa    142680
tttcagcagc aaaccctagc caccaaagtc ttcagtcgct ctcccctctt cagcctcctc    142740
cactcctctg acaccagcac cgcccctggt cactcccata ccgtctgcca ccgcatgctt    142800
ctcctccact tccctgacac ctccataccc tgaaaagaca gaagcagacc aaacagaata    142860
ggacaaaaaa taaataatat tttcctagtt ttgtagtcgg ctataaagtt gagaaataaa    142920
catttgtaag atggggggga ttttgctat gaaaacaaag attttctttc aatattaaca    142980
gattgaatac aagaaccatt cgaaaataca tatacaatca ggggctctaa caccaaatcg    143040
gagaatcaaa tctaaaacct aaggtgactt tttttttctt ttttctttac tgttttgagt    143100 ttgttttta cataaaaata ctaaaaaaat atcaaaacat aaaaacatat gtattattaa    143160
gcaaaaagaa aaaagaaatt ttacctttc cggccaccgc acggcgccgg cgagcctccg    143220
gtggccgtcc ggtgaccggc ccccatggcc ggagctcccc ccctcccctc tcttctttcc    143280
ccgttccctc ttttctctcc ctcctcttct gttttttttt ctttcatctg tttcaaatga    143340 aaaaagaac aaaaatttgg cttatatagg ggtccaaaac gcaccgtttt ggaccccccc    143400
ttttaaagta gaaaacgacg ccatttgat gcgggtcggg tcgacccgac ccgtccgacc    143460
aggggatccg cgtgttttta agggaggggc tatttgcgca gttggcccct ccgctttttc    143520
aacgttttat aatcaagttt ttttatattt taaattcggc cccgctgttt tgccctgatt    143580
tcgttctagt ccctccgtgc tgcgctgcgt tttagtaatt gagaatattg cacttttggt    143640
cctcgttgtt ttcacgcgtg tccatttag tcctttattt ctttatttct ttttaaattc    143700
gccctgaaat tctgttctta ttccgattta atccttttc gttatttc cttttttta    143760 catattacta atattgttac tattatatta tttattttca ctattattat tttcatcatt    143820
attatacata tatgtatata tttatgtaat attattaata ggcgtcccaa cattattatt    143880
atgtatgtat atacattttg ataccgtgca tgtgtaacac cccttacccg agaccgtttc    143940
cggagtcgag cacgaggcat tacttagctt atcttaccaa ttcggagcat aaaaactagg    144000
tttgaaaatt tatttcatta ttcgcagcaa atctgtccaa tcacacagca gttactaaat    144060
taattataac ttgagctaca gaactcgaaa tttaattccg taaattttcc ctgaaactat    144120
actcatatat ctactcacca taaaatttt agaattttg gttcagcaaa ttagtacagt    144180
ttattagtta aagtctcccc tatttcacca cctgactgcc ctgacctcta gtcactaaaa    144240
ataagttttc tcactgtagg attttcatat gaagttctta cttgtttcta cagaaaatac    144300
actcattaag aaatctaagc atgtaaattt caactcataa ccatttttgt acaatttgta    144360 attatttct aaactcagaa caggggactc caaaaacagt tctgacccta tcttactaaa    144420
attcacatat cttaaaatat aaatttcctt tttctacacc gttatttttc catgaaaata    144480
gactcaacaa gctttaattc catatattat tcaccctcta attcattta tactatcttg    144540 ggtgattttt caaattcacg tcactgtgct gtctgaattc tgtttctttg caaaattta    144600 tcctttcatg atttccatgc ataatttatc acctaatctt tcataacaac aaacaccttc    144660
```

```
atccttaatc attttaataa ccatacatca tcaaatactt acacatcact cattagcaaa   144720
atcatcatta caaacataca aaataactaa atccctatac atgccataac tcaaacgtgt   144780
ttcgatataa aataccgagc agttgtagtt gatagtgtgg acgatctccg acttctttag   144840
gatccttgaa gtagctttgc aatactataa gagaaagaga aataaaagaa gtaagcataa   144900
agcttagtaa gtttactagc aaataaataa caatatttaa cttaaataat taaactcaat   144960
gtctatatct ctagtttact ctttagttaa tctcatacta gttctcttac ttgtttactt   145020
agaatacttg tgtgcataac ttactcaatc cttgctgcat cgttgaacat caattgatag   145080
tataataagt tcttaagtct tacaacttac ctgagcttgt catttatgct ttaaactgaa   145140
ctttcatgaa catgattcgt ttacaagccc gttgagctac attggaataa taaggatact   145200
cgggtctctt ctgataataa catgccaaag ccatgtccca gacatggtct tacatgggat   145260
gttctcgtga tggtgcccat gccatgtccc agacatggtc ttataggga cctctcatct   145320 cggtgccaac gccatgtccc agacatggtc ttacatggga cctctcgtct cggtgcccat   145380
gccatgtccc agacatggtc ttacaggga cctctcatga tcttaaggat gccaatgcca   145440
tgccccagac atggtcttac atgggatctc tttacccaaa tgtcatgaca ttcgtatcca   145500
gtaccatcct tatgtatcaa cgggactttt aaattttaat tctctatcat ttcatgcttg   145560
gatcatcatc aaataaattc ataaaataaa ttcataattg ctggaaatta acagcattaa   145620
taataaatat tgaaatattg catttattta ccgtaaactt acctcggtac caattatagc   145680
caaattcacc aacttagtct tcaactttat tcttcccttt gtctaacctc gagtttcgta   145740
cttcttgatc taaaatagta aatttaactt atttaataat cacattcatc aaaacagccc   145800
tcgactctaa cttttcaaa attacaattt tgccctaaa cttttacata attacatttt   145860
tgccccaagg ctcggaaatt aaacttcatc tcttattctt atgttttata acattctgaa   145920
catttttccc ttctatggca acatcaaatt cccactctaa catgtactta tgaacattag   145980
gtatttttac cgattatgtc gttttactcg ttttcactta aaatcgctta gcaaaagttg   146040
tttaacataa tttatagctt catattctat cataaaacat caaaataaac acttttcacc   146100
tatgggtatt tttccaaata taaaccctag gttaaattat tgctagaata agctaaatta   146160
agctaccggg atctcaaaaa cgtaaagaac attaaaaacg gggcttggga tcacttacta   146220
tggagattgg aagcttgaaa accctaacta tggcttcccc ccttgctgat ttcgttcata   146280
tgaagaagat gatgattttt gccatctttt tccctttta ttcatttta ttactagatt   146340 accaaattgc ccctaactta aaaatttct atttcactta tctcatgtcc atttttgtct   146400
accaagttac caatggtata attaccatat aaggacctcc aatttaaagt ttcataacaa   146460
ttggacacct ctaacatgta gaactcaact tttgcacttt ttacaattta gtccttttga   146520
ctaaattgag tgcccaaacg ttgaaatttt cgaacgaaat tttcaaaaaa tcattttgtg   146580
aaattgtaga ccataaaaat ataagaaaaa taaaattttt cttatcggat ttgtggttcc   146640
gaaactactg ttccgataac ctcaaatttg ggccattaca gcatgtatat gattctatt   146700 aattgttagt tttgtatact aaattcatac gtatatttct catgtcattt catgtatcca   146760
tttttattat tatatatata ggtaataatt tttcaaaact tcgttttaat cttatgcatt   146820
atttgtttcg ttccctttca taatattatt atatatattg gtatatatat gttctttagg   146880
tgcatgtgtt cctcaatatt tattttatgt acatatgtaa atattatgaa tatatattta   146940
acattactag ttatatattt ttatgatctt atatatcttt ctaataccat taatatttat   147000
```

```
atatacatat tttacatgta tactcttaat tattttcatg tgtatattca tcgtattctc    147060
tttacgttct cgtattcaat gctaacattg catttgatct tgcatgcgcg gttattattt    147120
tccaatatca ttgtaatatt tgttatttgt ttcaaatatg tttatagttc ttccatttat    147180
ttatgtttat ttcatatcag cttgcttcac attatttcga aaaattatcc atgttttctt    147240
atttacttca ataatcaagg caatataccg atttaacatt aagtcatcga gttcgtcgct    147300
atgttgggtg aacgtcaatt gactcatgtt aaagcgatat acccttctaa aaaaaatgaa    147360
ataaaccaaa atttctcatt cttttaatcg gattatgact aaattttaca ttgaactctt    147420 attttttggaa attaagacaa cgcgtgttta tgagatacca atttgggcgt cgcgagggtg   147480
ctaataccTT cctcgcgcgt aaccgactcc cgaaccctag ttttctctg gcttttaacg     147540 tagacctaaa ttcagccttc cttttgtttt aaaaaatgaa tctaataggt gtccgatcac    147600
acctaggaaa aaggatcggt ggcgactccc tctttatttt aaaatcgaac ttcagtttcc    147660 aaacttttc actagatcgc cacaattagc gaccccggaa ccaattttta tgtcgctaca     147720
gggtagaaac acttaatgag atggtaagta tgggcatata tgctcatact ttggtgtcac   147780
cttgaaactc cttctacaat gtcacccaag cctcctttga tctagttgct tagttgctgt    147840
cataattctt ggaaaaatat cctcatgaag agctcgctga ataaaataa tgcttgtgca    147900 tccttttttct tattttctt cagtatggct acgtcatcga ggtcaacata cccatctcta    147960
ataagaaccc ggagatcgta ataagctttt catcatcatg ctccaaagtt cttatgtttc    148020
actaatcacc caaaaacaag atcaaactta gctctgatac taaatttgtc gaggggaaaa    148080
aagagagaat tcataaga gaaaatattg atcacataag agaaacaaa atactagcca     148140 cgttcgtctg aaaaaaaaaa catggcaact acgaatgctt gtccacagta tgggagtatt    148200
acaaagtcga aggatcatat tttcatagaa tgcaatgttg cccaagaaat ctggacgaa     148260 ctatgcgctt tgaatatcca agcgaacttc ttttcagtta gtttcgagga atagtttagg    148320
cgaaattgta agttagcaag tctgtcttat gattcaatat tccttggtgt gtactttcg    148380 ctatgatctt gtggggaatt tgaaaatgta gaaacgagtt gtatttcatg gtttgcatca   148440
gcaactgaca gttgcagtct ttttgtatga gaagtcttct gcacaagata tttgcaaggc    148500
agtgttaaat gatgtggcaa agatagcacg aataccgctt tgtgttcatt ggttgaaacc   148560
acacctgcag gaagctatat tcttaatatg aatggggctg tgaaatcgac ttcagcttgg   148620
gatttgatta aaacatgaca tgggtgacta ggttttaggt ttcatgatga agtcagcgca    148680
agggataatt tgcaagcgga gatctggggt gtttgagaag gttttagaat tgcattcaat   148740
tactcgtcat tgaattgatg ttatgacggt tgtgaagatt ctcccaacac cttacgcttt    148800
tactcatcct ttgactacac tcttattcaa tagttgaagt ttgattaatc aaggatgggt   148860
aattaaagta gagccaagag ggtaatatat gtgtgccgat tatctgacga atctcgacaa    148920
agccgatgct tgtggtaagg atgctcttag gatttagttt cctctagttt tcttcctta    148980 tgtataaaaa aaaatatatt gatcaaatgc tatcaaataa aaattcacac acactaaagt    149040
aaagttttct taatatctaa aaaaataaac cgagttattt gcaacataaa tccttttaat   149100
tttttcgcat tttctgttta ttaatttagt ttctaaagtt ttatagttat tctagattca   149160
aaaacaaaac ccctatatat tttcaatcac ttatgaaaaa attgttatt ttctcctttt     149220 tttttaattt ataaaatctt atttttataa aattaacata aaaattttaa taattaacat    149280
ataactcaaa taattaattg aaattttta ttttatatt taaaatttta actaataaat      149340
attaaaaatt atattacgta ttttaaacta agtattaaaa atttcactaa tgtatattaa   149400
```

```
aaattacatt tattttttaga tatcaaatgt aaattaaagt aatatttaat taatacatgt  149460
taaaaaacta tattttttgta atttttaaata aataaataaa ataattttct aataaataat  149520
gttcaataac ctaattaaat aaataataca tgttcatatt attttaacat tattttacta  149580
atatttaata tttacataac attattcaaa attatacatt tataatcaca caaaaaaata  149640
agtattgtta ttaaacattt tacaatccat aaattaacaa cactagtatt tattaatgct  149700
catgtacaaa ttttactatc ataatttaat attaacatta catgtttata taatttttta  149760
aattgtgaat tttttatttta aaattttttaa ataatacatt atcattattt gactttgaat  149820
atgttttcac aaatagaaaa caattcaaat ttgttttaaa tattaattttt ttattcttat  149880 attatattaa taataataca aaagtataaa gatttcaaaa tttaaatatt tatattatat  149940 tattttttaat ttcttaatca tagttttttct aaaatattac aattttgtag caattttttta  150000 agaaataaaa ataatatatt taatttatat atacaatcaa actcatacat cacacatgat  150060 aagaaaattag tgtgtatata tatatatata tatatataat attacaatat atttgatgca  150120
taagtctcat gcaccatcgg tgaataataa catgacacat catcattaaa taaaataaaa  150180
atataatgaa agacttataa ataaatacta ataactttat ttaaacataa ttaaataata  150240
attaattata aataaatagt aaaacccctta aacctaaata tcataaattc gagagctatt  150300
aatatttgtt tataatagtt ataattaatg tttaaataaa attattaata tttattaaca  150360
agtcctccat aattttatat ttaatttaat aaaaaattat catattatta tttactaata  150420
gtacatgaaa cttatacacc aacaatggat ataatatcgt tccttccata agttttttgg  150480
gtttgatata aaaggctata tatagtttttg gggcctattg agccgaggaa gagatttcgg  150540
gccataagaa gcctacttgt gctgggtttc ttacacttct ctgttagtcg caaaatttgc  150600
agatgcccaa accctaaact gtcttgatgt ttcttattta caattattat gaggatgatg  150660
ggtgatgggc agtgacattt ggaatcataa taaaaaacag ttggcaagaa aattggacat  150720
gtaggtccca aattttcaag tggcagtcgc tagcaaccaa tttgtatgtt tgatcaccat  150780
aatttctgtc caacaccaag atcttcttcc acgagaaaaa taaattgtat ttataaaaca  150840
ataatttcaa aattaaaaga cattgaaaac taactagaat gataagtctc attccatttc  150900
atttcagttt acctgttgat aggtttagct actcgtttaa gtctaaaaat ctattcgaaa  150960
tttagaagga tttaagcaaa aacattaggc tcgaaatatg agttcgggca aaaaatttag  151020 accctttttaa gatatgagtt tgactcgggc ttgaacattc aaggtcaaag cccgtcctaa  151080
ctagtaatgt tttatgttat tttatttttta tatattatat aatttataac acataaaaat  151140
taaatctata atagtattta taatattact accatgatgt aaacattaac aattgttaag  151200
gtgcctatat atgaaatttt aataaataaa aatatataaa attattaaat gataaattaa  151260
aaataacata aatatatatt tttgaaattt atatatatat atagacaggc ctaaaatggg  151320
ttattaggtt agtcatttac aaatataaac gagcttaagt aaaattttag gtcaatattt  151380
cgaatcttta cttgagcaag tataaagtat gttaatacca ttcgtaagcc gacttaaact  151440
caatccataa acacctctaa tataatccat aaaaccagtg catagtttaa gatttgggtc  151500
acctttataa tctaacaaaa ttgattcaaa ttgttatttta agttagctat aaaatatcaa  151560
acaatttaat taaacgataa agcaaatttc gggatgtatc aaatccttaa aagaaaaaat  151620
aaaataaatt attttacaac tcaaacttaa attgattcca tccttaacac tcaacagaca  151680
atagctcttt cactcttcca ctatatagct ggggatgttg acaacattgc cttccaataa  151740
```

```
aatcctgttc cattgctatg tatggttgtg tttcataact ttacaatctt taaaaatcaa   151800
cgcaatcatt caaactttt ttactcaata taatatattt aaaaataaaa taagaatta   151860 tatttgttct ttttaacaca aggtctaaaa ttagatatag cctttcctaa ctcataaata   151920
agaggataat acgcttcaac aaacttaaac ttttatcctc ctgcattgac gactatatcg   151980
atactaatca aactaaaact caatcaaaat aaaggtgatt aaacttacta ctcatgtgga   152040
agctcaaagt tgacactaaa ttgagtagta tattttggtg aaacaatttc caacagtaaa   152100
cttgattaaa cacactccac tataccaaaa cagaaatgat tatttaagat gatatatttt   152160
attttgatct ttccttaaaa aaaaaaaaag tgaaggagg caagtaggga actggaaaat   152220
gctatcataa actatgcctt tttctgaaga tagagacaat attacggtgt ggtacctta   152280 ccctgtctat aatcttcctt tgttttcctg aatataattt ctatgtagat ttagtagatg   152340
aataatggga tctttttat ttactaattt gttaaaggga agaaacgtg aatcatgcac   152400 agctcttggt gctgccactc acgttttcta gcatttctat gatataaaat aagaacaaat   152460
tgcatttaaa tataaatatt agggtagtga attcccacat atgtgctttc caataaacta   152520
aagattctgc tgcctaatct caagaaattc tctcacttac atgtaaaaca aagcattagt   152580
taaaatttaa taacaaaaag tagtattaga atagaataat cattcaacag ctttgttttt   152640
ggaattatat ctaaatgtaa atcccaatat aagcccccga cattgcggta aatggtaagt   152700
caaggctgag ccctatttct gtttaagatt agactgagct ttgaaataag ctgtttaagg   152760
ttacataata gcaggcagac agtacatctg attagacttt gcctgtgtct ttgccttcg   152820 gcttcaaccc tccaaactta aattaattta tgcacttcta tatctacttc attaaaaat   152880 agattttac tgcttcaaat tttatctaaa attaattcga gtttgtttaa aatttatata   152940 tattttaaa aattacattt tattttatt taaaatttaa aatttatttt ttattttgat   153000
caaatttctt tttgtttttg aaaattattt tgatcaacat tttaaatata aacaaattaa   153060
aaaaattata tttactaaat attaaataaa aatattatac tataaatatt atgaaaattt   153120
taaaaaatca acctcgctta actcacttaa atatttaaat tcgagcctag tttatgttta   153180
aaactttaaa tgagcttata caaatttatt tttcaagttt aatattaatt aaaccttttc   153240
taaatatctg ataaaattta aataaataac taaaccttg aataaatcta tttgagatta   153300
tcaaattaaa taagaataaa aaagttaaa taccctaaatt taaaataatt agttttttca   153360
gtatttagaa tttaggatta ccaacaaaaa cttaaatggc ataatgactt gtttggccct   153420 tcaacttat aaaaagtta ttttagccat ttatttaatt tttatttt ttaacccta   153480 aacttgtatt ttttgtcaaa tcaccctaaa atagatggaa aagttaacat tttttaactt   153540
tgctaatgtg gcatactcgt ggattgccat gtggatgaca cattagcatt taattaactt   153600
tttaaatttt taaaagttca aaaaatatat aataaattgt tttaaaaaac ttaaaattat   153660
taaaaatagt attttttaaa tttaaaaaaa taattaaata ttggcatgtc atctatttga   153720
taatccacgt gtatgtcaca ttcgcaaagt taaaaatat taacattttc atctatttg   153780 ggatgattta acaaaaaaaa atacaatttc aatggctaca aagaacaaaa attaaataaa   153840
agcctaaaat aattttttc ataaggttag agggacaact ttgaagagtt taaatttcca   153900 tgaaagaaa tgaatgggta ggaaaagaaa aatgtgaagc agaattagca atttcaatgc   153960
atccaaccaa cccacccctc cgcctaaatt actaaagtat ttctattaaa agaagaaata   154020
attaagtaca ataataatgc atgtatttgg gtcatcatag ggacatataa ttagggattc   154080
aagctacttt ttgttgcata tataaattaa tataaaattt taaattgggt agatgaaata   154140
```

-continued

```
taaataattg gtgtataaaa aaagaagaaa ttaattgttg ggggagatca tgtcccttc    154200 tagacaagcc tcatgtttgg tacgagtatg ccattttccc gacatggggt ggaaccacat   154260
ttaagaaaag gaaggcaaag agcccattag tctttatcaa tctcataatg taagcttccc   154320
ccttcgcatc attttagata tgtttggcta catgttttaa cttgtaatcc cacacaacac   154380
tccatgttat tcttgtggat gtctctattt tccttgagcc taaccccagc atgtatctct   154440
cacattttgt acttaaattt tttaccctcc tatcacatat tttattcata taaatcatat   154500
atattaaaat tttaataatt ttaataaaaa atttaataat ttgtttagct taaaaaaaaa   154560
atcatccata agggtggtct taagtagcaa gtaggagact ttacctttc aaaaagaca    154620 aatttttaat taaaaccttt taaaaattat aatattaaaa gttaatataa tagtaaaatt   154680 atattttca aaaatatatt gtttaagaat tctatacaca cccttgaggc cttaacttt    154740 tttttcaagt cctccaaagc aaaatgcagt aatccataag ggttatcatt agatttgaga   154800
tttataattg aaggatagtt tgaataaatt tgagaaaagg gttatgccta acctattaat   154860
tgtataatca aatttgatta ttctatgata ggttaacgta ataacctatt tttatgttga   154920
gaaattaatc atagtggtga atctgattca atttagttca atcaagattt ttggaatttt   154980
caaatcaatt attataatta aatatgactc tcgattttt atactaattt tatttttatg    155040
aacttgcttt gacaaaatta actttattta atagcttttg acattgaaaa aatttcgata   155100
taattttcaa atgaataaaa aataaaatta attataattt aaataaaaaa caaaattttg   155160
ttttgagtat attcccaaaa tcatgtaaac attgccgttg gaatcgactt ttgtttttag   155220 tttttatt tatttttc tttgtggagc ctaattaata gtgaagtttg aatttcataa     155280
ttagggacga aaaagttgct acaactctca tcacaataaa ttgaaaagaa gaagtaata   155340 atttcaatag cacatgcacc catgtactaa acctaaatta ttgcaaaaat ttgttggtca   155400
ttcattgata tttgatactt gtattcatca gtttccgccg ctatacaccc tccaccaatc   155460
tctaactatt cctttgaaaa tggctctccc ttctgcccta ggtatcaacc aaactcttgg   155520
aattgattta attaagttat acaaaatgtt gaaacagctt atattataag cggtacaaag   155580
agtcgttaaa atagagtgaa taatgtggag agccgctaga actaatggat tgagggagtc   155640
gaggccgtag ttgagcaaag tttgggtaat gagctttgtc tcttgtctgc aggttttatt   155700
gaaagaaggg atatctataa aggcttgaag tgtgccattt ttctcatgat aatatcttgg   155760
taaagtccac cttaagtcaa gattaaagta tgagttaaca aacttagcaa attaaaaaca   155820
ttaattagat tagatttgat aggatgatta ttattgacgg tgttgcagcg atatttcatc   155880
tctaaataca tttataataa cttgagatat tcaaatgaat atactaaaat ttgaatgcag   155940
aaacatagta cgaagcttaa tcaatcacaa ataataatc aaatacatag taattatttg    156000
ataattgtat ggtgtagttc tttattttc ataaacaggg ttagaatacc attaattaat    156060
ttaattgaac attttaaaaa caaattcgtt aataatgtag tcgctaatta tcagtacagt   156120
ggaattaatg tgacatgaat ataattgggg ttagggaggt aataaggagt tgttttcaag   156180
gcatttaacc aaagggaccg tcataattaa aaacgcactt catttttgaa ggcaatatat   156240
acctacttct atactatttg catgtgaaca gtcaccttcc attcttcatt attactcatt   156300
aaaaacttta ctagagatta gctctccctc ttatttatat agctgctgcc cagtggatca   156360
caaactagct aacctaacct aacctaacct aacctagcct tggattcagt ttcatgtatt   156420
aaactcccaa ctactactac gaaattcaag ttggaaccc aacatttcat agtcatcgta    156480
```

```
cgagataatt ctttagattc tcgccgatac acagaaattg aaggacttat ttctctttga   156540
tatatataca tgtagttcaa tatgaaataa attcatatat attagaggac atggcagaag   156600
caagtgtgga agagttggga aacattgcct gttattttct tgtttccatg agaaggtgtt   156660
gggggaacta tggttgaatt aggaaggagt caagtgggca ggcttgttga tgttcctggg   156720
cgtgcatgtg catgtgcatg tgcatgcatg gagattttgc caatacatgt tgacaaacta   156780
tggggttttt tgcgacagtt ttctttctac ggtgcttgct ggcaaatgca catgcacgtg   156840 cattttatt atgttttttg gttttagacc tattgctttc atatttatgc gtgtggactg   156900
tggacagcca atacaattta tgttaatata ttgataaaaa taatggaaat ttatctaaca   156960
cccccaaaat gtaaatttat ataaattata tgattatgac aataatattc cgattattaa   157020
ataaataaaa tcatgataat gtattcaatt atttatattc tttcttggta aacagatatg   157080
tccaatgatt gtcttgagct aacaaggcat atttttctgg tacatgtaaa aagataaata   157140
aacaaaaatt tcaaggaat gataaaataa tataatattt agttaacttc aatttcgaat   157200
ttaattcatg gattaactct acctcttaat aaggaacaat tttctaagat tgtattagca   157260
atcagtcaac agatcagata ttttaaaaa aatataacag tttaatgatt ttccttcctt   157320
tttcctagaa aattcaggaa caagaagcat taaaagaaaa tataaatatt aattagttgt   157380
tgttgcagct ttcttagata ccaaagaggg tttaattgaa aaacttttta ttttttgaa   157440 aatatttata aaaatattt tagaatttta tcgaataata tttaaaaatc ataaaacaaa   157500
ctaaagttaa tcaaaataat acctaaaatt aatataaact atatcattaa aacaagagtg   157560
ttgagattat taaatcaata aaatcatgat aatatagcca atttattgtc ttcaactaac   157620
aaggcatttt tctggtataa catgaagaat attaacagca tgtgaataat aaaaattcgt   157680
tttactgata aaatatttat atttaaaaat ctaaatcgt gtgagcaata attatatgct   157740
gctatagtca gcaagtcaga ttataaaaaa aataataata aagcagtttt ctgaattttc   157800 ttttccttt ttcctggaaa cttcagtaaa aaaaaaacat tagaagacaa gagaacaagt   157860
tttagtgagt tgtagttgca gctttcttag gtaacaaaga gagtttctcg tcactttcat   157920
gccatatgat gccgtatgct acaaaaactt gtttaacatt attaatttcc cttacattat   157980
taaaagaaaa agtgcatttt gagttattgt cagcgttagg tttattggaa aaattacggc   158040
ttttagatta ataaagcttg tagtaaatga aatgtctgcc tgccttgaca aaaaaggaca   158100
actctcgaaa tggccacttt attttaact caaaaagttg aatggggaga aattaagtgt   158160
taataattac actaaattct tccttttct attattgctg acctattcgc tatttgggta   158220
taaaatctga tatataacat tttaaaatct ttaatactgc tatcattcct gaaaatcacg   158280 ttttagaat atagttattt gtttaaaaat aatataattt attttaaata tgaaaaatta   158340
tttttataat tttttaatt gagttggtgt aattggctct taatataact tagtctgata   158400
ttttactaac agtataggta tatataatta atagagaata aaattaaaat gtaacaaatt   158460
aggccttggt tggatggtaa atttaatatt tttttaatat aattagcatg agtttaaatc   158520
tcattatatg tatattttta ttattttttt aaatttaaaa aatcttaaat taccatttaa   158580
taacttattt taaacacata aaggtttttt tttcttaagc gaattgatac ttgattgact   158640
tgttatacca acttaatcaa aaattttatt aataatatag acaaaatgat aaacgaattg   158700
ttagattaat taatttggat attgatccaa accaaacata agtatattat taaggaacgt   158760
agaattctaa taaacaattt tacatttcat gacccaacag tttgctttaa aggagtttat   158820
ttcaagccac tgtttgctag aaaaaatcta aaaaaaaaat gaaaatataa gtgagaatta   158880
```

```
tttcttcaaa aaaccaacaa attacacaaa tataatatga catttaaata tctaaattca  158940
aaacaaaaat taaaaaaata agtgggaatt atttttatt ttgagtaaag ccttatttaa  159000
aattcttgta caaattcaag caatattatc ctgttattta ttgatattat attttttttt  159060
aaaaacccct taaaagcctac atttttcttta ctccccactt gttctaatta aaactttcgg  159120
gtgaaatcaa gcctccaatg gcaaatatat gatcttctag agggaaccta gctatagact  159180
ttatttttta aaagaaaatt aaagttgtta aaaagtattt ttctttaata ttttcaaact  159240
tattaaattc atggacagta cttgatttag aaaccctaat caatcaagcc gattgagctt  159300
caacttagtt gatatcgtta ttgagttcaa gcacatttaa gcatattttt tttatataaa  159360
tattaaataa gaattttgaa aaaaaaaacc ttaatcaaga attgttgaaa aaaaattaac  159420
aaaaaaccca cttaatttgt agttacaaat atttgatgta tttaattaaa aatgctaaca  159480
ttttgaatat aatttgattt gaaggcatta aatatctcat gcgtcatcat cagttaataa  159540
taatataata tatttctaaa ttcaaaaatt gaaactttaa aaaacaatat ccgaaaccta  159600
aggcttgaaa gaaaaataaa ataaaataat tttaatttta attatgttta aaaatttgaa  159660
taaaaaactt gaaattcaaa accccaaatc tttaatttaa aataaaaaaa cttgaaactc  159720
aaaatttaaa cacagaaaga aaaacaaaat aattataatt aatatttaac tatctttaat  159780
acagttaata ttatttattt tcaagtcctt caattttttt ttcattttttt acaccaataa  159840 tgatgtaaaa caaatattaa tcatacatta aatttgtaaa ttagatctaa aaaataaaat  159900 atatacttttt atattaataa atattaggtg cgatgataaa ttatattata tgttttaaaa  159960 aaagaattc gagttcaaag attaaaagtg ttgattatta ggaaaacaac cgtgaactca  160020
aaaaaatatt aatttttata atttgaaaaa caaaaaaaaa atctgaataa tataaaaaac  160080
aataatactc ccatatgaca accaccacca taatgcttta attcaaaatg gtcccaactg  160140
gaaaacaaag aaagaaaaag ggcaggaaaa cagattaaat aaaatctttc cgtacaaaga  160200
tggatcgact gactgagttt ataaaatttt gttattattt attttagtaa acactgatat  160260 acttttttagg cattcaattg caggagaggc aacgcccacc taccttcaac cccaaacaga  160320
tctcgtctct gttaaaattt gcaggcctac gcctagctat ctcctaaacg tttctcctct  160380
cacgtcttcc actgtttggt tctcgagaaa taaatcaatt tacaaattta atgccattca  160440
tcttcaacta tctttacctc tttcaaccca aaattttcaa tttattgcac cgtcctactc  160500
gtatcgtatg ttccccgtgt atatttcgct ctacgttttt tttttaatca ttttgtaata  160560
atttggtttt cctttttata tatatatatt tatttattta gggcttgaat ttttttactt  160620
catttctatg aattattttt aaatatatat attttatgt ttattttatt gtctatattg  160680
gagatttgta aatatctctt ttaacaatgt tgtctcttta aactcgcgtt cttttcttgt  160740
taaaaaaata tatttaaatt attttttataa ttttaaatat aaaatatttt tacatcataa  160800
aaataaaaaa ttaataaaaa ataaaattcg ctccaattcg attttagtat ctacaacttt  160860
ttaatttaca tttcaaaaat aatccaaaca tcaattttca tttattttttc ttttttttca  160920 aaacccctat atatggttat gaattgagct taaaataagc cttgtagata agtaagatga  160980
attcgaatgc ttttggattc ttgtaagaga aacatgaagt ttgaaggaat cagagcataa  161040
gatttggaac actctctgat cttttaagtc aatctagaga ctttatcata agaaatgaa  161100 agaatagagt gaaaaagag actcaattaa aatttaaaaa ttatttatat taattattta  161160
aaaaatactt aaaatttata tttcatatac cacaatatta acaatgagtt gccgtgaatt  161220
```

```
attttattat atttacacta tcgttcaagt tgaattttt ttaataccaa aataatacta  161280
acttggcatc gtagtaataa taacatgtaa aactaagaat aatttacatt taattctatt  161340
attaatttta ttataattta agtttatata tttattctat atatcataat attaattact  161400
taatacatta ttttaaatat ttcgattata aattaagttt atatatttac tatattataa  161460
tattaatgaa attaaatatt aaacatggac attttatttt tgtaaaagca tttttaact   161520 tcaatggtaa actaaattaa tttcttgcta ttttggttct cctcgtaacc agatatgttt  161580
taatatagtt tttgtattgt acaaaaaaat aatttaatgt gattaagttg ttatgtattt  161640
gatattagtg taaataaata taaaactcgt ctaaatatcg attcaattt taaaatttta   161700 taatgtatgt atttatttat ttaaaaaaat tatatttttt taatatactt ttattattcg  161760
aaattattga tataattgta agttagattt tagtaaatta aaaatattat atgatataat  161820
aaaattgaaa atatcactaa accattattt agaaaaatat taatatattt aattatatat  161880
atattactat aaaagtttga ctgagttagt gttagccgtc aatcaagtcc caactcaatc  161940
ataaaaatat caaaatgtta attttttat aaagcaataa atattatttt gagggtattt   162000
gtatattttt ataaaataa atgaggagta tttggtacac tcagtgtact tttttttatt   162060
ctactagtag tcttaaaaaa ttgacatgtt ttttttaata tatattttt aataatttac   162120 tatattttt aataatttaa actaccataa catctctcta attcataaat aagtgaataa   162180
tacgttttag cgtattcgaa tctatctttt tataacaata cttattctaa gtgagataag  162240
actttatggg cataatttta ttttatgtaa taaaaaaaaa acctaaacgg taaatagaag  162300
tggcaaaggt tgaatctcat gggctagaag ggaaggaaa acattgtttt atgaaacaaa   162360
atgacatgac ggttctaatt tttccttctt tttttattgt atttgtggta ttgaggagaa  162420
gaaatatata gaaaatgaat aagttggtaa ttactaaatg tagcaaaacc cgaaaacatt  162480
ctttgactcg aacatccagg aataaataat gtataaatca gttgacttgt aaaataatct  162540
acccagggag ggaaaatatt tgtgaaactg gaagggataa acctataacc atatttcttt  162600
ttaatttatt gaccacattt ttggtttatt aaattgaatt atgaaaagag acagatcata  162660
tggaaaaagg tcccacttat caccagactc gtggctttgg gtctgcgcaa tcagacagta  162720
gaagctccca aaaagagaag taaggtcaaa agaaccccc aacccaacct ccctttaaat   162780
gaaaagcatc actctactgt ttccttagcc cgactttgac ccttccccca ttttcaatta  162840
aaataccaca cccttcccaa tatatgtctt cttgtttgtc cccccaaact tcgctttcat  162900
tatcattatt atccatataa tacgcgtaga ataatttagg tactattttg agttggtttt  162960
caagaggatt aaattaaaaa gaaacgacag cgcatctttc tcgcctttc atgtgattta   163020 aatttaaac ccccccaccct tgctctttca ctgcaaaaag aaaagcgaat gagcccccc   163080 ccccattttt tacttttca tatataaata aactgatcaa ataaataaaa gggaaaagag  163140
atgatgagac aatcccatgg cagtatggga cttctcactg atcctcctct tttataatt   163200 tatctcattc aatatatttt ttcttttaa gaaaaaactt ttaacaaaaa tatatctcac   163260
ccaaaaaaaa aatcatgata tttcccatct ccttgctata agctgtacac tttgttattc  163320
caagtttccc ctcttcacct ccctactttt taatctatct atctcttgga accatctgt   163380 tccctaaatc ttcacaaatt cacaaaattt ccaccccccat gaaaatcata acgaaattga  163440
ataaaataaa aacaaggaac cccaccataa tcccccaatt tctgtccccc cccaccctcc  163500
tttgaatgta caggagcttg caccatcaaa atcatgatga tgatgaatca atcctcactt  163560
caccccacca catttccaac cctgctgcag tcgactgaga ttgagctatc ccaagatgtt  163620
```

```
ttgctcacta gcttggtttt aagtgtgccc tgtggagtct tagctcaaag cttgtaacgg   163680
gggcctgaac gatttcccct atatgggaga actgaagtgg cattttcaga ctagacacag   163740
gccagatgtt ttattccaat tagccttctg atcatgctct actcttcttc aatgaaaatt   163800
cttcctataa aatcccgaaa cctcttcgag tagagttttg gaccaacagc tgatattgaa   163860
gaaggatcag cttgtagtga tttgtaggca tgctccaatt tcttgctgat gtcgtagtct   163920
tgtaagatgt caatgatgcc aaagtataac actacttcat aaacttcgcc actatgtgaa   163980
aagagaccga ctccaccctg tgtatactga tcaaagtcgc ttcttcttga cattcgcact   164040
gctcttgctg gcatgtttgc tcctagccgt atcaatggtt tcctgccaaa cgaaaaatac   164100
atagaaaatt atttagaatt tctgttaagt tttctttccc tacagaatca caactcgcag   164160
aagaggcatc aatccacaac acataaaatt ctaactgcat actatcaaag tccatttcag   164220
atccaattcc ctaaagtatc tcaaatgcgt atataatttt caccaagagg gtgatgaaca   164280
aatggtatgt catatggtga cagtccaaag atcattagaa gggaaagaga ccttaaaata   164340
gaactagtga tatgcaccaa accatcgggt cacattctcc accattctca tccactgagt   164400
tcatgaatca tttcctagaa actagataaa tgggtaacaa aaaatcaagg caacccttga   164460
ttcttatcta gtaggatcat aaagggccac aattgctaca tgccccacca aaaaaaaaat   164520
ttgtcttctg aattatttcc acaaaatcac tcagacaaca caatcaacct tcaattattc   164580
catcgaatat gatcaagtat caacagttga ccgagaaatt taaaatttaa gcatcatcat   164640
ggaggagcct tgcctaattc cacatctaca ataaggaaat aactagaacc aaaagtatta   164700
tctaaggaag agagcaaaac atactggcca gctaaaatcc gatccatgtc ctgtagctca   164760
gcttcaagga atctacagcc acgcataaac ttttcattct gatatgaatc cttttttgcct   164820
gcataggaa ggcatattca aatcccgatt cttatttcaa cagatattat ccattcaaat   164880
ttcatgagga atagtatggt tttctattaa cttacctgtg cgcaagagaa acggtgataa   164940
ccccattttta tcgcctctat tatcatcccg aaagtgtagt ccaaccaaaa gactataatc   165000
cataattctc tcagcctcca agaactcgca atctcgatca atttgcctat caccatgtag   165060
tcataggaaa ttagcaaaat acacgacact gacataactg gagtaaagta ataaaatata   165120
gcttacttca taagctcttg gaaccaattc ctctggaggc gaaacacata attaagatcc   165180
aggtctttaa gggtagtggt ttcatcaatt tcctcttctg gcttatcagt tgagcggcca   165240
tgggaggatc                                                          165250
```

<210> SEQ ID NO 54
<211> LENGTH: 1065
<212> TYPE: DNA
<213> ORGANISM: Gossypium barbadense
<220> FEATURE:
<221> NAME/KEY: CDS
<222> LOCATION: (50)..(589)

<400> SEQUENCE: 54

```
aatatagtga aatatgggtc caagattttc tgggttttta atctaagca atg ctg ttt      58
                                                     Met Leu Phe
                                                     1 tta act caa ctc ctc tct cta aca gat ggc cgt gat att ggt gtt tgc      106
Leu Thr Gln Leu Leu Ser Leu Thr Asp Gly Arg Asp Ile Gly Val Cys
        5                  10                  15 tat ggt ttg aac ggc aac aat ctt cca tct cca gga gat gtt att aat      154
Tyr Gly Leu Asn Gly Asn Asn Leu Pro Ser Pro Gly Asp Val Ile Asn
```

```
                20                  25                  30                  35
ctt ttc aaa act agt ggc ata aac aat atc agg ctc tac cag cct tac         202
Leu Phe Lys Thr Ser Gly Ile Asn Asn Ile Arg Leu Tyr Gln Pro Tyr
 40                  45                  50 cct gaa gtg ctc gaa gca gca agg gga tcg gga ata tcc ctc tcg atg         250
Pro Glu Val Leu Glu Ala Ala Arg Gly Ser Gly Ile Ser Leu Ser Met
 55                  60                  65 agt acg aca aac gag gac ata caa agc ctc gca acg gat caa act cat         298
Ser Thr Thr Asn Glu Asp Ile Gln Ser Leu Ala Thr Asp Gln Thr His
 70                  75                  80 caa agt gca gcc gat gca tgg gtt aac acc aac atc gtc cct tat aag         346
Gln Ser Ala Ala Asp Ala Trp Val Asn Thr Asn Ile Val Pro Tyr Lys
 85                  90                  95 gaa gat gtt caa ttc agg ttc atc atc att ggg aat gaa gcc att cca         394
Glu Asp Val Gln Phe Arg Phe Ile Ile Ile Gly Asn Glu Ala Ile Pro
100                 105                 110                 115 gga cag tca agc tct tac att cct ggt gcc atg aac aac ata atg aac         442
Gly Gln Ser Ser Ser Tyr Ile Pro Gly Ala Met Asn Asn Ile Met Asn
        120                 125                 130 tcg ctc gcc tca ttt ggg cta ggc acg acg aag gtt acg acc gtg gtc         490
Ser Leu Ala Ser Phe Gly Leu Gly Thr Thr Lys Val Thr Thr Val Val
135                 140                 145 ccg atg aat gcc cta agt acc tcg tac cct cct tca gac ggc gct ttt         538
Pro Met Asn Ala Leu Ser Thr Ser Tyr Pro Pro Ser Asp Gly Ala Phe
150                 155                 160 gga agc gat ata aca tcg atc atg act agt atc atg gcc att ctg gtt         586
Gly Ser Asp Ile Thr Ser Ile Met Thr Ser Ile Met Ala Ile Leu Val
165                 170                 175 tga caggattcgc ccctcctgat caatgtgtac ccttattttg cctatgcctc              639 agacccact catatttccc tcaactacgc cttgttcacc tcgaccgcac cggtggtggt        699
cgaccaaggc ttggaatact acaacctctt tgacggcata gtcgatgctt caatgccgc        759 cctagataag atcggcttcg gccaaattac tctcattgta gccgaaactg gatgccgac        819 cgccggtaac gagccttaca cgagtgtcgc gaacgctcaa acttataaca gaacttgtt        879 gaatcatgtg acgcagaaag gggctccgaa aagacctgaa tatataatgc cgacgttttt      939
cttcgagatg ttcaacgaga acttgaagca acccacagta gagcagatgt caacgagat       999 gttcaacgag aacttgaaat gttattgttg ctatttaaaa tcttttgcca gagacgcttc     1059
atatag                                                                1065

<210> SEQ ID NO 55
<211> LENGTH: 179
<212> TYPE: PRT
<213> ORGANISM: Gossypium barbadense

<400> SEQUENCE: 55

Met Leu Phe Leu Thr Gln Leu Leu Ser Leu Thr Asp Gly Arg Asp Ile
  1               5                  10                  15

Gly Val Cys Tyr Gly Leu Asn Gly Asn Asn Leu Pro Ser Pro Gly Asp
         20                  25                  30

Val Ile Asn Leu Phe Lys Thr Ser Gly Ile Asn Asn Ile Arg Leu Tyr
 35                  40                  45

Gln Pro Tyr Pro Glu Val Leu Glu Ala Ala Arg Gly Ser Gly Ile Ser
 50                  55                  60

Leu Ser Met Ser Thr Thr Asn Glu Asp Ile Gln Ser Leu Ala Thr Asp
 65                  70                  75                  80
```

```
Gln Thr His Gln Ser Ala Ala Asp Ala Trp Val Asn Thr Asn Ile Val
 85                  90                  95
Pro Tyr Lys Glu Asp Val Gln Phe Arg Phe Ile Ile Ile Gly Asn Glu
100                 105                 110
Ala Ile Pro Gly Gln Ser Ser Ser Tyr Ile Pro Gly Ala Met Asn Asn
115                 120                 125
Ile Met Asn Ser Leu Ala Ser Phe Gly Leu Gly Thr Thr Lys Val Thr
130                 135                 140
Thr Val Val Pro Met Asn Ala Leu Ser Thr Ser Tyr Pro Pro Ser Asp
145                 150                 155                 160
Gly Ala Phe Gly Ser Asp Ile Thr Ser Ile Met Thr Ser Ile Met Ala
165                 170                 175
Ile Leu Val

<210> SEQ ID NO 56
<211> LENGTH: 1239
<212> TYPE: DNA
<213> ORGANISM: Gossypium darwinii
<220> FEATURE:
<221> NAME/KEY: CDS
<222> LOCATION: (112)..(145)
<220> FEATURE:
<221> NAME/KEY: CDS
<222> LOCATION: (258)..(760)

<400> SEQUENCE: 56
aagaaacgag caccagttat tgactttcct ttgtaaaaaa aaaaaaagtg ctgagatcaa        60
gaaatatagt gaaatatggg tccaagattt tctgggtttt taatctaagc a atg ctg       117
                                                         Met Leu
                                                          1 ttt tta act caa ctc ctc tct cta aca g gtaaacaaa cttctctaca              165
Phe Leu Thr Gln Leu Leu Ser Leu Thr
 5                  10 gtgattttac agtaaatatg gctttgaaaa atatacaaca aaacattttat cttcaatcca      225 ttttaattac tgatctacta tatatgttgc ag at ggc cgt gat att ggt gtt          277
                                   Asp Gly Arg Asp Ile Gly Val
                                                        15 tgc tat ggt ttg aac ggc aac aat ctt cca tct cca gga gat gtt att         325
Cys Tyr Gly Leu Asn Gly Asn Asn Leu Pro Ser Pro Gly Asp Val Ile
 20                  25                  30 aat ctt ttc aaa act agt ggc ata aac aat atc agg ctc tac cag cct         373
Asn Leu Phe Lys Thr Ser Gly Ile Asn Asn Ile Arg Leu Tyr Gln Pro
 35                  40                  45                  50 tac cct gaa gtg ctc gaa gca gca agg gga tcg gga ata tcc ctc tcg         421
Tyr Pro Glu Val Leu Glu Ala Ala Arg Gly Ser Gly Ile Ser Leu Ser
         55                  60                  65 atg agt acg aca aac gag gac ata caa agc ctc gca acg gat caa act         469
Met Ser Thr Thr Asn Glu Asp Ile Gln Ser Leu Ala Thr Asp Gln Thr
 70                  75                  80 cat caa agt gca gcc gat gca tgg gtt aac acc aac atc gtc cct tat         517
His Gln Ser Ala Ala Asp Ala Trp Val Asn Thr Asn Ile Val Pro Tyr
 85                  90                  95 aag gaa gat gtt caa ttc agg ttc atc atc att ggg aat gaa gcc att         565
Lys Glu Asp Val Gln Phe Arg Phe Ile Ile Ile Gly Asn Glu Ala Ile
100                 105                 110 cca gga cag tca agc tct tac att cct ggt gcc atg aac aac ata atg         613
Pro Gly Gln Ser Ser Ser Tyr Ile Pro Gly Ala Met Asn Asn Ile Met
115                 120                 125                 130
```

| | |
|---|---|
| aac tcg ctc gcc tca ttt ggg cta ggc acg acg aag gtt acg acc gtg<br>Asn Ser Leu Ala Ser Phe Gly Leu Gly Thr Thr Lys Val Thr Thr Val<br>135                    140                   145 | 661 |
| gtc ccg atg aat gcc cta agt acc tcg tac cct cct tca gac ggc gct<br>Val Pro Met Asn Ala Leu Ser Thr Ser Tyr Pro Pro Ser Asp Gly Ala<br>150                    155                   160 | 709 |
| ttt gga agc gat ata aca tcg atc atg act agt atc atg gcc att ctg<br>Phe Gly Ser Asp Ile Thr Ser Ile Met Thr Ser Ile Met Ala Ile Leu<br>165                    170                   175 | 757 |
| gtt tgacaggatt cgcccctcct gatcaatgtg taccttatt ttgcctatgc<br>Val | 810 |
| ctcagacccc actcatattt ccctcaacta cgccttgttc acctcgaccg caccggtggt | 870 |
| ggtcgaccaa ggcttggaat actacaacct ctttgacggc atagtcgatg ctttcaatgc | 930 |
| cgccctagat aagatcggct tcggccaaat tactctcatt gtagccgaaa ctggatggcc | 990 |
| gaccgccggt aacgagcctt acacgagtgt cgcgaacgct caaacttata caagaacctt | 1050 |
| gttgaatcat gtgacgcaga aagggactcc gaaaagacct gaatatataa tgccgacgtt | 1110 |
| tttcttcgag atgttcaacg agaacttgaa gcaacccaca gttgagcaga tgttcaacga | 1170 |
| gatgttcaac gagaacttga atgttattg ttggctattt aaatcttttg ccagagacgc | 1230 |
| ttcatatag | 1239 |

<210> SEQ ID NO 57
<211> LENGTH: 179
<212> TYPE: PRT
<213> ORGANISM: Gossypium darwinii

<400> SEQUENCE: 57

Met Leu Phe Leu Thr Gln Leu Leu Ser Leu Thr Asp Gly Arg Asp Ile
1               5                   10                 15

Gly Val Cys Tyr Gly Leu Asn Gly Asn Asn Leu Pro Ser Pro Gly Asp
          20                   25                   30

Val Ile Asn Leu Phe Lys Thr Ser Gly Ile Asn Asn Ile Arg Leu Tyr
35                   40                   45

Gln Pro Tyr Pro Glu Val Leu Glu Ala Ala Arg Gly Ser Gly Ile Ser
50                   55                   60

Leu Ser Met Ser Thr Thr Asn Glu Asp Ile Gln Ser Leu Ala Thr Asp
65                   70                   75                 80

Gln Thr His Gln Ser Ala Ala Asp Ala Trp Val Asn Thr Asn Ile Val
85                   90                   95

Pro Tyr Lys Glu Asp Val Gln Phe Arg Phe Ile Ile Ile Gly Asn Glu
          100                105               110

Ala Ile Pro Gly Gln Ser Ser Ser Tyr Ile Pro Gly Ala Met Asn Asn
115                  120               125

Ile Met Asn Ser Leu Ala Ser Phe Gly Leu Gly Thr Thr Lys Val Thr
130                  135               140

Thr Val Val Pro Met Asn Ala Leu Ser Thr Ser Tyr Pro Pro Ser Asp
145                  150               155               160

Gly Ala Phe Gly Ser Asp Ile Thr Ser Ile Met Thr Ser Ile Met Ala
165                  170               175

Ile Leu Val

<210> SEQ ID NO 58
<211> LENGTH: 1234
<212> TYPE: DNA
<213> ORGANISM: Gossypium darwinii

```
<220> FEATURE:
<221> NAME/KEY: CDS
<222> LOCATION: (75)..(144)
<220> FEATURE:
<221> NAME/KEY: CDS
<222> LOCATION: (239)..(1179)

<400> SEQUENCE: 58
aagaaacgag caccagttat tgacattcct ttgtaaaaaa aagaagaagc tgagatcaag      60
aaatatagtg aaat atg ggt cca aca ttt tct ggg ttt tta atc tca gca      110
             Met Gly Pro Thr Phe Ser Gly Phe Leu Ile Ser Ala
             1               5                   10 atg gtg ttt tta act caa ctc ctc tct cta aca g gtaaaacaaa             154
Met Val Phe Leu Thr Gln Leu Leu Ser Leu Thr
15              20 cttctctaca gtgattttac ggtaagtatg gctttgaaaa atatacaaca aaacatttat    214
actgatctac catatatgtt gcag at  ggc cgt gat att ggt gtt tgc tat       264
                              Asp Gly Arg Asp Ile Gly Val Cys Tyr
                              25                  30 ggt ttg aac ggc aac aat ctt cca tct cca gga gat gtt att aat ctt      312
Gly Leu Asn Gly Asn Asn Leu Pro Ser Pro Gly Asp Val Ile Asn Leu
35                  40                  45 tac aaa act agt ggc ata aac aat atc agg ctc tac cag tct tac cct      360
Tyr Lys Thr Ser Gly Ile Asn Asn Ile Arg Leu Tyr Gln Ser Tyr Pro
50                  55                  60 gaa gtg ctc gaa gca gca agg gga tcg gga ata tcc ctc tcg atg ggt      408
Glu Val Leu Glu Ala Ala Arg Gly Ser Gly Ile Ser Leu Ser Met Gly
65                  70                  75                  80 ccg aga aac gag gac ata caa agc ctc gca aaa gat caa agt gca gcc      456
Pro Arg Asn Glu Asp Ile Gln Ser Leu Ala Lys Asp Gln Ser Ala Ala
85                  90                  95 gat gca tgg gtt aac acc aac atc gtc cct tat aag gac gat gtt cag      504
Asp Ala Trp Val Asn Thr Asn Ile Val Pro Tyr Lys Asp Asp Val Gln
100                 105                 110 ttc aag ttg atc act att ggg aat gaa gcc att tca gga caa tca agc      552
Phe Lys Leu Ile Thr Ile Gly Asn Glu Ala Ile Ser Gly Gln Ser Ser
115                 120                 125 tct tac att cct gat gcc atg aac aac ata atg aac tcg ctc gcc tta      600
Ser Tyr Ile Pro Asp Ala Met Asn Asn Ile Met Asn Ser Leu Ala Leu
130                 135                 140 ttt ggg tta ggc acg acg aag gtt acg acc gtg gtc ccg atg aat gcc      648
Phe Gly Leu Gly Thr Thr Lys Val Thr Thr Val Val Pro Met Asn Ala
145                 150                 155                 160 cta agt acc tcg tac cct cct tca gac ggc gct ttt gga agc gat ata      696
Leu Ser Thr Ser Tyr Pro Pro Ser Asp Gly Ala Phe Gly Ser Asp Ile
165                 170                 175 aca tcg atc atg act agt atc atg gcc att ctg gct gta cag gat tcg      744
Thr Ser Ile Met Thr Ser Ile Met Ala Ile Leu Ala Val Gln Asp Ser
180                 185                 190 ccc ctc ctg atc aat gtg tac cct tat ttt gcc tat gcc tca gac ccc      792
Pro Leu Leu Ile Asn Val Tyr Pro Tyr Phe Ala Tyr Ala Ser Asp Pro
195                 200                 205 act cat att tcc ctc gat tac gcc ttg ttc acc tcg acc gca ccg gtg      840
Thr His Ile Ser Leu Asp Tyr Ala Leu Phe Thr Ser Thr Ala Pro Val
210                 215                 220 gtg gtc gac caa ggc ttg gaa tac tac aac ctc ttt gac ggc atg gtc      888
Val Val Asp Gln Gly Leu Glu Tyr Tyr Asn Leu Phe Asp Gly Met Val
225                 230                 235                 240
```

```
gat gct ttc aat gcc gcc cta gat aag atc ggc ttc ggc caa att act    936
Asp Ala Phe Asn Ala Ala Leu Asp Lys Ile Gly Phe Gly Gln Ile Thr
245                 250                 255 ctc att gta gcc gaa act gga tgg ccg acc gcc ggt aac gag cct tac    984
Leu Ile Val Ala Glu Thr Gly Trp Pro Thr Ala Gly Asn Glu Pro Tyr
260                 265                 270 acg agt gtc gcg aac gct caa act tat aac aag aac ttg tta aat cat   1032
Thr Ser Val Ala Asn Ala Gln Thr Tyr Asn Lys Asn Leu Leu Asn His
275                 280                 285 gtg acg cag aag ggg act ccg aaa aga cct gaa tat ata atg ccg acg   1080
Val Thr Gln Lys Gly Thr Pro Lys Arg Pro Glu Tyr Ile Met Pro Thr
290                 295                 300 ttt ttc ttc gag atg ttc aac gag gat ttg aag caa ccc aca gtt gag   1128
Phe Phe Phe Glu Met Phe Asn Glu Asp Leu Lys Gln Pro Thr Val Glu
305                 310                 315                 320 cag aat ttc gga ttc ttc ttc ccc aat atg aac cct gtt tat cca ttt   1176
Gln Asn Phe Gly Phe Phe Phe Pro Asn Met Asn Pro Val Tyr Pro Phe
325                 330                 335 tgg tgaagttgaa atgttgttgg ctatttaaat cttttgccag agacgcttca tatag   1234
Trp

<210> SEQ ID NO 59
<211> LENGTH: 337
<212> TYPE: PRT
<213> ORGANISM: Gossypium darwinii

<400> SEQUENCE: 59

Met Gly Pro Thr Phe Ser Gly Phe Leu Ile Ser Ala Met Val Phe Leu
1               5                   10                  15

Thr Gln Leu Leu Ser Leu Thr Asp Gly Arg Asp Ile Gly Val Cys Tyr
            20                  25                  30

Gly Leu Asn Gly Asn Asn Leu Pro Ser Pro Gly Asp Val Ile Asn Leu
        35                  40                  45

Tyr Lys Thr Ser Gly Ile Asn Asn Ile Arg Leu Tyr Gln Ser Tyr Pro
    50                  55                  60

Glu Val Leu Glu Ala Ala Arg Gly Ser Gly Ile Ser Leu Ser Met Gly
65                  70                  75                  80

Pro Arg Asn Glu Asp Ile Gln Ser Leu Ala Lys Asp Gln Ser Ala Ala
                85                  90                  95

Asp Ala Trp Val Asn Thr Asn Ile Val Pro Tyr Lys Asp Asp Val Gln
            100                 105                 110

Phe Lys Leu Ile Thr Ile Gly Asn Glu Ala Ile Ser Gly Gln Ser Ser
        115                 120                 125

Ser Tyr Ile Pro Asp Ala Met Asn Asn Ile Met Asn Ser Leu Ala Leu
    130                 135                 140

Phe Gly Leu Gly Thr Thr Lys Val Thr Thr Val Pro Met Asn Ala
145                 150                 155                 160

Leu Ser Thr Ser Tyr Pro Pro Ser Asp Gly Ala Phe Gly Ser Asp Ile
                165                 170                 175

Thr Ser Ile Met Thr Ser Ile Met Ala Ile Leu Ala Val Gln Asp Ser
            180                 185                 190

Pro Leu Leu Ile Asn Val Tyr Pro Tyr Phe Ala Tyr Ala Ser Asp Pro
        195                 200                 205

Thr His Ile Ser Leu Asp Tyr Ala Leu Phe Thr Ser Thr Ala Pro Val
    210                 215                 220

Val Val Asp Gln Gly Leu Glu Tyr Tyr Asn Leu Phe Asp Gly Met Val
225                 230                 235                 240
```

-continued

Asp Ala Phe Asn Ala Ala Leu Asp Lys Ile Gly Phe Gly Gln Ile Thr
245                 250                 255

Leu Ile Val Ala Glu Thr Gly Trp Pro Thr Ala Gly Asn Glu Pro Tyr
260                 265                 270

Thr Ser Val Ala Asn Ala Gln Thr Tyr Asn Lys Asn Leu Leu Asn His
275                 280                 285

Val Thr Gln Lys Gly Thr Pro Lys Arg Pro Glu Tyr Ile Met Pro Thr
290                 295                 300

Phe Phe Phe Glu Met Phe Asn Glu Asp Leu Lys Gln Pro Thr Val Glu
305                 310                 315                 320

Gln Asn Phe Gly Phe Phe Pro Asn Met Asn Pro Val Tyr Pro Phe
325                 330                 335

Trp

<210> SEQ ID NO 60
<211> LENGTH: 15
<212> TYPE: DNA
<213> ORGANISM: Artificial
<220> FEATURE:
<223> OTHER INFORMATION: oligonucleotide

<400> SEQUENCE: 60
atcctgtcaa accag                                                        15

<210> SEQ ID NO 61
<211> LENGTH: 15
<212> TYPE: DNA
<213> ORGANISM: Artificial
<220> FEATURE:
<223> OTHER INFORMATION: oligonucleotide

<400> SEQUENCE: 61
atcctgtcaa accag                                                        15

<210> SEQ ID NO 62
<211> LENGTH: 25
<212> TYPE: DNA
<213> ORGANISM: Artificial
<220> FEATURE:
<223> OTHER INFORMATION: oligonucleotide

<400> SEQUENCE: 62
gcttttggaa gcgatataac atcga                                             25

<210> SEQ ID NO 63
<211> LENGTH: 25
<212> TYPE: DNA
<213> ORGANISM: Artificial
<220> FEATURE:
<223> OTHER INFORMATION: oligonucleotide

<400> SEQUENCE: 63
ggcataggca aaataagggt acaca                                             25

<210> SEQ ID NO 64
<211> LENGTH: 24
<212> TYPE: DNA
<213> ORGANISM: Artificial
<220> FEATURE:
<223> OTHER INFORMATION: oligonucleotide

<400> SEQUENCE: 64

```
aatatagtga aatatgggtc caag                                          24

<210> SEQ ID NO 65
<211> LENGTH: 24
<212> TYPE: DNA
<213> ORGANISM: Artificial
<220> FEATURE:
<223> OTHER INFORMATION: oligonucleotide

<400> SEQUENCE: 65
aagaaacgag caccagttat tgac                                          24
```